United States Patent
Wang et al.

[11] Patent Number: 5,861,244
[45] Date of Patent: Jan. 19, 1999

[54] GENETIC SEQUENCE ASSAY USING DNA TRIPLE STRAND FORMATION

[75] Inventors: Chia-Gee Wang, Millwood; Angus G. Hepburn, Verplanck, both of N.Y.

[73] Assignee: Profile Diagnostic Sciences, Inc., New York, N.Y.

[21] Appl. No.: 173,489

[22] Filed: Dec. 22, 1993

Related U.S. Application Data

[63] Continuation-in-part of Ser. No. 968,436, Oct. 29, 1992, abandoned.

[51] Int. Cl.$^6$ .............................. C12Q 1/68; C07H 21/04; C07H 21/02
[52] U.S. Cl. ............................... 435/6; 536/24.3; 935/77; 935/78
[58] Field of Search ............................... 435/6; 536/24.3; 935/77, 78

[56] References Cited

U.S. PATENT DOCUMENTS

| | | | |
|---|---|---|---|
| 4,436,826 | 3/1984 | Wang | 436/525 |
| 4,454,233 | 6/1984 | Wang | 436/525 |
| 4,766,062 | 8/1988 | Diamond et al. | 435/6 |
| 5,422,251 | 6/1995 | Fresco | 435/91.1 |
| 5,460,941 | 10/1995 | Camerini-Otero et al. | 435/6 |

FOREIGN PATENT DOCUMENTS

| | | |
|---|---|---|
| 0304845 | of 0000 | European Pat. Off. . |
| 0330185 | of 0000 | European Pat. Off. . |

*Primary Examiner*—Stephanie W. Zitomer
*Attorney, Agent, or Firm*—Ladas & Parry

[57] ABSTRACT

A method of assaying genetic sequences comprises introducing double stranded DNA to be assayed into an aqueous buffer medium containing complexes of an anchor DNA strand anchored to a support matrix and hybridized with a reporter DNA strand having a detectable label. A portion of the anchor strand or the reporter strand consists of a selected sequence of bases capable of forming a triple helix or triple strand structure with a portion of particular double stranded DNA. The reporter strand is displaced from the complex upon formation of a triple helix or triple strand structure, and displaced reporter strands are detected to determine the presence of the particular double stranded DNA. Gene probes, anchor/reporter hybrids, selected gene sequences and kits, useful in the assay method, are provided.

15 Claims, 6 Drawing Sheets

5'---CTCAGAGGAGGAGGATGAAATAGATGGTCC---3'
   |||||||||||||||||||||||||||||
3'---GAGTCTCCTCCTCCTACTTTATCTACCAGG---5'

FIG. 2

```
        5'tctcctcctcctgctttgtctgcc3'   third strand
          ........................
5'---CTCAGAGGAGGAGGATGAAATAGATGGTCC---3'
     |||||||||||||||||||||||||||||
3'---GAGTCTCCTCCTCCTACTTTATCTACCAGG---5'
```

FIG. 4

GENETIC SEQUENCE ASSAY USING DNA TRIPLE STRAND FORMATION

This is a continuation-in-part of application Ser. No. 07/968,436 filed on Oct. 29, 1992 now abandoned.

BACKGROUND OF THE INVENTION

1. Field of the Invention

This invention relates to a method for assaying genetic sequences to genetic sequences useful in the method, and to the relevant components of a kit for the assay of such sequences. It also embodies the selection and use of triple helix forming regions or triple strand forming regions in a number of genes of clinical importance.

The identification of genetic sequences is an important procedure in biological, medical and biotechnological research. Quantitative information about the copy number of genes in humans is particularly important in the early recognition of cancer and the prenatal identification of genetic defects. In the case of cancer cell recognition, such cells frequently have elevated copy numbers of regulatory genes and in some cases, the severity of the prognosis reflects the magnitude of the increase in copy number. Early detection while the copy number is still relatively low allows treatments that can give complete elimination of the cancer with minimum discomfort to the patient. The prenatal detection of genetic defects such as trisomy (three copies of a particular chromosome) or deletions or duplications of small portions can prepare parents and medical staff for later problems and the screening of high risk groups for such defects can help limit the number of births of children with low survival.

2. Description of the Related Art

A number of techniques exist for the detection of genes in human DNA but all of these are skilled techniques that are still principally used in the research laboratory environment. Southern blotting, Polymerase Chain Reaction and Ligase Chain Reaction have all been used to detect specific DNA sequences, but making the techniques quantitative is an extremely skilled process requiring considerable technical expertise and some statistical analysis. The technique described herein is part of a larger process that offers an easy-to-use alternative that combines sensitivity with reliability.

Triple helix formation is described in a publication of Moser, H. E. and Dervan, P. B. (1987) *Science*, Vol. 238, pages 645–650.

European Publication EP-A 0 330 185 of the present assignee describes a method for assaying genetic sequences in which a labelled reporter molecule is hybridized with a genetic probe and upon introduction of genetic material which more strongly hybridizes with the genetic probe, the reporter molecule disassociates from the genetic probe and is detected.

European Publication EP-A 0 304 845 of the present assignee describes and claims a method of assaying gene expressions which comprises linking MRNA molecules to a solid substrate and contacting the solid substrate with an aqueous suspension of labelled microbeads to which gene probe molecules are linked. The gene probe molecules comprise sequences which hybridize with sequences comprised by and characteristic of the unknown or target mRNA molecules to be assayed, so that the labelled microbeads are linked to the target MRNA molecules on the substrate. By separating the solid substrate from microbeads unlinked to target mRNA molecules and detecting labelled, linked microbeads, the gene expressions are assayed.

Labelled microbeads have been used in a number of analytical methods such as immunoassay methods. Extensive prior art concerning microbeads is described in U.S. Pat. Nos. 4,454,233 granted Jun. 12, 1984 and 4,436,826 granted Mar. 13, 1984, both assigned to the present assignee.

The method of the present invention for assaying genetic sequences is based on displacement of a reporter molecule hybridized to an anchored single-stranded DNA molecule. The displacement relies on the formation of a triple helical or triple strand DNA structure (triplex) between a portion of the sequence of the reporter and double-stranded DNA sequences in sample DNA. The reporter molecule in this case constitutes the "third strand" of the triple helix. The reporter/anchor hybrid is maintained in a suitable buffer in a reaction vessel. Double-stranded sample DNA is added to the buffer and the whole is incubated at a defined temperature. The free 5'-end of said reporter molecule forms a triple helical DNA segment with the sample DNA. The formation of the triple helix reduces the stability of the reporter/anchor stability and thus the reporter is displaced from the anchor DNA to the liquid phase where it can be assayed by means of the submicron particle attached to the reporter. The steps in this process are shown in diagrammatic form in FIG. 1.

According to the present invention there is provided a method for assaying genetic sequences which comprises the formation of a weak DNA-DNA duplex in aqueous solution where one of the strands (the anchor strand) is covalently bound to a solid phase and the other (the reporter strand) has an assayable molecule or particle comprising assayable groups attached to one end. A portion of the reporter molecule is not hybridized to the anchor molecule and has a DNA sequence such that it can form a triple-helical DNA structure with a double stranded duplex DNA molecule of suitable sequence. This double stranded DNA molecule would be found in the sample DNA added to the reaction vessel. When the triple helical DNA structure forms, it causes the reporter molecule to be displaced from the reporter/anchor duplex. The amount of said reporter molecule that is displaced, when compared with suitable standards, will then give a measure of the amount of the double helical sequences present in the sample. The use of specific DNA sequences allows for absolute specificity in the displacement reaction.

According to the present invention there is provided a method of assaying genetic sequences, which comprises introducing a sample containing double stranded DNA to be assayed into an aqueous medium containing at least one complex comprising an anchor DNA strand anchored to a support matrix, said anchor strand being hybridized with a reporter DNA strand having a detectable label, a portion of the anchor strand or the reporter strand consisting of a selected sequence of bases capable of forming a triple helix or triple strand structure with a portion of particular double stranded DNA, whereby said reporter strand is displaced from said complex upon formation of said triple helix or triple strand structure, and displaced reporter strands are detected to determine the presence of said particular double stranded DNA.

According to the invention there are also provided a DNA probe, a DNA complex, a kit and selected gene sequences, useful for assaying genetic material.

In an embodiment of the invention there also is provided a method of assaying genetic sequences, which comprises contacting a sample containing double stranded DNA to be assayed fixed to a support with an aqueous buffer medium containing a protein which promotes formation of a triple strand structure and containing at least one reporter DNA strand having a detectable label, a portion of the reporter strand consisting of a selected sequence of bases capable of forming a triple helix or triple strand structure with a portion of particular double stranded DNA, incubating the medium, washing to remove unbound reporter, and detecting bound reporter strands to determine the presence of said particular double stranded DNA.

Prior art techniques such as Southern blotting, polymerase chain reaction or ligase chain reaction involve many time-consuming steps. Also since all the steps in the process are performed in the diagnostic laboratory, the staff have to be highly skilled and trained scientists. In the present embodiment, the assay vessel would be supplied containing the preformed reporter/anchor hybrid duplex. In the diagnostic laboratory, the sample DNA is added to the reaction vessel and incubated at a controlled temperature for a defined period of time. These parameters are defined in the production laboratory. The amount of reporter released is then determined using technology not part of this invention. Thus the steps required are simple and rapid and do not require great technical skill on the part of the operator. As a result, the time taken for the assay is significantly reduced and the cost correspondingly reduced.

SUMMARY OF THE INVENTION

The invention relates to a method of assaying genetic sequences, in which a labelled DNA molecule which can form a triple strand DNA structure with certain duplex DNA sequences is displaced from an anchored hybrid, and detection of displaced labelled DNA enables determination of the presence and amount of the specific duplex DNA to be assayed.

BRIEF DESCRIPTION OF THE DRAWINGS

FIG. 2 schematically illustrates the nomenclature and organization of a DNA double helix. The sequence is derived from that of the human Papilloma Virus.

FIG. 4 schematically illustrates a duplex and triple-helix-forming third strand based on the sequence of the Human Pailloma Virus (HPV).

DESCRIPTION OF THE PREFERRED EMBODIMENTS

Figure 1A:
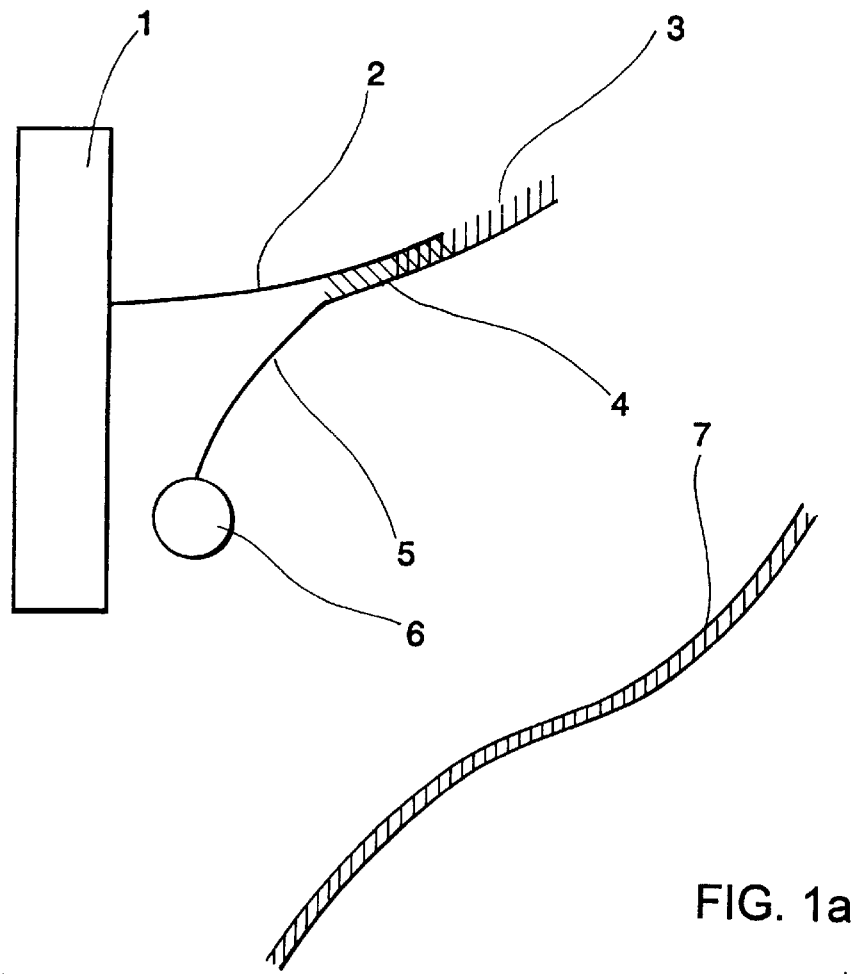
FIG. 1a is a diagrammatic illustration in accordance with the present invention of a reporter molecule which has a region capable of forming a triple strand structure with duplex DNA is hybridized to an anchored single stranded DNA molecule in proximity to a sample of double stranded DNA.

Nucleic acids as genetic material are found in all living cells. In higher organisms, the deoxyribonucleic acid (DNA) comprising genic and non-genic material is unique to that organism and can be used to identify that organism. The DNA exists as a double-stranded molecule where the two strands are antiparallel. The bases of the nucleotides that make up each strand are complementary to each other such that, in the double stranded form, a precise sequence of bases on one strand is paired with a precise sequence of bases on the other strand. It is this sequence bases that codes, in groups of three per amino acid, for the sequence of amino acids in proteins.

Four major nucleotides are found in DNA and these pair in a precise way. The base adenine pairs only with thymine (dA–dT); the base guanine pairs only with cytidine (dG–dC). If the sequence of bases in one strand of a DNA duplex is known, then the sequence of the other strand can be deduced. FIG. 2 shows a duplex sequence derived from the primary DNA sequence of Human Papilloma Virus strain 16 (Seedorf, K., Kraemmer, G., Duerst, M., Suhai, S. and Roewekamp, W. G. (1985) Virology 145:181–185). The individual nucleotides are joined by a phosphodiester bond between the 5'-carbon of the sugar residue in one nucleotide to the 3'-carbon of the sugar residue of the next. The polarity of the strand is then given by denoting which end of the molecule has a free 5'-carbon and which has a free 3'-carbon (FIG. 2). DNA double helix molecules normally exist in the B-form, as defined by the shape of the molecule (helix pitch, base angles etc.,). Other forms can also exist including the A-form, the Z-form amongst others. Although originally thought only to exist in non-biological ionic environments, it is now believed that many of these minor forms can exist in biological samples, often stabilized by proteins. The occurrence of non-random stretches of nucleotide sequence and base modifications (e.g., 5-methyl cytosine) can also help allow these unusual forms to exist in nature.

The other major type of nucleic acid molecule that exists in nature is ribonucleic acid (RNA). RNA differs from DNA in the use of ribose rather than deoxyribose as the sugar and the use of the base uracil instead of thymine. Although the vast majority of the RNA exists as single-stranded molecules, there is considerable intramolecular duplex formation. RNA duplexes exist in a shape and configuration comparable to the A-form of DNA. In 1954, it was observed that RNA can form triple helix structures and these have now also been observed in DNA. Only DNA duplexes with particular sequence structures are capable of binding a third strand. The sequences are those that comprise at least five contiguous purine nucleotides (A or G) in one strand (polypurine) and at least five contiguous pyrimidine nucleotides (T or C) in the other (polypyrimidine).

Two types of triple helix can exist. In the first, the polypyrimidine (comprising dT and dC) third strand is parallel to the polypurine (comprising dA and dG) strand of the duplex and the bases of these two strands pair (Mirkin, S. M., Lyamichev. V. I., Drushlyak, K. N., Dobrynin, V. N., Filippov, S. A. and Frank-Kamenetskii, M. D. (1987) Nature 330:495–497) to form triplets. In the second, a polypurine third strand (comprising dA and dG) binds antiparallel to the polypurine strand of the DNA double helix (Beal, P. A. and Dervan, P. B. (1991) Science 251:1360–1363). Of the two forms, the first, where the third strand has a polypyrimidine structure, is the best studied and therefore this is the preferred form for use in the invention.

Initially, two forms of triplet were identified, dT·dA–dT and dC$^+$·dG–dC with specificity conferred by Hoogsteen base pairing. The C in the third strand is protonated in the stable helix. Formation of the triple helix structure with a polypyrimidine third strand is promoted by acid pH. This favors the protonation of the dC and induces a structural shift to the A-form of DNA. This structural change shifts the helix axis 3 Å off-center and enlarges the major groove, and it is into this enlarged major groove that the third strand fits. The A-form of DNA strongly resembles the structural shape of RNA duplexes at neutral pH. There is the strong possibility that single-stranded RNA molecules may form triple helices with double-stranded DNA molecules and that such triple helices may play a regulatory role in gene expression in nature (Boles, T. C. and Hogan, M. E. (1987) Biochemistry 26:367–376).

Figure 3:
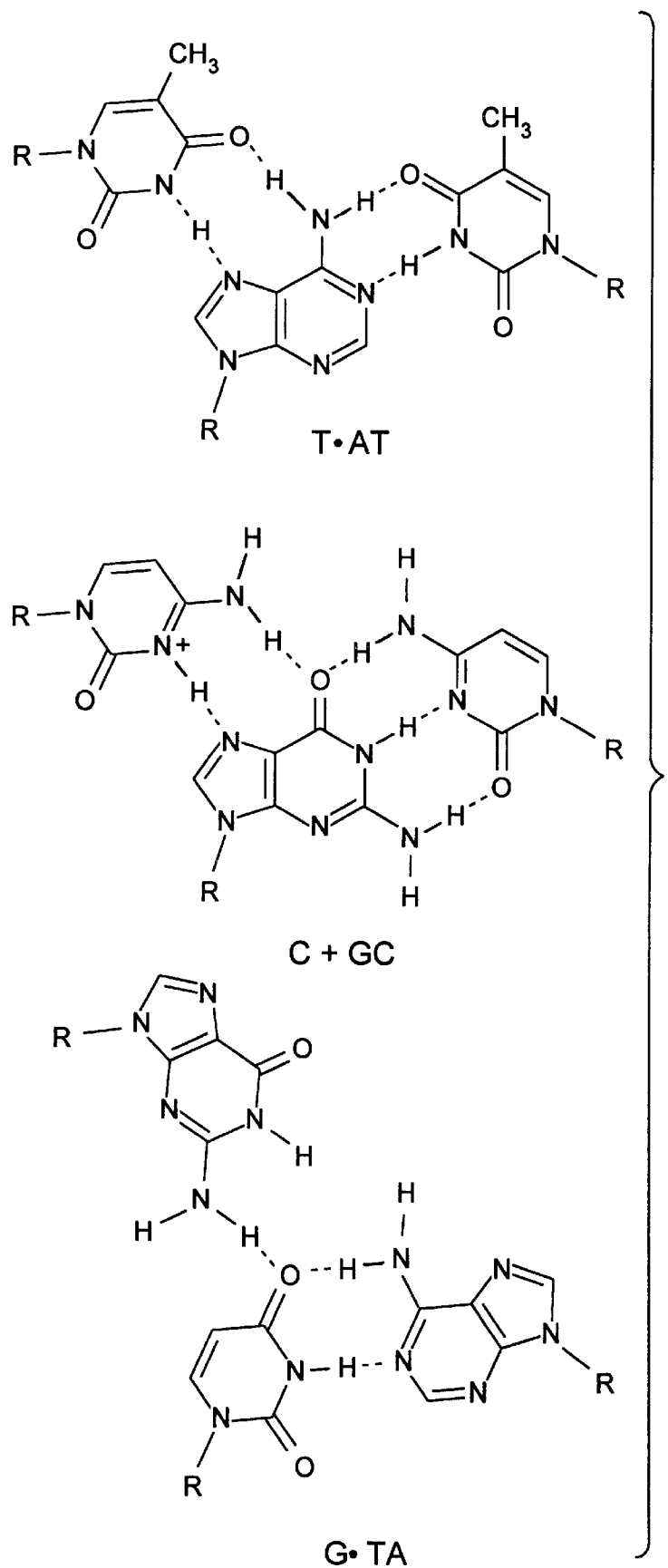
FIG. 3 taken from a hereinafter mentioned L. C. Griffin et al. publication (1989) shows at the top a Pyrimidine motif with isomorphous base triplets, T-AT and C+GC, and at the bottom a hypothetical model for G-TA base triplet within a pyrimidine triple helix motif.

Triplet recognition has recently been extended to include dG.dT-dA (Griffin, L. C. and Dervan, P. B. (1989) Science 242:967–971) which allows for exceptions to the strict polypurine-polypyrimidine rule. It appears, however, that only a limited number of purine interruptions to the duplex polypyrimidine strand can be tolerated, probably because too many such purine interruptions inhibit the formation of the A-form of DNA necessary for triple helix formation. The base pairs and the three corresponding stable triplet structures are shown in FIG. 3 (taken from page 968 of the above-mentioned Griffin et al. publication). The "R" indicates the sugar phosphate of the nucleotide and the broken lines show the hydrogen bonds between the bases.

Polypurine-polypyrimidine stretches of DNA are often found in and around the putative regulatory regions of genes and the potential for such regions to form intramolecular regions of triple-helical DNA has been associated with the anomalous S1-nuclease sensitivity of such regions. This is because S1-nuclease digests single stranded DNA and, when an intramolecular triple helix forms either under the appropriate ionic environment or in response to superhelical stress, the fourth strand of the two duplexes involved becomes single-stranded (Kohwi, Y. and Kohwi-Shigematsu, T. (1988) Proc. Natl. Acad. Sci. USA 85:3781–3785). Such an apparent regulation of the c-myc gene in vivo, by a single stranded RNA has been confirmed in vitro using a single stranded synthetic oligonucleotide (Cooney, M., Czernuszewicz, G., Postel, E. H., Flint, E. J. and Hogan, M. E. (1988) Science 241:456–459).

The fairly tight requirement for homopurine-homopyrimidine stretches for triple-helix formation can be artificially overcome in synthetic oligonucleotides by replacing dG with dI (deoxyinosine) since deoxyinosine in the third strand binds degenerately to all target sequences (Letai, A. G., Palladino, M. A., Fromm, E., Rizzo, V. and Fresco, J. R. (1988) Biochemistry 27:9108–9112). This is important in permitting the construction of oligonucleotides capable of forming triple helical regions with a wider range of sequences thus extending the structural constraint limits in probe design. Once again, however, too many deviations from the homopurine-homopyrimidine rule may limit the ability of the duplex component to adopt the correct conformation for triple helix formation.

In general, the triple helices studied show thermal denaturation profiles 30 or more degrees celsius below the comparable profile of the duplex alone (Shea, R. G., Ng, P. and Bischofberger, N. (1990) Nuc. Acids Res. 18:4859-4866). The use of 5-methyl cytosine instead of cytosine in the third strand can increase the Tm of the triple helix by as much as 10° C. (Maher, L. J., Wold, B. and Dervan, P. B. (1989) Science 245:725–730). Polyvalent cations and Mg$^{2+}$ can stabilize the triple helix but of course these also will stabilize duplexes. In particular, spermine and CO(NH$_3$)$_6^{3+}$ can give triple helix stability under conditions where Mg$^{2+}$ does not (Moser, H. E. and Dervan, P. B. (1987) Science 238:645–650). Several organic solvents (e.g., ethylene glycol, dimethyl formamide, ethanol etc.) also increase the stability of the triple helix probably because the increased organic concentration will promote the shift to the A-conformation needed for triple-helix formation (Moser, H. E. and Dervan, P. B. (1987) Science 238:645–650). Since many of these organic molecules also destabilize double helices, they are likely to assist in increasing the stability of triple helices even more relative to double helices and thus facilitating the displacement reaction.

DNA ligands also can increase the stability of the triple helix. A benzo[e]pyridoindole derivative was shown to increase the Tm of a (dT·dA–dT)$_{10}$ triple helical region by more than thirty degrees (Mergny, J. L., Duvak-Valentin, G., Nguyen, C. H., Perrouault, L., Faucon, B., Rougee, M., Montenay-Garestler, T., Blsagnl, E. and Helene, C. (1992) Science 256:1681–1684). If the triple helix contains dC$^+$·dG–dC triplets, the stability is greatly reduced, presumably because the protonated dC inhibits binding of the ligand (Mergny, J. L., Duvak-Valentin, G., Nguyen, C. H., Perrouault, L., Faucon, B., Rougee, M., Montenay-Garestler, T., Blsagnl, E. and Helene, C. (1992) Science 256:1681–1684). Such ligands are therefore of limited use with complex sequences.

The following description illustrates further embodiments of the present invention and techniques useful in carrying out the invention.

Synthesis of the DNA Strands

Once the required sequences for the anchor and reporter strands have been determined (the triple helix forming region and the duplex region holding the two together) the molecules can be synthesized. Additional sequences are included as spacer regions that ensure that the critical binding regions of the sequence are as far as possible from the solid matrix or assay particle to which the molecules are attached.

The DNA molecules are synthesized by standard, fully automated methods using, for example, phosphoramidite chemistry on controlled-pore glass supports. For use in the gene detection system, the molecules must be coupled to either solid supports or assay particles. This is normally facilitated by adding a reactable group to one end of the molecule. Linker arms terminating in an amino group can be added to either the 5'- or the 3'-end of the DNA molecule as part of the automated synthetic process. The DNA molecules can then be coupled to solid supports in a number of standard ways via this amino group. Such methods include the "carbodiimide method", the "glutaraldehyde method", the "cyano borohydride method" or the "tosylactivated method". These methods couple the amino group on the end of the DNA molecule to a reactive group on the solid support or assay particle and are used as standard methods for coupling proteins to solid supports or assayable molecules (e.g., biotin or fluorescent moieties).

Biotin can also be added directly to the 5'-end of the molecules as part of the synthesis process for use in streptavidin-coupled enzyme detection systems.

The anchor molecule is coupled to a solid matrix either contained within (e.g. coated glass beads) or part of (e.g. coated wall surfaces) the reaction vessel. Once the anchor molecules have been coupled, the anchor/reporter complex is formed by incubating reporter molecules in the reaction vessel containing the coupled anchor molecules. This is done at a suitable cation concentration (usually in the range 0.1 to 1.5M) and a suitable temperature (usually in the range 5° C. to 40° C.) for hybridization of the two molecules. Given the sizes of the two molecules, the rate of hybridization under these conditions is extremely fast and normally, an incubation time of no more than 5 or 6 hours would be needed. Excess reporter molecule is then removed by washing the vessel and any solid supports (e.g., glass beads) contained within it. The anchor/reporter complexes in the reaction vessels are stored under low temperature conditions until required.

The triple strand forming region should normally be located at the opposite end of the DNA molecule from the matrix or assay-particle attachment point. This is to limit possible interference with the displacement reaction resulting from steric hindrance due to the presence of large solid masses coupled to the DNA strands.

The triple strand forming sequence preferably should have 10 or more bases and should be at or near the end of either the anchor or reporter molecule. The other end of this triple strand forming sequence should overlap all or some of the nucleotides of a duplex forming region that is the duplex holding the anchor and reporter together. The DNA molecule that does not carry the triple strand forming region will end with the complementary sequence of the duplex forming region. There may or may not be a short (1–8 base) sequence with no complement between the duplex-forming region and the actual terminus of the molecule.

In one form, the anchor will be coupled to the solid support via its 5'-end. In another form, the anchor will be coupled to the solid support via its 3'-end.

Potential Triple Helix Forming Regions

Such regions can be identified on the basis of their sequence. It is preferred that the sequence to be used should be as long as possible. The following are further preferred features of the regions:

i) the sequence should be homopurine or homopyrimidine.

ii) the exception to i) is the limited allowance of the pyrimidine "T" in the homopurine strand or the purine "A" in the homopyrimidine strand. This T-A base pair will pair with a "G" in the otherwise polypyrimidine third strand. Too many T-A base pairs will, however, impair the ability of the triple helix to form.

iii) the final choice of sequence to be used is normally empirical. There is no constraint on sequence composition or on sequence size other than the minima required for stability.

Protein-assisted Triple Strand Formation

There are a number of proteins from different organisms which work in the same or a similar fashion. These include related proteins from the same or different organisms, either in their normal or modified (e.g. genetically engineered) form.

Protein-assisted triple strand formation requires its own unique buffer and suitable cofactors. Buffer composition:

A typical buffer for protein-assisted triple strand formation would comprise Tris buffer at near neutrality, $MgCl_2$ at approximately 10 mM, ATP (cofactor and source of energy) at approximately 4 mM and a reducing agent at approximately 1 mM. The preferred RecA protein concentration is 2 $\mu$M. Glycerol may be added for stability at concentrations up to 10%. E. coli single strand binding protein (SSB) may be at concentrations up to 2 $\mu$M to promote the strand transfer. Other cofactors may be used instead of ATP some of which may function only as cofactors and not energy donors (e.g., ATP$\gamma$(S)). The preferred incubation temperature is 37° C. but higher or lower temperatures may be used.

Conditions for Triple Helix Formation

A number of buffers may be used which can provide buffering for all or part of the range pH4.0 to pH7.5 (e.g., phosphate, citrate, acetate). The actual pH to be used depends on the sequence of the triple helix forming region. The preferred cation concentration is 200 mM. In order to promote the stability of triple helix versus the anchor/reporter duplex, the incubation medium may contain an organic solvent (e.g., dimethylformamide or ethanol) at concentrations up to 10%. The preferred range of temperatures to be used in the reaction is from 0° C. to 30° C. Temperatures in excess of 30° C. are normally only used with the protein-assisted reaction.

Thus a typical reaction would involve the assay vessel containing the anchor/reporter hybrid in 25 mM sodium acetate buffer, pH 4.5 containing 10 mM $MgCl_2$ and 5% dimethylformamide. The sample DNA in the same buffer would be added and the mixture incubated at 25° C. for 4 hours. Then liquid phase would then be collected and assayed for the presence of reporter.

Sample Preparation

Total DNA is isolated from solid tissue, blood or fecal samples by standard methods involving a homogenization or lysis step followed by deproteinization and precipitation. The DNA in a dilute buffer (normally 10 mM Tris-HCl, 1 mM EDTA, pH8.0) is adjusted to the appropriate reaction buffer for either normal or protein-assisted triple strand formation.

Suitable Standards

In each set of assays, it is desirable to include a DNA standard from an individual classed as "normal" or "wild-type" for the gene or viral sequence to be determined. This constitutes a system external standard. It is also preferred that each reaction vessel contain a second anchor/reporter complex for a gene or DNA sequence classed as "normal" in relation to the potentially altered sequence that is being assayed for. This provides an internal control or standard and accounts for any sample problems that may affect the reaction. These standards shall normally be provided in the system kit for each assay and have been calibrated for use with the system.

The Assay System

Following the completion of the reaction, it is desirable that the liquid in the vessel be automatically removed and passed, in a narrow tube, through a laser beam. The fluorescence from the particles attached to the reporter molecules can then be determined. Since a number of different fluorescent particles are commercially available, several anchor/reporter complexes can be set up in the same vessel, each using a different fluorescent molecule attached to the reporter. This allows for internal standards to be used in the reactions.

Other detection methods may also be used. The reporter DNA molecule labels for example may be colored compounds; compounds which are fluorescent under light, laser beams or ultraviolet illumination; enzyme molecules; or metal elements or compounds detectable by X-ray fluorescence. The labels may comprise a polymeric microsphere containing detectable compounds or elements. These microspheres or microbeads are small latex beads preferably 0.3 micrometers in diameter or less such as 0.25 micrometers or 0.1 micrometers on smaller. A preferred label comprises fluorescent compounds which fluoresce under a laser beam. Automatic equipment for detection of fluorescent particles may be used to advantage.

In the drawings, FIG. 1a shows solid matrix 1 for attachment, anchor DNA strand 2, potential triple helix forming region 3, duplex region 4 holding reporter to anchor, reporter DNA strand 5, assayable particle 6 attached to reporter, and input sample duplex DNA 7. The region of the reporter molecule 2 capable of forming a triple helix 3 with the input sample DNA 7 overlaps with the region of DNA duplex that holds the reporter to the anchor 4.

Figure 1B:
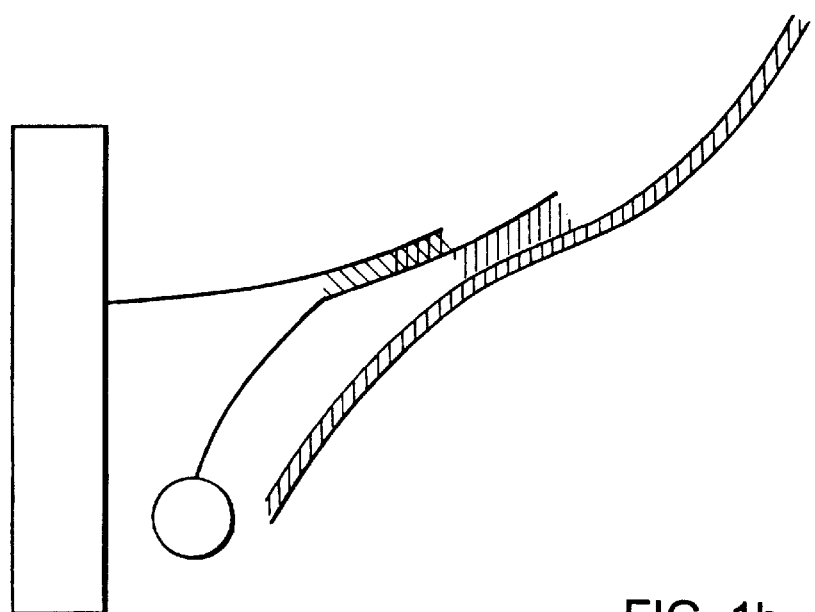
FIG. 1b diagrammatically illustrates the reporter molecule shown in FIG. 1a forming a triple stranded structure with the double stranded DNA.

FIG. 1b shows that the input sample DNA forms a triple stranded structure with the region of the reporter molecular capable of pairing with the duplex sequence. In the first phase of this reaction, the triple stranded region is limited to the single-stranded portion of the reporter sequence.

Figure 1C:
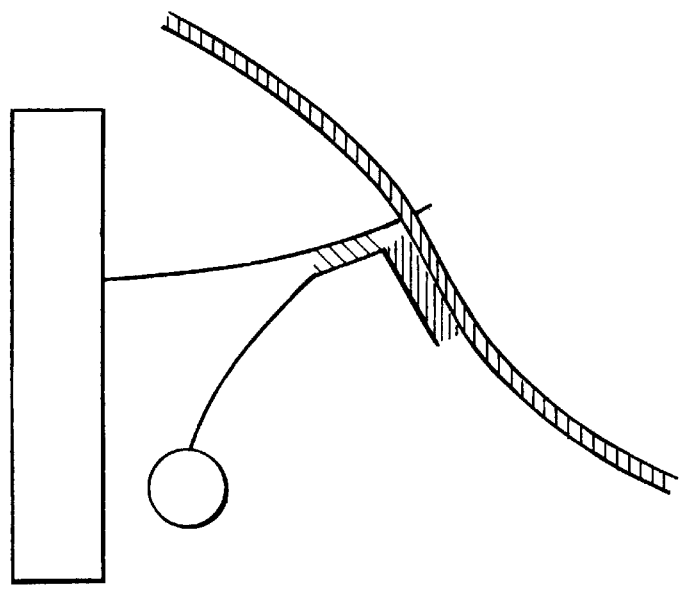
FIG. 1c diagrammatically illustrates the start of separation of the reporter molecule shown in FIG. 1a from the anchored molecule.

As shown in FIG. 1c, during the course of the incubation, the reporter strand region of the duplex holding the anchor and reporter together that also has triple-strand forming capability, converts to triple strand. This increases the size and stability of the triple helix and reduces the size and stability of the duplex holding the anchor and reporter together.

Figure 1D:
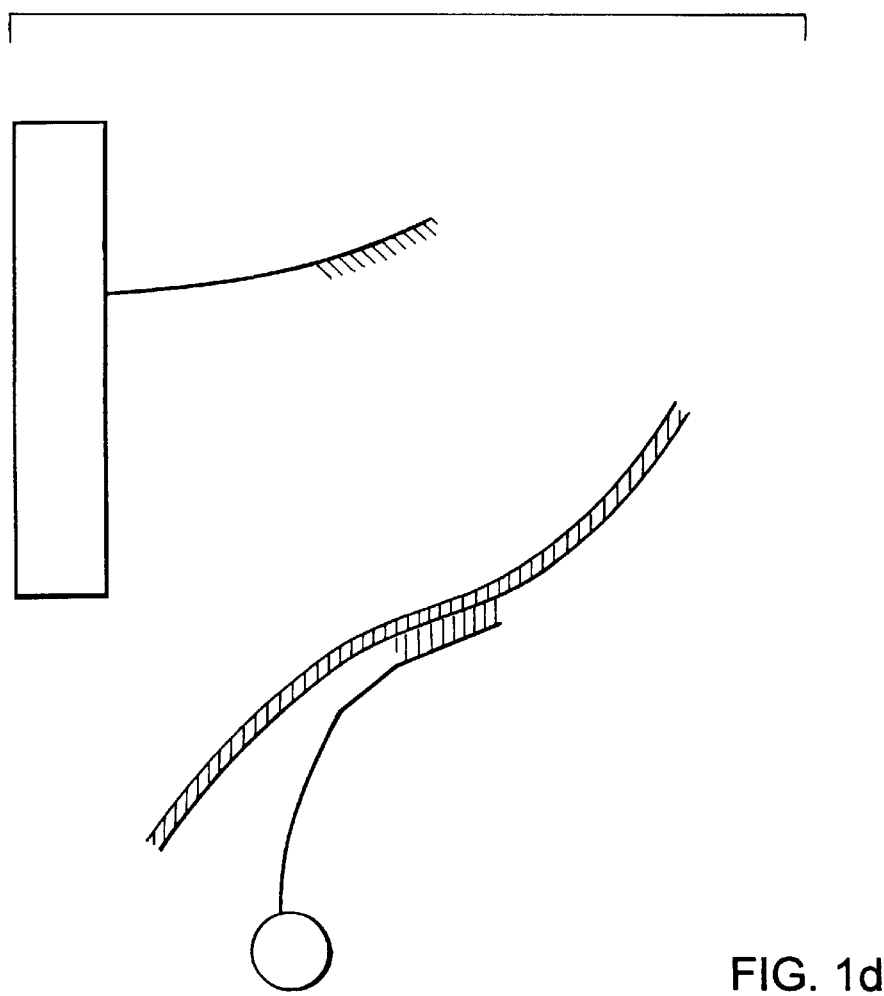
FIG. 1d diagrammatically illustrates the displacement of the reporter molecule shown in FIG. 1a from the anchored molecule.

FIG. 1d illustrates that as a result of the reduction in size the duplex holding the anchor and reporter together, the stability is reduced to a pint where the two strands fall apart. The reporter attached to the input duplex DNA by region of triple helix is now free in the solution where it can be collected and assayed.

Figure 1E:
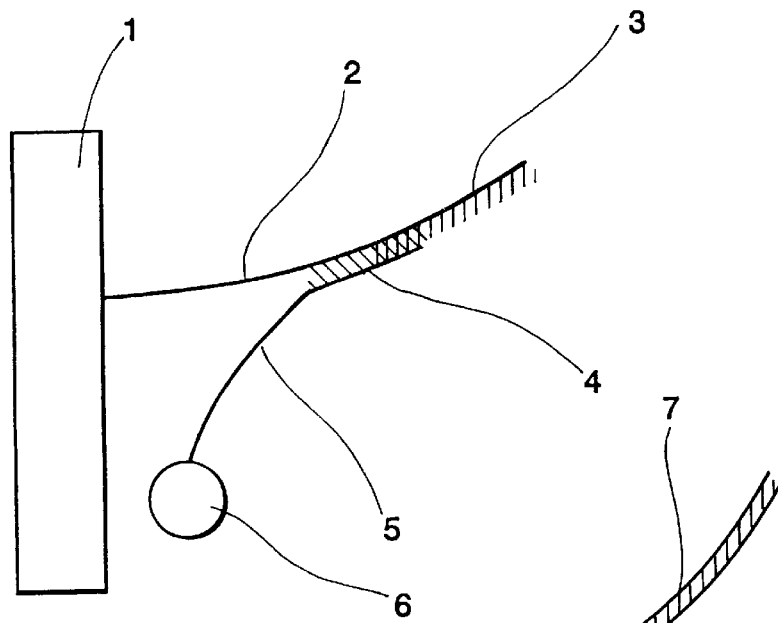
FIG. 1e is a diagrammatic illustration of an embodiment of the present invention in which an anchored DNA molecule has a region capable of forming a triple strand DNA structure with duplex DNA shown being separately introduced.

FIG. 1e shows a second embodiment of the invention. The numbering of components is the same as for FIG. 1a. The difference is that the region capable of forming a triple strand region 3 is on the anchor DNA strand 2.

Figure 1F:
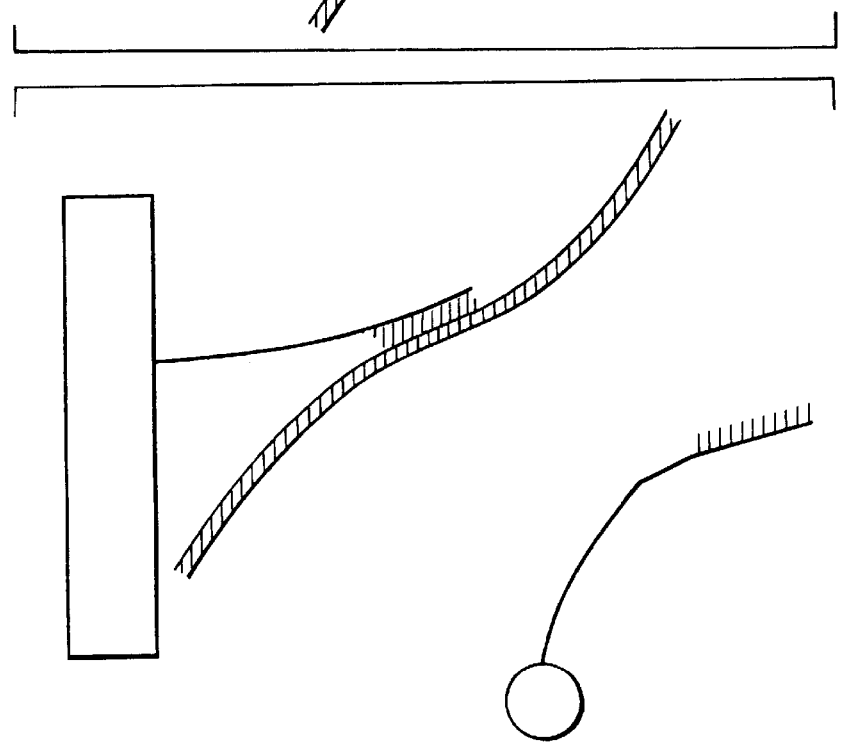
FIG. 1f diagrammatically illustrates the anchored molecule shown in FIG. 1e having formed a triple strand structure with duplex DNA and a reporter molecule having been displaced from the anchored molecule.

FIG. 1f illustrates the result of the reaction following incubation of the components in FIG. 1c. The reporter is released free into the solution where it can be assayed. The input sample DNA fragment is left bound to the anchor strand by the triple stranded region.

Figure 5:
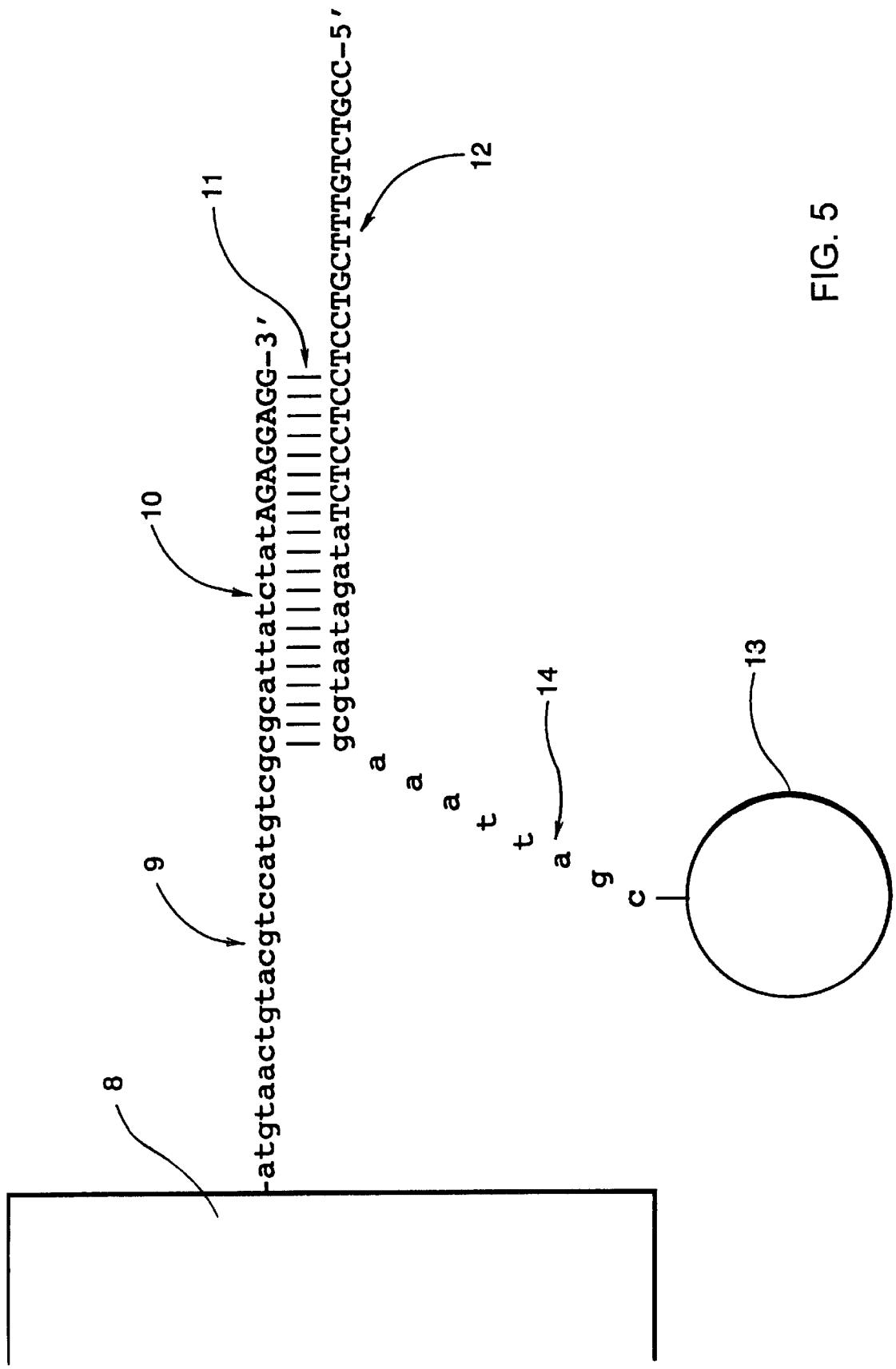
FIG. 5 schematically illustrates an anchor/reporter complex in accordance with the present nvention, based on the HPV sequence shown in FIG. 4.

FIG. 5 illustrates an anchor/reporter combination based on the HPV sequence shown in FIG. 4.

In FIG. 5 there is shown a solid matrix 8 for attachment, anchor DNA strand 9, duplex region 10 holding reporter to anchor, duplex region base pairs 11, potential triple helix forming region 12, assayable particle 13 attached to reporter and reporter DNA strand 14. The extent of the region capable of forming a triple stranded structure is denoted by upper case letters. This is the only region with any DNA sequence homology to the input sample DNA (HPV sequences in this case). The reporter component of the triple strand forming region has the sequence of the 'third strand' shown in FIG. 4.

The DNA sequence shown in FIG. 2 is capable of supporting a triple helix over part of its length. The predicted triple helix is shown in FIG. 4 where the third strand is computed to use all three possible triplets known to be stable. Comparable potential triple helix forming regions can be derived from the sequence of many genes of clinical significance and can therefore be utilized by the gene detection system described in the invention.

The anchor DNA has a primary nucleotide sequence arbitrarily derived and contains a region of homology with a portion of the reporter sequence. The 3'-terminal region of this homology is related to a portion of the sequence of the gene or DNA region of interest and comprises part of a region of potential triple helix formation from that sequence. The reporter contains the whole sequence capable of forming a triple helix. FIG. 5 shows such a configuration based on the triple helix region shown in FIG. 4 (from the Human Papilloma Virus).

RecA Protein-Assisted Triple-Strand Formation

The formation of a triple stranded DNA structure is promoted by the RecA protein of *Escherichia coli* (Ferrin and Camerini-Otero, 1991). In the case of RecA-assisted triple-strand formation, however, there is no strict homopurine-homopyrimidine requirement. The single-stranded third strand must be homologous to the input sample duplex. RecA protein will bind to single-stranded regions of DNA, and, where homology exists between such single-stranded regions and a double stranded DNA molecule, will catalyze the formation of a triple-stranded structure (Cox and Lehman, 1987).

In this embodiment, purified RecA protein is added to the anchor/reporter hybrid in a suitable buffer containing a divalent cation with ribonucleoside or deoxyribonucleoside triphosphate as the cofactor and the double stranded sample DNA is added to the mixture. The single strand tail on the anchor/reporter complex that is homologous to the desired region of the input sample DNA will then form a triple-stranded structure with the sample DNA with the RecA protein initially bound to the structure, stabilizing it. As with the unassisted triple-helix formation, the sequence of the anchor/reporter complex that is homologous to the sample DNA overlaps the duplex region that holds the anchor/reporter complex together. Thus, the first interaction between the RecA:ssDNA (single-stranded DNA) structure of the anchor/reporter complex forms the first portion of the triple strand structure. As the triple strand formation continues, it will lead to displacement of the reporter from the anchor. The RecA protein will thus assist or promote the transfer of the strand containing the extended homology to the sample duplex, thus displacing the reporter molecule.

The sample-homologous region can be on either the anchor (in which case the reporter is "displaced") or the reporter (in which case the reporter is "captured").

With regard to the above, reference is made to:

Cox, M. M. and Lehman, I. R. (1987) Enzymes of general recombination. Annual Review of Biochemistry 56:229–262; and Ferrin, L. J. and Camerini-Otero, R. D. (1991) Selective cleavage of human DNA: RecA-assisted restriction endonuclease (RARE) cleavage.

Protein-Assisted Triple Strand Formation for in situ Hybridization

In situ gene analyses involve the probing of biological specimens fixed and mounted on microscope slides. Current technology involves denaturation of the DNA in the sample material and hybridization or PCR amplification in situ, that is in place on the slide. If DNA sequences homologous to the hybridization probe or PCR primers are present, they can be detected by an assay for the probe or the amplified products. The triple strand technology can be used to greatly simplify this process, cutting down on the number of steps and increasing the sensitivity by using a reporter coupled to an assayable particle.

The preparation of biological material on a microscope slide is modified to omit the DNA denaturation step. Since this step can present problems in sample preparation, this omission is a significant advantage. As a final step, the material is equilibrated in RecA buffer (see above).

Reporter DNA coupled to an assayable particle is mixed with RecA protein in RecA assay buffer and added to the equilibrated material on the microscope slide. After incubation for a period of time normally in excess of 1 hour, excess reporter is washed off the preparation and the presence of bound reporter is determined under a fluorescence microscope.

The process generates triple-stranded structures at the site of homology between the DNA in the material and the reporter. The process requires fewer steps than existing technology. The steps that are eliminated (e.g., DNA denaturation and enzyme-coupled signal amplification) are also prone to variability. Their elimination thus creates a reliable and sensitive technique.

This approach requires that the double-stranded DNA in the sample material be available for interaction with the RecA/reporter complex. DNA in such samples has been demonstrated in the past to be available for interaction with a number of DNA modifying enzymes, for example restriction endonucleases. Such observations show that the recognition of the double-helix in fixed samples is not obscured by the remaining proteins and that modification and/or digestion of DNA in such samples is possible.

Bacterial Strain Identification

The ribosomal genes are the sequences of choice because:
a) they exist in 2–5 copies in many species.
b) they do not code for proteins but code for RNA species that exist as 40,000 copies per cell.
c) the rRNA products are of the order of 70% double-stranded.
d) because of their use as a standardized, universal sequence analysis for molecular evolutionary studies, there is a large and rapidly expanding database of sequences available.

Bacterial Identification

The triple helical DNA assay can also be used to identify bacterial species using the genes for the two major ribosomal RNA species (rDNAs) and their RNA products (rRNAs). In many species of bacteria, these genes exist as a small family comprising 1–5 copies. The products are known as the 23S and 16S RNA species and are present at 40,000 copies per cell. The primary nucleotide sequences of these genes are used extensively for molecular evolutionary analyses of both prokaryotic and eukaryotic organisms and there is therefore a rapidly expanding database of these sequences available. The primary sequences of the prokaryotic rDNAs are very different from those of eukaryotic rDNA. They contain regions of very high homology between species and regions of very low homology. Potential triple helix forming regions in the sequences with low inter-species homology can therefore be used to identify individual bacterial species associated with disease symptoms. This approach for bacterial identification can be done with bacterial DNA to identify the genes themselves. Since the rRNA is present in high concentration per cell and is up to 70% double stranded as a result of intra-molecular pairing, it can also be used with RNA preparations from the bacteria. The second approach will give higher sensitivity (10,000 times) but limits the potential triple helix forming regions to those contained completely within the double-helical loops in the rRNA.

Identification of Eubacteria using Protein-Assisted Triple Strand Formation

Although many eubacteria species can be distinguished on the basis of the variable regions of the 16s ribosomal genes, in some cases there is not enough variation for unequivocal species identification. The spacer region between the 23s and 16s genes on the other hand is much more variable. PCR techniques can be used (Barry et al., 1991) to identify differences in the spacer region based on size using primers in the flanking constant regions of the 16s and 23s genes. A PCR run then results in the amplification of the spacer region and the differences can be seen as differences in the size of the amplified region. This approach can only detect differences when they are large enough to affect the mobility of the resulting fragment on a gel. Amplified fragments of the almost the same size may be indistinguishable but still have different nucleotide sequences. In some cases, these can be identified from different patterns of fragments resulting from restriction endonuclease digestion of the amplified fragment. For more accurate results, the spacer region can be sequenced, but sequencing errors mean that at least 10 determinations are needed. While this is an acceptable effort for determining the sequence, it is not practical in a diagnostic environment. Accurate sequence information can, however be used to generate spacer region-specific primers for more routine PCR analyses.

As with other PCR techniques, this approach is technically skilled and the results difficult to analyze. The spacer regions, however, rarely have large enough homopurine/homopyrimidine regions for potential triple-helix formation and so the unassisted triple-strand approach is not a suitable alternative in this instance.. The protein-assisted triple-strand formation approach is, however, ideal for this diagnostic approach.

Because the protein-assisted approach does not impose any sequence constraints other than that the sequence be unique, it is applicable to almost all diagnostic developments related to eubacterial identification. The only practical limitation is the availability of sequence information for designing the anchor and reporter sequences. Where such sequences are not available, however, they can be obtained very simply using standard primers in the adjacent 16s and 23s genes and reading into the spacer. Using sequence information, anchor/reporter combinations can be developed which could distinguish, for example, between pathogenic and nonpathogenic clostridium species.

The approach of protein-assisted triple strand formation would use DNA extracted from cultured bacteria or total DNA from potentially contaminated clinical samples. This DNA is then added to the anchor/reporter RecA protein complex where the triple-strand forming single strand tail is homologous to a unique region in the 23s-16s spacer. Incubation would then release the reporter as the triple-stranded structure forms with the input double-stranded sample DNA. The technique would give a simple Yes/No determination of bacterial contamination. If concentration standards are included, the technique will also give a measure of the degree of pathogen contamination. With the availability of different assayable fluorescent particle tags for the reporter, more than one bacterial strain can be screened in each assay. In some instances, for example, where a disease is linked to more than one bacterial species, all candidates could be checked in one assay. The simplicity of the protein-assisted triple-strand formation approach allows this identification scheme for pathogenic bacterial to be transferred readily to the diagnostic environment. Reference is made in regard to the above to Barry, T., Colleran, G., Glennon, M., Dunican, L. K. and Gannon, F. (1991) "The 16s/23s ribosomal spacer region as a target for DNA probes to identify bacteria." PCR Methods and Applications 1:51–56.

The following describes the selection of triple helix or triple strand forming regions, and illustrates specifically selected regions.

DNA sequences are given based on the 5' to 3' direction. For a gene this means that the gene starts at the left and goes to the right. All databases normally contain such sequences in this orientation with only the top (5' to 3') strand listed. For viral sequences, the orientation is often arbitrarily defined since the genes contained within them can be orientated in different directions. The potential triple helical forming regions are given hereinafter as they appear in the source of the sequence (database or published manuscript). In line with convention, the top strand is listed from left to right, 5' to 3'. In some cases, this lists the homopurine strand and in some cases the homopyrimidine strand. In each case the appropriate second strand can be deduced from the base pairing that will result. The next two columns list the length of the triple-helix forming regions and the sequence location, again based on the numbering of the source listing. The final column lists the "third strand" that will form the triple helix. No matter what the orientation of the duplex region of the source sequence is, the third strand will always be a homopyrimidine with the 5' to 3' direction parallel to the homopurine strand of the duplex. This is the sequence that will be synthesized with appropriate 5' and 3' tails for coupling to the solid matrix or the assayable particle.

As noted in the main text, the possibility exists for the stable presence of a dG·dT–dA triplet in triple helices. This,. however, disrupts the homopurine homopyrimidine structure since the third (homopyrimide) strand would contain a purine (G) which would pair with a T (pyrimidine) in the homopurine strand of the duplex. Because the inclusion of this triplet can frequently increase the size of triple-helix forming regions quite considerably, these are used in the present screening process, and the number is limited as much as possible. In general only those sequences with 5 or more purines (A or G) on each side of the pyrimidine (T) as shown in the third strand should probably be used since published reports indicate that 5 bases are needed to nucleate the formation of the triple helix. In order to make these bases easier to identify in the sequences listed, they are shown in a different case to the rest of the sequence.

Criteria for Sequence use

In general, sequences with long stretches of poly(A) or poly(G) are not advisable because such sequences appear in many locations. Sequences with mixtures of A and G are preferred since they will give better specificity and reduce the chance of "slippage" during alignment. Sequences that result in relatively high preponderances of C in the third strand are preferred to allow the extensive use of '$5^M$C' instead of 'C' during oligonucleotide synthesis to increase the stability of the triplex helix.

POTENTIAL TRIPLE-HELIX FORMING REGIONS

Sequence sources are given either as the EMBL/Genbank database accession number(s) or the source reference. The sequence is listed as the 5'3' direction and the size and sequence location are given. Any special notes are shown together with the 3rd strand sequence. In general, C is replaced by 5-methylcytosine in the third strand for increased triple helix stability. The lists represent a "most likely" but not exhaustive listing of potential Triple helix forming sequences.

| Sequence | Size | Location | Third Strand |
|---|---|---|---|

1) c-myc
Gene sequence from EMBL X00364, K01908, V00501; update
Rel. 27, Version 2.

| | | | |
|---|---|---|---|
| SEQUENCE ID NO: 1 | | | SEQUENCE ID NO: 2 |
| ctcctctcctcttcttt | 17 | 1047 . . . 1063 | TTTCTTCTCCTCTCCTC |
| SEQUENCE ID NO: 3 | | | SEQUENCE ID NO: 4 |
| agagaaagggagaggg | 16 | 2055 . . . 2070 | TCTCTTTCCCTCTCCC |
| SEQUENCE ID NO: 5 | | | SEQUENCE ID NO: 6 |
| aggggaaaagggagg | 15 | 3546 . . . 3560 | TCCCCTTTTCCCTCC |
| SEQUENCE ID NO: 7 | | | SEQUENCE ID NO: 8 |
| tcttcccctAcccctctc | 17 | 5101 . . . 5117 | CTCTCCCgTCCCCTTCT |
| SEQUENCE ID NO: 9 | | | SEQUENCE ID NO: 10 |
| aaagaggaggaa | 12 | 6650 . . . 6661 | TTTCTCCTCCTT |
| SEQUENCE ID NO: 11 | | | SEQUENCE ID NO: 12 |
| aagaagaTgaggaagaaa | 18 | 6663 . . . 6680 | TTCTTCTgCTCCTTCTTT |

2) n-myc
Gene sequence from EMBL Y00664; update Re. 26, Version 2.

| | | | |
|---|---|---|---|
| SEQUENCE ID NO: 13 | | | SEQUENCE ID NO: 14 |
| ctttcctctccttctctccctccccctt | 27 | 1746 . . . 1772 | TTCCCCCTCCCTCTTTCCTCTCCTTTC |
| SEQUENCE ID NO: 15 | | | SEQUENCE ID NO: 16 |
| ccccttctctcccc | 15 | 1786 . . . 1800 | CCCCTCTCTTCCCCC |
| SEQUENCE ID NO: 17 | | | SEQUENCE ID NO: 18 |
| ggaggaagaagagggggga | 20 | 2407 . . . 2426 | CCTCCTTCTTCTCCCCCCCT |
| SEQUENCE ID NO: 19 | | | SEQUENCE ID NO: 20 |
| ttttctAttcttttctttttttttttttttc | 35 | 4791 . . . 4725 | CTTTTTTTTTTTTTTTTTCTTTTTCTTGTCTTTT |
| SEQUENCE ID NO: 21 | | | SEQUENCE ID NO: 22 |
| gaggagagggggaagaa | 18 | 5419 . . . 5437 | CTCCTCTCTCCCCTTCTT |

-continued

| | | | | SEQUENCE ID NO: 24 |
|---|---|---|---|---|
| SEQUENCE ID NO: 23 | | | | TCCCTCTCCCCC |
| cccectcect | | 12 | 6708 ... 6719 | |
| 3) dystrophin (Xp21.3–p21.1) | | | | |
| Gene (mRNA) sequence from M18533, M17154, M18026; update Rel. 23, | | | | |
| Version 1 | | | | |
| SEQUENCE ID NO: 25 | | | | SEQUENCE ID NO: 26 |
| cttcttcect | | 11 | 1074 ... 1084 | TCCCCTTCTTC |
| Picks up MS deletion 473-1168 | | | | |
| SEQUENCE ID NO: 27 | | | | SEQUENCE ID NO: 28 |
| aaggaaaaTggaggaagag | | 19 | 1621 ... 1639 | TTCCTTTTgCCTCCTTCTC |
| Picks up two MS deletions (302-2200 & 1169-3011) | | | | |
| SEQUENCE ID NO: 29 | | | | SEQUENCE ID NO: 30 |
| gaagagaTgaagagag | | 16 | 3800 ... 3815 | CTTCTCTgCTTCTCTC |
| SEQUENCE ID NO: 31 | | | | SEQUENCE ID NO: 32 |
| agaagaaaTgaagaaa | | 16 | 4480 ... 4495 | TCTTCTTTgCTTCTTT |
| SEQUENCE ID NO: 33 | | | | SEQUENCE ID NO: 34 |
| gagagaaagagagaggaaaTaaaga | | 25 | 5729 ... 5753 | CTCTCCTTTCTCTCTCCTTTgTTTCT |
| SEQUENCE ID NO: 25 | | | | SEQUENCE ID NO: 36 |
| aaagaagaaaaaaagg | | 15 | 5808 ... 5822 | TTTCTTCTTTTTTCC |
| SEQUENCE ID NO: 37 | | | | SEQUENCE ID NO: 38 |
| agaagaagaaagaggag | | 17 | 5967 ... 5983 | TCTTCTTCTTTCTCCCTC |
| SEQUENCE ID NO: 39 | | | | SEQUENCE ID NO: 40 |
| agagagTgaggaaagaggggag | | 22 | 10702 ... 10723 | TCTCTCgCTCCTTTCTCCCCTC |
| SEQUENCE ID NO: 41 | | | | SEQUENCE ID NO: 42 |
| tcctctccttctAcctctct | | 20 | 11042 ... 11061 | TCTCTCCgTCTTCCTCTCCT |
| SEQUENCE ID NO: 43 | | | | SEQUENCE ID NO: 44 |
| aaaaaagaggagaaaaag | | 17 | 12923 ... 12939 | TTTTTTCTCCTCTTTC |
| SEQUENCE ID NO: 45 | | | | SEQUENCE ID NO: 46 |
| ttttcttttcettt | | 15 | 13280 ... 13294 | TTTCCTTTTTCTTTT |
| SEQUENCE ID NO: 47 | | | | SEQUENCE ID NO: 48 |
| ttctttcttttcette | | 17 | 13299 ... 13315 | CTTCCTTTTTCTTTCTT |
| 4) HER-2 | | | | |
| Gene (mRNA) sequences from EMBL #M11730 | | | | |
| SEQUENCE ID NO: 49 | | | | SEQUENCE ID NO: 50 |
| gaaaggagggg | | 11 | 597 ... 607 | CTTTCCTCCCC |
| SEQUENCE ID NO: 51 | | | | SEQUENCE ID NO: 52 |
| gagaggTgaggg | | 11 | 1202 ... 1213 | CTCTCCgCTCCC |
| SEQUENCE ID NO: 53 | | | | SEQUENCE ID NO: 54 |
| ccctccettct | | 11 | 1926 ... 1936 | TCTTCCCTCCC |
| SEQUENCE ID NO: 55 | | | | SEQUENCE ID NO: 56 |
| ggaaaagggggag | | 13 | 2955 ... 2967 | CCTTTTCCCCCTC |
| SEQUENCE ID NO: 57 | | | | SEQUENCE ID NO: 58 |
| ccctttccttcc | | 12 | 4201 ... 4212 | CCTTCCTTTCCC |
| SEQUENCE ID NO: 59 | | | | SEQUENCE ID NO: 60 |
| gagaggggaag | | 11 | 4250 ... 4260 | CTCTCCCCTTC |
| 5) γ-crystallin (2q33–q35) (γ-3) | | | | |
| part 1:exons 1 and 2:K03003 | | | | |
| SEQUENCE ID NO: 61 | | | | SEQUENCE ID NO: 62 |
| aaaaTgaaaaaaag | | 15 | 144 ... 158 | TTTTgCTTTTTTTC |
| part 2:exon 3:K03004 | | | | |
| SEQUENCE ID NO: 63 | | | | SEQUENCE ID NO: 64 |
| tttcccAtttt | | 11 | 301 ... 311 | TTTgCCCTTT |
| γ-crystallin (2q33–q35) (γ-4) | | | | |
| Part 2:exon 3:K03006 | | | | |
| SEQUENCE ID NO: 65 | | | | SEQUENCE ID NO: 66 |
| cttttcttctcttttAtttct | | 22 | 9 ... 30 | TCTTTgTTTTTCTCTTCTTTTC |
| 6) Esterase D (13q14.1–14.2) | | | | |
| RNA sequence from EMBL M13450 | | | | |
| SEQUENCE ID NO: 67 | | | | SEQUENCE ID NO: 68 |
| aggaaaagaa | | 10 | 34 ... 43 | TCCTTTTCTT |
| SEQUENCE ID NO: 69 | | | | SEQUENCE ID NO: 70 |
| aaaggTgaagaTgagag | | 17 | 316 ... 332 | TTTCCgCTTCTgCTCTC |
| SEQUENCE ID NO: 71 | | | | SEQUENCE ID NO: 72 |
| aagggaaaga | | 10 | 710 ... 719 | TTCCCTTTCT |
| SEQUENCE ID NO: 73 | | | | SEQUENCE ID NO: 74 |
| agaaagaaaa | | 11 | 777 ... 787 | TCTTTTCTTTT |
| SEQUENCE ID NO: 75 | | | | SEQUENCE ID NO: 76 |
| aaaaaaaaaaaaaa | | 14 | 962 ... 975 | TTTTTTTTTTTTTT |
| 7) Retinoblastoma (13q14.2) | | | | |
| RNA sequence from EMBL M33647, J02994 | | | | |
| SEQUENCE ID NO: 77 | | | | SEQUENCE ID NO: 78 |
| aaaagaaaaaggaa | | 14 | 281 ... 394 | TTTTCTTTTTCCTT |
| SEQUENCE ID NO: 79 | | | | SEQUENCE ID NO: 80 |
| gaaagagTgaagga | | 15 | 1251 ... 1265 | CTTTTCgCTTCCT |
| SEQUENCE ID NO: 81 | | | | SEQUENCE ID NO: 82 |
| tcttcctctcc | | 11 | 1781 ... 1791 | CCTCTCCTTCT |
| SEQUENCE ID NO: 83 | | | | SEQUENCE ID NO: 84 |
| aaagaaaaaagg | | 12 | 1842 ... 1853 | TTTCTTTTTTCC |
| SEQUENCE ID NO: 85 | | | | SEQUENCE ID NO: 86 |
| aaagaagaggag | | 12 | 2236 ... 2247 | TTTCTTCTCCTC |

| | | | |
|---|---|---|---|
| SEQUENCE ID NO: 87 | | | SEQUENCE ID NO: 88 |
| ctttctccccctccct | 15 | 4062 ... 4076 | TCCCCTCCCCTCTTC |
| 8) SOD1 (extracellular) (21q22.1) | | | |
| RNA sequence from EMBL J02947 | | | |
| SEQUENCE ID NO: 89 | | | SEQUENCE ID NO: 90 |
| aggagagaaag | 11 | 21 ... 31 | TCCTCTCTTT |
| SEQUENCE ID NO: 91 | | | SEQUENCE ID NO: 92) |
| ccctccttccccAcccc | 17 | 1084 ... 1110 | CCCCgCCCCTTCCTCCC |
| SEQUENCE ID NO: 93) | | | SEQUENCE ID NO: 94 |
| tcttccccttccc | 14 | 1145 ... 1158 | CCCTTCCCCCTTCT |
| SEQUENCE ID NO: 95 | | | SEQUENCE ID NO: 96 |
| tccccAcccctcccc | 17 | 1205 ... 1218 | CCCTCCCCgCCCCCCT |
| 9) Prealbumin gene (18q11.2–12.1) | | | |
| DAN in three sections: | | | |
| #1 exons 1 and 2:M15515 | | | |
| SEQUENCE ID NO: 97 | | | SEQUENCE ID NO: 98 |
| gagggaggaaaaa | 14 | 250 ... 263 | CTCCCTCCTTTTTT |
| SEQUENCE ID NO: 99 | | | SEQUENCE ID NO: 100 |
| ttttctccctt | 11 | 1344 ... 1354 | TTCCCTCTTTT |
| #2 exon 3:M15516 | | | |
| SEQUENCE ID NO: 101 | | | SEQUENCE ID NO: 102 |
| ttctcttctt | 10 | 166 ... 175 | TTCTTCTCTT |
| SEQUENCE ID NO: 103 | | | SEQUENCE ID NO: 104 |
| agagaaaaaaa | 11 | 179 ... 189 | TCTCTTTTTTT |
| SEQUENCE ID NO: 105 | | | SEQUENCE ID NO: 106 |
| ttcccttcct | 11 | 658 ... 668 | TCCTTTCCCTT |
| #3 exon 4:M15517 | | | |
| SEQUENCE ID NO: 107 | | | SEQUENCE ID NO: 108 |
| cttttcttcttc | 12 | 133 ... 144 | CTTCTTCTTTTC |
| SEQUENCE ID NO: 109 | | | SEQUENCE ID NO: 110 |
| aggagggTgggggaa | 15 | 166 ... 180 | TCCTCCCgCCCCCTT |
| SEQUENCE ID NO: 111 | | | SEQUENCE ID NO: 112 |
| ccttttttttct | 12 | 391 ... 402 | TCTTTTTTTTCC |
| SEQUENCE ID NO: 113 | | | SEQUENCE ID NO: 114 |
| aaaaaaaagagaa | 13 | 1020 ... 1032 | TTTTTTTTCTCTT |
| 10) β-globin gene mRNA | | | |
| for deletion based thalassemia. From EMBL:V00499 | | | |
| SEQUENCE ID NO: 115 | | | SEQUENCE ID NO: 116 |
| ttttctttcccttctttct | 21 | 742 ... 762 | TCTTTTCTTCCCCTTTCTTTT |
| SEQUENCE ID NO: 117 | | | SEQUENCE ID NO: 118 |
| ctttcttttttttcttctcc | 21 | 917 ... 937 | CCTCTTCTTTTTTTTCTTTC |
| SEQUENCE ID NO: 119 | | | SEQUENCE ID NO: 120 |
| tctctttctttc | 12 | 1284 ... 1295 | CTTTCTTTCTCT |
| 11) α-globin gene mRNA α-2-globin | | | |
| for deletion-based thalassemia. From EMBL:V00516 | | | |
| Note probe sequences work for α-1-globin and α-2-globin. | | | |
| SEQUENCE ID NO: 121 | | | SEQUENCE ID NO: 122 |
| ctccctccccct | 11 | 139 ... 149 | TCCCCTCCCTC |
| SEQUENCE ID NO: 123 | | | SEQUENCE ID NO: 124 |
| ccctcttctct | 11 | 580 ... 590 | TCTCTTCTCCC |
| SEQUENCE ID NO: 125 | | | SEQUENCE ID NO: 126 |
| ccctcctccccctcctt | 16 | 775 ... 790 | TTCCTCCCCTCCTCCC |
| note last sequence is different in α-1-globin:V00491 | | | |
| SEQUENCE ID NO: 127 | | | SEQUENCE ID NO: 128 |
| ccccctcctccccttcct | 17 | 827 ... 843 | TCCTTCCCCTCCTCCCC |
| 12) Hepatitis B virus adr isolate | | | |
| SEQUENCE ID NO: 129 | | | SEQUENCE ID NO: 130 |
| ctttcActttctc | 13 | 961 ... 973 | CTCTTCgCTTTC |
| SEQUENCE ID NO: 131 | | | SEQUENCE ID NO: 132 |
| tccccttcttc | 11 | 1360 ... 1370 | CTTCTTCCCCT |
| SEQUENCE ID NO: 133 | | | SEQUENCE ID NO: 134 |
| gggggaggaga | 11 | 1614 ... 1624 | CCCCCTCCTCT |
| SEQUENCE ID NO: 135 | | | SEQUENCE ID NO: 136 |
| cttttcAcctct | 13 | 1692 ... 1704 | TCTCCgCTTTTC |
| SEQUENCE ID NO: 137 | | | SEQUENCE ID NO: 138 |
| ctctcttttt | 11 | 1818 ... 1828 | TTTTTCTCTC |
| SEQUENCE ID NO: 139 | | | SEQUENCE ID NO: 140 |
| cttcttttccttct | 13 | 1838 ... 1850 | TCTTCCTTTCTTC |
| SEQUENCE ID NO: 141 | | | SEQUENCE ID NO: 142 |
| ctccctccttcctc | 15 | 2405 ... 2419 | CTCCTTTCCTCCCTC |
| SEQUENCE ID NO: 143 | | | SEQUENCE ID NO: 144 |
| gaaaaaaggaga | 12 | 2485 ... 2496 | CTTTTTTCCTCT |
| Hepatitis B Triple helix forming regions | | | |
| Three major strains of Hepatitis B are considered: | | | |
| ayw | | | |
| Galibert, F., Mandart, E., Fitoussi, F., Tiollais, P. | | | |
| and Charnay, P. (1979) Nucleotide sequence of the | | | |
| Hepatitis B virus genome (subtype ayw) cloned in *E.* | | | |
| *coli.* Nature 281:646–650. | | | |

-continued

| # | sequence | size | location | third strand | note |
|---|---|---|---|---|---|
| | SEQUENCE ID NO: 145 | | | SEQUENCE ID NO: 146 | |
| 1 | tttctctctt | 10 | 395 . . . 404 | TTCTCTCTTT | adr #15 |
| | SEQUENCE ID NO: 147 | | | SEQUENCE ID NO: 148 | |
| 2 | tcttcttttctc | 12 | 561 . . . 572 | CTCTTTTCTTCT | |
| | SEQUENCE ID NO: 149 | | | SEQUENCE ID NO: 150 | |
| 3 | ttcccctcctt | 11 | 706 . . . 716 | TTCCTCCCCTT | |
| | SEQUENCE ID NO: 151 | | | SEQUENCE ID NO: 152 | |
| 4 | ttcttcttct | 10 | 807 . . . 816 | TCTTCTTCTT | adw #3 |
| | SEQUENCE ID NO: 153 | | | SEQUENCE ID NO: 154 | |
| 5 | tttctcttcc | 10 | 945 . . . 954 | CCTTCTCTTT | adr #10, adw #12 |
| | SEQUENCE ID NO: 155 | | | SEQUENCE ID NO: 156 | |
| 6 | gaaggaaagaag | 12 | 1208 . . . 1219 | CTTCCTTTCTTC | |
| | SEQUENCE ID NO: 157 | | | SEQUENCE ID NO: 158 | |
| 7 | agaggTgaaaaag | 13 | 1353 . . . 1365 | TCTCCgCTTTTC | |
| | SEQUENCE ID NO: 159 | | | SEQUENCE ID NO: 160 | |
| 8 | tctcctccccc | 11 | 1433 . . . 1443 | CCCCCTCCTCT | adw #13 |
| | SEQUENCE ID NO: 161 | | | SEQUENCE ID NO: 162 | |
| 9 | ggagaaggga | 11 | 1687 . . . 1697 | CCTCTTCCCCT | adw #12 |
| | SEQUENCE ID NO: 163 | | | SEQUENCE ID NO: 164 | |
| 10 | gagaaagTgaaag | 13 | 2085 . . . 2097 | CTCTTTCgCTTTC | adw #11, adr #3 |
| | SEQUENCE ID NO: 165 | | | SEQUENCE ID NO: 166 | |
| 11 | aagaagaTgagg | 12 | 2750 . . . 2761 | TTCTTCTgCTCC | adw #9 |
| | SEQUENCE ID NO: 167 | | | SEQUENCE ID NO: 168 | |
| 12 | aggaTgaagaggaaga | 16 | 2771 . . . 2786 | TCCTgCTTCTCCTTCT | |
| | SEQUENCE ID NO: 169 | | | SEQUENCE ID NO: 170 | |
| 13 | aagggagagg | 10 | 3071 . . . 3080 | TTCCCTCTCC | | adw2
Valenzuela, P. Quiroga, M., Zaldivar, J., Gray, P. and Ruter, W. J.
(1980) The nucleotide sequence of the Hepatitis B viral genome and the
identification of the major viral genes. In "Animal Virus Genetics"
Fields, B. N., Jaenisch, R and Fox, C. F., eds. pp 55–70. Academic
Press, New York.

| # | sequence | size | location | third strand | note |
|---|---|---|---|---|---|
| | SEQUENCE ID NO: 171 | | | SEQUENCE ID NO: 172 | |
| 1 | cttctttccttcc | 13 | 154 . . . 166 | CCTTCCTTTCTTC | ayw #6 (−2) |
| | SEQUENCE ID NO: 173 | | | SEQUENCE ID NO: 174 | |
| 2 | ggaagagaga | 10 | 419 . . . 428 | CCTCTCTCT | adr #10, ayw #5 |
| | SEQUENCE ID NO: 175 | | | SEQUENCE ID NO: 176 | |
| 3 | agaagaagaa | 10 | 563 . . . 572 | TCTTCTTCTT | adr #11, ayw #4 |
| | SEQUENCE ID NO: 177 | | | SEQUENCE ID NO: 178 | |
| 4 | aaggTgggaaa | 11 | 663 . . 673 | TTCCgCCCTTT | adr #12 |
| | SEQUENCE ID NO: 179 | | | SEQUENCE ID NO: 180 | |
| 5 | ctccttccttcct | 14 | 727 . . . 740 | TCCTTTCCTTCCTC | |
| | SEQUENCE ID NO: 181 | | | SEQUENCE ID NO: 182 | |
| 6 | ga2aaagagaaga | 12 | 807 . . . 818 | CTTTTCTCTTCT | |
| | SEQUENCE ID NO: 183 | | | SEQUENCE ID NO: 184 | |
| 7 | aggagTgggag | 11 | 1215 . . . 1225 | TCCTCgCCCTC | |
| | SEQUENCE ID NO: 185 | | | SEQUENCE ID NO: 186 | |
| 8 | ttcctcttcAtccct | 14 | 1810 . . . 1823 | TCCTgCTTCTCCTT | ayw #12 (−2), adr #1 |
| | SEQUENCE ID NO: 187 | | | SEQUENCE ID NO: 188 | |
| 8 | cctcAtcttctt | 12 | 1833 . . . 1844 | TTCTTCTgCTCC | ayw #11 |
| | SEQUENCE ID NO: 189 | | | SEQUENCE ID NO: 190 | |
| 9 | aaaaagaTgggg | 12 | 2258 . . . 2269 | TTTTTCTgCCCC | |
| | SEQUENCE ID NO: 191 | | | SEQUENCE ID NO: 192 | |
| 10 | ctttcActttctc | 13 | 2497 . . . 2507 | CCTCTTCCCCT | ayw #10, adr #3 |
| | SEQUENCE ID NO: 193 | | | SEQUENCE ID NO: 194 | |
| 11 | tccccttctcc | 11 | 2897 . . . 2907 | CCTCTTCCCCT | ayw #9 |
| | SEQUENCE ID NO: 195 | | | SEQUENCE ID NO: 196 | |
| 12 | gggggaggaga | 11 | 3151 . . . 3161 | CCCCCTCCTCT | ayw #8 | adr
Fujiyama, A., Miyanchara, A., Nozaki, C., Yoneyama, T., Chromo,
N. and Matsubara, K. (1983) Cloning and structural anaylsis of
Hepatitis B virus DNAs subtype adr. Nucleic Acids Research
11:4601–4610.

| # | sequence | size | location | third strand | note |
|---|---|---|---|---|---|
| | SEQUENCE ID NO: 197 | | | SEQUENCE ID NO: 198 | |
| 1 | ttcctccttcAtcct | 14 | 274 . . . 287 | TCCTgCTTCTCCTT | adw #8, ayw #11(−2) |
| | SEQUENCE ID NO: 199 | | | SEQUENCE ID NO: 200 | |
| 2 | tttccctctt | 10 | 427 . . . 436 | TTCTCCCTTT | |
| | SEQUENCE ID NO: 201 | | | SEQUENCE ID NO: 202 | |
| 4 | cctcctttcc | 10 | 1236 . . . 1245 | CCTTTCCTCC | |
| | SEQUENCE ID NO: 131 | | | SEQUENCE ID NO: 132 | |
| 5 | tccccttcttc | 11 | 1360 . . . 1370 | CTTCTTCCCCT | |
| | SEQUENCE ID NO: 203 | | | SEQUENCE ID NO: 204 | |
| 10 | ggaagagaaa | 10 | 2103 . . . 2112 | CCTTCTCTTT | adw #2, ayw #5 |
| | SEQUENCE ID NO: 205 | | | SEQUENCE ID NO: 206 | |
| 11 | agaagaagaa | 10 | 2241 . . . 2250 | TCTTCTTCTT | adw #3, ayw #4 |
| | SEQUENCE ID NO: 207 | | | SEQUENCE ID NO: 208 | |
| 12 | aaggTgggaaa | 11 | 2341 . . . 2351 | TTCCgCCCTTT | adw #4 |
| | SEQUENCE ID NO: 209 | | | SEQUENCE ID NO: 210 | |

| | | | | | |
|---|---|---|---|---|---|
| 13 | ctttAttcttct | 12 | 2362 ... 2373 | TCTTCTTgTTTC | |
| | SEQUENCE ID NO: 211 | | | SEQUENCE ID NO: 212 | |
| 15 | aagagagaaa | 10 | 2653 ... 2662 | TTCTCTCTTT | ayw #1 |
| | SEQUENCE ID NO: 213 | | | SEQUENCE ID NO: 214 | |
| 16 | ctcccAtctctccAcctct | 19 | 3036 ... 3054 | TCTCCgCCTCTCTgCCCTC | |

The three sequences have been taken from the original publications. They each start at a different place on the viral genome and one of them (ayw) is listed in a different polarity from the other two. For this reason, the numbering of the locations is not easy to relate between the three sequences. If a particular region capable of triple helix formation can be found in more than one strain, this is listed in the "note" column. Some regions are common to all three strains (e.g., ayw #5 and ayw #10). Others are common to only two out of the three strains. These regions with cross-strain homologies can be used to identify all or some of the common hepatitis B strains. The others are strain-specific.

In selecting the particular sequence for use, the normal guidelines apply. Long stretches of the same nucleotide are avoided, and a mix of 50%C or more is preferred. Where the third triplet is needed to provide length of complexity, (putting a G into the third strand), it should be at least five nucleotides from either end.

Bacterial ribosomal gene sequences.
LARGE RIBOSOMAL (23S) sequences
*Escherichia coli*                                            Sequence #M25458
Sequence 2894 BP; 762 A; 633 C; 909 G; 590 T; 0 other;

| | | | | |
|---|---|---|---|---|
| SEQUENCE ID NO: 215 | | | | SEQUENCE ID NO: 216 |
| gaggaaaagaaa | 12 | 212 ... 223 | | CTCCTTTTCTTT |
| SEQUENCE ID NO: 217 | | | | SEQUENCE ID NO: 218 |
| gaggggagTgaaaaagaa | 18 | 493 ... 510 | | CTCCCCTCgCTTTTTCTT |
| SEQUENCE ID NO: 219 | | | | SEQUENCE ID NO: 220 |
| gggggTgaaagg | 12 | 785 ... 796 | | CCCCCgCTTTCC |
| SEQUENCE ID NO: 221 | | | | SEQUENCE ID NO: 222 |
| gaagaggaaa | 11 | 982 ... 992 | | CTTCTCCCTTT |
| SEQUENCE ID NO: 223 | | | | SEQUENCE ID NO: 224 |
| gaagggggga | 10 | 1410 ... 1419 | | CTTCCCCCCT |

*Halococcus morrhuae*                                  Sequence #X05481
Sequence 2927 BP; 711 A; 771 C; 939 G; 506 T; 0 other;

| | | | | |
|---|---|---|---|---|
| SEQUENCE ID NO: 225 | | | | SEQUENCE ID NO: 226 |
| aggaagagaaa | 11 | 181 ... 191 | | TCCTTCTCTTT |
| SEQUENCE ID NO: 227 | | | | SEQUENCE ID NO: 228 |
| gaaaaTgaaagg | 12 | 880 ... 891 | | TCCCCgCTTTCC |
| SEQUENCE ID NO: 229 | | | | SEQUENCE ID NO: 230 |
| gagaTagagaaa | 12 | 1628 ... 1639 | | CTCTgTCTCTTT |
| SEQUENCE ID NO: 231 | | | | SEQUENCE ID NO: 232 |
| ttccctccAtcct | 13 | 2551 ... 1563 | | TCCTgCCTCCCTT |

*Leptosphira interrogans*                          Sequence #X14249
Sequence 3244 BP; 928 A; 680 C; 944 G; 692 T; 0 other;

| | | | | |
|---|---|---|---|---|
| SEQUENCE ID NO: 233 | | | | SEQUENCE ID NO: 234 |
| agagggTgaaaag | 12 | 384 ... 395 | | TCTCCCgCTTTC |
| SEQUENCE ID NO: 235 | | | | SEQUENCE ID NO: 236 |
| gagggaaaggTgaaaaag | 17 | 530 ... 546 | | CTCCCTTTCCgCTTTTC |
| SEQUENCE ID NO: 237 | | | | SEQUENCE ID NO: 238 |
| aggggTgaaagg | 12 | 842 ... 853 | | TCCCCgCTTTCC |
| SEQUENCE ID NO: 239 | | | | SEQUENCE ID NO: 240 |
| ttctttcttcc | 11 | 1258 ... 1268 | | CCTTCTTTCTT |
| SEQUENCE ID NO: 241 | | | | SEQUENCE ID NO: 242 |
| ggaggagTaagaaaTgaaga | 20 | 1295 ... 1314 | | CCTTCCTCgTTCTTTgCTTCT |
| SEQUENCE ID NO: 243 | | | | SEQUENCE ID NO: 244 |
| gggaTaagggaga | 13 | 1758 ... 1770 | | CCCTgTTCCCTCT |

*Micrococcus luteus*                                      Sequence #X06484
Sequence 3094 BP; 736 A; 704 C; 1029 G; 625 T; 0 other;

| | | | | |
|---|---|---|---|---|
| SEQUENCE ID NO: 245 | | | | SEQUENCE ID NO: 246 |
| aggaagagaaaa | 12 | 214 ... 225 | | TCCTTCTCTTTT |
| SEQUENCE ID NO: 247 | | | | SEQUENCE ID NO: 248 |
| gggaggggagTgaaa | 15 | 572 ... 586 | | CCCTCCCCTCgCTTT |
| SEQUENCE ID NO: 249 | | | | SEQUENCE ID NO: 250 |
| aggggTgaaagg | 12 | 859 ... 870 | | TCCCCgCTTTCC |
| SEQUENCE ID NO: 251 | | | | SEQUENCE ID NO: 252 |
| gggaagTgagag | 12 | 1009 ... 1020 | | CCCTTCgCTCTC |
| SEQUENCE ID NO: 253 | | | | SEQUENCE ID NO: 254 |
| gggagaaggggg | 13 | 1884 ... 1896 | | CCCTCTTCCCCCC |
| SEQUENCE ID NO: 255 | | | | SEQUENCE ID NO: 256 |
| tccctAtcctct | 12 | 2795 ... 2806 | | TCTCCTgTCCCT |

*Frankia sp.*                                                    Sequence #M55343
rRNA
Sequence 6481 BP; 1333 A; 1592 C; 2268 G; 1288 T; 0 other;

| | | | | |
|---|---|---|---|---|
| SEQUENCE ID NO: 257 | | | | SEQUENCE ID NO: 258 |
| gagggaaaggTgaaaag | 17 | 3002 ... 3018 | | CTCCCTTTCCgCTTTTTC |
| SEQUENCE ID NO: 259 | | | | SEQUENCE ID NO: 260 |

-continued

| | | | |
|---|---|---|---|
| aggggTgaaagg | 12 | 3314 ... 3325 | TCCCCgCTTTCC |
| SEQUENCE ID NO: 261 | | | SEQUENCE ID NO: 262 |
| ggagaagggggg | 12 | 5444 ... 5455 | CCTCTTCCCCCC |

*Rhodobacter capsulatus*  Sequence #X06485
Sequence 2884 BP; 737 A; 679 C; 893 G; 575 T; 0 other;

| | | | |
|---|---|---|---|
| SEQUENCE ID NO: 263 | | | SEQUENCE ID NO: 264 |
| aggggTgaaagg | 12 | 842 ... 853 | TCCCCgCTTTCC |
| SEQUENCE ID NO: 265 | | | SEQUENCE ID NO: 266 |
| gaagagggaaa | 11 | 1038 ... 1048 | CTTCTCCCTTT |
| SEQUENCE ID NO: 267 | | | SEQUENCE ID NO: 268 |
| aaagagggTgagaga | 15 | 1401 ... 1415 | TTTCTCCCgCTCTCT |

SMALL RIBOSMAL (16S) sequence
*Alcaligenes faecalis*  Sequence #M22508; M22467
Sequence 1476 BP; 373 A; 339 C; 449 G; 295 T; 20 other;

| | | | |
|---|---|---|---|
| SEQUENCE ID NO: 269 | | | SEQUENCE ID NO: 270 |
| gggggaaaggggga | 16 | 190 ... 205 | CCCCCTTTCCCCCCT |
| SEQUENCE ID NO: 271 | | | SEQUENCE ID NO: 272 |
| agagaagaaaagg | 13 | 444 ... 456 | TCTCTTCTTTCC |
| SEQUENCE ID NO: 273 | | | SEQUENCE ID NO: 274 |
| ggaaagaaaga | 11 | 592 ... 602 | CCAAACAAACA |
| SEQUENCE ID NO: 275 | | | SEQUENCE ID NO: 276 |
| agaggggggTagaa | 14 | 663 ... 676 | TCTCCCCCCgTCTT |
| SEQUENCE ID NO: 277 | | | SEQUENCE ID NO: 278 |
| ggaggaaggTgggga | 15 | 1169 ... 1183 | CCTCCTTCCgCCCCT* |

*Coxiella burnetii*  Sequence #M21291
Sequence 1484 BP; 369 A; 330 C; 461 G; 311 T; 13 other;

| | | | |
|---|---|---|---|
| SEQUENCE ID NO: 279 | | | SEQUENCE ID NO: 280 |
| ggggaagaaa | 10 | 444 ... 453 | CCCCTTCTTT |
| SEQUENCE ID NO: 281 | | | SEQUENCE ID NO: 282 |
| ttcccttctt | 10 | 841 ... 850 | TTCTTCCCTT |
| SEQUENCE ID NO: 283 | | | SEQUENCE ID NO: 284 |
| ggaggaaggTgggga | 15 | 1174 ... 1188 | CCTCCTTCCgCCCCCT* |

*Clostridium pasteurianum*  Sequence #M23930
Sequence 1511 BP; 391 A; 320 C; 450 G; 317 T; 33 other;

| | | | |
|---|---|---|---|
| SEQUENCE ID NO: 285 | | | SEQUENCE ID NO: 286 |
| aaagaggggaa | 11 | 129 ... 139 | TTTCTCCCCTT |
| SEQUENCE ID NO: 287 | | | SEQUENCE ID NO: 288 |
| gaaagggaga | 10 | 149 ... 158 | CTTTCCCTCT |
| SEQUENCE ID NO: 289 | | | SEQUENCE ID NO: 290 |
| aaaggaggaag | 11 | 459 ... 469 | TTTCCTCCTTC |
| SEQUENCE ID NO: 291 | | | SEQUENCE ID NO: 292 |
| aggagaggaaag | 12 | 629 ... 640 | TCCTCTCCTTTC |
| SEQUENCE ID NO: 293 | | | SEQUENCE ID NO: 294 |
| [ggNaggaaggCgggga | 16 | 1141 ... 1156 | CCNTCCTTCCGCCCCT |

*Chlamydia psittaci*  Sequence #M13769
Sequence 1552 BP; 411 A; 324 C; 454 G; 363 T; 0 other;

| | | | |
|---|---|---|---|
| SEQUENCE ID NO: 295 | | | SEQUENCE ID NO: 296 |
| aaagaagggga | 11 | 203 ... 213 | TTTCTTCCCT |
| SEQUENCE ID NO: 297 | | | SEQUENCE ID NO: 298 |
| gggaaTaagagaga | 14 | 453 ... 466 | CCCTTgTTCTCTCT |
| SEQUENCE ID NO: 299 | | | SEQUENCE ID NO: 300 |
| ggaaaggaaag | 11 | 595 ... 605 | CCTTTCCTTTC |
| SEQUENCE ID NO: 301 | | | SEQUENCE ID NO: 302 |
| agagggTagaTggagaaaagggaa | 24 | 661 ... 684 | TCTCCCgTCTgCCTCTTTTCCCTT |
| SEQUENCE ID NO: 303 | | | SEQUENCE ID NO: 304 |
| aggaggaagg | 10 | 1181 ... 1190 | TCCTCCTTCC (related to *) |

*Corynebacterium renale*  Sequence #M29553
Sequence 1366 BP; 290 A; 301 C; 455 G; 298 T; 22 other;

| | | | |
|---|---|---|---|
| SEQUENCE ID NO: 305 | | | SEQUENCE ID NO: 306 |
| gagagggTgga | 11 | 291 ... 301 | CTCTCCCgCCT |
| SEQUENCE ID NO: 307 | | | SEQUENCE ID NO: 308 |
| tctttcccttt | 11 | 997 ... 1007 | TTTCCCTTTCT |
| SEQUENCE ID NO: 309 | | | SEQUENCE ID NO: 310 |
| agaaggTgggga | 13 | 1151 ... 1164 | TCCTTCCgCCCCT |
| SEQUENCE ID NO: 311 | | | SEQUENCE ID NO: 312 |
| gNaggaaggTgggga | 15 | 1150 ... 1164 | CnTCCTTCCgCCCCT |

*Haemophilus influenze*  Sequence #M35019; M59433
Sequence 1487 BP; 384 A; 304 C; 468 G; 324 T; 7 other;

| | | | |
|---|---|---|---|
| SEQUENCE ID NO: 313 | | | SEQUENCE ID NO: 314 |
| ggaagaTgaaag | 12 | 187 ... 198 | CCTTCTgCTTTC |
| SEQUENCE ID NO: 315 | | | SEQUENCE ID NO: 316 |
| gaaTgaagaagg | 12 | 406 ... 417 | CTTgCTTCTTCC |
| SEQUENCE ID NO: 317 | | | SEQUENCE ID NO: 318 |
| agggaggggTagaa | 14 | 663 ... 676 | TCCCTCCCCgTCTT |
| SEQUENCE ID NO: 319 | | | SEQUENCE ID NO: 320 |
| cccttAtccttt | 12 | 1110 ... 1121 | TTTCCTgTTCCC |
| SEQUENCE ID NO: 321 | | | SEQUENCE ID NO: 322 |
| ggaggaaggTNggga | 15 | 1172 ... 1186 | CCTCCTTCCgnCCCT (related to *) |

*Mycobacterium paratuberculosis*  Sequence #M29569
Sequence 1367 BP; 297 A; 316 C; 461 G; 285 T; 8 other;

-continued

| Sequence | Size | Location | Third strand |
|---|---|---|---|
| SEQUENCE ID NO: 323 | | | SEQUENCE ID NO: 324 |
| aggTggagaagaag | 14 | 471 ... 484 | TCCgCCTCTTCTTC |
| SEQUENCE ID NO: 325 | | | SEQUENCE ID NO: 326 |
| tttccttcctt | 11 | 821 ... 831 | TTCCTTCCTTT |
| SEQUENCE ID NO: 327 | | | SEQUENCE ID NO: 328 |
| ggaggaaggTgggga | 15 | 1159 ... 1173 | CCTCCTTCCgCCCCT* |
| *Mycoplasma pneumoniae* | | Sequence #M29061 | |
| Sequence 1465 BP; 426 A; 272 C; 396 G; 367 T; 4 other; | | | |
| SEQUENCE ID NO: 329 | | | SEQUENCE ID NO: 330 |
| ggaggaaggaaggga | 15 | 1150 ... 1164 | CCTCCTTCCgTTCCCT (related to *) |
| *Neisseria gonorrhoeae* | | Sequence #X07714 | |
| Sequence 1544 BP; 380 A; 357 C; 492 G; 315 T; 0 other; | | | |
| SEQUENCE ID NO: 331 | | | SEQUENCE ID NO: 332 |
| gagagggaaag | 11 | 189 ... 199 | CTCTCCCTTTC |
| SEQUENCE ID NO: 333 | | | SEQUENCE ID NO: 334 |
| agggaagaaaagg | 13 | 445 ... 457 | TCCCTTCTTTTCC |
| SEQUENCE ID NO: 335 | | | SEQUENCE ID NO: 336 |
| agagggaggTggaa | 14 | 664 ... 677 | TCTCCCTCCgCCTT |
| SEQUENCE ID NO: 337 | | | SEQUENCE ID NO: 338 |
| ggaggaaggTggga | 15 | 1174 ... 1188 | CCTCCTTCCgCCCCT |
| SEQUENCE ID NO: 339 | | | SEQUENCE ID NO: 340 |
| gggagTggggga | 12 | 1415 ... 1426 | CCCCTCgCCCCCT |
| *Pseudomonas cepacea* | | Sequence #M22518; M22467 | |
| Sequence 1473 BP; 365 A; 334 C; 457 G; 289 T; 28 other; | | | |
| SEQUENCE ID NO: 341 | | | SEQUENCE ID NO: 342 |
| ggaagaaTaag | 11 | 486 ... 496 | CCTTCTTgTTC |
| SEQUENCE ID NO: 343 | | | SEQUENCE ID NO: 344 |
| ggaggaaggTgggga | 15 | 1165 ... 1179 | CCTCCTTCCgCCCCT* |
| *Streptococcus parasanguis* | | Sequence #X53652 | |
| Sequence 1480; BP; 365 A; 320 C; 439 G; 310 T; 46 other; | | | |
| SEQUENCE ID NO: 345 | | | SEQUENCE ID NO: 346 |
| agaaggggagagTggaa | 17 | 665 ... 681 | TCTTCCCCTCTCgCCTT |
| SEQUENCE ID NO: 347 | | | SEQUENCE ID NO: 348 |
| ggaggaaggTgggga | 15 | 1178 ... 1192 | CCTCCTTCCgCCCCT |

Sequences marked "*" are common to a number of species.
In most of those species where the sequence does not appear intact, it is present in a mutated form.
Triple helix-forming regions from the human p53 gene
Sequence taken from:
Harlow, E., Williamson, N. M., Ralston, R., Helfman, D. M. and Adams, T. E. (1985) "Molecular cloning and in vitro expression of a cDNA clone for human cellular tumor antigen p53." Molecular and Cellular Biology 5:1601–1610.

| Sequence | Size | Location | Third strand |
|---|---|---|---|
| SEQUENCE ID NO: 349 | | | SEQUENCE ID NO: 350 |
| gagTggaaggaaa | 13 | 901 ... 913 | CTCgCCTTCCTTT |
| SEQUENCE ID NO: 351 | | | SEQUENCE ID NO: 352 |
| agaggaagagaa | 12 | 1066 ... 1077 | TCTCCTTCTCTT |
| SEQUENCE ID NO: 353 | | | SEQUENCE ID NO: 354 |
| aagaaaggggag | 12 | 1085 ... 1096 | TTCTTTCCCCTC |
| SEQUENCE ID NO: 355 | | | SEQUENCE ID NO: 356 |
| ctcctctcccc | 11 | 1153 ... 1163 | CCCCTCTCCTC |
| SEQUENCE ID NO: 357 | | | SEQUENCE ID NO: 348 |
| aaagaagaaa | 10 | 1168 ... 1177 | TTTCTTCTTT |
| SEQUENCE ID NO: 359 | | | SEQUENCE ID NO: 360 |
| cctcccAccccccAtctctccctccct | 27 | 1427 ... 1453 | TCCCCCTCCCTCTCTgCCCCCgCCCTCC |
| SEQUENCE ID NO: 361 | | | SEQUENCE ID NO: 362 |
| ggggaggaggaTggggagTagga | 23 | 1581 ... 1603 | CCCCTCCTCCTgCCCCTCgTCCT |

The suppressor gene called P53 produces a protein which has a molecular weight of 53,000 dalton. The suppressors can prevent oncogenesis and are very important to cancer therapy.

EXAMPLE 1

Sample DNA containing the duplex sequence shown in FIG. 2 is then incubated with the anchor/reporter hybrid for several hours in buffer at a pH between 4.5 and 6.8 with an Na$^+$ concentration in excess of 0.1M, and containing dimethyl formamide or ethanol at concentrations up to 10%. The temperature range for incubation is from 0° C. to 25° C. These conditions represent the range for a number of different sequence combinations (base composition, triplex length etc.). During this incubation, the duplex region binds to the free tail of the reporter to form a triple helix. The initial nucleation then extends into the overlap region between the triple-helical portion and the anchor-reporter hybrid duplex. Since the conditions used strongly favor triple helix formation, the anchor/reporter duplex is reduced as the triple-helix forms and the reporter is displaced from the anchor as a result of capture by the sample duplex. FIGS. 1a through 1d illustrate these steps.

A defined amount of reporter is thus released into the liquid phase of the reaction where its concentration can be determined. The reporter release reflects the concentration of the triple-helix forming duplex sequences in the sample DNA added to the reaction vessel and, by comparison with suitable internal standards, gives an accurate measure of the concentration of these.

EXAMPLE 2

In order to test the displacement hybridization system, three molecular components were designed whose sequences are derived from the E6-gene of Human Papilloma Virus (HPV) strain 16. The selected DNA sequences are:

Collector

5'-gcaagcaacagttactgcgacgtgaggtatatg-3' SEQUENCE ID NO: 363

Reporter

5'-agttgaacgtcgcatcc-3' SEQUENCE ID NO: 364

Tester

5'-atacctcacgtcgcagtaactg-3' SEQUENCE ID NO: 365

The relationship between the sequence in terms of their complementarity and overlap, are:

```
                        Tester
                        3'-gtcaatgacgctgcactccata-5' SEQUENCE ID NO: 365
Collector
5'-(amino)-gcaagcaacagttactgcgacgtgaggtatatg-3' SEQUENCE ID NO: 363
                           acgctgca
                        t           a
                         c         g
                         c           t
                         3'            t
                       Reporter      g
                                    a
                                   biotin
                                   5' SEQUENCE ID NO: 364
```

The "COLLECTOR" sequence was coupled to a solid matrix via a 5'-amino group. The "REPORTER" molecule can be detected in a number of ways by making use of the 5'-terminal biotin group. The reporter molecule was hybridized to the collector molecule in 10×SSC (SSC is 0.15M NaCl, 0.015M sodium citrate) overnight at 35° Celsius. 2.5% (w/v) low fat milk powder was included in all reactions to reduce non-specific binding of DNA. Although the extent of hybridization is significant over a wide range of temperatures, the amount of hybridization increases with time. The hybrid can be melted from the collector by increasing the temperature of incubation with a Tm of approximately 50° C. The displacement reaction requires that the melting of this hybrid be done in the presence of sequences that bind to the same region of DNA as does the reporter but with a much greater linear extent of homology. Under these conditions, the reporter should be eluted from the collector at a lower temperature when the test sequence is present as compared with its absence. In order to test this, magnetic beads to which reporter had been hybridized were incubated in 10×SSC in the presence of the test sequence and the amount of reporter that was eluted with increasing temperature was recorded. The reporter DNA eluted from the. collector at temperatures that were significantly lower than those seen when no test DNA sequences were present. In order to confirm this phenomenon, three temperatures were examined in more detail and the incubation time increased to 19 hr. Even at 0° C., the test DNA displaces significant amounts of reporter DNA over a 19 hr incubation. At 25° C., displacement occurs even within 15 min. In these assays, following elution at the experimental temperatures, all samples were incubated at 90° C. to strip the remaining reporter. From the data it is clear that the displacement hybridization system can be used to test for the presence of sequences complementary to the collector molecule.

In order to test the efficiency of the Solid Phase Amplification (labelled microbeads) system to detect reporter sequences, assays were done to obtain an indication of the sensitivity of the technique. Streptavidin was coupled to Dynabeads using standard protocols. Biotin was coupled to 0.3 $\mu$ titanium oxide particles. A fixed amount of biotin-$TiO_2$ was mixed with known amounts of biotinylated reporter sequences and the mixture was added to 50 $\mu$g of the streptavidin-coated Dynabeads. After two hours incubation the beads were collected magnetically and the amount of $TiO_2$ per unit magnetic beads determined. Extrapolation from the data obtained indicates that the technique has a sensitivity of at least 1–5 pg DNA. It is likely that more detailed optimization of the amounts of streptavidin and biotin coupled to the dynabeads and $TiO_2$ respectively will increase this sensitivity. The simplicity of this technique and the system accuracy (machine analytical reproducibility of +/−2%) means that the Solid Phase Amplification approach offers significant advantages over alternative technologies.

SEQUENCE LISTING ( 1 ) GENERAL INFORMATION:

( i i i ) NUMBER OF SEQUENCES: 365

( 2 ) INFORMATION FOR SEQ ID NO:1:

( i ) SEQUENCE CHARACTERISTICS:
    ( A ) LENGTH: 17 base pairs
    ( B ) TYPE: Nucleic Acid
    ( C ) STRANDEDNESS: double
    ( D ) TOPOLOGY: linear ( i i ) MOLECULE TYPE: Genomic DNA
    ( A ) DESCRIPTION: c-myc gene (Accession #X00364, K01908, V00501) nucleotides 1047 to 1063

( i i i ) HYPOTHETICAL: No ( i v ) ANTI-SENSE: No ( v i ) ORIGINAL SOURCE:
    ( A ) ORGANISM: Homo sapiens ( x ) PUBLICATION INFORMATION:
    ( A ) AUTHORS: Gazin, C, Dupont, S, de Dinechin, D, Hampe, A, Masson, J M, Martin, P, Stehelin, D, Galibert, F.
    ( B ) TITLE: Nucleotide sequence of the human c-myc locus: provocative open reading frame within the first exon.
    ( C ) JOURNAL: EMBO Journal
    ( D ) VOLUME: 3
    ( F ) PAGES: 383-387
    ( G ) DATE: 1984
    ( A ) AUTHORS: Colby, W W, Chen, E Y, Smith, D H, Levinson, A D.
    ( B ) TITLE: Identification and nucleotide sequence of a human locus homologous to the v-myc oncogene of avian myelocytomatosis virus MC29
    ( C ) JOURNAL: Nature
    ( D ) VOLUME: 301
    ( F ) PAGES: 722-725
    ( G ) DATE: 1983
    ( A ) AUTHORS: Saito, H, Hayday, A C, Wiman, K G, Hayward, W S, Tonegawa, S.
    ( B ) TITLE: Activation of the c-myc gene by translocation: a model for translational control
    ( C ) JOURNAL: Proceedings of the National Academy of Sciences, USA
    ( D ) VOLUME: 80
    ( F ) PAGES: 7476-7480
    ( G ) DATE: 1983
    ( A ) AUTHORS: Gazin, C, Rigolet, M, Briand, J P, Van Regenmortel, M H V, Galibert, F.
    ( B ) TITLE: Immunochemical detection of proteins related to the human c-myc exon 1
    ( C ) JOURNAL: EMBO Journal
    ( D ) VOLUME: 5
    ( F ) PAGES: 2241-2250
    ( G ) DATE: 1986
    ( K ) RELEVANT RESIDUES IN SEQ ID NO: 1 :FROM 1 TO 17

( x i ) SEQUENCE DESCRIPTION: SEQ ID NO: 1 :

C T C C T C T C C T   C T T C T T T                   1 7

( 2 ) INFORMATION FOR SEQ ID NO:2:

( i ) SEQUENCE CHARACTERISTICS:
    ( A ) LENGTH: 17 bases
    ( B ) TYPE: Nucleic Acid
    ( C ) STRANDEDNESS: single stranded
    ( D ) TOPOLOGY: linear (ii) MOLECULE TYPE: other nucleic acid
   (A) DESCRIPTION: third strand derived from c-myc
      sequence region in Seq ID No 2

(iii) HYPOTHETICAL: Yes (iv) ANTI-SENSE: No (x) PUBLICATION INFORMATION:
   (K) RELEVANT RESIDUES IN SEQ ID NO: 2 :FROM 1 TO 17

(xi) SEQUENCE DESCRIPTION: SEQ ID NO: 2 :

TTTCTTCTCC TCTCCTC                                                         17

(2) INFORMATION FOR SEQ ID NO:3:

(i) SEQUENCE CHARACTERISTICS:
      (A) LENGTH: 16 base pairs
      (B) TYPE: Nucleic Acid
      (C) STRANDEDNESS: double
      (D) TOPOLOGY: linear (ii) MOLECULE TYPE: Genomic DNA
      (A) DESCRIPTION: c-myc gene (Accession #X00364,
         K01908, V00501) nucleotides 2055 to 2070

(iii) HYPOTHETICAL: No (iv) ANTI-SENSE: No (vi) ORIGINAL SOURCE:
      (A) ORGANISM: Homo sapiens (x) PUBLICATION INFORMATION:
      (A) AUTHORS: Gazin, C, Dupont, S, de Dinechin, D,
         Hampe, A, Masson, J M, Martin, P, Stehelin,
         D, Galibert, F.
      (B) TITLE: Nucleotide sequence of the
         human c-myc locus: provocative open reading
         frame within the first exon.
      (C) JOURNAL: EMBO Journal
      (D) VOLUME: 3
      (F) PAGES: 383-387
      (G) DATE: 1984
      (A) AUTHORS: Colby, W W, Chen, E Y, Smith, D H,
         Levinson, A D.
      (B) TITLE: Identification and nucleotide
         sequence of a human locus homologous to the v-
         myc oncogene of avian myelocytomatosis virus
         MC29
      (C) JOURNAL: Nature
      (D) VOLUME: 301
      (F) PAGES: 722-725
      (G) DATE: 1983
      (A) AUTHORS: Saito, H, Hayday, A C, Wiman, K G,
         Hayward, W S, Tonegawa, S.
      (B) TITLE: Activation of the c-myc gene
         by translocation: a model for translational
         control
      (C) JOURNAL: Proceedings of the National Academy of
         Sciences, USA
      (D) VOLUME: 80
      (F) PAGES: 7476-7480
      (G) DATE: 1983
      (A) AUTHORS: Gazin, C, Rigolet, M, Briand, J P, Van
         Regenmortel, M H V, Galibert, F.
      (B) TITLE: Immunochemical detection of
         proteins related to the human c-myc exon 1
      (C) JOURNAL: EMBO Journal
      (D) VOLUME: 5
      (F) PAGES: 2241-2250
      (G) DATE: 1986
      (K) RELEVANT RESIDUES IN SEQ ID NO: 3 :FROM 1 TO 16

(xi) SEQUENCE DESCRIPTION: SEQ ID NO: 3 :

AGAGAAAGGG AGAGGG                                                           16

( 2 ) INFORMATION FOR SEQ ID NO:4:

( i ) SEQUENCE CHARACTERISTICS:
        ( A ) LENGTH: 16 bases
        ( B ) TYPE: Nucleic Acid
        ( C ) STRANDEDNESS: single stranded
        ( D ) TOPOLOGY: linear ( i i ) MOLECULE TYPE: other nucleic acid
        ( A ) DESCRIPTION: third strand derived from c-myc
            sequence region in Seq ID No 3

( i i i ) HYPOTHETICAL: Yes ( i v ) ANTI-SENSE: No ( x ) PUBLICATION INFORMATION:
        ( K ) RELEVANT RESIDUES IN SEQ ID NO: 4 :FROM 1 TO 16

( x i ) SEQUENCE DESCRIPTION: SEQ ID NO: 4 :

TCTCTTTCCC TCTCCC              16

( 2 ) INFORMATION FOR SEQ ID NO:5:

( i ) SEQUENCE CHARACTERISTICS:
        ( A ) LENGTH: 15 base pairs
        ( B ) TYPE: Nucleic Acid
        ( C ) STRANDEDNESS: double
        ( D ) TOPOLOGY: linear ( i i ) MOLECULE TYPE: Genomic DNA
        ( A ) DESCRIPTION: c-myc gene (Accession #X00364,
            K01908, V00501) nucleotides 3546 to 3560

( i i i ) HYPOTHETICAL: No ( i v ) ANTI-SENSE: No ( v i ) ORIGINAL SOURCE:
        ( A ) ORGANISM: Homo sapiens ( x ) PUBLICATION INFORMATION:
        ( A ) AUTHORS: Gazin, C, Dupont, S, de Dinechin, D,
            Hampe, A, Masson, J M, Martin, P, Stehelin,
            D, Galibert, F.
        ( B ) TITLE: Nucleotide sequence of the
            human c-myc locus: provocative open reading
            frame within the first exon.
        ( C ) JOURNAL: EMBO Journal
        ( D ) VOLUME: 3
        ( F ) PAGES: 383-387
        ( G ) DATE: 1984
        ( A ) AUTHORS: Colby, W W, Chen, E Y, Smith, D H,
            Levinson, A D.
        ( B ) TITLE: Identification and nucleotide
            sequence of a human locus homologous to the v-
            myc oncogene of avian myelocytomatosis virus
            MC29
        ( C ) JOURNAL: Nature
        ( D ) VOLUME: 301
        ( F ) PAGES: 722-725
        ( G ) DATE: 1983
        ( A ) AUTHORS: Saito, H, Hayday, A C, Wiman, K G,
            Hayward, W S, Tonegawa, S.
        ( B ) TITLE: Activation of the c-myc gene
            by translocation: a model for translational
            control
        ( C ) JOURNAL: Proceedings of the National Academy of
            Sciences, USA
        ( D ) VOLUME: 80
        ( F ) PAGES: 7476-7480
        ( G ) DATE: 1983
        ( A ) AUTHORS: Gazin, C, Rigolet, M, Briand, J P, Van
            Regenmortel, M H V, Galibert, F.
        ( B ) TITLE: Immunochemical detection of
            proteins related to the human c-myc exon 1

(C) JOURNAL: EMBO Journal
(D) VOLUME: 5
(F) PAGES: 2241-2250
(G) DATE: 1986
(K) RELEVANT RESIDUES IN SEQ ID NO: 5 :FROM 1 TO 15

(xi) SEQUENCE DESCRIPTION: SEQ ID NO: 5 :

AGGGGAAAAG GGAGG 15

(2) INFORMATION FOR SEQ ID NO:6:

(i) SEQUENCE CHARACTERISTICS:
(A) LENGTH: 15 bases
(B) TYPE: Nucleic Acid
(C) STRANDEDNESS: single stranded
(D) TOPOLOGY: linear (ii) MOLECULE TYPE: other nucleic acid
(A) DESCRIPTION: third strand derived from c-myc
sequence region in Seq ID No 5

(iii) HYPOTHETICAL: Yes (iv) ANTI-SENSE: No (x) PUBLICATION INFORMATION:
(K) RELEVANT RESIDUES IN SEQ ID NO: 6 :FROM 1 TO 15

(xi) SEQUENCE DESCRIPTION: SEQ ID NO: 6 :

TCCCCTTTTC CCTCC 15

(2) INFORMATION FOR SEQ ID NO:7:

(i) SEQUENCE CHARACTERISTICS:
(A) LENGTH: 17 base pairs
(B) TYPE: Nucleic Acid
(C) STRANDEDNESS: double
(D) TOPOLOGY: linear (ii) MOLECULE TYPE: Genomic DNA
(A) DESCRIPTION: c-myc gene (Accession #X00364,
K01908, V00501) nucleotides 5101 to 5117

(iii) HYPOTHETICAL: No (iv) ANTI-SENSE: No (vi) ORIGINAL SOURCE:
(A) ORGANISM: Homo sapiens (x) PUBLICATION INFORMATION:
(A) AUTHORS: Gazin, C, Dupont, S, de Dinechin, D,
Hampe, A, Masson, J M, Martin, P, Stehelin,
D, Galibert, F.
(B) TITLE: Nucleotide sequence of the
human c-myc locus: provocative open reading
frame within the first exon.
(C) JOURNAL: EMBO Journal
(D) VOLUME: 3
(F) PAGES: 383-387
(G) DATE: 1984
(A) AUTHORS: Colby, W W, Chen, E Y, Smith, D H,
Levinson, A D.
(B) TITLE: Identification and nucleotide
sequence of a human locus homologous to the v-
myc oncogene of avian myelocytomatosis virus
MC29
(C) JOURNAL: Nature
(D) VOLUME: 301
(F) PAGES: 722-725
(G) DATE: 1983
(A) AUTHORS: Saito, H, Hayday, A C, Wiman, K G,
Hayward, W S, Tonegawa, S.
(B) TITLE: Activation of the c-myc gene
by translocation: a model for translational
control (C) JOURNAL: Proceedings of the National Academy of
    Sciences, USA
(D) VOLUME: 80
(F) PAGES: 7476-7480
(G) DATE: 1983
(A) AUTHORS: Gazin, C, Rigolet, M, Briand, J P, Van
    Regenmortel, M H V, Galibert, F.
(B) TITLE: Immunochemical detection of
    proteins related to the human c-myc exon 1
(C) JOURNAL: EMBO Journal
(D) VOLUME: 5
(F) PAGES: 2241-2250
(G) DATE: 1986
(K) RELEVANT RESIDUES IN SEQ ID NO: 7 :FROM 1 TO 17

(x i) SEQUENCE DESCRIPTION: SEQ ID NO: 7 :

TCTTCCCCTA CCCTCTC                                                          17

(2) INFORMATION FOR SEQ ID NO:8:

(i) SEQUENCE CHARACTERISTICS:
    (A) LENGTH: 17 bases
    (B) TYPE: Nucleic Acid
    (C) STRANDEDNESS: single stranded
    (D) TOPOLOGY: linear (i i) MOLECULE TYPE: other nucleic acid
    (A) DESCRIPTION: third strand derived from c-myc
        sequence region in Seq ID No 7

(i i i) HYPOTHETICAL: Yes (i v) ANTI-SENSE: No (x) PUBLICATION INFORMATION:
    (K) RELEVANT RESIDUES IN SEQ ID NO: 8 :FROM 1 TO 17

(x i) SEQUENCE DESCRIPTION: SEQ ID NO: 8 :

CTCTCCCGTC CCCTTCT                                                          17

(2) INFORMATION FOR SEQ ID NO:9:

(i) SEQUENCE CHARACTERISTICS:
    (A) LENGTH: 12 base pairs
    (B) TYPE: Nucleic Acid
    (C) STRANDEDNESS: double
    (D) TOPOLOGY: linear (i i) MOLECULE TYPE: Genomic DNA
    (A) DESCRIPTION: c-myc gene (Accession #X00364,
        K01908, V00501) nucleotides 6650 to 6661

(i i i) HYPOTHETICAL: No (i v) ANTI-SENSE: No (v i) ORIGINAL SOURCE:
    (A) ORGANISM: Homo sapiens (x) PUBLICATION INFORMATION:
    (A) AUTHORS: Gazin, C, Dupont, S, de Dinechin, D,
        Hampe, A, Masson, J M, Martin, P, Stehelin,
        D, Galibert, F.
    (B) TITLE: Nucleotide sequence of the
        human c-myc locus: provocative open reading
        frame within the first exon.
    (C) JOURNAL: EMBO Journal
    (D) VOLUME: 3
    (F) PAGES: 383-387
    (G) DATE: 1984
    (A) AUTHORS: Colby, W W, Chen, E Y, Smith, D H,
        Levinson, A D.
    (B) TITLE: Identification and nucleotide
        sequence of a human locus homologous to the v-
        myc oncogene of avian myelocytomatosis virus
        MC29

(C) JOURNAL: Nature
                    (D) VOLUME: 301
                    (F) PAGES: 722-725
                    (G) DATE: 1983
                    (A) AUTHORS: Saito, H, Hayday, A C, Wiman, K G,
                            Hayward, W S, Tonegawa, S.
                    (B) TITLE: Activation of the c-myc gene
                            by translocation: a model for translational
                            control
                    (C) JOURNAL: Proceedings of the National Academy of
                            Sciences, USA
                    (D) VOLUME: 80
                    (F) PAGES: 7476-7480
                    (G) DATE: 1983
                    (A) AUTHORS: Gazin, C, Rigolet, M, Briand, J P, Van
                            Regenmortel, M H V, Galibert, F.
                    (B) TITLE: Immunochemical detection of
                            proteins related to the human c-myc exon 1
                    (C) JOURNAL: EMBO Journal
                    (D) VOLUME: 5
                    (F) PAGES: 2241-2250
                    (G) DATE: 1986
                    (K) RELEVANT RESIDUES IN SEQ ID NO: 9 :FROM 1 TO 12

(x i) SEQUENCE DESCRIPTION: SEQ ID NO: 9 :

AAAGAGGAGG AA                                                                                               1 2

(2) INFORMATION FOR SEQ ID NO:10:

(i) SEQUENCE CHARACTERISTICS:
                    (A) LENGTH: 12 bases
                    (B) TYPE: Nucleic Acid
                    (C) STRANDEDNESS: single stranded
                    (D) TOPOLOGY: linear (i i) MOLECULE TYPE: other nucleic acid
                    (A) DESCRIPTION: third strand derived from c-myc
                            sequence region in Seq ID No 9

(i i i) HYPOTHETICAL: Yes (i v) ANTI-SENSE: No (x) PUBLICATION INFORMATION:
                    (K) RELEVANT RESIDUES IN SEQ ID NO: 10 :FROM 1 TO 12

(x i) SEQUENCE DESCRIPTION: SEQ ID NO: 10 :

TTTCTCCTCC TT                                                                                               1 2

(2) INFORMATION FOR SEQ ID NO:11:

(i) SEQUENCE CHARACTERISTICS:
                    (A) LENGTH: 18 base pairs
                    (B) TYPE: Nucleic Acid
                    (C) STRANDEDNESS: double
                    (D) TOPOLOGY: linear (i i) MOLECULE TYPE: Genomic DNA
                    (A) DESCRIPTION: c-myc gene (Accession #X00364,
                            K01908, V00501) nucleotides 6663 to 6680

(i i i) HYPOTHETICAL: No (i v) ANTI-SENSE: No (v i) ORIGINAL SOURCE:
                    (A) ORGANISM: Homo sapiens (x) PUBLICATION INFORMATION:
                    (A) AUTHORS: Gazin, C, Dupont, S, de Dinechin, D,
                            Hampe, A, Masson, J M, Martin, P, Stehelin,
                            D, Galibert, F.
                    (B) TITLE: Nucleotide sequence of the
                            human c-myc locus: provocative open reading
                            frame within the first exon.
                    (C) JOURNAL: EMBO Journal (D) VOLUME: 3
              (F) PAGES: 383-387
              (G) DATE: 1984
              (A) AUTHORS: Colby, W W, Chen, E Y, Smith, D H,
                    Levinson, A D.
              (B) TITLE: Identification and nucleotide
                    sequence of a human locus homologous to the v-
                    myc oncogene of avian myelocytomatosis virus
                    MC29
              (C) JOURNAL: Nature
              (D) VOLUME: 301
              (F) PAGES: 722-725
              (G) DATE: 1983
              (A) AUTHORS: Saito, H, Hayday, A C, Wiman, K G,
                    Hayward, W S, Tonegawa, S.
              (B) TITLE: Activation of the c-myc gene
                    by translocation: a model for translational
                    control
              (C) JOURNAL: Proceedings of the National Academy of
                    Sciences, USA
              (D) VOLUME: 80
              (F) PAGES: 7476-7480
              (G) DATE: 1983
              (A) AUTHORS: Gazin, C, Rigolet, M, Briand, J P, Van
                    Regenmortel, M H V, Galibert, F.
              (B) TITLE: Immunochemical detection of
                    proteins related to the human c-myc exon 1
              (C) JOURNAL: EMBO Journal
              (D) VOLUME: 5
              (F) PAGES: 2241-2250
              (G) DATE: 1986
              (K) RELEVANT RESIDUES IN SEQ ID NO: 11 :FROM 1 TO 18

(xi) SEQUENCE DESCRIPTION: SEQ ID NO: 11 :

AAGAAGATGA GGAAGAAA                                                                         18

(2) INFORMATION FOR SEQ ID NO:12:

(i) SEQUENCE CHARACTERISTICS:
              (A) LENGTH: 18 bases
              (B) TYPE: Nucleic Acid
              (C) STRANDEDNESS: single stranded
              (D) TOPOLOGY: linear (ii) MOLECULE TYPE: other nucleic acid
              (A) DESCRIPTION: third strand derived from c-myc
                    sequence region in Seq ID No 11

(iii) HYPOTHETICAL: Yes (iv) ANTI-SENSE: No (x) PUBLICATION INFORMATION:
              (K) RELEVANT RESIDUES IN SEQ ID NO: 12 :FROM 1 TO 18

(xi) SEQUENCE DESCRIPTION: SEQ ID NO: 12 :

TTCTTCTGCT CCTTCTTT                                                                         18

(2) INFORMATION FOR SEQ ID NO:13:

(i) SEQUENCE CHARACTERISTICS:
              (A) LENGTH: 27 base pairs
              (B) TYPE: Nucleic Acid
              (C) STRANDEDNESS: double
              (D) TOPOLOGY: linear (ii) MOLECULE TYPE: Genomic DNA
              (A) DESCRIPTION: n-myc gene (Accession #Y00664)
                    nucleotides 1746 to 1772

(iii) HYPOTHETICAL: No (iv) ANTI-SENSE: No (vi) ORIGINAL SOURCE:
              (A) ORGANISM: Homo sapiens (x) PUBLICATION INFORMATION:
    (A) AUTHORS: Ibson, J M, Rabbitts, P H.
    (B) TITLE: Sequence of a germ-line N- myc
        gene and amplification as a mechanism of
        activation
    (C) JOURNAL: Oncogene
    (D) VOLUME: 2
    (F) PAGES: 399-402
    (G) DATE: 1988
    (K) RELEVANT RESIDUES IN SEQ ID NO: 13 :FROM 1 TO 27

(xi) SEQUENCE DESCRIPTION: SEQ ID NO: 13:

CTTTCCTCTC CTTTCTCCCT CCCCCTT 27

(2) INFORMATION FOR SEQ ID NO:14:

(i) SEQUENCE CHARACTERISTICS:
    (A) LENGTH: 27 bases
    (B) TYPE: Nucleic Acid
    (C) STRANDEDNESS: single stranded
    (D) TOPOLOGY: linear (ii) MOLECULE TYPE: other nucleic acid
    (A) DESCRIPTION: third strand derived from n-myc
        sequence region in Seq ID No 13

(iii) HYPOTHETICAL: Yes (iv) ANTI-SENSE: No (x) PUBLICATION INFORMATION:
    (K) RELEVANT RESIDUES IN SEQ ID NO: 14 :FROM 1 TO 27

(xi) SEQUENCE DESCRIPTION: SEQ ID NO: 14:

TTCCCCCTCC CTCTTTCCTC TCCTTTC 27

(2) INFORMATION FOR SEQ ID NO:15:

(i) SEQUENCE CHARACTERISTICS:
    (A) LENGTH: 15 base pairs
    (B) TYPE: Nucleic Acid
    (C) STRANDEDNESS: double
    (D) TOPOLOGY: linear (ii) MOLECULE TYPE: Genomic DNA
    (A) DESCRIPTION: n-myc gene (Accession #Y00664)
        nucleotides 1786 to 1800

(iii) HYPOTHETICAL: No (iv) ANTI-SENSE: No (vi) ORIGINAL SOURCE:
    (A) ORGANISM: Homo sapiens (x) PUBLICATION INFORMATION:
    (A) AUTHORS: Ibson, J M, Rabbitts, P H.
    (B) TITLE: Sequence of a germ-line N- myc
        gene and amplification as a mechanism of
        activation
    (C) JOURNAL: Oncogene
    (D) VOLUME: 2
    (F) PAGES: 399-402
    (G) DATE: 1988
    (K) RELEVANT RESIDUES IN SEQ ID NO: 15 :FROM 1 TO 15

(xi) SEQUENCE DESCRIPTION: SEQ ID NO: 15:

CCCCCTTCTC TCCCC 15

(2) INFORMATION FOR SEQ ID NO:16:

(i) SEQUENCE CHARACTERISTICS:
    (A) LENGTH: 15 bases (B) TYPE: Nucleic Acid
(C) STRANDEDNESS: single stranded
(D) TOPOLOGY: linear (i i) MOLECULE TYPE: other nucleic acid
(A) DESCRIPTION: third strand derived from n-myc
sequence region in Seq ID No 15

(i i i) HYPOTHETICAL: Yes (i v) ANTI-SENSE: No (x) PUBLICATION INFORMATION:
(K) RELEVANT RESIDUES IN SEQ ID NO: 16 :FROM 1 TO 15

(x i) SEQUENCE DESCRIPTION: SEQ ID NO: 16 :

CCCCTCTCTT CCCCC  15

(2) INFORMATION FOR SEQ ID NO:17:

(i) SEQUENCE CHARACTERISTICS:
(A) LENGTH: 20 base pairs
(B) TYPE: Nucleic Acid
(C) STRANDEDNESS: double
(D) TOPOLOGY: linear (i i) MOLECULE TYPE: Genomic DNA
(A) DESCRIPTION: n-myc gene (Accession #Y00664)
nucleotides 2407 to 2426

(i i i) HYPOTHETICAL: No (i v) ANTI-SENSE: No (v i) ORIGINAL SOURCE:
(A) ORGANISM: Homo sapiens (x) PUBLICATION INFORMATION:
(A) AUTHORS: Ibson, J M, Rabbitts, P H.
(B) TITLE: Sequence of a germ-line N- myc
gene and amplification as a mechanism of
activation
(C) JOURNAL: Oncogene
(D) VOLUME: 2
(F) PAGES: 399-402
(G) DATE: 1988
(K) RELEVANT RESIDUES IN SEQ ID NO: 17 :FROM 1 TO 20

(x i) SEQUENCE DESCRIPTION: SEQ ID NO: 17:

GGAGGAAGAA GAGGGGGGGA  20

(2) INFORMATION FOR SEQ ID NO:18:

(i) SEQUENCE CHARACTERISTICS:
(A) LENGTH: 20 bases
(B) TYPE: Nucleic Acid
(C) STRANDEDNESS: single stranded
(D) TOPOLOGY: linear (i i) MOLECULE TYPE: other nucleic acid
(A) DESCRIPTION: third strand derived from n-myc
sequence region in Seq ID No 17

(i i i) HYPOTHETICAL: Yes (i v) ANTI-SENSE: No (x) PUBLICATION INFORMATION:
(K) RELEVANT RESIDUES IN SEQ ID NO: 18 :FROM 1 TO 20

(x i) SEQUENCE DESCRIPTION: SEQ ID NO: 18 :

CCTCCTTCTT CTCCCCCCCT  20

(2) INFORMATION FOR SEQ ID NO:19:

( i ) SEQUENCE CHARACTERISTICS:
    ( A ) LENGTH: 35 base pairs
    ( B ) TYPE: Nucleic Acid
    ( C ) STRANDEDNESS: double
    ( D ) TOPOLOGY: linear ( i i ) MOLECULE TYPE: Genomic DNA
    ( A ) DESCRIPTION: n-myc gene (Accession #Y00664)
    nucleotides 4691 to 4725

( i i i ) HYPOTHETICAL: No ( i v ) ANTI-SENSE: No ( v i ) ORIGINAL SOURCE:
    ( A ) ORGANISM: Homo sapiens ( x ) PUBLICATION INFORMATION:
    ( A ) AUTHORS: Ibson, J M, Rabbitts, P H.
    ( B ) TITLE: Sequence of a germ-line N- myc
    gene and amplification as a mechanism of
    activation
    ( C ) JOURNAL: Oncogene
    ( D ) VOLUME: 2
    ( F ) PAGES: 399-402
    ( G ) DATE: 1988
    ( K ) RELEVANT RESIDUES IN SEQ ID NO: 19 :FROM 1 TO 35

( x i ) SEQUENCE DESCRIPTION: SEQ ID NO: 19:

TTTTCTATTC TTTTCTTTT TTTTTTTTT TTTTC    35

( 2 ) INFORMATION FOR SEQ ID NO:20:

( i ) SEQUENCE CHARACTERISTICS:
    ( A ) LENGTH: 35 bases
    ( B ) TYPE: Nucleic Acid
    ( C ) STRANDEDNESS: single stranded
    ( D ) TOPOLOGY: linear ( i i ) MOLECULE TYPE: other nucleic acid
    ( A ) DESCRIPTION: third strand derived from n-myc
    sequence region in Seq ID No 19

( i i i ) HYPOTHETICAL: Yes ( i v ) ANTI-SENSE: No ( x ) PUBLICATION INFORMATION:
    ( K ) RELEVANT RESIDUES IN SEQ ID NO: 20 :FROM 1 TO 35

( x i ) SEQUENCE DESCRIPTION: SEQ ID NO: 20 :

CTTTTTTTT TTTTTTTTC TTTTCTTGT CTTTT    35

( 2 ) INFORMATION FOR SEQ ID NO:21:

( i ) SEQUENCE CHARACTERISTICS:
    ( A ) LENGTH: 18 base pairs
    ( B ) TYPE: Nucleic Acid
    ( C ) STRANDEDNESS: double
    ( D ) TOPOLOGY: linear ( i i ) MOLECULE TYPE: Genomic DNA
    ( A ) DESCRIPTION: n-myc gene (Accession #Y00664)
    nucleotides 5619 to 5636

( i i i ) HYPOTHETICAL: No ( i v ) ANTI-SENSE: No ( v i ) ORIGINAL SOURCE:
    ( A ) ORGANISM: Homo sapiens ( x ) PUBLICATION INFORMATION:
    ( A ) AUTHORS: Ibson, J M, Rabbitts, P H.
    ( B ) TITLE: Sequence of a germ-line N- myc gene and amplification as a mechanism of
activation
(C) JOURNAL: Oncogene
(D) VOLUME: 2
(F) PAGES: 399-402
(G) DATE: 1988
(K) RELEVANT RESIDUES IN SEQ ID NO: 21 :FROM 1 TO 18

(xi) SEQUENCE DESCRIPTION: SEQ ID NO: 21:

GAGGAGAGAG GGGAAGAA 18

(2) INFORMATION FOR SEQ ID NO:22:

(i) SEQUENCE CHARACTERISTICS:
(A) LENGTH: 18 bases
(B) TYPE: Nucleic Acid
(C) STRANDEDNESS: single stranded
(D) TOPOLOGY: linear (ii) MOLECULE TYPE: other nucleic acid
(A) DESCRIPTION: third strand derived from n-myc
sequence region in Seq ID No 21

(iii) HYPOTHETICAL: Yes (iv) ANTI-SENSE: No (x) PUBLICATION INFORMATION:
(K) RELEVANT RESIDUES IN SEQ ID NO: 22 :FROM 1 TO 18

(xi) SEQUENCE DESCRIPTION: SEQ ID NO: 22 :

CTCCTCTCTC CCCTTCTT 18

(2) INFORMATION FOR SEQ ID NO:23:

(i) SEQUENCE CHARACTERISTICS:
(A) LENGTH: 12 base pairs
(B) TYPE: Nucleic Acid
(C) STRANDEDNESS: double
(D) TOPOLOGY: linear (ii) MOLECULE TYPE: Genomic DNA
(A) DESCRIPTION: n-myc gene (Accession #Y00664)
nucleotides 7008 to 7019

(iii) HYPOTHETICAL: No (iv) ANTI-SENSE: No (vi) ORIGINAL SOURCE:
(A) ORGANISM: Homo sapiens (x) PUBLICATION INFORMATION:
(A) AUTHORS: Ibson, J M, Rabbitts, P H.
(B) TITLE: Sequence of a germ-line N- myc
gene and amplification as a mechanism of
activation
(C) JOURNAL: Oncogene
(D) VOLUME: 2
(F) PAGES: 399-402
(G) DATE: 1988
(K) RELEVANT RESIDUES IN SEQ ID NO: 23 :FROM 1 TO 12

(xi) SEQUENCE DESCRIPTION: SEQ ID NO: 23:

CCCCCTCTCC CT 12

(2) INFORMATION FOR SEQ ID NO:24:

(i) SEQUENCE CHARACTERISTICS:
(A) LENGTH: 12 bases
(B) TYPE: Nucleic Acid
(C) STRANDEDNESS: single stranded
(D) TOPOLOGY: linear (ii) MOLECULE TYPE: other nucleic acid
    (A) DESCRIPTION: third strand derived from n-myc
        sequence region in Seq ID No 23

(iii) HYPOTHETICAL: Yes (iv) ANTI-SENSE: No (x) PUBLICATION INFORMATION:
    (K) RELEVANT RESIDUES IN SEQ ID NO: 24 :FROM 1 TO 12

(xi) SEQUENCE DESCRIPTION: SEQ ID NO: 24 :

T C C C T C T C C C  C C                                                                            1 2

(2) INFORMATION FOR SEQ ID NO:25:

(i) SEQUENCE CHARACTERISTICS:
        (A) LENGTH: 11 base pairs
        (B) TYPE: Nucleic Acid
        (C) STRANDEDNESS: double stranded
        (D) TOPOLOGY: linear (ii) MOLECULE TYPE: Genomic DNA
        (A) DESCRIPTION: dystrophin gene (Accession #M18533,
            M17154, M18026) nucleotides 1074 to 1084

(iii) HYPOTHETICAL: No (iv) ANTI-SENSE: No (vi) ORIGINAL SOURCE:
        (A) ORGANISM: Homo sapiens (vii) POSITION IN GENOME:
        (A) CHROMOSOME/SEGMENT: X- chromosome
        (B) MAP POSITION: Xp21.3-p21.1

(x) PUBLICATION INFORMATION:
        (A) AUTHORS: Koenig, M, Hoffman, E P, Bertelson, C J,
            Monaco, A P, Feener, C, Kunkel, L M.
        (B) TITLE: Complete cloning of the
            Duchenne muscular dystrophy (DMD) cDNA and
            preliminary genomic organization of the DMD
            gene in normal and affected individuals
        (C) JOURNAL: Cell
        (D) VOLUME: 50
        (F) PAGES: 509-517
        (G) DATE: 1987
        (A) AUTHORS: Hoffman, E P, Monaco, A P, Feener, C C,
            Kunkel, L M.
        (B) TITLE: Conservation of the Duchenne
            muscular dystrophy gene in mice and humans
        (C) JOURNAL: Science
        (D) VOLUME: 238
        (F) PAGES: 347-350
        (G) DATE: 1987
        (A) AUTHORS: Koenig, M, Monaco, A P, Kunkel, L M.
        (B) TITLE: The complete sequence of
            dystrophin predicts a rod-shaped cytoskeletal
            protein
        (C) JOURNAL: Cell
        (D) VOLUME: 53
        (F) PAGES: 219-228
        (G) DATE: 1988
        (K) RELEVANT RESIDUES IN SEQ ID NO: 25 :FROM 1 TO 11

(xi) SEQUENCE DESCRIPTION: SEQ ID NO: 25:

C T T C T T C C C C  T                                                                              1 1

(2) INFORMATION FOR SEQ ID NO:26:

(i) SEQUENCE CHARACTERISTICS:
        (A) LENGTH: 11 bases
        (B) TYPE: Nucleic Acid
        (C) STRANDEDNESS: single stranded
        (D) TOPOLOGY: linear (i i) MOLECULE TYPE: other nucleic acid
    (A) DESCRIPTION: third strand derived from dystrophin
        sequence region in Seq ID No 25

(i i i) HYPOTHETICAL: Yes (i v) ANTI-SENSE: No (x) PUBLICATION INFORMATION:
    (K) RELEVANT RESIDUES IN SEQ ID NO: 26 :FROM 1 TO 11

(x i) SEQUENCE DESCRIPTION: SEQ ID NO: 26 :

TCCCCTTCTT C                                                                11

(2) INFORMATION FOR SEQ ID NO:27:

(i) SEQUENCE CHARACTERISTICS:
    (A) LENGTH: 19 base pairs
    (B) TYPE: Nucleic Acid
    (C) STRANDEDNESS: double stranded
    (D) TOPOLOGY: linear (i i) MOLECULE TYPE: Genomic DNA
    (A) DESCRIPTION: dystrophin gene (Accession #M18533,
        M17154, M18026) nucleotides 1621 to 1639

(i i i) HYPOTHETICAL: No (i v) ANTI-SENSE: No (v i) ORIGINAL SOURCE:
    (A) ORGANISM: Homo sapiens (v i i) POSITION IN GENOME:
    (A) CHROMOSOME/SEGMENT: X- chromosome
    (B) MAP POSITION: Xp21.3-p21.1

(x) PUBLICATION INFORMATION:
    (A) AUTHORS: Koenig, M, Hoffman, E P, Bertelson, C J,
        Monaco, A P, Feener, C, Kunkel, L M.
    (B) TITLE: Complete cloning of the
        Duchenne muscular dystrophy (DMD) cDNA and
        preliminary genomic organization of the DMD
        gene in normal and affected individuals
    (C) JOURNAL: Cell
    (D) VOLUME: 50
    (F) PAGES: 509-517
    (G) DATE: 1987
    (A) AUTHORS: Hoffman, E P, Monaco, A P, Feener, C C,
        Kunkel, L M.
    (B) TITLE: Conservation of the Duchenne
        muscular dystrophy gene in mice and humans
    (C) JOURNAL: Science
    (D) VOLUME: 238
    (F) PAGES: 347-350
    (G) DATE: 1987
    (A) AUTHORS: Koenig, M, Monaco, A P, Kunkel, L M.
    (B) TITLE: The complete sequence of
        dystrophin predicts a rod-shaped cytoskeletal
        protein
    (C) JOURNAL: Cell
    (D) VOLUME: 53
    (F) PAGES: 219-228
    (G) DATE: 1988
    (K) RELEVANT RESIDUES IN SEQ ID NO: 27 :FROM 1 TO 19

(x i) SEQUENCE DESCRIPTION: SEQ ID NO: 27:

AAGGAAAATG GAGGAAGAG                                                        19

(2) INFORMATION FOR SEQ ID NO:28:

(i) SEQUENCE CHARACTERISTICS:
    (A) LENGTH: 19bases
    (B) TYPE: Nucleic Acid
    (C) STRANDEDNESS: single stranded (D) TOPOLOGY: linear (ii) MOLECULE TYPE: other nucleic acid
    (A) DESCRIPTION: third strand derived from dystrophin
        sequence region in Seq ID No 27

(iii) HYPOTHETICAL: Yes (iv) ANTI-SENSE: No (x) PUBLICATION INFORMATION:
    (K) RELEVANT RESIDUES IN SEQ ID NO: 28:FROM 1 TO 19

(xi) SEQUENCE DESCRIPTION: SEQ ID NO: 28:

TTCCTTTTGC CTCCTTCTC                          19

(2) INFORMATION FOR SEQ ID NO:29:

(i) SEQUENCE CHARACTERISTICS:
    (A) LENGTH: 16 base pairs
    (B) TYPE: Nucleic Acid
    (C) STRANDEDNESS: double stranded
    (D) TOPOLOGY: linear (ii) MOLECULE TYPE: Genomic DNA
    (A) DESCRIPTION: dystrophin gene (Accession #M18533,
        M17154, M18026) nucleotides 3800 to 3815

(iii) HYPOTHETICAL: No (iv) ANTI-SENSE: No (vi) ORIGINAL SOURCE:
    (A) ORGANISM: Homo sapiens (vii) POSITION IN GENOME:
    (A) CHROMOSOME/SEGMENT: X- chromosome
    (B) MAP POSITION: Xp21.3-p21.1

(x) PUBLICATION INFORMATION:
    (A) AUTHORS: Koenig, M, Hoffman, E P, Bertelson, C J,
        Monaco, A P, Feener, C, Kunkel, L M.
    (B) TITLE: Complete cloning of the
        Duchenne muscular dystrophy (DMD) cDNA and
        preliminary genomic organization of the DMD
        gene in normal and affected individuals
    (C) JOURNAL: Cell
    (D) VOLUME: 50
    (F) PAGES: 509-517
    (G) DATE: 1987
    (A) AUTHORS: Hoffman, E P, Monaco, A P, Feener, C C,
        Kunkel, L M.
    (B) TITLE: Conservation of the Duchenne
        muscular dystrophy gene in mice and humans
    (C) JOURNAL: Science
    (D) VOLUME: 238
    (F) PAGES: 347-350
    (G) DATE: 1987
    (A) AUTHORS: Koenig, M, Monaco, A P, Kunkel, L M.
    (B) TITLE: The complete sequence of
        dystrophin predicts a rod-shaped cytoskeletal
        protein
    (C) JOURNAL: Cell
    (D) VOLUME: 53
    (F) PAGES: 219-228
    (G) DATE: 1988
    (K) RELEVANT RESIDUES IN SEQ ID NO: 29 :FROM 1 TO 16

(xi) SEQUENCE DESCRIPTION: SEQ ID NO: 29:

GAAGAGATGA AGAGAG                             16

(2) INFORMATION FOR SEQ ID NO:30:

(i) SEQUENCE CHARACTERISTICS:
    (A) LENGTH: 16 bases
    (B) TYPE: Nucleic Acid (C) STRANDEDNESS: single stranded
        (D) TOPOLOGY: linear (ii) MOLECULE TYPE: other nucleic acid
        (A) DESCRIPTION: third strand derived from dystrophin
            sequence region in Seq ID No 29

(iii) HYPOTHETICAL: Yes (iv) ANTI-SENSE: No (x) PUBLICATION INFORMATION:
        (K) RELEVANT RESIDUES IN SEQ ID NO: 30 :FROM 1 TO 16

(xi) SEQUENCE DESCRIPTION: SEQ ID NO: 30 :

CTTCTCTGCT TCTCTC                                                                                       16

(2) INFORMATION FOR SEQ ID NO:31:

(i) SEQUENCE CHARACTERISTICS:
        (A) LENGTH: 16 base pairs
        (B) TYPE: Nucleic Acid
        (C) STRANDEDNESS: double stranded
        (D) TOPOLOGY: linear (ii) MOLECULE TYPE: Genomic DNA
        (A) DESCRIPTION: dystrophin gene (Accession #M18533,
            M17154, M18026) nucleotides 4480 to 4495

(iii) HYPOTHETICAL: No (iv) ANTI-SENSE: No (vi) ORIGINAL SOURCE:
        (A) ORGANISM: Homo sapiens (vii) POSITION IN GENOME:
        (A) CHROMOSOME/SEGMENT: X- chromosome
        (B) MAP POSITION: Xp21.3-p21.1

(x) PUBLICATION INFORMATION:
        (A) AUTHORS: Koenig, M, Hoffman, E P, Bertelson, C J,
            Monaco, A P, Feener, C, Kunkel, L M.
        (B) TITLE: Complete cloning of the
            Duchenne muscular dystrophy (DMD) cDNA and
            preliminary genomic organization of the DMD
            gene in normal and affected individuals
        (C) JOURNAL: Cell
        (D) VOLUME: 50
        (F) PAGES: 509-517
        (G) DATE: 1987
        (A) AUTHORS: Hoffman, E P, Monaco, A P, Feener, C C,
            Kunkel, L M.
        (B) TITLE: Conservation of the Duchenne
            muscular dystrophy gene in mice and humans
        (C) JOURNAL: Science
        (D) VOLUME: 238
        (F) PAGES: 347-350
        (G) DATE: 1987
        (A) AUTHORS: Koenig, M, Monaco, A P, Kunkel, L M.
        (B) TITLE: The complete sequence of
            dystrophin predicts a rod-shaped cytoskeletal
            protein
        (C) JOURNAL: Cell
        (D) VOLUME: 53
        (F) PAGES: 219-228
        (G) DATE: 1988
        (K) RELEVANT RESIDUES IN SEQ ID NO: 31 :FROM 1 TO 16

(xi) SEQUENCE DESCRIPTION: SEQ ID NO: 31:

AGAAGAAATG AAGAAA                                                                                       16

(2) INFORMATION FOR SEQ ID NO:32:

(i) SEQUENCE CHARACTERISTICS:
        (A) LENGTH: 16 bases ( B ) TYPE: Nucleic Acid
                    ( C ) STRANDEDNESS: single stranded
                    ( D ) TOPOLOGY: linear ( i i ) MOLECULE TYPE: other nucleic acid
                    ( A ) DESCRIPTION: third strand derived from dystrophin
                            sequence region in Seq ID No 31

( i i i ) HYPOTHETICAL: Yes ( i v ) ANTI-SENSE: No ( x ) PUBLICATION INFORMATION:
                    ( K ) RELEVANT RESIDUES IN SEQ ID NO: 32 :FROM 1 TO 16

( x i ) SEQUENCE DESCRIPTION: SEQ ID NO: 32 :

TCTTCTTTGC TTCTTT                                                                                               1 6

( 2 ) INFORMATION FOR SEQ ID NO:33:

( i ) SEQUENCE CHARACTERISTICS:
                    ( A ) LENGTH: 25 base pairs
                    ( B ) TYPE: Nucleic Acid
                    ( C ) STRANDEDNESS: double stranded
                    ( D ) TOPOLOGY: linear ( i i ) MOLECULE TYPE: Genomic DNA
                    ( A ) DESCRIPTION: dystrophin gene (Accession #M18533,
                            M17154, M18026) nucleotides 5729 to 5753

( i i i ) HYPOTHETICAL: No ( i v ) ANTI-SENSE: No ( v i ) ORIGINAL SOURCE:
                    ( A ) ORGANISM: Homo sapiens ( v i i ) POSITION IN GENOME:
                    ( A ) CHROMOSOME/SEGMENT: X- chromosome
                    ( B ) MAP POSITION: Xp21.3-p21.1

( x ) PUBLICATION INFORMATION:
                    ( A ) AUTHORS: Koenig, M, Hoffman, E P, Bertelson, C J,
                            Monaco, A P, Feener, C, Kunkel, L M.
                    ( B ) TITLE: Complete cloning of the
                            Duchenne muscular dystrophy (DMD) cDNA and
                            preliminary genomic organization of the DMD
                            gene in normal and affected individuals
                    ( C ) JOURNAL: Cell
                    ( D ) VOLUME: 50
                    ( F ) PAGES: 509-517
                    ( G ) DATE: 1987
                    ( A ) AUTHORS: Hoffman, E P, Monaco, A P, Feener, C C,
                            Kunkel, L M.
                    ( B ) TITLE: Conservation of the Duchenne
                            muscular dystrophy gene in mice and humans
                    ( C ) JOURNAL: Science
                    ( D ) VOLUME: 238
                    ( F ) PAGES: 347-350
                    ( G ) DATE: 1987
                    ( A ) AUTHORS: Koenig, M, Monaco, A P, Kunkel, L M.
                    ( B ) TITLE: The complete sequence of
                            dystrophin predicts a rod-shaped cytoskeletal
                            protein
                    ( C ) JOURNAL: Cell
                    ( D ) VOLUME: 53
                    ( F ) PAGES: 219-228
                    ( G ) DATE: 1988
                    ( K ) RELEVANT RESIDUES IN SEQ ID NO: 33 :FROM 1 TO 25

( x i ) SEQUENCE DESCRIPTION: SEQ ID NO: 33:

GAGAGAAAGA GAGAGGAAAT AAAGA                                                                                     2 5

( 2 ) INFORMATION FOR SEQ ID NO:34:

( i ) SEQUENCE CHARACTERISTICS:

(A) LENGTH: 25 bases
(B) TYPE: Nucleic Acid
(C) STRANDEDNESS: single stranded
(D) TOPOLOGY: linear (i i) MOLECULE TYPE: other nucleic acid
(A) DESCRIPTION: third strand derived from dystrophin sequence region in Seq ID No 33

(i i i) HYPOTHETICAL: Yes (i v) ANTI-SENSE: No (x) PUBLICATION INFORMATION:
(K) RELEVANT RESIDUES IN SEQ ID NO: 34 :FROM 1 TO 25

(x i) SEQUENCE DESCRIPTION: SEQ ID NO: 34 :

CTCTCTTTCT CTCTCCTTTG TTTCT                                    25

(2) INFORMATION FOR SEQ ID NO:35:

(i) SEQUENCE CHARACTERISTICS:
(A) LENGTH: 15 base pairs
(B) TYPE: Nucleic Acid
(C) STRANDEDNESS: double stranded
(D) TOPOLOGY: linear (i i) MOLECULE TYPE: Genomic DNA
(A) DESCRIPTION: dystrophin gene (Accession #M18533, M17154, M18026) nucleotides 5808 to 5822

(i i i) HYPOTHETICAL: No (i v) ANTI-SENSE: No (v i) ORIGINAL SOURCE:
(A) ORGANISM: Homo sapiens (v i i) POSITION IN GENOME:
(A) CHROMOSOME/SEGMENT: X- chromosome
(B) MAP POSITION: Xp21.3-p21.1

(x) PUBLICATION INFORMATION:
(A) AUTHORS: Koenig, M, Hoffman, E P, Bertelson, C J, Monaco, A P, Feener, C, Kunkel, L M.
(B) TITLE: Complete cloning of the Duchenne muscular dystrophy (DMD) cDNA and preliminary genomic organization of the DMD gene in normal and affected individuals
(C) JOURNAL: Cell
(D) VOLUME: 50
(F) PAGES: 509-517
(G) DATE: 1987
(A) AUTHORS: Hoffman, E P, Monaco, A P, Feener, C C, Kunkel, L M.
(B) TITLE: Conservation of the Duchenne muscular dystrophy gene in mice and humans
(C) JOURNAL: Science
(D) VOLUME: 238
(F) PAGES: 347-350
(G) DATE: 1987
(A) AUTHORS: Koenig, M, Monaco, A P, Kunkel, L M.
(B) TITLE: The complete sequence of dystrophin predicts a rod-shaped cytoskeletal protein
(C) JOURNAL: Cell
(D) VOLUME: 53
(F) PAGES: 219-228
(G) DATE: 1988
(K) RELEVANT RESIDUES IN SEQ ID NO: 35 :FROM 1 TO 15

(x i) SEQUENCE DESCRIPTION: SEQ ID NO: 35:

AAAGAAGAAA AAAGG                                                15

(2) INFORMATION FOR SEQ ID NO:36:

( i ) SEQUENCE CHARACTERISTICS:
    ( A ) LENGTH: 15 bases
    ( B ) TYPE: Nucleic Acid
    ( C ) STRANDEDNESS: single stranded
    ( D ) TOPOLOGY: linear ( i i ) MOLECULE TYPE: other nucleic acid
    ( A ) DESCRIPTION: third strand derived from dystrophin
        sequence region in Seq ID No 35

( i i i ) HYPOTHETICAL: Yes ( i v ) ANTI-SENSE: No ( x ) PUBLICATION INFORMATION:
    ( K ) RELEVANT RESIDUES IN SEQ ID NO: 36 :FROM 1 TO 15

( x i ) SEQUENCE DESCRIPTION: SEQ ID NO: 36 :

TTTCTTCTTT TTTCC    15

( 2 ) INFORMATION FOR SEQ ID NO:37:

( i ) SEQUENCE CHARACTERISTICS:
    ( A ) LENGTH: 17 base pairs
    ( B ) TYPE: Nucleic Acid
    ( C ) STRANDEDNESS: double stranded
    ( D ) TOPOLOGY: linear ( i i ) MOLECULE TYPE: Genomic DNA
    ( A ) DESCRIPTION: dystrophin gene (Accession #M18533,
        M17154, M18026) nucleotides 5967 to 5983

( i i i ) HYPOTHETICAL: No ( i v ) ANTI-SENSE: No ( v i ) ORIGINAL SOURCE:
    ( A ) ORGANISM: Homo sapiens ( v i i ) POSITION IN GENOME:
    ( A ) CHROMOSOME/SEGMENT: X- chromosome
    ( B ) MAP POSITION: Xp21.3-p21.1

( x ) PUBLICATION INFORMATION:
    ( A ) AUTHORS: Koenig, M, Hoffman, E P, Bertelson, C J,
        Monaco, A P, Feener, C, Kunkel, L M.
    ( B ) TITLE: Complete cloning of the
        Duchenne muscular dystrophy (DMD) cDNA and
        preliminary genomic organization of the DMD
        gene in normal and affected individuals
    ( C ) JOURNAL: Cell
    ( D ) VOLUME: 50
    ( F ) PAGES: 509-517
    ( G ) DATE: 1987
    ( A ) AUTHORS: Hoffman, E P, Monaco, A P, Feener, C C,
        Kunkel, L M.
    ( B ) TITLE: Conservation of the Duchenne
        muscular dystrophy gene in mice and humans
    ( C ) JOURNAL: Science
    ( D ) VOLUME: 238
    ( F ) PAGES: 347-350
    ( G ) DATE: 1987
    ( A ) AUTHORS: Koenig, M, Monaco, A P, Kunkel, L M.
    ( B ) TITLE: The complete sequence of
        dystrophin predicts a rod-shaped cytoskeletal
        protein
    ( C ) JOURNAL: Cell
    ( D ) VOLUME: 53
    ( F ) PAGES: 219-228
    ( G ) DATE: 1988
    ( K ) RELEVANT RESIDUES IN SEQ ID NO: 37 :FROM 1 TO 17

( x i ) SEQUENCE DESCRIPTION: SEQ ID NO: 37:

AGAAGAAGAA AGAGGAG    17

( 2 ) INFORMATION FOR SEQ ID NO:38:

( i ) SEQUENCE CHARACTERISTICS:
                ( A ) LENGTH: 17 bases
                ( B ) TYPE: Nucleic Acid
                ( C ) STRANDEDNESS: single stranded
                ( D ) TOPOLOGY: linear ( i i ) MOLECULE TYPE: other nucleic acid
                ( A ) DESCRIPTION: third strand derived from dystrophin
                        sequence region in Seq ID No 37

( i i i ) HYPOTHETICAL: Yes ( i v ) ANTI-SENSE: No ( x ) PUBLICATION INFORMATION:
                ( K ) RELEVANT RESIDUES IN SEQ ID NO: 38 :FROM 1 TO 17

( x i ) SEQUENCE DESCRIPTION: SEQ ID NO: 38 :

TCTTCTTCTT TCTCCTC                                                                                                    17

( 2 ) INFORMATION FOR SEQ ID NO:39:

( i ) SEQUENCE CHARACTERISTICS:
                ( A ) LENGTH: 22 base pairs
                ( B ) TYPE: Nucleic Acid
                ( C ) STRANDEDNESS: double stranded
                ( D ) TOPOLOGY: linear ( i i ) MOLECULE TYPE: Genomic DNA
                ( A ) DESCRIPTION: dystrophin gene (Accession #M18533,
                        M17154, M18026) nucleotides 10702 to 10723

( i i i ) HYPOTHETICAL: No ( i v ) ANTI-SENSE: No ( v i ) ORIGINAL SOURCE:
                ( A ) ORGANISM: Homo sapiens ( v i i ) POSITION IN GENOME:
                ( A ) CHROMOSOME/SEGMENT: X- chromosome
                ( B ) MAP POSITION: Xp21.3-p21.1

( x ) PUBLICATION INFORMATION:
                ( A ) AUTHORS: Koenig, M, Hoffman, E P, Bertelson, C J,
                        Monaco, A P, Feener, C, Kunkel, L M.
                ( B ) TITLE: Complete cloning of the
                        Duchenne muscular dystrophy (DMD) cDNA and
                        preliminary genomic organization of the DMD
                        gene in normal and affected individuals
                ( C ) JOURNAL: Cell
                ( D ) VOLUME: 50
                ( F ) PAGES: 509-517
                ( G ) DATE: 1987
                ( A ) AUTHORS: Hoffman, E P, Monaco, A P, Feener, C C,
                        Kunkel, L M.
                ( B ) TITLE: Conservation of the Duchenne
                        muscular dystrophy gene in mice and humans
                ( C ) JOURNAL: Science
                ( D ) VOLUME: 238
                ( F ) PAGES: 347-350
                ( G ) DATE: 1987
                ( A ) AUTHORS: Koenig, M, Monaco, A P, Kunkel, L M.
                ( B ) TITLE: The complete sequence of
                        dystrophin predicts a rod-shaped cytoskeletal
                        protein
                ( C ) JOURNAL: Cell
                ( D ) VOLUME: 53
                ( F ) PAGES: 219-228
                ( G ) DATE: 1988
                ( K ) RELEVANT RESIDUES IN SEQ ID NO: 39 :FROM 1 TO 22

( x i ) SEQUENCE DESCRIPTION: SEQ ID NO: 39:

AGAGAGTGAG GAAAGAGGGG AG                                                                                              22

( 2 ) INFORMATION FOR SEQ ID NO:40:

( i ) SEQUENCE CHARACTERISTICS:
        ( A ) LENGTH: 22 bases
        ( B ) TYPE: Nucleic Acid
        ( C ) STRANDEDNESS: single stranded
        ( D ) TOPOLOGY: linear ( i i ) MOLECULE TYPE: other nucleic acid
        ( A ) DESCRIPTION: third strand derived from dystrophin
        sequence region in Seq ID No 39

( i i i ) HYPOTHETICAL: Yes ( i v ) ANTI-SENSE: No ( x ) PUBLICATION INFORMATION:
        ( K ) RELEVANT RESIDUES IN SEQ ID NO: 40 :FROM 1 TO 22

( x i ) SEQUENCE DESCRIPTION: SEQ ID NO: 40 :

TCTCTCGCTC CTTTCTCCCC TC        22

( 2 ) INFORMATION FOR SEQ ID NO:41:

( i ) SEQUENCE CHARACTERISTICS:
        ( A ) LENGTH: 20 base pairs
        ( B ) TYPE: Nucleic Acid
        ( C ) STRANDEDNESS: double stranded
        ( D ) TOPOLOGY: linear ( i i ) MOLECULE TYPE: Genomic DNA
        ( A ) DESCRIPTION: dystrophin gene (Accession #M18533,
        M17154, M18026) nucleotides 11042 to 11061

( i i i ) HYPOTHETICAL: No ( i v ) ANTI-SENSE: No ( v i ) ORIGINAL SOURCE:
        ( A ) ORGANISM: Homo sapiens ( v i i ) POSITION IN GENOME:
        ( A ) CHROMOSOME/SEGMENT: X- chromosome
        ( B ) MAP POSITION: Xp21.3-p21.1

( x ) PUBLICATION INFORMATION:
        ( A ) AUTHORS: Koenig, M, Hoffman, E P, Bertelson, C J,
        Monaco, A P, Feener, C, Kunkel, L M.
        ( B ) TITLE: Complete cloning of the
        Duchenne muscular dystrophy (DMD) cDNA and
        preliminary genomic organization of the DMD
        gene in normal and affected individuals
        ( C ) JOURNAL: Cell
        ( D ) VOLUME: 50
        ( F ) PAGES: 509-517
        ( G ) DATE: 1987
        ( A ) AUTHORS: Hoffman, E P, Monaco, A P, Feener, C C,
        Kunkel, L M.
        ( B ) TITLE: Conservation of the Duchenne
        muscular dystrophy gene in mice and humans
        ( C ) JOURNAL: Science
        ( D ) VOLUME: 238
        ( F ) PAGES: 347-350
        ( G ) DATE: 1987
        ( A ) AUTHORS: Koenig, M, Monaco, A P, Kunkel, L M.
        ( B ) TITLE: The complete sequence of
        dystrophin predicts a rod-shaped cytoskeletal
        protein
        ( C ) JOURNAL: Cell
        ( D ) VOLUME: 53
        ( F ) PAGES: 219-228
        ( G ) DATE: 1988
        ( K ) RELEVANT RESIDUES IN SEQ ID NO: 41 :FROM 1 TO 20

( x i ) SEQUENCE DESCRIPTION: SEQ ID NO: 41:

TCCTCTCCTT CTACCTCTCT        20

( 2 ) INFORMATION FOR SEQ ID NO:42:

( i ) SEQUENCE CHARACTERISTICS:
        ( A ) LENGTH: 20 bases
        ( B ) TYPE: Nucleic Acid
        ( C ) STRANDEDNESS: single stranded
        ( D ) TOPOLOGY: linear ( i i ) MOLECULE TYPE: other nucleic acid
        ( A ) DESCRIPTION: third strand derived from dystrophin
            sequence region in Seq ID No 41

( i i i ) HYPOTHETICAL: Yes ( i v ) ANTI-SENSE: No ( x ) PUBLICATION INFORMATION:
        ( K ) RELEVANT RESIDUES IN SEQ ID NO: 42 :FROM 1 TO 20

( x i ) SEQUENCE DESCRIPTION: SEQ ID NO: 42 :

TCTCTCCGTC TTCCTCTCCT    20

( 2 ) INFORMATION FOR SEQ ID NO:43:

( i ) SEQUENCE CHARACTERISTICS:
        ( A ) LENGTH: 17 base pairs
        ( B ) TYPE: Nucleic Acid
        ( C ) STRANDEDNESS: double stranded
        ( D ) TOPOLOGY: linear ( i i ) MOLECULE TYPE: Genomic DNA
        ( A ) DESCRIPTION: dystrophin gene (Accession #M18533,
            M17154, M18026) nucleotides 12923 to 12939

( i i i ) HYPOTHETICAL: No ( i v ) ANTI-SENSE: No ( v i ) ORIGINAL SOURCE:
        ( A ) ORGANISM: Homo sapiens ( v i i ) POSITION IN GENOME:
        ( A ) CHROMOSOME/SEGMENT: X- chromosome
        ( B ) MAP POSITION: Xp21.3-p21.1

( x ) PUBLICATION INFORMATION:
        ( A ) AUTHORS: Koenig, M, Hoffman, E P, Bertelson, C J,
            Monaco, A P, Feener, C, Kunkel, L M.
        ( B ) TITLE: Complete cloning of the
            Duchenne muscular dystrophy (DMD) cDNA and
            preliminary genomic organization of the DMD
            gene in normal and affected individuals
        ( C ) JOURNAL: Cell
        ( D ) VOLUME: 50
        ( F ) PAGES: 509-517
        ( G ) DATE: 1987
        ( A ) AUTHORS: Hoffman, E P, Monaco, A P, Feener, C C,
            Kunkel, L M.
        ( B ) TITLE: Conservation of the Duchenne
            muscular dystrophy gene in mice and humans
        ( C ) JOURNAL: Science
        ( D ) VOLUME: 238
        ( F ) PAGES: 347-350
        ( G ) DATE: 1987
        ( A ) AUTHORS: Koenig, M, Monaco, A P, Kunkel, L M.
        ( B ) TITLE: The complete sequence of
            dystrophin predicts a rod-shaped cytoskeletal
            protein
        ( C ) JOURNAL: Cell
        ( D ) VOLUME: 53
        ( F ) PAGES: 219-228
        ( G ) DATE: 1988
        ( K ) RELEVANT RESIDUES IN SEQ ID NO: 43 :FROM 1 TO 17

( x i ) SEQUENCE DESCRIPTION: SEQ ID NO: 43:

AAAAAGAGG AGAAAAG    17

( 2 ) INFORMATION FOR SEQ ID NO:44:

( i ) SEQUENCE CHARACTERISTICS:
      ( A ) LENGTH: 17 bases
      ( B ) TYPE: Nucleic Acid
      ( C ) STRANDEDNESS: single stranded
      ( D ) TOPOLOGY: linear ( i i ) MOLECULE TYPE: other nucleic acid
      ( A ) DESCRIPTION: third strand derived from dystrophin
            sequence region in Seq ID No 43

( i i i ) HYPOTHETICAL: Yes ( i v ) ANTI-SENSE: No ( x ) PUBLICATION INFORMATION:
      ( K ) RELEVANT RESIDUES IN SEQ ID NO: 44 :FROM 1 TO 17

( x i ) SEQUENCE DESCRIPTION: SEQ ID NO: 44 :

TTTTTCTCC TCTTTTC                                                        17

( 2 ) INFORMATION FOR SEQ ID NO:45:

( i ) SEQUENCE CHARACTERISTICS:
      ( A ) LENGTH: 15 base pairs
      ( B ) TYPE: Nucleic Acid
      ( C ) STRANDEDNESS: double stranded
      ( D ) TOPOLOGY: linear ( i i ) MOLECULE TYPE: Genomic DNA
      ( A ) DESCRIPTION: dystrophin gene (Accession #M18533,
            M17154, M18026) nucleotides 13280 to 13294

( i i i ) HYPOTHETICAL: No ( i v ) ANTI-SENSE: No ( v i ) ORIGINAL SOURCE:
      ( A ) ORGANISM: Homo sapiens ( v i i ) POSITION IN GENOME:
      ( A ) CHROMOSOME/SEGMENT: X- chromosome
      ( B ) MAP POSITION: Xp21.3-p21.1

( x ) PUBLICATION INFORMATION:
      ( A ) AUTHORS: Koenig, M, Hoffman, E P, Bertelson, C J,
            Monaco, A P, Feener, C, Kunkel, L M.
      ( B ) TITLE: Complete cloning of the
            Duchenne muscular dystrophy (DMD) cDNA and
            preliminary genomic organization of the DMD
            gene in normal and affected individuals
      ( C ) JOURNAL: Cell
      ( D ) VOLUME: 50
      ( F ) PAGES: 509-517
      ( G ) DATE: 1987
      ( A ) AUTHORS: Hoffman, E P, Monaco, A P, Feener, C C,
            Kunkel, L M.
      ( B ) TITLE: Conservation of the Duchenne
            muscular dystrophy gene in mice and humans
      ( C ) JOURNAL: Science
      ( D ) VOLUME: 238
      ( F ) PAGES: 347-350
      ( G ) DATE: 1987
      ( A ) AUTHORS: Koenig, M, Monaco, A P, Kunkel, L M.
      ( B ) TITLE: The complete sequence of
            dystrophin predicts a rod-shaped cytoskeletal
            protein
      ( C ) JOURNAL: Cell
      ( D ) VOLUME: 53
      ( F ) PAGES: 219-228
      ( G ) DATE: 1988
      ( K ) RELEVANT RESIDUES IN SEQ ID NO: 45 :FROM 1 TO 15

( x i ) SEQUENCE DESCRIPTION: SEQ ID NO: 45:

TTTCTTTTT CCTTT                                                                 15

( 2 ) INFORMATION FOR SEQ ID NO:46:

( i ) SEQUENCE CHARACTERISTICS:
        ( A ) LENGTH: 15 bases
        ( B ) TYPE: Nucleic Acid
        ( C ) STRANDEDNESS: single stranded
        ( D ) TOPOLOGY: linear ( i i ) MOLECULE TYPE: other nucleic acid
        ( A ) DESCRIPTION: third strand derived from dystrophin
            sequence region in Seq ID No 45

( i i i ) HYPOTHETICAL: Yes ( i v ) ANTI-SENSE: No ( x ) PUBLICATION INFORMATION:
        ( K ) RELEVANT RESIDUES IN SEQ ID NO: 46 :FROM 1 TO 15

( x i ) SEQUENCE DESCRIPTION: SEQ ID NO: 46 :

TTTCCTTTTT CTTTT                                                                15

( 2 ) INFORMATION FOR SEQ ID NO:47:

( i ) SEQUENCE CHARACTERISTICS:
        ( A ) LENGTH: 17 base pairs
        ( B ) TYPE: Nucleic Acid
        ( C ) STRANDEDNESS: double stranded
        ( D ) TOPOLOGY: linear ( i i ) MOLECULE TYPE: Genomic DNA
        ( A ) DESCRIPTION: dystrophin gene (Accession #M18533,
            M17154, M18026) nucleotides 13299 to 13315

( i i i ) HYPOTHETICAL: No ( i v ) ANTI-SENSE: No ( v i ) ORIGINAL SOURCE:
        ( A ) ORGANISM: Homo sapiens ( v i i ) POSITION IN GENOME:
        ( A ) CHROMOSOME/SEGMENT: X- chromosome
        ( B ) MAP POSITION: Xp21.3-p21.1

( x ) PUBLICATION INFORMATION:
        ( A ) AUTHORS: Koenig, M, Hoffman, E P, Bertelson, C J,
            Monaco, A P, Feener, C, Kunkel, L M.
        ( B ) TITLE: Complete cloning of the
            Duchenne muscular dystrophy (DMD) cDNA and
            preliminary genomic organization of the DMD
            gene in normal and affected individuals
        ( C ) JOURNAL: Cell
        ( D ) VOLUME: 50
        ( F ) PAGES: 509-517
        ( G ) DATE: 1987
        ( A ) AUTHORS: Hoffman, E P, Monaco, A P, Feener, C C,
            Kunkel, L M.
        ( B ) TITLE: Conservation of the Duchenne
            muscular dystrophy gene in mice and humans
        ( C ) JOURNAL: Science
        ( D ) VOLUME: 238
        ( F ) PAGES: 347-350
        ( G ) DATE: 1987
        ( A ) AUTHORS: Koenig, M, Monaco, A P, Kunkel, L M.
        ( B ) TITLE: The complete sequence of
            dystrophin predicts a rod-shaped cytoskeletal
            protein
        ( C ) JOURNAL: Cell
        ( D ) VOLUME: 53
        ( F ) PAGES: 219-228
        ( G ) DATE: 1988
        ( K ) RELEVANT RESIDUES IN SEQ ID NO: 47 :FROM 1 TO 17

( x i ) SEQUENCE DESCRIPTION: SEQ ID NO: 47:

TTCTTTCTTT TTCCTTC                                                                                          17

( 2 ) INFORMATION FOR SEQ ID NO:48:

( i ) SEQUENCE CHARACTERISTICS:
        ( A ) LENGTH: 17 bases
        ( B ) TYPE: Nucleic Acid
        ( C ) STRANDEDNESS: single stranded
        ( D ) TOPOLOGY: linear ( i i ) MOLECULE TYPE: other nucleic acid
        ( A ) DESCRIPTION: third strand derived from dystrophin
              sequence region in Seq ID No 47

( i i i ) HYPOTHETICAL: Yes ( i v ) ANTI-SENSE: No ( x ) PUBLICATION INFORMATION:
        ( K ) RELEVANT RESIDUES IN SEQ ID NO: 48 :FROM 1 TO 17

( x i ) SEQUENCE DESCRIPTION: SEQ ID NO: 48 :

CTTCCTTTTT CTTTCTT                                                                                          17

( 2 ) INFORMATION FOR SEQ ID NO:49:

( i ) SEQUENCE CHARACTERISTICS:
        ( A ) LENGTH: 11 base pairs
        ( B ) TYPE: Nucleic Acid
        ( C ) STRANDEDNESS: double stranded
        ( D ) TOPOLOGY: linear ( i i ) MOLECULE TYPE: Genomic DNA
        ( A ) DESCRIPTION: HER-2 gene (Accession #M11730)
              nucleotides 597to 607

( i i i ) HYPOTHETICAL: No ( i v ) ANTI-SENSE: No ( v i ) ORIGINAL SOURCE:
        ( A ) ORGANISM: Homo sapiens ( x ) PUBLICATION INFORMATION:
        ( A ) AUTHORS: Coussens, L, Yang- Feng, T L, Liao, Y C,
              Chen, E, Gray, A, McGrath, J, Seeburg, P H,
              Libermann, T A, Schlessinger, J, Francke, U,
              Levinson, A, Ullrich, A.
        ( B ) TITLE: Tyrosine kinase receptor with
              extensive homology to EGF receptor shares
              chromosomal location with neu oncogene
        ( C ) JOURNAL: Science
        ( D ) VOLUME: 230
        ( F ) PAGES: 1132-1139
        ( G ) DATE: 1985
        ( K ) RELEVANT RESIDUES IN SEQ ID NO: 49 :FROM 1 TO 11

( x i ) SEQUENCE DESCRIPTION: SEQ ID NO: 49:

GAAAGGAGGG G                                                                                                11

( 2 ) INFORMATION FOR SEQ ID NO:50:

( i ) SEQUENCE CHARACTERISTICS:
        ( A ) LENGTH: 11 bases
        ( B ) TYPE: Nucleic Acid
        ( C ) STRANDEDNESS: single stranded
        ( D ) TOPOLOGY: linear ( i i ) MOLECULE TYPE: other nucleic acid
        ( A ) DESCRIPTION: third strand derived from HER-2
              sequence region in Seq ID No 49

( i i i ) HYPOTHETICAL: Yes (i v) ANTI-SENSE: No (x) PUBLICATION INFORMATION:
(K) RELEVANT RESIDUES IN SEQ ID NO: 50 :FROM 1 TO 11

(x i) SEQUENCE DESCRIPTION: SEQ ID NO: 50 :

CTTTCCTCCC C                                                                                                   11

(2) INFORMATION FOR SEQ ID NO:51:

(i) SEQUENCE CHARACTERISTICS:
(A) LENGTH: 12 base pairs
(B) TYPE: Nucleic Acid
(C) STRANDEDNESS: double stranded
(D) TOPOLOGY: linear (i i) MOLECULE TYPE: Genomic DNA
(A) DESCRIPTION: HER-2 gene (Accession #M11730)
nucleotides 1202 to 1213

(i i i) HYPOTHETICAL: No (i v) ANTI-SENSE: No (v i) ORIGINAL SOURCE:
(A) ORGANISM: Homo sapiens (x) PUBLICATION INFORMATION:
(A) AUTHORS: Coussens, L, Yang- Feng, T L, Liao, Y C,
Chen, E, Gray, A, McGrath, J, Seeburg, P H,
Libermann, T A, Schlessinger, J, Francke, U,
Levinson, A, Ullrich, A.
(B) TITLE: Tyrosine kinase receptor with
extensive homology to EGF receptor shares
chromosomal location with neu oncogene
(C) JOURNAL: Science
(D) VOLUME: 230
(F) PAGES: 1132-1139
(G) DATE: 1985
(K) RELEVANT RESIDUES IN SEQ ID NO: 51 :FROM 1 TO 12

(x i) SEQUENCE DESCRIPTION: SEQ ID NO: 51:

GAGAGGTGAG GG                                                                                                  12

(2) INFORMATION FOR SEQ ID NO:52:

(i) SEQUENCE CHARACTERISTICS:
(A) LENGTH: 12 bases
(B) TYPE: Nucleic Acid
(C) STRANDEDNESS: single stranded
(D) TOPOLOGY: linear (i i) MOLECULE TYPE: other nucleic acid
(A) DESCRIPTION: third strand derived from HER-2
sequence region in Seq ID No 51

(i i i) HYPOTHETICAL: Yes (i v) ANTI-SENSE: No (x) PUBLICATION INFORMATION:
(K) RELEVANT RESIDUES IN SEQ ID NO: 52 :FROM 1 TO 12

(x i) SEQUENCE DESCRIPTION: SEQ ID NO: 52 :

CTCTCCGCTC CC                                                                                                  12

(2) INFORMATION FOR SEQ ID NO:53:

(i) SEQUENCE CHARACTERISTICS:
(A) LENGTH: 11 base pairs
(B) TYPE: Nucleic Acid
(C) STRANDEDNESS: double stranded
(D) TOPOLOGY: linear (i i) MOLECULE TYPE: Genomic DNA
    (A) DESCRIPTION: HER-2 gene (Accession #M11730)
        nucleotides 1926 to 1936

(i i i) HYPOTHETICAL: No (i v) ANTI-SENSE: No (v i) ORIGINAL SOURCE:
    (A) ORGANISM: Homo sapiens (x) PUBLICATION INFORMATION:
    (A) AUTHORS: Coussens, L, Yang- Feng, T L, Liao, Y C,
        Chen, E, Gray, A, McGrath, J, Seeburg, P H,
        Libermann, T A, Schlessinger, J, Francke, U,
        Levinson, A, Ullrich, A.
    (B) TITLE: Tyrosine kinase receptor with
        extensive homology to EGF receptor shares
        chromosomal location with neu oncogene
    (C) JOURNAL: Science
    (D) VOLUME: 230
    (F) PAGES: 1132-1139
    (G) DATE: 1985
    (K) RELEVANT RESIDUES IN SEQ ID NO: 53 :FROM 1 TO 11

(x i) SEQUENCE DESCRIPTION: SEQ ID NO: 53:

CCCTCCCTTC T                                                    11

(2) INFORMATION FOR SEQ ID NO:54:

(i) SEQUENCE CHARACTERISTICS:
        (A) LENGTH: 11 bases
        (B) TYPE: Nucleic Acid
        (C) STRANDEDNESS: single stranded
        (D) TOPOLOGY: linear (i i) MOLECULE TYPE: other nucleic acid
        (A) DESCRIPTION: third strand derived from HER-2
            sequence region in Seq ID No 53

(i i i) HYPOTHETICAL: Yes (i v) ANTI-SENSE: No (x) PUBLICATION INFORMATION:
        (K) RELEVANT RESIDUES IN SEQ ID NO: 54 :FROM 1 TO 11

(x i) SEQUENCE DESCRIPTION: SEQ ID NO: 54 :

TCTTCCCTCC C                                                    11

(2) INFORMATION FOR SEQ ID NO:55:

(i) SEQUENCE CHARACTERISTICS:
        (A) LENGTH: 13 base pairs
        (B) TYPE: Nucleic Acid
        (C) STRANDEDNESS: double stranded
        (D) TOPOLOGY: linear (i i) MOLECULE TYPE: Genomic DNA
        (A) DESCRIPTION: HER-2 gene (Accession #M11730)
            nucleotides 2955 to 2967

(i i i) HYPOTHETICAL: No (i v) ANTI-SENSE: No (v i) ORIGINAL SOURCE:
        (A) ORGANISM: Homo sapiens (x) PUBLICATION INFORMATION:
        (A) AUTHORS: Coussens, L, Yang- Feng, T L, Liao, Y C,
            Chen, E, Gray, A, McGrath, J, Seeburg, P H,
            Libermann, T A, Schlessinger, J, Francke, U,
            Levinson, A, Ullrich, A.
        (B) TITLE: Tyrosine kinase receptor with
            extensive homology to EGF receptor shares chromosomal location with neu oncogene
(C) JOURNAL: Science
(D) VOLUME: 230
(F) PAGES: 1132-1139
(G) DATE: 1985
(K) RELEVANT RESIDUES IN SEQ ID NO: 55 :FROM 1 TO 13

(x i) SEQUENCE DESCRIPTION: SEQ ID NO: 55:

GGAAAAGGGG GAG 13

(2) INFORMATION FOR SEQ ID NO:56:

(i) SEQUENCE CHARACTERISTICS:
(A) LENGTH: 13 bases
(B) TYPE: Nucleic Acid
(C) STRANDEDNESS: single stranded
(D) TOPOLOGY: linear (i i) MOLECULE TYPE: other nucleic acid
(A) DESCRIPTION: third strand derived from HER-2
sequence region in Seq ID No 55

(i i i) HYPOTHETICAL: Yes (i v) ANTI-SENSE: No (x) PUBLICATION INFORMATION:
(K) RELEVANT RESIDUES IN SEQ ID NO: 56 :FROM 1 TO 13

(x i) SEQUENCE DESCRIPTION: SEQ ID NO: 56 :

CCTTTTCCCC CTC 13

(2) INFORMATION FOR SEQ ID NO:57:

(i) SEQUENCE CHARACTERISTICS:
(A) LENGTH: 12 base pairs
(B) TYPE: Nucleic Acid
(C) STRANDEDNESS: double stranded
(D) TOPOLOGY: linear (i i) MOLECULE TYPE: Genomic DNA
(A) DESCRIPTION: HER-2 gene (Accession #M11730)
nucleotides 4201 to 4212

(i i i) HYPOTHETICAL: No (i v) ANTI-SENSE: No (v i) ORIGINAL SOURCE:
(A) ORGANISM: Homo sapiens (x) PUBLICATION INFORMATION:
(A) AUTHORS: Coussens, L, Yang- Feng, T L, Liao, Y C,
Chen, E, Gray, A, McGrath, J, Seeburg, P H,
Libermann, T A, Schlessinger, J, Francke, U,
Levinson, A, Ullrich, A.
(B) TITLE: Tyrosine kinase receptor with
extensive homology to EGF receptor shares
chromosomal location with neu oncogene
(C) JOURNAL: Science
(D) VOLUME: 230
(F) PAGES: 1132-1139
(G) DATE: 1985
(K) RELEVANT RESIDUES IN SEQ ID NO: 57 :FROM 1 TO 12

(x i) SEQUENCE DESCRIPTION: SEQ ID NO: 57:

CCCTTTCCTT CC 12

(2) INFORMATION FOR SEQ ID NO:58:

(i) SEQUENCE CHARACTERISTICS:
(A) LENGTH: 12 bases
(B) TYPE: Nucleic Acid
(C) STRANDEDNESS: single stranded (D) TOPOLOGY: linear (ii) MOLECULE TYPE: other nucleic acid
                (A) DESCRIPTION: third strand derived from HER-2
                        sequence region in Seq ID No 57

(iii) HYPOTHETICAL: Yes (iv) ANTI-SENSE: No (x) PUBLICATION INFORMATION:
                (K) RELEVANT RESIDUES IN SEQ ID NO: 58 :FROM 1 TO 12

(xi) SEQUENCE DESCRIPTION: SEQ ID NO: 58 :

CCTTCCTTTC CC                                                                                        12

(2) INFORMATION FOR SEQ ID NO:59:

(i) SEQUENCE CHARACTERISTICS:
                (A) LENGTH: 11 base pairs
                (B) TYPE: Nucleic Acid
                (C) STRANDEDNESS: double stranded
                (D) TOPOLOGY: linear (ii) MOLECULE TYPE: Genomic DNA
                (A) DESCRIPTION: HER-2 gene (Accession #M11730)
                        nucleotides 4250 to 4260

(iii) HYPOTHETICAL: No (iv) ANTI-SENSE: No (vi) ORIGINAL SOURCE:
                (A) ORGANISM: Homo sapiens (x) PUBLICATION INFORMATION:
                (A) AUTHORS: Coussens, L, Yang- Feng, T L, Liao, Y C,
                        Chen, E, Gray, A, McGrath, J, Seeburg, P H,
                        Libermann, T A, Schlessinger, J, Francke, U,
                        Levinson, A, Ullrich, A.
                (B) TITLE: Tyrosine kinase receptor with
                        extensive homology to EGF receptor shares
                        chromosomal location with neu oncogene
                (C) JOURNAL: Science
                (D) VOLUME: 230
                (F) PAGES: 1132-1139
                (G) DATE: 1985
                (K) RELEVANT RESIDUES IN SEQ ID NO: 59 :FROM 1 TO 11

(xi) SEQUENCE DESCRIPTION: SEQ ID NO: 59:

GAGAGGGGAA G                                                                                         11

(2) INFORMATION FOR SEQ ID NO:60:

(i) SEQUENCE CHARACTERISTICS:
                (A) LENGTH: 11 bases
                (B) TYPE: Nucleic Acid
                (C) STRANDEDNESS: single stranded
                (D) TOPOLOGY: linear (ii) MOLECULE TYPE: other nucleic acid
                (A) DESCRIPTION: third strand derived from HER-2
                        sequence region in Seq ID No 59

(iii) HYPOTHETICAL: Yes (iv) ANTI-SENSE: No (x) PUBLICATION INFORMATION:
                (K) RELEVANT RESIDUES IN SEQ ID NO: 60 :FROM 1 TO 11

(xi) SEQUENCE DESCRIPTION: SEQ ID NO: 60 :

CTCTCCCCTT C                                                                                         11

( 2 ) INFORMATION FOR SEQ ID NO:61:

( i ) SEQUENCE CHARACTERISTICS:
        ( A ) LENGTH: 15 base pairs
        ( B ) TYPE: Nucleic Acid
        ( C ) STRANDEDNESS: double stranded
        ( D ) TOPOLOGY: linear ( i i ) MOLECULE TYPE: Genomic DNA
        ( A ) DESCRIPTION: gamma-crystallin gene exons 1 and 2
        ( A c c e s s i o n # K 0 3 0 0 3 ) nucleotides 144 to 158

( i i i ) HYPOTHETICAL: No ( i v ) ANTI-SENSE: No ( v i ) ORIGINAL SOURCE:
        ( A ) ORGANISM: Homo sapiens ( v i i ) POSITION IN GENOME:
        ( A ) CHROMOSOME/SEGMENT: chromosome 2
        ( B ) MAP POSITION: 2q33-q35

( x ) PUBLICATION INFORMATION:
        ( A ) AUTHORS: Meakin, S O, Breitman, M L, Tsui, L C.
        ( B ) TITLE: Structural and evolutionary
            relationships among five members of the human
            gamma- crystallin gene family
        ( C ) JOURNAL: Molecular and Cellular Biology
        ( D ) VOLUME: 5
        ( F ) PAGES: 1408-1414
        ( G ) DATE: 1985
        ( K ) RELEVANT RESIDUES IN SEQ ID NO: 61 :FROM 1 TO 15

( x i ) SEQUENCE DESCRIPTION: SEQ ID NO: 61:

A A A A T G A A A A   A A A A G                                                                                   1 5

( 2 ) INFORMATION FOR SEQ ID NO:62:

( i ) SEQUENCE CHARACTERISTICS:
        ( A ) LENGTH: 15 bases
        ( B ) TYPE: Nucleic Acid
        ( C ) STRANDEDNESS: single stranded
        ( D ) TOPOLOGY: linear ( i i ) MOLECULE TYPE: other nucleic acid
        ( A ) DESCRIPTION: third strand derived from gamma-
            crystallin sequence region in Seq ID No 61

( i i i ) HYPOTHETICAL: Yes ( i v ) ANTI-SENSE: No ( x ) PUBLICATION INFORMATION:
        ( K ) RELEVANT RESIDUES IN SEQ ID NO: 62 :FROM 1 TO 15

( x i ) SEQUENCE DESCRIPTION: SEQ ID NO: 62 :

T T T T G C T T T T   T T T T C                                                                                   1 5

( 2 ) INFORMATION FOR SEQ ID NO:63:

( i ) SEQUENCE CHARACTERISTICS:
        ( A ) LENGTH: 11 base pairs
        ( B ) TYPE: Nucleic Acid
        ( C ) STRANDEDNESS: double stranded
        ( D ) TOPOLOGY: linear ( i i ) MOLECULE TYPE: Genomic DNA
        ( A ) DESCRIPTION: gamma-crystallin gene exon 3
        ( A c c e s s i o n # K 0 3 0 0 4 ) nucleotides 301 to 311

( i i i ) HYPOTHETICAL: No ( i v ) ANTI-SENSE: No ( v i ) ORIGINAL SOURCE:

(A) ORGANISM: Homo sapiens (vii) POSITION IN GENOME:
    (A) CHROMOSOME/SEGMENT: chromosome 2
    (B) MAP POSITION: 2q33-q35

(x) PUBLICATION INFORMATION:
    (A) AUTHORS: Meakin, S O, Breitman, M L, Tsui, L C.
    (B) TITLE: Structural and evolutionary
        relationships among five members of the human
        gamma- crystallin gene family
    (C) JOURNAL: Molecular and Cellular Biology
    (D) VOLUME: 5
    (F) PAGES: 1408-1414
    (G) DATE: 1985
    (K) RELEVANT RESIDUES IN SEQ ID NO: 63 :FROM 1 TO 11

(xi) SEQUENCE DESCRIPTION: SEQ ID NO: 63:

TTTCCCATTT T                            11

(2) INFORMATION FOR SEQ ID NO:64:

(i) SEQUENCE CHARACTERISTICS:
        (A) LENGTH: 11 bases
        (B) TYPE: Nucleic Acid
        (C) STRANDEDNESS: single stranded
        (D) TOPOLOGY: linear (ii) MOLECULE TYPE: other nucleic acid
        (A) DESCRIPTION: third strand derived from gamma-
        crystallin sequence region in Seq ID No 63

(iii) HYPOTHETICAL: Yes (iv) ANTI-SENSE: No (x) PUBLICATION INFORMATION:
        (K) RELEVANT RESIDUES IN SEQ ID NO: 64 :FROM 1 TO 11

(xi) SEQUENCE DESCRIPTION: SEQ ID NO: 64 :

TTTTGCCCTT T                            11

(2) INFORMATION FOR SEQ ID NO:65:

(i) SEQUENCE CHARACTERISTICS:
        (A) LENGTH: 22 base pairs
        (B) TYPE: Nucleic Acid
        (C) STRANDEDNESS: double stranded
        (D) TOPOLOGY: linear (ii) MOLECULE TYPE: Genomic DNA
        (A) DESCRIPTION: gamma-crystallin gene exon 3
        (Accession # K03006) nucleotides 9 to 30

(iii) HYPOTHETICAL: No (iv) ANTI-SENSE: No (vi) ORIGINAL SOURCE:
        (A) ORGANISM: Homo sapiens (vii) POSITION IN GENOME:
        (A) CHROMOSOME/SEGMENT: chromosome 2
        (B) MAP POSITION: 2q33-q35

(x) PUBLICATION INFORMATION:
        (A) AUTHORS: Meakin, S O, Breitman, M L, Tsui, L C.
        (B) TITLE: Structural and evolutionary
            relationships among five members of the human
            gamma- crystallin gene family
        (C) JOURNAL: Molecular and Cellular Biology
        (D) VOLUME: 5
        (F) PAGES: 1408-1414
        (G) DATE: 1985
        (K) RELEVANT RESIDUES IN SEQ ID NO: 65 :FROM 1 TO 22

(x i) SEQUENCE DESCRIPTION: SEQ ID NO: 65:

CTTTTCTTCT CTTTTTATTT CT 22

(2) INFORMATION FOR SEQ ID NO:66:

(i) SEQUENCE CHARACTERISTICS:
        (A) LENGTH: 22 bases
        (B) TYPE: Nucleic Acid
        (C) STRANDEDNESS: single stranded
        (D) TOPOLOGY: linear (i i) MOLECULE TYPE: other nucleic acid
        (A) DESCRIPTION: third strand derived from gamma-
            crystallin sequence region in Seq ID No 65

(i i i) HYPOTHETICAL: Yes (i v) ANTI-SENSE: No (x) PUBLICATION INFORMATION:
        (K) RELEVANT RESIDUES IN SEQ ID NO: 66 :FROM 1 TO 22

(x i) SEQUENCE DESCRIPTION: SEQ ID NO: 66 :

TCTTTGTTTT TCTCTTCTTT TC 22

(2) INFORMATION FOR SEQ ID NO:67:

(i) SEQUENCE CHARACTERISTICS:
        (A) LENGTH: 10 base pairs
        (B) TYPE: Nucleic Acid
        (C) STRANDEDNESS: double stranded
        (D) TOPOLOGY: linear (i i) MOLECULE TYPE: Genomic DNA
        (A) DESCRIPTION: esterase D gene (Accession #M13450)
            nucleotides 34 to 43

(i i i) HYPOTHETICAL: No (i v) ANTI-SENSE: No (v i) ORIGINAL SOURCE:
        (A) ORGANISM: Homo sapiens (v i i) POSITION IN GENOME:
        (A) CHROMOSOME/SEGMENT: chromosome 13
        (B) MAP POSITION: 13q14.1- q14.2

(x) PUBLICATION INFORMATION:
        (A) AUTHORS: Lee, E Y H P, Lee, W H.
        (B) TITLE: Molecular cloning of the
            human esterase D gene, a genetic marker of
            retinoblastoma
        (C) JOURNAL: Proceedings of the National Academy of
            Sciences, USA
        (D) VOLUME: 83
        (F) PAGES: 6337-6341
        (G) DATE: 1986
        (K) RELEVANT RESIDUES IN SEQ ID NO: 67 :FROM 1 TO 10

(x i) SEQUENCE DESCRIPTION: SEQ ID NO: 67:

AGGAAAAGAA 10

(2) INFORMATION FOR SEQ ID NO:68:

(i) SEQUENCE CHARACTERISTICS:
        (A) LENGTH: 10 bases
        (B) TYPE: Nucleic Acid
        (C) STRANDEDNESS: single stranded
        (D) TOPOLOGY: linear (i i) MOLECULE TYPE: other nucleic acid
        (A) DESCRIPTION: third strand derived from esterase D
            sequence region in Seq ID No 67

( i i i ) HYPOTHETICAL: Yes ( i v ) ANTI-SENSE: No ( x ) PUBLICATION INFORMATION:
( K ) RELEVANT RESIDUES IN SEQ ID NO: 68 :FROM 1 TO 10

( x i ) SEQUENCE DESCRIPTION: SEQ ID NO: 68 :

TCCTTTTCTT 10

( 2 ) INFORMATION FOR SEQ ID NO:69:

( i ) SEQUENCE CHARACTERISTICS:
( A ) LENGTH: 17 base pairs
( B ) TYPE: Nucleic Acid
( C ) STRANDEDNESS: double stranded
( D ) TOPOLOGY: linear ( i i ) MOLECULE TYPE: Genomic DNA
( A ) DESCRIPTION: esterase D gene (Accession #M13450)
nucleotides 316 to 332

( i i i ) HYPOTHETICAL: No ( i v ) ANTI-SENSE: No ( v i ) ORIGINAL SOURCE:
( A ) ORGANISM: Homo sapiens ( v i i ) POSITION IN GENOME:
( A ) CHROMOSOME/SEGMENT: chromosome 13
( B ) MAP POSITION: 13q14.1- q14.2

( x ) PUBLICATION INFORMATION:
( A ) AUTHORS: Lee, E Y H P, Lee, W H.
( B ) TITLE: Molecular cloning of the
human esterase D gene, a genetic marker of
retinoblastoma
( C ) JOURNAL: Proceedings of the National Academy of
Sciences, USA
( D ) VOLUME: 83
( F ) PAGES: 6337-6341
( G ) DATE: 1986
( K ) RELEVANT RESIDUES IN SEQ ID NO: 69 :FROM 1 TO 17

( x i ) SEQUENCE DESCRIPTION: SEQ ID NO: 69:

AAAGGTGAAG ATGAGAG 17

( 2 ) INFORMATION FOR SEQ ID NO:70:

( i ) SEQUENCE CHARACTERISTICS:
( A ) LENGTH: 17 bases
( B ) TYPE: Nucleic Acid
( C ) STRANDEDNESS: single stranded
( D ) TOPOLOGY: linear ( i i ) MOLECULE TYPE: other nucleic acid
( A ) DESCRIPTION: third strand derived from esterase D
sequence region in Seq ID No 69

( i i i ) HYPOTHETICAL: Yes ( i v ) ANTI-SENSE: No ( x ) PUBLICATION INFORMATION:
( K ) RELEVANT RESIDUES IN SEQ ID NO: 70 :FROM 1 TO 17

( x i ) SEQUENCE DESCRIPTION: SEQ ID NO: 70 :

TTTCCGCTTC TGCTCTC 17

( 2 ) INFORMATION FOR SEQ ID NO:71:

( i ) SEQUENCE CHARACTERISTICS:

( A ) LENGTH: 10 base pairs
                    ( B ) TYPE: Nucleic Acid
                    ( C ) STRANDEDNESS: double stranded
                    ( D ) TOPOLOGY: linear ( i i ) MOLECULE TYPE: Genomic DNA
                    ( A ) DESCRIPTION: esterase D gene (Accession #M13450)
                              nucleotides 710 to 719

( i i i ) HYPOTHETICAL: No ( i v ) ANTI-SENSE: No ( v i ) ORIGINAL SOURCE:
                    ( A ) ORGANISM: Homo sapiens ( v i i ) POSITION IN GENOME:
                    ( A ) CHROMOSOME/SEGMENT: chromosome 13
                    ( B ) MAP POSITION: 13q14.1- q14.2

( x ) PUBLICATION INFORMATION:
                    ( A ) AUTHORS: Lee, E Y H P, Lee, W H.
                    ( B ) TITLE: Molecular cloning of the
                              human esterase D gene, a genetic marker of
                              retinoblastoma
                    ( C ) JOURNAL: Proceedings of the National Academy of
                              Sciences, USA
                    ( D ) VOLUME: 83
                    ( F ) PAGES: 6337-6341
                    ( G ) DATE: 1986
                    ( K ) RELEVANT RESIDUES IN SEQ ID NO: 71 :FROM 1 TO 10

( x i ) SEQUENCE DESCRIPTION: SEQ ID NO: 71:

AAGGGAAAGA                                                                                                10

( 2 ) INFORMATION FOR SEQ ID NO:72:

( i ) SEQUENCE CHARACTERISTICS:
                    ( A ) LENGTH: 10 bases
                    ( B ) TYPE: Nucleic Acid
                    ( C ) STRANDEDNESS: single stranded
                    ( D ) TOPOLOGY: linear ( i i ) MOLECULE TYPE: other nucleic acid
                    ( A ) DESCRIPTION: third strand derived from esterase D
                              sequence region in Seq ID No 71

( i i i ) HYPOTHETICAL: Yes ( i v ) ANTI-SENSE: No ( x ) PUBLICATION INFORMATION:
                    ( K ) RELEVANT RESIDUES IN SEQ ID NO: 72 :FROM 1 TO 10

( x i ) SEQUENCE DESCRIPTION: SEQ ID NO: 72 :

TTCCCTTTCT                                                                                                10

( 2 ) INFORMATION FOR SEQ ID NO:73:

( i ) SEQUENCE CHARACTERISTICS:
                    ( A ) LENGTH: 11 base pairs
                    ( B ) TYPE: Nucleic Acid
                    ( C ) STRANDEDNESS: double stranded
                    ( D ) TOPOLOGY: linear ( i i ) MOLECULE TYPE: Genomic DNA
                    ( A ) DESCRIPTION: esterase D gene (Accession #M13450)
                              nucleotides 777 to 787

( i i i ) HYPOTHETICAL: No ( i v ) ANTI-SENSE: No ( v i ) ORIGINAL SOURCE:
                    ( A ) ORGANISM: Homo sapiens (  v i i ) POSITION IN GENOME:
    ( A ) CHROMOSOME/SEGMENT: chromosome 13
    ( B ) MAP POSITION: 13q14.1- q14.2

( x ) PUBLICATION INFORMATION:
    ( A ) AUTHORS: Lee, E Y H P, Lee, W H.
    ( B ) TITLE: Molecular cloning of the
            human esterase D gene, a genetic marker of
            retinoblastoma
    ( C ) JOURNAL: Proceedings of the National Academy of
            Sciences, USA
    ( D ) VOLUME: 83
    ( F ) PAGES: 6337-6341
    ( G ) DATE: 1986
    ( K ) RELEVANT RESIDUES IN SEQ ID NO: 73 :FROM 1 TO 11

( x i ) SEQUENCE DESCRIPTION: SEQ ID NO: 73:

AGAAAAGAAA A    11

( 2 ) INFORMATION FOR SEQ ID NO:74:

( i ) SEQUENCE CHARACTERISTICS:
        ( A ) LENGTH: 11 bases
        ( B ) TYPE: Nucleic Acid
        ( C ) STRANDEDNESS: single stranded
        ( D ) TOPOLOGY: linear ( i i ) MOLECULE TYPE: other nucleic acid
        ( A ) DESCRIPTION: third strand derived from esterase D
                sequence region in Seq ID No 73

( i i i ) HYPOTHETICAL: Yes ( i v ) ANTI-SENSE: No ( x ) PUBLICATION INFORMATION:
        ( K ) RELEVANT RESIDUES IN SEQ ID NO: 74 :FROM 1 TO 11

( x i ) SEQUENCE DESCRIPTION: SEQ ID NO: 74 :

TCTTTTCTTT T    11

( 2 ) INFORMATION FOR SEQ ID NO:75:

( i ) SEQUENCE CHARACTERISTICS:
        ( A ) LENGTH: 14 base pairs
        ( B ) TYPE: Nucleic Acid
        ( C ) STRANDEDNESS: double stranded
        ( D ) TOPOLOGY: linear ( i i ) MOLECULE TYPE: Genomic DNA
        ( A ) DESCRIPTION: esterase D gene (Accession #M13450)
                nucleotides 962 to 975

( i i i ) HYPOTHETICAL: No ( i v ) ANTI-SENSE: No ( v i ) ORIGINAL SOURCE:
        ( A ) ORGANISM: Homo sapiens ( v i i ) POSITION IN GENOME:
        ( A ) CHROMOSOME/SEGMENT: chromosome 13
        ( B ) MAP POSITION: 13q14.1- q14.2

( x ) PUBLICATION INFORMATION:
        ( A ) AUTHORS: Lee, E Y H P, Lee, W H.
        ( B ) TITLE: Molecular cloning of the
                human esterase D gene, a genetic marker of
                retinoblastoma
        ( C ) JOURNAL: Proceedings of the National Academy of
                Sciences, USA
        ( D ) VOLUME: 83
        ( F ) PAGES: 6337-6341
        ( G ) DATE: 1986
        ( K ) RELEVANT RESIDUES IN SEQ ID NO: 75 :FROM 1 TO 14

( x i ) SEQUENCE DESCRIPTION: SEQ ID NO: 75:

AAAAAAAAA AAAA 14

( 2 ) INFORMATION FOR SEQ ID NO:76:

( i ) SEQUENCE CHARACTERISTICS:
        ( A ) LENGTH: 14 bases
        ( B ) TYPE: Nucleic Acid
        ( C ) STRANDEDNESS: single stranded
        ( D ) TOPOLOGY: linear ( i i ) MOLECULE TYPE: other nucleic acid
        ( A ) DESCRIPTION: third strand derived from esterase D
            sequence region in Seq ID No 75

( i i i ) HYPOTHETICAL: Yes ( i v ) ANTI-SENSE: No ( x ) PUBLICATION INFORMATION:
        ( K ) RELEVANT RESIDUES IN SEQ ID NO: 76 :FROM 1 TO 14

( x i ) SEQUENCE DESCRIPTION: SEQ ID NO: 76 :

TTTTTTTTT TTTT 14

( 2 ) INFORMATION FOR SEQ ID NO:77:

( i ) SEQUENCE CHARACTERISTICS:
        ( A ) LENGTH: 14 base pairs
        ( B ) TYPE: Nucleic Acid
        ( C ) STRANDEDNESS: double stranded
        ( D ) TOPOLOGY: linear ( i i ) MOLECULE TYPE: Genomic DNA
        ( A ) DESCRIPTION: retinoblastoma gene (Accession #
            M33647, J02994) nucleotides 281 to 394

( i i i ) HYPOTHETICAL: No ( i v ) ANTI-SENSE: No ( v i ) ORIGINAL SOURCE:
        ( A ) ORGANISM: Homo sapiens ( v i i ) POSITION IN GENOME:
        ( A ) CHROMOSOME/SEGMENT: chromosome 13
        ( B ) MAP POSITION: 13q14.2

( x ) PUBLICATION INFORMATION:
        ( A ) AUTHORS: Friend, S H, Horowitz, J M, Gerber, M R,
            Wang X F, Bogenmann, E, Li, F P, Weinberg,
            R A.
        ( B ) TITLE: Deletions of a DNA sequence
            in retinoblastomas and mesenchymal tumors:
            Organization of the sequence and its encoded
            protein
        ( C ) JOURNAL: Proceedings of the National Academy of
            Sciences, USA
        ( D ) VOLUME: 84
        ( F ) PAGES: 9059-9063
        ( G ) DATE: 1987
        ( K ) RELEVANT RESIDUES IN SEQ ID NO: 77 :FROM 1 TO 14

( x i ) SEQUENCE DESCRIPTION: SEQ ID NO: 77:

AAAAGAAAAA GGAA 14

( 2 ) INFORMATION FOR SEQ ID NO:78:

( i ) SEQUENCE CHARACTERISTICS:
        ( A ) LENGTH: 14 bases
        ( B ) TYPE: Nucleic Acid
        ( C ) STRANDEDNESS: single stranded
        ( D ) TOPOLOGY: linear (ii) MOLECULE TYPE: other nucleic acid
    (A) DESCRIPTION: third strand derived from
        retinoblastoma sequence region in Seq ID No 77

(iii) HYPOTHETICAL: Yes (iv) ANTI-SENSE: No (x) PUBLICATION INFORMATION:
    (K) RELEVANT RESIDUES IN SEQ ID NO: 78 :FROM 1 TO 14

(xi) SEQUENCE DESCRIPTION: SEQ ID NO: 78 :

TTTTCTTTTT CCTT     14

(2) INFORMATION FOR SEQ ID NO:79:

(i) SEQUENCE CHARACTERISTICS:
    (A) LENGTH: 15 base pairs
    (B) TYPE: Nucleic Acid
    (C) STRANDEDNESS: double stranded
    (D) TOPOLOGY: linear (ii) MOLECULE TYPE: Genomic DNA
    (A) DESCRIPTION: retinoblastoma gene (Accession #
        M33647, J02994) nucleotides 1251 to 1265

(iii) HYPOTHETICAL: No (iv) ANTI-SENSE: No (vi) ORIGINAL SOURCE:
    (A) ORGANISM: Homo sapiens (vii) POSITION IN GENOME:
    (A) CHROMOSOME/SEGMENT: chromosome 13
    (B) MAP POSITION: 13q14.2

(x) PUBLICATION INFORMATION:
    (A) AUTHORS: Friend, S H, Horowitz, J M, Gerber, M R,
        Wang X F, Bogenmann, E, Li, F P, Weinberg,
        R A.
    (B) TITLE: Deletions of a DNA sequence
        in retinoblastomas and mesenchymal tumors:
        Organization of the sequence and its encoded
        protein
    (C) JOURNAL: Proceedings of the National Academy of
        Sciences, USA
    (D) VOLUME: 84
    (F) PAGES: 9059-9063
    (G) DATE: 1987
    (K) RELEVANT RESIDUES IN SEQ ID NO: 79 :FROM 1 TO 15

(xi) SEQUENCE DESCRIPTION: SEQ ID NO: 79:

GAAAAGAGTG AAGGA     15

(2) INFORMATION FOR SEQ ID NO:80:

(i) SEQUENCE CHARACTERISTICS:
    (A) LENGTH: 15 bases
    (B) TYPE: Nucleic Acid
    (C) STRANDEDNESS: single stranded
    (D) TOPOLOGY: linear (ii) MOLECULE TYPE: other nucleic acid
    (A) DESCRIPTION: third strand derived from
        retinoblastoma sequence region in Seq ID No 79

(iii) HYPOTHETICAL: Yes (iv) ANTI-SENSE: No (x) PUBLICATION INFORMATION:
    (K) RELEVANT RESIDUES IN SEQ ID NO: 80 :FROM 1 TO 15

(xi) SEQUENCE DESCRIPTION: SEQ ID NO: 80 :

CTTTTCTCGC TTCCT                                                                 15

( 2 ) INFORMATION FOR SEQ ID NO:81:

( i ) SEQUENCE CHARACTERISTICS:
           ( A ) LENGTH: 11 base pairs
           ( B ) TYPE: Nucleic Acid
           ( C ) STRANDEDNESS: double stranded
           ( D ) TOPOLOGY: linear ( i i ) MOLECULE TYPE: Genomic DNA
           ( A ) DESCRIPTION: retinoblastoma gene (Accession #
               M33647, J02994) nucleotides 1782 to 1792

( i i i ) HYPOTHETICAL: No ( i v ) ANTI-SENSE: No ( v i ) ORIGINAL SOURCE:
           ( A ) ORGANISM: Homo sapiens ( v i i ) POSITION IN GENOME:
           ( A ) CHROMOSOME/SEGMENT: chromosome 13
           ( B ) MAP POSITION: 13q14.2

( x ) PUBLICATION INFORMATION:
           ( A ) AUTHORS: Friend, S H, Horowitz, J M, Gerber, M R,
               Wang X F, Bogenmann, E, Li, F P, Weinberg,
               R A.
           ( B ) TITLE: Deletions of a DNA sequence
               in retinoblastomas and mesenchymal tumors:
               Organization of the sequence and its encoded
               protein
           ( C ) JOURNAL: Proceedings of the National Academy of
               Sciences, USA
           ( D ) VOLUME: 84
           ( F ) PAGES: 9059-9063
           ( G ) DATE: 1987
           ( K ) RELEVANT RESIDUES IN SEQ ID NO: 81 :FROM 1 TO 11

( x i ) SEQUENCE DESCRIPTION: SEQ ID NO: 81:

TCTTCCTCTC C                                                                     11

( 2 ) INFORMATION FOR SEQ ID NO:82:

( i ) SEQUENCE CHARACTERISTICS:
           ( A ) LENGTH: 11 bases
           ( B ) TYPE: Nucleic Acid
           ( C ) STRANDEDNESS: single stranded
           ( D ) TOPOLOGY: linear ( i i ) MOLECULE TYPE: other nucleic acid
           ( A ) DESCRIPTION: third strand derived from
               retinoblastoma sequence region in Seq ID No 81

( i i i ) HYPOTHETICAL: Yes ( i v ) ANTI-SENSE: No ( x ) PUBLICATION INFORMATION:
           ( K ) RELEVANT RESIDUES IN SEQ ID NO: 82 :FROM 1 TO 11

( x i ) SEQUENCE DESCRIPTION: SEQ ID NO: 82 :

CCTCTCCTTC T                                                                     11

( 2 ) INFORMATION FOR SEQ ID NO:83:

( i ) SEQUENCE CHARACTERISTICS:
           ( A ) LENGTH: 12 base pairs
           ( B ) TYPE: Nucleic Acid
           ( C ) STRANDEDNESS: double stranded
           ( D ) TOPOLOGY: linear ( i i ) MOLECULE TYPE: Genomic DNA
           ( A ) DESCRIPTION: retinoblastoma gene (Accession #

M33647, J02994) nucleotides 1842 to 1853

(iii) HYPOTHETICAL: No (iv) ANTI-SENSE: No (vi) ORIGINAL SOURCE:
    (A) ORGANISM: Homo sapiens (vii) POSITION IN GENOME:
    (A) CHROMOSOME/SEGMENT: chromosome 13
    (B) MAP POSITION: 13q14.2

(x) PUBLICATION INFORMATION:
    (A) AUTHORS: Friend, S H, Horowitz, J M, Gerber, M R,
        Wang X F, Bogenmann, E, Li, F P, Weinberg,
        R A.
    (B) TITLE: Deletions of a DNA sequence
        in retinoblastomas and mesenchymal tumors:
        Organization of the sequence and its encoded
        protein
    (C) JOURNAL: Proceedings of the National Academy of
        Sciences, USA
    (D) VOLUME: 84
    (F) PAGES: 9059-9063
    (G) DATE: 1987
    (K) RELEVANT RESIDUES IN SEQ ID NO: 83 :FROM 1 TO 12

(xi) SEQUENCE DESCRIPTION: SEQ ID NO: 83:

AAAGAAAAAA GG 12

(2) INFORMATION FOR SEQ ID NO:84:

(i) SEQUENCE CHARACTERISTICS:
        (A) LENGTH: 12 bases
        (B) TYPE: Nucleic Acid
        (C) STRANDEDNESS: single stranded
        (D) TOPOLOGY: linear (ii) MOLECULE TYPE: other nucleic acid
        (A) DESCRIPTION: third strand derived from
            retinoblastoma sequence region in Seq ID No 83

(iii) HYPOTHETICAL: Yes (iv) ANTI-SENSE: No (x) PUBLICATION INFORMATION:
        (K) RELEVANT RESIDUES IN SEQ ID NO: 84 :FROM 1 TO 12

(xi) SEQUENCE DESCRIPTION: SEQ ID NO: 84 :

TTTCTTTTTT CC 12

(2) INFORMATION FOR SEQ ID NO:85:

(i) SEQUENCE CHARACTERISTICS:
        (A) LENGTH: 12 base pairs
        (B) TYPE: Nucleic Acid
        (C) STRANDEDNESS: double stranded
        (D) TOPOLOGY: linear (ii) MOLECULE TYPE: Genomic DNA
        (A) DESCRIPTION: retinoblastoma gene (Accession #
            M33647, J02994) nucleotides 2236 to 2247

(iii) HYPOTHETICAL: No (iv) ANTI-SENSE: No (vi) ORIGINAL SOURCE:
        (A) ORGANISM: Homo sapiens (vii) POSITION IN GENOME:
        (A) CHROMOSOME/SEGMENT: chromosome 13
        (B) MAP POSITION: 13q14.2

(x) PUBLICATION INFORMATION:
  (A) AUTHORS: Friend, S H, Horowitz, J M, Gerber, M R,
       Wang X F, Bogenmann, E, Li, F P, Weinberg,
       R A.
  (B) TITLE: Deletions of a DNA sequence
       in retinoblastomas and mesenchymal tumors:
       Organization of the sequence and its encoded
       protein
  (C) JOURNAL: Proceedings of the National Academy of
       Sciences, USA
  (D) VOLUME: 84
  (F) PAGES: 9059-9063
  (G) DATE: 1987
  (K) RELEVANT RESIDUES IN SEQ ID NO: 85 :FROM 1 TO 12

(xi) SEQUENCE DESCRIPTION: SEQ ID NO: 85:

AAAGAAGAGG AG                                                                                     12

(2) INFORMATION FOR SEQ ID NO:86:

(i) SEQUENCE CHARACTERISTICS:
       (A) LENGTH: 12 bases
       (B) TYPE: Nucleic Acid
       (C) STRANDEDNESS: single stranded
       (D) TOPOLOGY: linear (ii) MOLECULE TYPE: other nucleic acid
       (A) DESCRIPTION: third strand derived from
            retinoblastoma sequence region in Seq ID No 85

(iii) HYPOTHETICAL: Yes (iv) ANTI-SENSE: No (x) PUBLICATION INFORMATION:
       (K) RELEVANT RESIDUES IN SEQ ID NO: 86 :FROM 1 TO 12

(xi) SEQUENCE DESCRIPTION: SEQ ID NO: 86 :

TTTCTTCTCC TC                                                                                     12

(2) INFORMATION FOR SEQ ID NO:87:

(i) SEQUENCE CHARACTERISTICS:
       (A) LENGTH: 15 base pairs
       (B) TYPE: Nucleic Acid
       (C) STRANDEDNESS: double stranded
       (D) TOPOLOGY: linear (ii) MOLECULE TYPE: Genomic DNA
       (A) DESCRIPTION: retinoblastoma gene (Accession #
            M33647, J02994) nucleotides 4062 to 4076

(iii) HYPOTHETICAL: No (iv) ANTI-SENSE: No (vi) ORIGINAL SOURCE:
       (A) ORGANISM: Homo sapiens (vii) POSITION IN GENOME:
       (A) CHROMOSOME/SEGMENT: chromosome 13
       (B) MAP POSITION: 13q14.2

(x) PUBLICATION INFORMATION:
       (A) AUTHORS: Friend, S H, Horowitz, J M, Gerber, M R,
            Wang X F, Bogenmann, E, Li, F P, Weinberg,
            R A.
       (B) TITLE: Deletions of a DNA sequence
            in retinoblastomas and mesenchymal tumors:
            Organization of the sequence and its encoded
            protein
       (C) JOURNAL: Proceedings of the National Academy of
            Sciences, USA
       (D) VOLUME: 84
       (F) PAGES: 9059-9063
       (G) DATE: 1987

( K ) RELEVANT RESIDUES IN SEQ ID NO: 87 :FROM 1 TO 15

( x i ) SEQUENCE DESCRIPTION: SEQ ID NO: 87:

CTTCTCCCCT CCCCT                                                                                    15

( 2 ) INFORMATION FOR SEQ ID NO:88:

( i ) SEQUENCE CHARACTERISTICS:
                ( A ) LENGTH: 15 bases
                ( B ) TYPE: Nucleic Acid
                ( C ) STRANDEDNESS: single stranded
                ( D ) TOPOLOGY: linear ( i i ) MOLECULE TYPE: other nucleic acid
                ( A ) DESCRIPTION: third strand derived from
                        retinoblastoma sequence region in Seq ID No 87

( i i i ) HYPOTHETICAL: Yes ( i v ) ANTI-SENSE: No ( x ) PUBLICATION INFORMATION:
                ( K ) RELEVANT RESIDUES IN SEQ ID NO: 88 :FROM 1 TO 15

( x i ) SEQUENCE DESCRIPTION: SEQ ID NO: 88 :

TCCCCTCCCC TCTTC                                                                                    15

( 2 ) INFORMATION FOR SEQ ID NO:89:

( i ) SEQUENCE CHARACTERISTICS:
                ( A ) LENGTH: 11 base pairs
                ( B ) TYPE: nucleic acid
                ( C ) STRANDEDNESS: double stranded
                ( D ) TOPOLOGY: linear ( i i ) MOLECULE TYPE: genomic DNA
                ( A ) DESCRIPTION: superoxide dismutase gene (accession #
                        J02947) nucleotides 21 to 31

( i i i ) HYPOTHETICAL: no ( i v ) ANTI-SENSE: no ( v i ) ORIGINAL SOURCE:
                ( A ) ORGANISM: Homo sapiens ( v i i ) POSITION IN GENOME:
                ( A ) CHROMOSOME/SEGMENT: chromosome 21
                ( B ) MAP POSITION: 21q22.1

( x ) PUBLICATION INFORMATION:
                ( A ) AUTHORS: Hjalmarsson, K, Marklund, S L,
                        Engstroem, A, Edlund, T.
                ( B ) TITLE: Isolation and sequence of
                        complementary dna encoding human extracellular-
                        superoxide dismutase
                ( C ) JOURNAL: Proceedings of the National Academy of
                        Sciences, USA
                ( D ) VOLUME: 84
                ( F ) PAGES: 6340-6344
                ( G ) DATE: 1987
                ( K ) RELEVANT RESIDUES IN SEQ ID NO: 89 :FROM 1 TO 11

( x i ) SEQUENCE DESCRIPTION: SEQ ID NO: 89:

AGGAGAGAAA G                                                                                        11

( 2 ) INFORMATION FOR SEQ ID NO:90:

( i ) SEQUENCE CHARACTERISTICS:
                ( A ) LENGTH: 11 bases
                ( B ) TYPE: nucleic acid
                ( C ) STRANDEDNESS: single stranded
                ( D ) TOPOLOGY: linear (  i  i  ) MOLECULE TYPE: other nucleic acid
    ( A ) DESCRIPTION: third strand derived from superoxide
        dismutase sequence region in Seq ID No 89

(  i  i  i  ) HYPOTHETICAL: yes (  i  v  ) ANTI-SENSE: no ( x ) PUBLICATION INFORMATION:
    ( K ) RELEVANT RESIDUES IN SEQ ID NO: 90 :FROM 1 TO 11

( x i ) SEQUENCE DESCRIPTION: SEQ ID NO: 90 :

TCCTCTCTTT C                                                                                            11

( 2 ) INFORMATION FOR SEQ ID NO:91:

( i ) SEQUENCE CHARACTERISTICS:
        ( A ) LENGTH: 17 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: superoxide dismutase gene (accession #
            J02947) nucleotides 1094 to 1110

( i i i ) HYPOTHETICAL: no ( i v ) ANTI-SENSE: no ( v i ) ORIGINAL SOURCE:
        ( A ) ORGANISM: Homo sapiens ( v i i ) POSITION IN GENOME:
        ( A ) CHROMOSOME/SEGMENT: chromosome 21
        ( B ) MAP POSITION: 21q22.1

( x ) PUBLICATION INFORMATION:
        ( A ) AUTHORS: Hjalmarsson, K, Marklund, S L,
            Engstroem, A, Edlund, T.
        ( B ) TITLE: Isolation and sequence of
            complementary dna encoding human extracellular-
            superoxide dismutase
        ( C ) JOURNAL: Proceedings of the National Academy of
            Sciences, USA
        ( D ) VOLUME: 84
        ( F ) PAGES: 6340-6344
        ( G ) DATE: 1987
        ( K ) RELEVANT RESIDUES IN SEQ ID NO: 91 :FROM 1 TO 17

( x i ) SEQUENCE DESCRIPTION: SEQ ID NO: 91:

CCCTCCTTCC CCACCCC                                                                                      17

( 2 ) INFORMATION FOR SEQ ID NO:92:

( i ) SEQUENCE CHARACTERISTICS:
        ( A ) LENGTH: 17 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from superoxide
            dismutase sequence region in Seq ID No 91

( i i i ) HYPOTHETICAL: yes ( i v ) ANTI-SENSE: no ( x ) PUBLICATION INFORMATION:
        ( K ) RELEVANT RESIDUES IN SEQ ID NO: 92 :FROM 1 TO 17

( x i ) SEQUENCE DESCRIPTION: SEQ ID NO: 92 :

CCCCGCCCCT TCCTCCC                                                                                      17

( 2 ) INFORMATION FOR SEQ ID NO:93:

( i ) SEQUENCE CHARACTERISTICS:
        ( A ) LENGTH: 14 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: superoxide dismutase gene (accession #
            J02947) nucleotides 1145 to 1158

( i i i ) HYPOTHETICAL: no ( i v ) ANTI-SENSE: no ( v i ) ORIGINAL SOURCE:
        ( A ) ORGANISM: Homo sapiens ( v i i ) POSITION IN GENOME:
        ( A ) CHROMOSOME/SEGMENT: chromosome 21
        ( B ) MAP POSITION: 21q22.1

( x ) PUBLICATION INFORMATION:
        ( A ) AUTHORS: Hjalmarsson, K, Marklund, S L,
            Engstroem, A, Edlund, T.
        ( B ) TITLE: Isolation and sequence of
            complementary dna encoding human extracellular-
            superoxide dismutase
        ( C ) JOURNAL: Proceedings of the National Academy of
            Sciences, USA
        ( D ) VOLUME: 84
        ( F ) PAGES: 6340-6344
        ( G ) DATE: 1987
        ( K ) RELEVANT RESIDUES IN SEQ ID NO: 93 :FROM 1 TO 14

( x i ) SEQUENCE DESCRIPTION: SEQ ID NO: 93:

TCTTCCCCCT TCCC        14

( 2 ) INFORMATION FOR SEQ ID NO:94:

( i ) SEQUENCE CHARACTERISTICS:
        ( A ) LENGTH: 14 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from superoxide
            dismutase sequence region in Seq ID No 93

( i i i ) HYPOTHETICAL: yes ( i v ) ANTI-SENSE: no ( x ) PUBLICATION INFORMATION:
        ( K ) RELEVANT RESIDUES IN SEQ ID NO: 94 :FROM 1 TO 14

( x i ) SEQUENCE DESCRIPTION: SEQ ID NO: 94 :

CCCTTCCCCC TTCT        14

( 2 ) INFORMATION FOR SEQ ID NO:95:

( i ) SEQUENCE CHARACTERISTICS:
        ( A ) LENGTH: 17 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: superoxide dismutase gene (accession #
            J02947) nucleotides 1212 to 1228

( i i i ) HYPOTHETICAL: no ( i v ) ANTI-SENSE: no ( v i ) ORIGINAL SOURCE:
    ( A ) ORGANISM: Homo sapiens ( v i i ) POSITION IN GENOME:
    ( A ) CHROMOSOME/SEGMENT: chromosome 21
    ( B ) MAP POSITION: 21q22.1

( x ) PUBLICATION INFORMATION:
    ( A ) AUTHORS: Hjalmarsson, K, Marklund, S L,
        Engstroem, A, Edlund, T.
    ( B ) TITLE: Isolation and sequence of
        complementary dna encoding human extracellular-
        superoxide dismutase
    ( C ) JOURNAL: Proceedings of the National Academy of
        Sciences, USA
    ( D ) VOLUME: 84
    ( F ) PAGES: 6340-6344
    ( G ) DATE: 1987
    ( K ) RELEVANT RESIDUES IN SEQ ID NO: 95 :FROM 1 TO 17

( x i ) SEQUENCE DESCRIPTION: SEQ ID NO: 95:

TCCCCCCACC CCTCCCC                                                                 17

( 2 ) INFORMATION FOR SEQ ID NO:96:

( i ) SEQUENCE CHARACTERISTICS:
        ( A ) LENGTH: 17 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from superoxide
        dismutase sequence region in Seq ID No 95

( i i i ) HYPOTHETICAL: yes ( i v ) ANTI-SENSE: no ( x ) PUBLICATION INFORMATION:
        ( K ) RELEVANT RESIDUES IN SEQ ID NO: 96 :FROM 1 TO 17

( x i ) SEQUENCE DESCRIPTION: SEQ ID NO: 96 :

CCCCTCCCCG CCCCCCT                                                                 17

( 2 ) INFORMATION FOR SEQ ID NO:97:

( i ) SEQUENCE CHARACTERISTICS:
        ( A ) LENGTH: 14 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: prealbumin gene exons 1 and 2
        (accession # M15515) nucleotides 250 to 263

( i i i ) HYPOTHETICAL: no ( i v ) ANTI-SENSE: no ( v i ) ORIGINAL SOURCE:
        ( A ) ORGANISM: Homo sapiens ( v i i ) POSITION IN GENOME:
        ( A ) CHROMOSOME/SEGMENT: chromosome 18
        ( B ) MAP POSITION: 18q11.2-12.1

( x ) PUBLICATION INFORMATION:
        ( A ) AUTHORS: Maeda, S, Mita, S, Araki, S, Shimada,
        K.
        ( B ) TITLE: Structure and expression of
        the mutant prealbumin gene associated with
        familial amyloidotic polyneuropathy (C) JOURNAL: Molecular Biological Medicine
(D) VOLUME: 3
(F) PAGES: 329-338
(G) DATE: 1986
(K) RELEVANT RESIDUES IN SEQ ID NO: 97 :FROM 1 TO 14

(xi) SEQUENCE DESCRIPTION: SEQ ID NO: 97:

GAGGGAGGAA AAAA 14

(2) INFORMATION FOR SEQ ID NO:98:

(i) SEQUENCE CHARACTERISTICS:
(A) LENGTH: 14 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from superoxide
dismutase sequence region in Seq ID No 97

(iii) HYPOTHETICAL: yes (iv) ANTI-SENSE: no (x) PUBLICATION INFORMATION:
(K) RELEVANT RESIDUES IN SEQ ID NO: 98 :FROM 1 TO 14

(xi) SEQUENCE DESCRIPTION: SEQ ID NO: 98 :

CTCCCTCCTT TTTT 14

(2) INFORMATION FOR SEQ ID NO:99:

(i) SEQUENCE CHARACTERISTICS:
(A) LENGTH: 11 base pairs
(B) TYPE: nucleic acid
(C) STRANDEDNESS: double stranded
(D) TOPOLOGY: linear (ii) MOLECULE TYPE: genomic DNA
(A) DESCRIPTION: prealbumin gene exons 1 and 2
(accession # M15515) nucleotides 1344 to 1354

(iii) HYPOTHETICAL: no (iv) ANTI-SENSE: no (vi) ORIGINAL SOURCE:
(A) ORGANISM: Homo sapiens (vii) POSITION IN GENOME:
(A) CHROMOSOME/SEGMENT: chromosome 18
(B) MAP POSITION: 18q11.2-12.1

(x) PUBLICATION INFORMATION:
(A) AUTHORS: Maeda, S, Mita, S, Araki, S, Shimada,
K.
(B) TITLE: Structure and expression of
the mutant prealbumin gene associated with
familial amyloidotic polyneuropathy
(C) JOURNAL: Molecular Biological Medicine
(D) VOLUME: 3
(F) PAGES: 329-338
(G) DATE: 1986
(K) RELEVANT RESIDUES IN SEQ ID NO: 99 :FROM 1 TO 11

(xi) SEQUENCE DESCRIPTION: SEQ ID NO: 99:

TTTTCTCCCT T 11

(2) INFORMATION FOR SEQ ID NO:100:

(i) SEQUENCE CHARACTERISTICS:
(A) LENGTH: 11 bases
(B) TYPE: nucleic acid (C) STRANDEDNESS: single stranded
(D) TOPOLOGY: linear (ii) MOLECULE TYPE: other nucleic acid
(A) DESCRIPTION: third strand derived from superoxide dismutase sequence region in Seq ID No 99

(iii) HYPOTHETICAL: yes (iv) ANTI-SENSE: no (x) PUBLICATION INFORMATION:
(K) RELEVANT RESIDUES IN SEQ ID NO: 100 :FROM 1 TO 11

(xi) SEQUENCE DESCRIPTION: SEQ ID NO: 100:

TTCCCTCTTT T　　　　　　　　　　　　　　　　　　　　　　　　　　11

(2) INFORMATION FOR SEQ ID NO:101:

(i) SEQUENCE CHARACTERISTICS:
(A) LENGTH: 10 base pairs
(B) TYPE: nucleic acid
(C) STRANDEDNESS: double stranded
(D) TOPOLOGY: linear (ii) MOLECULE TYPE: genomic DNA
(A) DESCRIPTION: prealbumin gene exon 3 (accession # M15516) nucleotides 166 to 175

(iii) HYPOTHETICAL: no (iv) ANTI-SENSE: no (vi) ORIGINAL SOURCE:
(A) ORGANISM: Homo sapiens (vii) POSITION IN GENOME:
(A) CHROMOSOME/SEGMENT: chromosome 18
(B) MAP POSITION: 18q11.2-12.1

(x) PUBLICATION INFORMATION:
(A) AUTHORS: Maeda, S, Mita, S, Araki, S, Shimada, K.
(B) TITLE: Structure and expression of the mutant prealbumin gene associated with familial amyloidotic polyneuropathy
(C) JOURNAL: Molecular Biological Medicine
(D) VOLUME: 3
(F) PAGES: 329-338
(G) DATE: 1986
(K) RELEVANT RESIDUES IN SEQ ID NO: 101 :FROM 1 TO 10

(xi) SEQUENCE DESCRIPTION: SEQ ID NO: 101:

TTCTCTTCTT　　　　　　　　　　　　　　　　　　　　　　　　　　10

(2) INFORMATION FOR SEQ ID NO:102:

(i) SEQUENCE CHARACTERISTICS:
(A) LENGTH: 10 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from superoxide dismutase sequence region in Seq ID No 101

(iii) HYPOTHETICAL: yes (iv) ANTI-SENSE: no (x) PUBLICATION INFORMATION:
(K) RELEVANT RESIDUES IN SEQ ID NO: 102 :FROM 1 TO 10

(xi) SEQUENCE DESCRIPTION: SEQ ID NO: 102:

TTCTTCTCTT 10

( 2 ) INFORMATION FOR SEQ ID NO:103:

( i ) SEQUENCE CHARACTERISTICS:
        ( A ) LENGTH: 11 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: prealbumin gene exon 3 (accession #
            M15516) nucleotides 179 to 189

( i i i ) HYPOTHETICAL: no ( i v ) ANTI-SENSE: no ( v i ) ORIGINAL SOURCE:
        ( A ) ORGANISM: Homo sapiens ( v i i ) POSITION IN GENOME:
        ( A ) CHROMOSOME/SEGMENT: chromosome 18
        ( B ) MAP POSITION: 18q11.2-12.1

( x ) PUBLICATION INFORMATION:
        ( A ) AUTHORS: Maeda, S, Mita, S, Araki, S, Shimada,
            K.
        ( B ) TITLE: Structure and expression of
            the mutant prealbumin gene associated with
            familial amyloidotic polyneuropathy
        ( C ) JOURNAL: Molecular Biological Medicine
        ( D ) VOLUME: 3
        ( F ) PAGES: 329-338
        ( G ) DATE: 1986
        ( K ) RELEVANT RESIDUES IN SEQ ID NO: 103 :FROM 1 TO 11

( x i ) SEQUENCE DESCRIPTION: SEQ ID NO: 103 :

AGAGAAAAAA A 11

( 2 ) INFORMATION FOR SEQ ID NO:104:

( i ) SEQUENCE CHARACTERISTICS:
        ( A ) LENGTH: 11 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from superoxide
            dismutase sequence region in Seq ID No 103

( i i i ) HYPOTHETICAL: yes ( i v ) ANTI-SENSE: no ( x ) PUBLICATION INFORMATION:
        ( K ) RELEVANT RESIDUES IN SEQ ID NO: 104 :FROM 1 TO 11

( x i ) SEQUENCE DESCRIPTION: SEQ ID NO: 104 :

TCTCTTTTTT T 11

( 2 ) INFORMATION FOR SEQ ID NO:105:

( i ) SEQUENCE CHARACTERISTICS:
        ( A ) LENGTH: 11 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: prealbumin gene exon 3 (accession #
            M15516) nucleotides 658 to 668

( i i i ) HYPOTHETICAL: no (iv) ANTI-SENSE: no (vi) ORIGINAL SOURCE:
    (A) ORGANISM: Homo sapiens (vii) POSITION IN GENOME:
    (A) CHROMOSOME/SEGMENT: chromosome 18
    (B) MAP POSITION: 18q11.2-12.1

(x) PUBLICATION INFORMATION:
    (A) AUTHORS: Maeda, S, Mita, S, Araki, S, Shimada, K.
    (B) TITLE: Structure and expression of the mutant prealbumin gene associated with familial amyloidotic polyneuropathy
    (C) JOURNAL: Molecular Biological Medicine
    (D) VOLUME: 3
    (F) PAGES: 329-338
    (G) DATE: 1986
    (K) RELEVANT RESIDUES IN SEQ ID NO: 105 :FROM 1 TO 11

(xi) SEQUENCE DESCRIPTION: SEQ ID NO: 105 :

TTCCTTTCC T            11

(2) INFORMATION FOR SEQ ID NO:106:

(i) SEQUENCE CHARACTERISTICS:
        (A) LENGTH: 11 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from superoxide dismutase sequence region in Seq ID No 105

(iii) HYPOTHETICAL: yes (iv) ANTI-SENSE: no (x) PUBLICATION INFORMATION:
        (K) RELEVANT RESIDUES IN SEQ ID NO: 106 :FROM 1 TO 11

(xi) SEQUENCE DESCRIPTION: SEQ ID NO: 106 :

TCCTTTCCCT T            11

(2) INFORMATION FOR SEQ ID NO:107:

(i) SEQUENCE CHARACTERISTICS:
        (A) LENGTH: 12 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: prealbumin gene exon 4 (accession # M15517) nucleotides 133 to 144

(iii) HYPOTHETICAL: no (iv) ANTI-SENSE: no (vi) ORIGINAL SOURCE:
        (A) ORGANISM: Homo sapiens (vii) POSITION IN GENOME:
        (A) CHROMOSOME/SEGMENT: chromosome 18
        (B) MAP POSITION: 18q11.2-12.1

(x) PUBLICATION INFORMATION:
        (A) AUTHORS: Maeda, S, Mita, S, Araki, S, Shimada, K.
        (B) TITLE: Structure and expression of the mutant prealbumin gene associated with familial amyloidotic polyneuropathy (C) JOURNAL: Molecular Biological Medicine
(D) VOLUME: 3
(F) PAGES: 329-338
(G) DATE: 1986
(K) RELEVANT RESIDUES IN SEQ ID NO: 107 :FROM 1 TO 12

(xi) SEQUENCE DESCRIPTION: SEQ ID NO: 107 :

CTTTTCTTCT TC 12

(2) INFORMATION FOR SEQ ID NO:108:

(i) SEQUENCE CHARACTERISTICS:
(A) LENGTH: 12 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from superoxide
dismutase sequence region in Seq ID No 107

(iii) HYPOTHETICAL: yes (iv) ANTI-SENSE: no (x) PUBLICATION INFORMATION:
(K) RELEVANT RESIDUES IN SEQ ID NO: 108 :FROM 1 TO 12

(xi) SEQUENCE DESCRIPTION: SEQ ID NO: 108 :

CTTCTTCTTT TC 12

(2) INFORMATION FOR SEQ ID NO:109:

(i) SEQUENCE CHARACTERISTICS:
(A) LENGTH: 15 base pairs
(B) TYPE: nucleic acid
(C) STRANDEDNESS: double stranded
(D) TOPOLOGY: linear (ii) MOLECULE TYPE: genomic DNA
(A) DESCRIPTION: prealbumin gene exon 4 (accession #
M15517) nucleotides 166 to 180

(iii) HYPOTHETICAL: no (iv) ANTI-SENSE: no (vi) ORIGINAL SOURCE:
(A) ORGANISM: Homo sapiens (vii) POSITION IN GENOME:
(A) CHROMOSOME/SEGMENT: chromosome 18
(B) MAP POSITION: 18q11.2-12.1

(x) PUBLICATION INFORMATION:
(A) AUTHORS: Maeda, S, Mita, S, Araki, S, Shimada,
K.
(B) TITLE: Structure and expression of
the mutant prealbumin gene associated with
familial amyloidotic polyneuropathy
(C) JOURNAL: Molecular Biological Medicine
(D) VOLUME: 3
(F) PAGES: 329-338
(G) DATE: 1986
(K) RELEVANT RESIDUES IN SEQ ID NO: 109 :FROM 1 TO 15

(xi) SEQUENCE DESCRIPTION: SEQ ID NO: 109 :

AGGAGGGTGG GGGAA 15

(2) INFORMATION FOR SEQ ID NO:110:

(i) SEQUENCE CHARACTERISTICS:
(A) LENGTH: 15 bases
(B) TYPE: nucleic acid (C) STRANDEDNESS: single stranded
(D) TOPOLOGY: linear (ii) MOLECULE TYPE: other nucleic acid
(A) DESCRIPTION: third strand derived from superoxide dismutase sequence region in Seq ID No 109

(iii) HYPOTHETICAL: yes (iv) ANTI-SENSE: no (x) PUBLICATION INFORMATION:
(K) RELEVANT RESIDUES IN SEQ ID NO: 110 :FROM 1 TO 15

(xi) SEQUENCE DESCRIPTION: SEQ ID NO: 110 :

TCCTCCCGCC CCCTT    15

(2) INFORMATION FOR SEQ ID NO:111:

(i) SEQUENCE CHARACTERISTICS:
(A) LENGTH: 12 base pairs
(B) TYPE: nucleic acid
(C) STRANDEDNESS: double stranded
(D) TOPOLOGY: linear (ii) MOLECULE TYPE: genomic DNA
(A) DESCRIPTION: prealbumin gene exon 4 (accession # M15517) nucleotides 391 to 402

(iii) HYPOTHETICAL: no (iv) ANTI-SENSE: no (vi) ORIGINAL SOURCE:
(A) ORGANISM: Homo sapiens (vii) POSITION IN GENOME:
(A) CHROMOSOME/SEGMENT: chromosome 18
(B) MAP POSITION: 18q11.2-12.1

(x) PUBLICATION INFORMATION:
(A) AUTHORS: Maeda, S, Mita, S, Araki, S, Shimada, K.
(B) TITLE: Structure and expression of the mutant prealbumin gene associated with familial amyloidotic polyneuropathy
(C) JOURNAL: Molecular Biological Medicine
(D) VOLUME: 3
(F) PAGES: 329-338
(G) DATE: 1986
(K) RELEVANT RESIDUES IN SEQ ID NO: 111 :FROM 1 TO 12

(xi) SEQUENCE DESCRIPTION: SEQ ID NO: 111 :

CCTTTTTTTT CT    12

(2) INFORMATION FOR SEQ ID NO:112:

(i) SEQUENCE CHARACTERISTICS:
(A) LENGTH: 12 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from superoxide dismutase sequence region in Seq ID No 111

(iii) HYPOTHETICAL: yes (iv) ANTI-SENSE: no (x) PUBLICATION INFORMATION:
(K) RELEVANT RESIDUES IN SEQ ID NO: 112 :FROM 1 TO 12

(xi) SEQUENCE DESCRIPTION: SEQ ID NO: 112 :

TCTTTTTTTT CC 12

(2) INFORMATION FOR SEQ ID NO:113:

(i) SEQUENCE CHARACTERISTICS:
        (A) LENGTH: 13 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: prealbumin gene exon 4 (accession # M15517) nucleotides 1020 to 1032

(iii) HYPOTHETICAL: no (iv) ANTI-SENSE: no (vi) ORIGINAL SOURCE:
        (A) ORGANISM: Homo sapiens (vii) POSITION IN GENOME:
        (A) CHROMOSOME/SEGMENT: chromosome 18
        (B) MAP POSITION: 18q11.2-12.1

(x) PUBLICATION INFORMATION:
        (A) AUTHORS: Maeda, S, Mita, S, Araki, S, Shimada, K.
        (B) TITLE: Structure and expression of the mutant prealbumin gene associated with familial amyloidotic polyneuropathy
        (C) JOURNAL: Molecular Biological Medicine
        (D) VOLUME: 3
        (F) PAGES: 329-338
        (G) DATE: 1986
        (K) RELEVANT RESIDUES IN SEQ ID NO: 113 :FROM 1 TO 13

(xi) SEQUENCE DESCRIPTION: SEQ ID NO: 113 :

AAAAAAAGA GAA 13

(2) INFORMATION FOR SEQ ID NO:114:

(i) SEQUENCE CHARACTERISTICS:
        (A) LENGTH: 13 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from superoxide dismutase sequence region in Seq ID No 113

(iii) HYPOTHETICAL: yes (iv) ANTI-SENSE: no (x) PUBLICATION INFORMATION:
        (K) RELEVANT RESIDUES IN SEQ ID NO: 114 :FROM 1 TO 13

(xi) SEQUENCE DESCRIPTION: SEQ ID NO: 114 :

TTTTTTTCT CTT 13

(2) INFORMATION FOR SEQ ID NO:115:

(i) SEQUENCE CHARACTERISTICS:
        (A) LENGTH: 21 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: beta-globin gene (accession #V00499) nucleotides 742 to 762

(iii) HYPOTHETICAL: no (iv) ANTI-SENSE: no (vi) ORIGINAL SOURCE:
    (A) ORGANISM: Homo sapiens (x) PUBLICATION INFORMATION:
    (A) AUTHORS: Lawn, R M, Efstratiadis, A, O'Connell,
        C, Maniatis, T.
    (B) TITLE: The nucleotide sequence of
        the human beta-globin gene
    (C) JOURNAL: Cell
    (D) VOLUME: 2178
    (F) PAGES: 647-651
    (G) DATE: 1980
    (K) RELEVANT RESIDUES IN SEQ ID NO: 115 :FROM 1 TO 21

(xi) SEQUENCE DESCRIPTION: SEQ ID NO: 115 :

TTTCTTTCC CCTTCTTTTC T                        21

(2) INFORMATION FOR SEQ ID NO:116:

(i) SEQUENCE CHARACTERISTICS:
        (A) LENGTH: 21 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from beta-globin
        sequence region in Seq ID No 115

(iii) HYPOTHETICAL: yes (iv) ANTI-SENSE: no (x) PUBLICATION INFORMATION:
        (K) RELEVANT RESIDUES IN SEQ ID NO: 116 :FROM 1 TO 21

(xi) SEQUENCE DESCRIPTION: SEQ ID NO: 116 :

TCTTTTCTTC CCCTTTCTTT T                       21

(2) INFORMATION FOR SEQ ID NO:117:

(i) SEQUENCE CHARACTERISTICS:
        (A) LENGTH: 21 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: beta-globin gene (accession #V00499)
        nucleotides 918 to 938

(iii) HYPOTHETICAL: no (iv) ANTI-SENSE: no (vi) ORIGINAL SOURCE:
        (A) ORGANISM: Homo sapiens (x) PUBLICATION INFORMATION:
        (A) AUTHORS: Lawn, R M, Efstratiadis, A, O'Connell,
        C, Maniatis, T.
        (B) TITLE: The nucleotide sequence of
        the human beta-globin gene
        (C) JOURNAL: Cell
        (D) VOLUME: 21
        (F) PAGES: 647-651
        (G) DATE: 1980
        (K) RELEVANT RESIDUES IN SEQ ID NO: 117 :FROM 1 TO 21

(xi) SEQUENCE DESCRIPTION: SEQ ID NO: 117 :

CTTTCTTTTT TTTCTTCTC C                        21

( 2 ) INFORMATION FOR SEQ ID NO:118:

( i ) SEQUENCE CHARACTERISTICS:
        ( A ) LENGTH: 21 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from beta-globin
            sequence region in Seq ID No 117

( i i i ) HYPOTHETICAL: yes ( i v ) ANTI-SENSE: no ( x ) PUBLICATION INFORMATION:
        ( K ) RELEVANT RESIDUES IN SEQ ID NO: 118 :FROM 1 TO 21

( x i ) SEQUENCE DESCRIPTION: SEQ ID NO: 118 :

CCTCTTCTTT TTTTTCTTT C     21

( 2 ) INFORMATION FOR SEQ ID NO:119:

( i ) SEQUENCE CHARACTERISTICS:
        ( A ) LENGTH: 12 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: beta-globin gene (accession #V00499)
            nucleotides 1284 to 1295

( i i i ) HYPOTHETICAL: no ( i v ) ANTI-SENSE: no ( v i ) ORIGINAL SOURCE:
        ( A ) ORGANISM: Homo sapiens ( x ) PUBLICATION INFORMATION:
        ( A ) AUTHORS: Lawn, R M, Efstratiadis, A, O'Connell,
            C, Maniatis, T.
        ( B ) TITLE: The nucleotide sequence of
            the human beta-globin gene
        ( C ) JOURNAL: Cell
        ( D ) VOLUME: 21
        ( F ) PAGES: 647-651
        ( G ) DATE: 1980
        ( K ) RELEVANT RESIDUES IN SEQ ID NO: 119 :FROM 1 TO 12

( x i ) SEQUENCE DESCRIPTION: SEQ ID NO: 119 :

TCTCTTTCTT TC     12

( 2 ) INFORMATION FOR SEQ ID NO:120:

( i ) SEQUENCE CHARACTERISTICS:
        ( A ) LENGTH: 12 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from beta-globin
            sequence region in Seq ID No 119

( i i i ) HYPOTHETICAL: yes ( i v ) ANTI-SENSE: no ( x ) PUBLICATION INFORMATION:
        ( K ) RELEVANT RESIDUES IN SEQ ID NO: 120 :FROM 1 TO 12

( x i ) SEQUENCE DESCRIPTION: SEQ ID NO: 120 :

CTTTCTTTCT CT    12

(2) INFORMATION FOR SEQ ID NO:121:

(i) SEQUENCE CHARACTERISTICS:
        (A) LENGTH: 11 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: alpha-2-globin gene (accession #
            V00516) nucleotides 139 to 149

(iii) HYPOTHETICAL: no (iv) ANTI-SENSE: no (vi) ORIGINAL SOURCE:
        (A) ORGANISM: Homo sapiens (x) PUBLICATION INFORMATION:
        (A) AUTHORS: Orkin, S H, Goff, S C, Hechtman, R L.
        (B) TITLE: Mutation in an intervening
            sequence splice junction in man
        (C) JOURNAL: Proceedings of the National Academy of
            Sciences, USA
        (D) VOLUME: 78
        (F) PAGES: 5041-5045
        (G) DATE: 1981
        (K) RELEVANT RESIDUES IN SEQ ID NO: 121 :FROM 1 TO 11

(xi) SEQUENCE DESCRIPTION: SEQ ID NO: 121 :

CTCCCTCCCC T    11

(2) INFORMATION FOR SEQ ID NO:122:

(i) SEQUENCE CHARACTERISTICS:
        (A) LENGTH: 11 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from alpha-2-
            globin sequence region in Seq ID No 121

(iii) HYPOTHETICAL: yes (iv) ANTI-SENSE: no (x) PUBLICATION INFORMATION:
        (K) RELEVANT RESIDUES IN SEQ ID NO: 122 :FROM 1 TO 11

(xi) SEQUENCE DESCRIPTION: SEQ ID NO: 122 :

TCCCCTCCCT C    11

(2) INFORMATION FOR SEQ ID NO:123:

(i) SEQUENCE CHARACTERISTICS:
        (A) LENGTH: 11 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: alpha-2-globin gene (accession #
            V00516) nucleotides 580 to 590

(iii) HYPOTHETICAL: no (iv) ANTI-SENSE: no (vi) ORIGINAL SOURCE:

(A) ORGANISM: Homo sapiens (x) PUBLICATION INFORMATION:
                (A) AUTHORS: Orkin, S H, Goff, S C, Hechtman, R L.
                (B) TITLE: Mutation in an intervening
                    sequence splice junction in man
                (C) JOURNAL: Proceedings of the National Academy of
                    Sciences, USA
                (D) VOLUME: 78
                (F) PAGES: 5041-5045
                (G) DATE: 1981
                (K) RELEVANT RESIDUES IN SEQ ID NO: 123 :FROM 1 TO 11

(xi) SEQUENCE DESCRIPTION: SEQ ID NO: 123 :

CCCTCTTCTC T                                                                                    11

(2) INFORMATION FOR SEQ ID NO:124:

(i) SEQUENCE CHARACTERISTICS:
                (A) LENGTH: 11 bases
                (B) TYPE: nucleic acid
                (C) STRANDEDNESS: single stranded
                (D) TOPOLOGY: linear (ii) MOLECULE TYPE: other nucleic acid
                (A) DESCRIPTION: third strand derived from alpha-2-
                    globin sequence region in Seq ID No 123

(iii) HYPOTHETICAL: yes (iv) ANTI-SENSE: no (x) PUBLICATION INFORMATION:
                (K) RELEVANT RESIDUES IN SEQ ID NO: 124 :FROM 1 TO 11

(xi) SEQUENCE DESCRIPTION: SEQ ID NO: 124 :

TCTCTTCTCC C                                                                                    11

(2) INFORMATION FOR SEQ ID NO:125:

(i) SEQUENCE CHARACTERISTICS:
                (A) LENGTH: 16 base pairs
                (B) TYPE: nucleic acid
                (C) STRANDEDNESS: double stranded
                (D) TOPOLOGY: linear (ii) MOLECULE TYPE: genomic DNA
                (A) DESCRIPTION: alpha-2-globin gene (accession #
                    V00516) nucleotides 775 to 790

(iii) HYPOTHETICAL: no (iv) ANTI-SENSE: no (vi) ORIGINAL SOURCE:
                (A) ORGANISM: Homo sapiens (x) PUBLICATION INFORMATION:
                (A) AUTHORS: Orkin, S H, Goff, S C, Hechtman, R L.
                (B) TITLE: Mutation in an intervening
                    sequence splice junction in man
                (C) JOURNAL: Proceedings of the National Academy of
                    Sciences, USA
                (D) VOLUME: 78
                (F) PAGES: 5041-5045
                (G) DATE: 1981
                (K) RELEVANT RESIDUES IN SEQ ID NO: 125 :FROM 1 TO 16

(xi) SEQUENCE DESCRIPTION: SEQ ID NO: 125 :

CCCTCCTCCC CTCCTT                                                                               16

(2) INFORMATION FOR SEQ ID NO:126:

(i) SEQUENCE CHARACTERISTICS:

(A) LENGTH: 16 bases
(B) TYPE: nucleic acid
(C) STRANDEDNESS: single stranded
(D) TOPOLOGY: linear (i i) MOLECULE TYPE: other nucleic acid
(A) DESCRIPTION: third strand derived from alpha-2-
globin sequence region in Seq ID No 125

(i i i) HYPOTHETICAL: yes (i v) ANTI-SENSE: no (x) PUBLICATION INFORMATION:
(K) RELEVANT RESIDUES IN SEQ ID NO: 126 :FROM 1 TO 16

(x i) SEQUENCE DESCRIPTION: SEQ ID NO: 126 :

TTCTCCCCT CCTCCC    16

(2) INFORMATION FOR SEQ ID NO:127:

(i) SEQUENCE CHARACTERISTICS:
(A) LENGTH: 17 base pairs
(B) TYPE: nucleic acid
(C) STRANDEDNESS: double stranded
(D) TOPOLOGY: linear (i i) MOLECULE TYPE: genomic DNA
(A) DESCRIPTION: alpha-1-globin gene (accession #
V00491) nucleotides 827 to 843

(i i i) HYPOTHETICAL: no (i v) ANTI-SENSE: no (v i) ORIGINAL SOURCE:
(A) ORGANISM: Homo sapiens (x) PUBLICATION INFORMATION:
(A) AUTHORS: Michelson, A M, Orkin, S H.
(B) TITLE: The 3'untranslated regions
of the duplicated human alpha-globin genes are
unexpectedly divergent
(C) JOURNAL: Cell
(D) VOLUME: 22
(F) PAGES: 371-377
(G) DATE: 1980
(K) RELEVANT RESIDUES IN SEQ ID NO: 127 :FROM 1 TO 17

(x i) SEQUENCE DESCRIPTION: SEQ ID NO: 127 :

CCCCTCCTCC CCTTCCT    17

(2) INFORMATION FOR SEQ ID NO:128:

(i) SEQUENCE CHARACTERISTICS:
(A) LENGTH: 17 bases
(B) TYPE: nucleic acid
(C) STRANDEDNESS: single stranded
(D) TOPOLOGY: linear (i i) MOLECULE TYPE: other nucleic acid
(A) DESCRIPTION: third strand derived from alpha-1-
globin sequence region in Seq ID No 127

(i i i) HYPOTHETICAL: yes (i v) ANTI-SENSE: no (x) PUBLICATION INFORMATION:
(K) RELEVANT RESIDUES IN SEQ ID NO: 128 :FROM 1 TO 17

(x i) SEQUENCE DESCRIPTION: SEQ ID NO: 128 :

TCCTTCCCCT CCTCCCC    17

( 2 ) INFORMATION FOR SEQ ID NO:129:

( i ) SEQUENCE CHARACTERISTICS:
        ( A ) LENGTH: 13 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus adr isolate,
            nucleotides 961 to 973

( i i i ) HYPOTHETICAL: no ( i v ) ANTI-SENSE: no ( v i ) ORIGINAL SOURCE:
        ( A ) ORGANISM: Hepatitis B virus
        ( C ) INDIVIDUAL ISOLATE: adr ( x ) PUBLICATION INFORMATION:
        ( A ) AUTHORS: Fujiyama, A, Miyanchara, A, Nozaki, C,
            Yoneyama, T, Ohromo, N, Matsubara, K.
        ( B ) TITLE: Cloning and structural
            analysis of Hepatitis B virus DNAs subtype adr
        ( C ) JOURNAL: Nucleic Acids Research
        ( D ) VOLUME: 11
        ( F ) PAGES: 4601-4610
        ( G ) DATE: 1983
        ( K ) RELEVANT RESIDUES IN SEQ ID NO: 129 :FROM 1 TO 13

( x i ) SEQUENCE DESCRIPTION: SEQ ID NO: 129 :

CTTTCACTTT CTC                                    13

( 2 ) INFORMATION FOR SEQ ID NO:130:

( i ) SEQUENCE CHARACTERISTICS:
        ( A ) LENGTH: 13 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from Hepatitis B
            isolate adr sequence region in Seq ID No 129

( i i i ) HYPOTHETICAL: yes ( i v ) ANTI-SENSE: no ( x ) PUBLICATION INFORMATION:
        ( K ) RELEVANT RESIDUES IN SEQ ID NO: 130 :FROM 1 TO 13

( x i ) SEQUENCE DESCRIPTION: SEQ ID NO: 130 :

CTCTTTCGCT TTC                                    13

( 2 ) INFORMATION FOR SEQ ID NO:131:

( i ) SEQUENCE CHARACTERISTICS:
        ( A ) LENGTH: 11 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus adr isolate,
            nucleotides 1360 to 1370

( i i i ) HYPOTHETICAL: no ( i v ) ANTI-SENSE: no ( v i ) ORIGINAL SOURCE:
        ( A ) ORGANISM: Hepatitis B virus
        ( C ) INDIVIDUAL ISOLATE: adr (x) PUBLICATION INFORMATION:
    (A) AUTHORS: Fujiyama, A, Miyanchara, A, Nozaki, C,
        Yoneyama, T, Ohromo, N, Matsubara, K.
    (B) TITLE: Cloning and structural
        analysis of Hepatitis B virus DNAs subtype adr
    (C) JOURNAL: Nucleic Acids Research
    (D) VOLUME: 11
    (F) PAGES: 4601-4610
    (G) DATE: 1983
    (K) RELEVANT RESIDUES IN SEQ ID NO: 131 :FROM 1 TO 11

(xi) SEQUENCE DESCRIPTION: SEQ ID NO: 131 :

TCCCCTTCTT C								11

(2) INFORMATION FOR SEQ ID NO:132:

(i) SEQUENCE CHARACTERISTICS:
        (A) LENGTH: 11 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
            isolate adr sequence region in Seq ID No 131

(iii) HYPOTHETICAL: yes (iv) ANTI-SENSE: no (x) PUBLICATION INFORMATION:
        (K) RELEVANT RESIDUES IN SEQ ID NO: 132 :FROM 1 TO 11

(xi) SEQUENCE DESCRIPTION: SEQ ID NO: 132 :

CTTCTTCCCC T								11

(2) INFORMATION FOR SEQ ID NO:133:

(i) SEQUENCE CHARACTERISTICS:
        (A) LENGTH: 11 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: hepatitis B virus adr isolate,
            nucleotides 1614 to 1624

(iii) HYPOTHETICAL: no (iv) ANTI-SENSE: no (vi) ORIGINAL SOURCE:
        (A) ORGANISM: Hepatitis B virus
        (C) INDIVIDUAL ISOLATE: adr (x) PUBLICATION INFORMATION:
        (A) AUTHORS: Fujiyama, A, Miyanchara, A, Nozaki, C,
            Yoneyama, T, Ohromo, N, Matsubara, K.
        (B) TITLE: Cloning and structural
            analysis of Hepatitis B virus DNAs subtype adr
        (C) JOURNAL: Nucleic Acids Research
        (D) VOLUME: 11
        (F) PAGES: 4601-4610
        (G) DATE: 1983
        (K) RELEVANT RESIDUES IN SEQ ID NO: 133 :FROM 1 TO 11

(xi) SEQUENCE DESCRIPTION: SEQ ID NO: 133 :

GGGGGAGGAG A								11

(2) INFORMATION FOR SEQ ID NO:134:

(i) SEQUENCE CHARACTERISTICS:
        (A) LENGTH: 11 bases (B) TYPE: nucleic acid
(C) STRANDEDNESS: single stranded
(D) TOPOLOGY: linear (i i) MOLECULE TYPE: other nucleic acid
(A) DESCRIPTION: third strand derived from Hepatitis B
isolate adr sequence region in Seq ID No 133

(i i i) HYPOTHETICAL: yes (i v) ANTI-SENSE: no (x) PUBLICATION INFORMATION:
(K) RELEVANT RESIDUES IN SEQ ID NO: 134 :FROM 1 TO 11

(x i) SEQUENCE DESCRIPTION: SEQ ID NO: 134 :

CCCCCTCCTC T 11

(2) INFORMATION FOR SEQ ID NO:135:

(i) SEQUENCE CHARACTERISTICS:
(A) LENGTH: 13 base pairs
(B) TYPE: nucleic acid
(C) STRANDEDNESS: double stranded
(D) TOPOLOGY: linear (i i) MOLECULE TYPE: genomic DNA
(A) DESCRIPTION: hepatitis B virus adr isolate,
nucleotides 1692 to 1704

(i i i) HYPOTHETICAL: no (i v) ANTI-SENSE: no (v i) ORIGINAL SOURCE:
(A) ORGANISM: Hepatitis B virus
(C) INDIVIDUAL ISOLATE: adr (x) PUBLICATION INFORMATION:
(A) AUTHORS: Fujiyama, A, Miyanchara, A, Nozaki, C,
Yoneyama, T, Ohromo, N, Matsubara, K.
(B) TITLE: Cloning and structural
analysis of Hepatitis B virus DNAs subtype adr
(C) JOURNAL: Nucleic Acids Research
(D) VOLUME: 11
(F) PAGES: 4601-4610
(G) DATE: 1983
(K) RELEVANT RESIDUES IN SEQ ID NO: 135 :FROM 1 TO 13

(x i) SEQUENCE DESCRIPTION: SEQ ID NO: 135 :

CTTTTTCACC TCT 13

(2) INFORMATION FOR SEQ ID NO:136:

(i) SEQUENCE CHARACTERISTICS:
(A) LENGTH: 13 bases
(B) TYPE: nucleic acid
(C) STRANDEDNESS: single stranded
(D) TOPOLOGY: linear (i i) MOLECULE TYPE: other nucleic acid
(A) DESCRIPTION: third strand derived from Hepatitis B
isolate adr sequence region in Seq ID No 135

(i i i) HYPOTHETICAL: yes (i v) ANTI-SENSE: no (x) PUBLICATION INFORMATION:
(K) RELEVANT RESIDUES IN SEQ ID NO: 136 :FROM 1 TO 13

(x i) SEQUENCE DESCRIPTION: SEQ ID NO: 136 :

TCTCCGCTTT TTC 13

( 2 ) INFORMATION FOR SEQ ID NO:137:

( i ) SEQUENCE CHARACTERISTICS:
        ( A ) LENGTH: 11 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus adr isolate,
            nucleotides 1818 to 1828

( i i i ) HYPOTHETICAL: no ( i v ) ANTI-SENSE: no ( v i ) ORIGINAL SOURCE:
        ( A ) ORGANISM: Hepatitis B virus
        ( C ) INDIVIDUAL ISOLATE: adr ( x ) PUBLICATION INFORMATION:
        ( A ) AUTHORS: Fujiyama, A, Miyanchara, A, Nozaki, C,
            Yoneyama, T, Ohromo, N, Matsubara, K.
        ( B ) TITLE: Cloning and structural
            analysis of Hepatitis B virus DNAs subtype adr
        ( C ) JOURNAL: Nucleic Acids Research
        ( D ) VOLUME: 11
        ( F ) PAGES: 4601-4610
        ( G ) DATE: 1983
        ( K ) RELEVANT RESIDUES IN SEQ ID NO: 137 :FROM 1 TO 11

( x i ) SEQUENCE DESCRIPTION: SEQ ID NO: 137 :

C T C T C T T T T T  T                                      1 1

( 2 ) INFORMATION FOR SEQ ID NO:138:

( i ) SEQUENCE CHARACTERISTICS:
        ( A ) LENGTH: 11 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from Hepatitis B
            isolate adr sequence region in Seq ID No 137

( i i i ) HYPOTHETICAL: yes ( i v ) ANTI-SENSE: no ( x ) PUBLICATION INFORMATION:
        ( K ) RELEVANT RESIDUES IN SEQ ID NO: 138 :FROM 1 TO 11

( x i ) SEQUENCE DESCRIPTION: SEQ ID NO: 138 :

T T T T T T C T C T  C                                      1 1

( 2 ) INFORMATION FOR SEQ ID NO:139:

( i ) SEQUENCE CHARACTERISTICS:
        ( A ) LENGTH: 13 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus adr isolate,
            nucleotides 1838 to 1850

( i i i ) HYPOTHETICAL: no ( i v ) ANTI-SENSE: no ( v i ) ORIGINAL SOURCE:
        ( A ) ORGANISM: Hepatitis B virus
        ( C ) INDIVIDUAL ISOLATE: adr (x) PUBLICATION INFORMATION:
    (A) AUTHORS: Fujiyama, A, Miyanchara, A, Nozaki, C,
        Yoneyama, T, Ohromo, N, Matsubara, K.
    (B) TITLE: Cloning and structural
        analysis of Hepatitis B virus DNAs subtype adr
    (C) JOURNAL: Nucleic Acids Research
    (D) VOLUME: 11
    (F) PAGES: 4601-4610
    (G) DATE: 1983
    (K) RELEVANT RESIDUES IN SEQ ID NO: 139 :FROM 1 TO 13

(xi) SEQUENCE DESCRIPTION: SEQ ID NO: 139 :

CTTCTTTCCT TCT         13

(2) INFORMATION FOR SEQ ID NO:140:

(i) SEQUENCE CHARACTERISTICS:
        (A) LENGTH: 13 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
        isolate adr sequence region in Seq ID No 139

(iii) HYPOTHETICAL: yes (iv) ANTI-SENSE: no (x) PUBLICATION INFORMATION:
        (K) RELEVANT RESIDUES IN SEQ ID NO: 140 :FROM 1 TO 13

(xi) SEQUENCE DESCRIPTION: SEQ ID NO: 140 :

TCTTCCTTTC TTC         13

(2) INFORMATION FOR SEQ ID NO:141:

(i) SEQUENCE CHARACTERISTICS:
        (A) LENGTH: 15 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: hepatitis B virus adr isolate,
        nucleotides 2405 to 2419

(iii) HYPOTHETICAL: no (iv) ANTI-SENSE: no (vi) ORIGINAL SOURCE:
        (A) ORGANISM: Hepatitis B virus
        (C) INDIVIDUAL ISOLATE: adr (x) PUBLICATION INFORMATION:
        (A) AUTHORS: Fujiyama, A, Miyanchara, A, Nozaki, C,
        Yoneyama, T, Ohromo, N, Matsubara, K.
        (B) TITLE: Cloning and structural
        analysis of Hepatitis B virus DNAs subtype adr
        (C) JOURNAL: Nucleic Acids Research
        (D) VOLUME: 11
        (F) PAGES: 4601-4610
        (G) DATE: 1983
        (K) RELEVANT RESIDUES IN SEQ ID NO: 141 :FROM 1 TO 15

(xi) SEQUENCE DESCRIPTION: SEQ ID NO: 141 :

CTCCCTCCTT TCCTC         15

(2) INFORMATION FOR SEQ ID NO:142:

(i) SEQUENCE CHARACTERISTICS:
        (A) LENGTH: 15 bases (B) TYPE: nucleic acid
                (C) STRANDEDNESS: single stranded
                (D) TOPOLOGY: linear (ii) MOLECULE TYPE: other nucleic acid
                (A) DESCRIPTION: third strand derived from Hepatitis B
                    isolate adr sequence region in Seq ID No 141

(iii) HYPOTHETICAL: yes (iv) ANTI-SENSE: no (x) PUBLICATION INFORMATION:
                (K) RELEVANT RESIDUES IN SEQ ID NO: 142 :FROM 1 TO 15

(xi) SEQUENCE DESCRIPTION: SEQ ID NO: 142 :

CTCCTTTCCT CCCTC                                                                15

(2) INFORMATION FOR SEQ ID NO:143:

(i) SEQUENCE CHARACTERISTICS:
                (A) LENGTH: 12 base pairs
                (B) TYPE: nucleic acid
                (C) STRANDEDNESS: double stranded
                (D) TOPOLOGY: linear (ii) MOLECULE TYPE: genomic DNA
                (A) DESCRIPTION: hepatitis B virus adr isolate,
                    nucleotides 2485 to 2496

(iii) HYPOTHETICAL: no (iv) ANTI-SENSE: no (vi) ORIGINAL SOURCE:
                (A) ORGANISM: Hepatitis B virus
                (C) INDIVIDUAL ISOLATE: adr (x) PUBLICATION INFORMATION:
                (A) AUTHORS: Fujiyama, A, Miyanchara, A, Nozaki, C,
                    Yoneyama, T, Ohromo, N, Matsubara, K.
                (B) TITLE: Cloning and structural
                    analysis of Hepatitis B virus DNAs subtype adr
                (C) JOURNAL: Nucleic Acids Research
                (D) VOLUME: 11
                (F) PAGES: 4601-4610
                (G) DATE: 1983
                (K) RELEVANT RESIDUES IN SEQ ID NO: 143 :FROM 1 TO 12

(xi) SEQUENCE DESCRIPTION: SEQ ID NO: 143 :

GAAAAAAGGA GA                                                                   12

(2) INFORMATION FOR SEQ ID NO:144:

(i) SEQUENCE CHARACTERISTICS:
                (A) LENGTH: 12 bases
                (B) TYPE: nucleic acid
                (C) STRANDEDNESS: single stranded
                (D) TOPOLOGY: linear (ii) MOLECULE TYPE: other nucleic acid
                (A) DESCRIPTION: third strand derived from Hepatitis B
                    isolate adr sequence region in Seq ID No 143

(iii) HYPOTHETICAL: yes (iv) ANTI-SENSE: no (x) PUBLICATION INFORMATION:
                (K) RELEVANT RESIDUES IN SEQ ID NO: 144 :FROM 1 TO 12

(xi) SEQUENCE DESCRIPTION: SEQ ID NO: 144 :

CTTTTTTCCT CT                                                                   12

( 2 ) INFORMATION FOR SEQ ID NO:145:

( i ) SEQUENCE CHARACTERISTICS:
        ( A ) LENGTH: 10 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus ayw isolate,
            nucleotides 395 to 404

( i i i ) HYPOTHETICAL: no ( i v ) ANTI-SENSE: no ( v i ) ORIGINAL SOURCE:
        ( A ) ORGANISM: Hepatitis B virus
        ( C ) INDIVIDUAL ISOLATE: ayw ( x ) PUBLICATION INFORMATION:
        ( A ) AUTHORS: Galibert, F, Mandart, E, Fitoussi, F,
            Tiollais, P, Charnay, P.
        ( B ) TITLE: Nucleotide sequence of the
            Hepatitis B virus genome (subtype ayw) cloned
            in E coli
        ( C ) JOURNAL: Nature
        ( D ) VOLUME: 281
        ( F ) PAGES: 646-650
        ( G ) DATE: 1979
        ( K ) RELEVANT RESIDUES IN SEQ ID NO: 145 :FROM 1 TO 10

( x i ) SEQUENCE DESCRIPTION: SEQ ID NO: 145 :

T T T C T C T C T T        10

( 2 ) INFORMATION FOR SEQ ID NO:146:

( i ) SEQUENCE CHARACTERISTICS:
        ( A ) LENGTH: 10 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from Hepatitis B
            isolate ayw sequence region in Seq ID No 145

( i i i ) HYPOTHETICAL: yes ( i v ) ANTI-SENSE: no ( x ) PUBLICATION INFORMATION:
        ( K ) RELEVANT RESIDUES IN SEQ ID NO: 146 :FROM 1 TO 10

( x i ) SEQUENCE DESCRIPTION: SEQ ID NO: 146 :

T T C T C T C T T T        10

( 2 ) INFORMATION FOR SEQ ID NO:147:

( i ) SEQUENCE CHARACTERISTICS:
        ( A ) LENGTH: 12 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus ayw isolate,
            nucleotides 561 to 572

( i i i ) HYPOTHETICAL: no ( i v ) ANTI-SENSE: no ( v i ) ORIGINAL SOURCE:
        ( A ) ORGANISM: Hepatitis B virus
        ( C ) INDIVIDUAL ISOLATE: ayw ( x ) PUBLICATION INFORMATION:
- ( A ) AUTHORS: Galibert, F, Mandart, E, Fitoussi, F,
    Tiollais, P, Charnay, P.
- ( B ) TITLE: Nucleotide sequence of the
    Hepatitis B virus genome (subtype ayw) cloned
    in E coli
- ( C ) JOURNAL: Nature
- ( D ) VOLUME: 281
- ( F ) PAGES: 646-650
- ( G ) DATE: 1979
- ( K ) RELEVANT RESIDUES IN SEQ ID NO: 147 :FROM 1 TO 12

( x i ) SEQUENCE DESCRIPTION: SEQ ID NO: 147 :

TCTTCTTTTC TC                                                                12

( 2 ) INFORMATION FOR SEQ ID NO:148:

- ( i ) SEQUENCE CHARACTERISTICS:
    - ( A ) LENGTH: 12 bases
    - ( B ) TYPE: nucleic acid
    - ( C ) STRANDEDNESS: single stranded
    - ( D ) TOPOLOGY: linear

- ( i i ) MOLECULE TYPE: other nucleic acid
    - ( A ) DESCRIPTION: third strand derived from Hepatitis B
        isolate ayw sequence region in Seq ID No 147

- ( i i i ) HYPOTHETICAL: yes

- ( i v ) ANTI-SENSE: no

- ( x ) PUBLICATION INFORMATION:
    - ( K ) RELEVANT RESIDUES IN SEQ ID NO: 148 :FROM 1 TO 12

( x i ) SEQUENCE DESCRIPTION: SEQ ID NO: 148 :

CTCTTTTCTT CT                                                                12

( 2 ) INFORMATION FOR SEQ ID NO:149:

- ( i ) SEQUENCE CHARACTERISTICS:
    - ( A ) LENGTH: 11 base pairs
    - ( B ) TYPE: nucleic acid
    - ( C ) STRANDEDNESS: double stranded
    - ( D ) TOPOLOGY: linear

- ( i i ) MOLECULE TYPE: genomic DNA
    - ( A ) DESCRIPTION: hepatitis B virus ayw isolate,
        nucleotides 706 to 716

- ( i i i ) HYPOTHETICAL: no

- ( i v ) ANTI-SENSE: no

- ( v i ) ORIGINAL SOURCE:
    - ( A ) ORGANISM: Hepatitis B virus
    - ( C ) INDIVIDUAL ISOLATE: ayw

- ( x ) PUBLICATION INFORMATION:
    - ( A ) AUTHORS: Galibert, F, Mandart, E, Fitoussi, F,
        Tiollais, P, Charnay, P.
    - ( B ) TITLE: Nucleotide sequence of the
        Hepatitis B virus genome (subtype ayw) cloned
        in E coli
    - ( C ) JOURNAL: Nature
    - ( D ) VOLUME: 281
    - ( F ) PAGES: 646-650
    - ( G ) DATE: 1979
    - ( K ) RELEVANT RESIDUES IN SEQ ID NO: 149 :FROM 1 TO 11

( x i ) SEQUENCE DESCRIPTION: SEQ ID NO: 149 :

TTCCCCTCCT T                                                                 11

( 2 ) INFORMATION FOR SEQ ID NO:150:

( i ) SEQUENCE CHARACTERISTICS:
    ( A ) LENGTH: 11 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from Hepatitis B
        isolate ayw sequence region in Seq ID No 149

( i i i ) HYPOTHETICAL: yes ( i v ) ANTI-SENSE: no ( x ) PUBLICATION INFORMATION:
    ( K ) RELEVANT RESIDUES IN SEQ ID NO: 150 :FROM 1 TO 11

( x i ) SEQUENCE DESCRIPTION: SEQ ID NO: 150 :

TTCCTCCCCT T          11

( 2 ) INFORMATION FOR SEQ ID NO:151:

( i ) SEQUENCE CHARACTERISTICS:
    ( A ) LENGTH: 10 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: hepatitis B virus ayw isolate,
        nucleotides 807 to 816

( i i i ) HYPOTHETICAL: no ( i v ) ANTI-SENSE: no ( v i ) ORIGINAL SOURCE:
    ( A ) ORGANISM: Hepatitis B virus
    ( C ) INDIVIDUAL ISOLATE: ayw ( x ) PUBLICATION INFORMATION:
    ( A ) AUTHORS: Galibert, F, Mandart, E, Fitoussi, F,
        Tiollais, P, Charnay, P.
    ( B ) TITLE: Nucleotide sequence of the
        Hepatitis B virus genome (subtype ayw) cloned
        in E coli
    ( C ) JOURNAL: Nature
    ( D ) VOLUME: 281
    ( F ) PAGES: 646-650
    ( G ) DATE: 1979
    ( K ) RELEVANT RESIDUES IN SEQ ID NO: 151 :FROM 1 TO 10

( x i ) SEQUENCE DESCRIPTION: SEQ ID NO: 151 :

TTCTTCTTCT          10

( 2 ) INFORMATION FOR SEQ ID NO:152:

( i ) SEQUENCE CHARACTERISTICS:
    ( A ) LENGTH: 10 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from Hepatitis B
        isolate ayw sequence region in Seq ID No 151

( i i i ) HYPOTHETICAL: yes ( i v ) ANTI-SENSE: no ( x ) PUBLICATION INFORMATION:
    ( K ) RELEVANT RESIDUES IN SEQ ID NO: 152 :FROM 1 TO 10

( x i ) SEQUENCE DESCRIPTION: SEQ ID NO: 152 :

T C T T C T T C T T 10

( 2 ) INFORMATION FOR SEQ ID NO:153:

( i ) SEQUENCE CHARACTERISTICS:
        ( A ) LENGTH: 10 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus ayw isolate,
            nucleotides 945 to 954

( i i i ) HYPOTHETICAL: no ( i v ) ANTI-SENSE: no ( v i ) ORIGINAL SOURCE:
        ( A ) ORGANISM: Hepatitis B virus
        ( C ) INDIVIDUAL ISOLATE: ayw ( x ) PUBLICATION INFORMATION:
        ( A ) AUTHORS: Galibert, F, Mandart, E, Fitoussi, F,
            Tiollais, P, Charnay, P.
        ( B ) TITLE: Nucleotide sequence of the
            Hepatitis B virus genome (subtype ayw) cloned
            in E coli
        ( C ) JOURNAL: Nature
        ( D ) VOLUME: 281
        ( F ) PAGES: 646-650
        ( G ) DATE: 1979
        ( K ) RELEVANT RESIDUES IN SEQ ID NO: 153 :FROM 1 TO 10

( x i ) SEQUENCE DESCRIPTION: SEQ ID NO: 153 :

T T T C T C T T C C 10

( 2 ) INFORMATION FOR SEQ ID NO:154:

( i ) SEQUENCE CHARACTERISTICS:
        ( A ) LENGTH: 10 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from Hepatitis B
            isolate ayw sequence region in Seq ID No 153

( i i i ) HYPOTHETICAL: yes ( i v ) ANTI-SENSE: no ( x ) PUBLICATION INFORMATION:
        ( K ) RELEVANT RESIDUES IN SEQ ID NO: 154 :FROM 1 TO 10

( x i ) SEQUENCE DESCRIPTION: SEQ ID NO: 154 :

C C T T C T C T T T 10

( 2 ) INFORMATION FOR SEQ ID NO:155:

( i ) SEQUENCE CHARACTERISTICS:
        ( A ) LENGTH: 12 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus ayw isolate,
            nucleotides 1208 to 1219

( i i i ) HYPOTHETICAL: no ( i v ) ANTI-SENSE: no ( v i ) ORIGINAL SOURCE:
  ( A ) ORGANISM: Hepatitis B virus
  ( C ) INDIVIDUAL ISOLATE: ayw ( x ) PUBLICATION INFORMATION:
  ( A ) AUTHORS: Galibert, F, Mandart, E, Fitoussi, F,
       Tiollais, P, Charnay, P.
  ( B ) TITLE: Nucleotide sequence of the
       Hepatitis B virus genome (subtype ayw) cloned
       in E coli
  ( C ) JOURNAL: Nature
  ( D ) VOLUME: 281
  ( F ) PAGES: 646-650
  ( G ) DATE: 1979
  ( K ) RELEVANT RESIDUES IN SEQ ID NO: 155 :FROM 1 TO 12

( x i ) SEQUENCE DESCRIPTION: SEQ ID NO: 155 :

GAAGGAAAGA AG                                                                  12

( 2 ) INFORMATION FOR SEQ ID NO:156:

( i ) SEQUENCE CHARACTERISTICS:
    ( A ) LENGTH: 12 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from Hepatitis B
         isolate ayw sequence region in Seq ID No 155

( i i i ) HYPOTHETICAL: yes ( i v ) ANTI-SENSE: no ( x ) PUBLICATION INFORMATION:
    ( K ) RELEVANT RESIDUES IN SEQ ID NO: 156 :FROM 1 TO 12

( x i ) SEQUENCE DESCRIPTION: SEQ ID NO: 156 :

CTTCCTTTCT TC                                                                  12

( 2 ) INFORMATION FOR SEQ ID NO:157:

( i ) SEQUENCE CHARACTERISTICS:
    ( A ) LENGTH: 13 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: hepatitis B virus ayw isolate,
         nucleotides 1353 to 1365

( i i i ) HYPOTHETICAL: no ( i v ) ANTI-SENSE: no ( v i ) ORIGINAL SOURCE:
    ( A ) ORGANISM: Hepatitis B virus
    ( C ) INDIVIDUAL ISOLATE: ayw ( x ) PUBLICATION INFORMATION:
    ( A ) AUTHORS: Galibert, F, Mandart, E, Fitoussi, F,
         Tiollais, P, Charnay, P.
    ( B ) TITLE: Nucleotide sequence of the
         Hepatitis B virus genome (subtype ayw) cloned
         in E coli
    ( C ) JOURNAL: Nature
    ( D ) VOLUME: 281
    ( F ) PAGES: 646-650
    ( G ) DATE: 1979
    ( K ) RELEVANT RESIDUES IN SEQ ID NO: 157 :FROM 1 TO 13

( x i ) SEQUENCE DESCRIPTION: SEQ ID NO: 157 :

| | |
|---|---|
| AGAGGTGAAA AAG | 13 |

(2) INFORMATION FOR SEQ ID NO:158:

(i) SEQUENCE CHARACTERISTICS:
        (A) LENGTH: 13 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
            isolate ayw sequence region in Seq ID No 157

(iii) HYPOTHETICAL: yes (iv) ANTI-SENSE: no (x) PUBLICATION INFORMATION:
        (K) RELEVANT RESIDUES IN SEQ ID NO: 158 :FROM 1 TO 13

(xi) SEQUENCE DESCRIPTION: SEQ ID NO: 158 :

| | |
|---|---|
| TCTCCGCTTT TTC | 13 |

(2) INFORMATION FOR SEQ ID NO:159:

(i) SEQUENCE CHARACTERISTICS:
        (A) LENGTH: 11 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: hepatitis B virus ayw isolate,
            nucleotides 1433 to 1443

(iii) HYPOTHETICAL: no (iv) ANTI-SENSE: no (vi) ORIGINAL SOURCE:
        (A) ORGANISM: Hepatitis B virus
        (C) INDIVIDUAL ISOLATE: ayw (x) PUBLICATION INFORMATION:
        (A) AUTHORS: Galibert, F, Mandart, E, Fitoussi, F,
            Tiollais, P, Charnay, P.
        (B) TITLE: Nucleotide sequence of the
            Hepatitis B virus genome (subtype ayw) cloned
            in E coli
        (C) JOURNAL: Nature
        (D) VOLUME: 281
        (F) PAGES: 646-650
        (G) DATE: 1979
        (K) RELEVANT RESIDUES IN SEQ ID NO: 159 :FROM 1 TO 11

(xi) SEQUENCE DESCRIPTION: SEQ ID NO: 159 :

| | |
|---|---|
| TCTCCTCCCC C | 11 |

(2) INFORMATION FOR SEQ ID NO:160:

(i) SEQUENCE CHARACTERISTICS:
        (A) LENGTH: 11 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
            isolate ayw sequence region in Seq ID No 159

(iii) HYPOTHETICAL: yes (iv) ANTI-SENSE: no (x) PUBLICATION INFORMATION:
    (K) RELEVANT RESIDUES IN SEQ ID NO: 160 :FROM 1 TO 11

(xi) SEQUENCE DESCRIPTION: SEQ ID NO: 160 :

CCCCCTCCTC T                                                                11

(2) INFORMATION FOR SEQ ID NO:161:

(i) SEQUENCE CHARACTERISTICS:
        (A) LENGTH: 11 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: hepatitis B virus ayw isolate,
            nucleotides 1687 to 1697

(iii) HYPOTHETICAL: no (iv) ANTI-SENSE: no (vi) ORIGINAL SOURCE:
        (A) ORGANISM: Hepatitis B virus
        (C) INDIVIDUAL ISOLATE: ayw (x) PUBLICATION INFORMATION:
        (A) AUTHORS: Galibert, F, Mandart, E, Fitoussi, F,
            Tiollais, P, Charnay, P.
        (B) TITLE: Nucleotide sequence of the
            Hepatitis B virus genome (subtype ayw) cloned
            in E coli
        (C) JOURNAL: Nature
        (D) VOLUME: 281
        (F) PAGES: 646-650
        (G) DATE: 1979
        (K) RELEVANT RESIDUES IN SEQ ID NO: 161 :FROM 1 TO 11

(xi) SEQUENCE DESCRIPTION: SEQ ID NO: 161 :

GGAGAAGGGG A                                                                11

(2) INFORMATION FOR SEQ ID NO:162:

(i) SEQUENCE CHARACTERISTICS:
        (A) LENGTH: 11 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
            isolate ayw sequence region in Seq ID No 161

(iii) HYPOTHETICAL: yes (iv) ANTI-SENSE: no (x) PUBLICATION INFORMATION:
        (K) RELEVANT RESIDUES IN SEQ ID NO: 162 :FROM 1 TO 11

(xi) SEQUENCE DESCRIPTION: SEQ ID NO: 162 :

CCTCTTCCCC T                                                                11

(2) INFORMATION FOR SEQ ID NO:163:

(i) SEQUENCE CHARACTERISTICS:
        (A) LENGTH: 13 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: hepatitis B virus ayw isolate,
            nucleotides 2085 to 2097

(  i i i ) HYPOTHETICAL: no (  i v ) ANTI-SENSE: no (  v i ) ORIGINAL SOURCE:
      ( A ) ORGANISM: Hepatitis B virus
      ( C ) INDIVIDUAL ISOLATE: ayw (  x ) PUBLICATION INFORMATION:
      ( A ) AUTHORS: Galibert, F, Mandart, E, Fitoussi, F,
            Tiollais, P, Charnay, P.
      ( B ) TITLE: Nucleotide sequence of the
            Hepatitis B virus genome (subtype ayw) cloned
            in E coli
      ( C ) JOURNAL: Nature
      ( D ) VOLUME: 281
      ( F ) PAGES: 646-650
      ( G ) DATE: 1979
      ( K ) RELEVANT RESIDUES IN SEQ ID NO: 163 :FROM 1 TO 13

(  x i ) SEQUENCE DESCRIPTION: SEQ ID NO: 163 :

G A G A A A G T G A   A A G                                                 1 3

( 2 ) INFORMATION FOR SEQ ID NO:164:

( i ) SEQUENCE CHARACTERISTICS:
        ( A ) LENGTH: 13 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from Hepatitis B
            isolate ayw sequence region in Seq ID No 163

( i i i ) HYPOTHETICAL: yes ( i v ) ANTI-SENSE: no ( x ) PUBLICATION INFORMATION:
        ( K ) RELEVANT RESIDUES IN SEQ ID NO: 164 :FROM 1 TO 13

( x i ) SEQUENCE DESCRIPTION: SEQ ID NO: 164 :

C T C T T T C G C T   T T C                                                1 3

( 2 ) INFORMATION FOR SEQ ID NO:165:

( i ) SEQUENCE CHARACTERISTICS:
        ( A ) LENGTH: 12 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus ayw isolate,
            nucleotides 2750 to 2761

( i i i ) HYPOTHETICAL: no ( i v ) ANTI-SENSE: no ( v i ) ORIGINAL SOURCE:
        ( A ) ORGANISM: Hepatitis B virus
        ( C ) INDIVIDUAL ISOLATE: ayw ( x ) PUBLICATION INFORMATION:
        ( A ) AUTHORS: Galibert, F, Mandart, E, Fitoussi, F,
            Tiollais, P, Charnay, P.
        ( B ) TITLE: Nucleotide sequence of the
            Hepatitis B virus genome (subtype ayw) cloned
            in E coli
        ( C ) JOURNAL: Nature
        ( D ) VOLUME: 281
        ( F ) PAGES: 646-650
        ( G ) DATE: 1979

(K) RELEVANT RESIDUES IN SEQ ID NO: 165 :FROM 1 TO 12

(xi) SEQUENCE DESCRIPTION: SEQ ID NO: 165 :

AAGAAGATGA GG                                                                      12

(2) INFORMATION FOR SEQ ID NO:166:

(i) SEQUENCE CHARACTERISTICS:
        (A) LENGTH: 12 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
            isolate ayw sequence region in Seq ID No 165

(iii) HYPOTHETICAL: yes (iv) ANTI-SENSE: no (x) PUBLICATION INFORMATION:
        (K) RELEVANT RESIDUES IN SEQ ID NO: 166 :FROM 1 TO 12

(xi) SEQUENCE DESCRIPTION: SEQ ID NO: 166 :

TTCTTCTGCT CC                                                                      12

(2) INFORMATION FOR SEQ ID NO:167:

(i) SEQUENCE CHARACTERISTICS:
        (A) LENGTH: 16 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: hepatitis B virus ayw isolate,
            nucleotides 2771 to 2786

(iii) HYPOTHETICAL: no (iv) ANTI-SENSE: no (vi) ORIGINAL SOURCE:
        (A) ORGANISM: Hepatitis B virus
        (C) INDIVIDUAL ISOLATE: ayw (x) PUBLICATION INFORMATION:
        (A) AUTHORS: Galibert, F, Mandart, E, Fitoussi, F,
            Tiollais, P, Charnay, P.
        (B) TITLE: Nucleotide sequence of the
            Hepatitis B virus genome (subtype ayw) cloned
            in E coli
        (C) JOURNAL: Nature
        (D) VOLUME: 281
        (F) PAGES: 646-650
        (G) DATE: 1979
        (K) RELEVANT RESIDUES IN SEQ ID NO: 167 :FROM 1 TO 16

(xi) SEQUENCE DESCRIPTION: SEQ ID NO: 167 :

AGGATGAAGA GGAAGA                                                                  16

(2) INFORMATION FOR SEQ ID NO:168:

(i) SEQUENCE CHARACTERISTICS:
        (A) LENGTH: 16 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
            isolate ayw sequence region in Seq ID No 167

-continued (iii) HYPOTHETICAL: yes (iv) ANTI-SENSE: no (x) PUBLICATION INFORMATION:
                (K) RELEVANT RESIDUES IN SEQ ID NO: 168 :FROM 1 TO 16

(xi) SEQUENCE DESCRIPTION: SEQ ID NO: 168 :

TCCTGCTTCT CCTTCT                                                                                       16

(2) INFORMATION FOR SEQ ID NO:169:

(i) SEQUENCE CHARACTERISTICS:
                (A) LENGTH: 10 base pairs
                (B) TYPE: nucleic acid
                (C) STRANDEDNESS: double stranded
                (D) TOPOLOGY: linear (ii) MOLECULE TYPE: genomic DNA
                (A) DESCRIPTION: hepatitis B virus ayw isolate,
                        nucleotides 3071 to 3080

(iii) HYPOTHETICAL: no (iv) ANTI-SENSE: no (vi) ORIGINAL SOURCE:
                (A) ORGANISM: Hepatitis B virus
                (C) INDIVIDUAL ISOLATE: ayw (x) PUBLICATION INFORMATION:
                (A) AUTHORS: Galibert, F, Mandart, E, Fitoussi, F,
                        Tiollais, P, Charnay, P.
                (B) TITLE: Nucleotide sequence of the
                        Hepatitis B virus genome (subtype ayw) cloned
                        in E coli
                (C) JOURNAL: Nature
                (D) VOLUME: 281
                (F) PAGES: 646-650
                (G) DATE: 1979
                (K) RELEVANT RESIDUES IN SEQ ID NO: 169 :FROM 1 TO 10

(xi) SEQUENCE DESCRIPTION: SEQ ID NO: 169 :

AAGGGAGAGG                                                                                              10

(2) INFORMATION FOR SEQ ID NO:170:

(i) SEQUENCE CHARACTERISTICS:
                (A) LENGTH: 10 bases
                (B) TYPE: nucleic acid
                (C) STRANDEDNESS: single stranded
                (D) TOPOLOGY: linear (ii) MOLECULE TYPE: other nucleic acid
                (A) DESCRIPTION: third strand derived from Hepatitis B
                        isolate ayw sequence region in Seq ID No 169

(iii) HYPOTHETICAL: yes (iv) ANTI-SENSE: no (x) PUBLICATION INFORMATION:
                (K) RELEVANT RESIDUES IN SEQ ID NO: 170 :FROM 1 TO 10

(xi) SEQUENCE DESCRIPTION: SEQ ID NO: 170 :

TTCCCTCTCC                                                                                              10

(2) INFORMATION FOR SEQ ID NO:171:

(i) SEQUENCE CHARACTERISTICS:
                (A) LENGTH: 13 base pairs
                (B) TYPE: nucleic acid
                (C) STRANDEDNESS: double stranded
                (D) TOPOLOGY: linear (ii) MOLECULE TYPE: genomic DNA
    (A) DESCRIPTION: hepatitis B virus adw2 isolate,
        nucleotides 154 to 166

(iii) HYPOTHETICAL: no (iv) ANTI-SENSE: no (vi) ORIGINAL SOURCE:
    (A) ORGANISM: Hepatitis B virus
    (C) INDIVIDUAL ISOLATE: adw2

(x) PUBLICATION INFORMATION:
    (A) AUTHORS: Valenzuela, P, Quiroga, M, Zaldivar, J,
        Gray, P, Ruter, W J.
    (B) TITLE: The nucleotide sequence of
        the Hepatitis B viral genome and the
        identification of the major viral genes
    (C) JOURNAL: In "Animal Virus Genetics", Fields, B N,
        Jaenisch, R, Fox C F eds
    (D) VOLUME:
    (F) PAGES: 57-70
    (G) DATE: 1980
    (K) RELEVANT RESIDUES IN SEQ ID NO: 171 :FROM 1 TO 13

(xi) SEQUENCE DESCRIPTION: SEQ ID NO: 171 :

CTTCTTTCCT TCC                                                          13

(2) INFORMATION FOR SEQ ID NO:172:

(i) SEQUENCE CHARACTERISTICS:
        (A) LENGTH: 13 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
            isolate adw2 sequence region in Seq ID No 171

(iii) HYPOTHETICAL: yes (iv) ANTI-SENSE: no (x) PUBLICATION INFORMATION:
        (K) RELEVANT RESIDUES IN SEQ ID NO: 172 :FROM 1 TO 13

(xi) SEQUENCE DESCRIPTION: SEQ ID NO: 172 :

CCTTCCTTTC TTC                                                          13

(2) INFORMATION FOR SEQ ID NO:173:

(i) SEQUENCE CHARACTERISTICS:
        (A) LENGTH: 10 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: hepatitis B virus adw2 isolate,
            nucleotides 419 to 428

(iii) HYPOTHETICAL: no (iv) ANTI-SENSE: no (vi) ORIGINAL SOURCE:
        (A) ORGANISM: Hepatitis B virus
        (C) INDIVIDUAL ISOLATE: adw2

(x) PUBLICATION INFORMATION:
        (A) AUTHORS: Valenzuela, P, Quiroga, M, Zaldivar, J,
            Gray, P, Ruter, W J.
        (B) TITLE: The nucleotide sequence of
            the Hepatitis B viral genome and the identification of the major viral genes
(C) JOURNAL: In "Animal Virus Genetics", Fields, B N,
Jaenisch, R, Fox C F eds
(D) VOLUME:
(F) PAGES: 57-70
(G) DATE: 1980
(K) RELEVANT RESIDUES IN SEQ ID NO: 173 :FROM 1 TO 10

(x i) SEQUENCE DESCRIPTION: SEQ ID NO: 173 :

GGAAGAGAGA 10

(2) INFORMATION FOR SEQ ID NO:174:

(i) SEQUENCE CHARACTERISTICS:
(A) LENGTH: 10 bases
(B) TYPE: nucleic acid
(C) STRANDEDNESS: single stranded
(D) TOPOLOGY: linear (i i) MOLECULE TYPE: other nucleic acid
(A) DESCRIPTION: third strand derived from Hepatitis B
isolate adw2 sequence region in Seq ID No 173

(i i i) HYPOTHETICAL: yes (i v) ANTI-SENSE: no (x) PUBLICATION INFORMATION:
(K) RELEVANT RESIDUES IN SEQ ID NO: 174 :FROM 1 TO 10

(x i) SEQUENCE DESCRIPTION: SEQ ID NO: 174 :

CCTTCTCTCT 10

(2) INFORMATION FOR SEQ ID NO:175:

(i) SEQUENCE CHARACTERISTICS:
(A) LENGTH: 10 base pairs
(B) TYPE: nucleic acid
(C) STRANDEDNESS: double stranded
(D) TOPOLOGY: linear (i i) MOLECULE TYPE: genomic DNA
(A) DESCRIPTION: hepatitis B virus adw2 isolate,
nucleotides 563 to 572

(i i i) HYPOTHETICAL: no (i v) ANTI-SENSE: no (v i) ORIGINAL SOURCE:
(A) ORGANISM: Hepatitis B virus
(C) INDIVIDUAL ISOLATE: adw2

(x) PUBLICATION INFORMATION:
(A) AUTHORS: Valenzuela, P, Quiroga, M, Zaldivar, J,
Gray, P, Ruter, W J.
(B) TITLE: The nucleotide sequence of
the Hepatitis B viral genome and the
identification of the major viral genes
(C) JOURNAL: In "Animal Virus Genetics", Fields, B N,
Jaenisch, R, Fox C F eds
(D) VOLUME:
(F) PAGES: 57-70
(G) DATE: 1980
(K) RELEVANT RESIDUES IN SEQ ID NO: 175 :FROM 1 TO 10

(x i) SEQUENCE DESCRIPTION: SEQ ID NO: 175 :

AGAAGAAGAA 10

(2) INFORMATION FOR SEQ ID NO:176:

(i) SEQUENCE CHARACTERISTICS:
(A) LENGTH: 10 bases
(B) TYPE: nucleic acid ( C ) STRANDEDNESS: single stranded
            ( D ) TOPOLOGY: linear ( i i ) MOLECULE TYPE: other nucleic acid
            ( A ) DESCRIPTION: third strand derived from Hepatitis B
                    isolate adw2 sequence region in Seq ID No 175

( i i i ) HYPOTHETICAL: yes ( i v ) ANTI-SENSE: no ( x ) PUBLICATION INFORMATION:
            ( K ) RELEVANT RESIDUES IN SEQ ID NO: 176 :FROM 1 TO 10

( x i ) SEQUENCE DESCRIPTION: SEQ ID NO: 176 :

T C T T C T T C T T                                                                                     1 0

( 2 ) INFORMATION FOR SEQ ID NO:177:

( i ) SEQUENCE CHARACTERISTICS:
            ( A ) LENGTH: 11 base pairs
            ( B ) TYPE: nucleic acid
            ( C ) STRANDEDNESS: double stranded
            ( D ) TOPOLOGY: linear ( i i ) MOLECULE TYPE: genomic DNA
            ( A ) DESCRIPTION: hepatitis B virus adw2 isolate,
                    nucleotides 663 to 673

( i i i ) HYPOTHETICAL: no ( i v ) ANTI-SENSE: no ( v i ) ORIGINAL SOURCE:
            ( A ) ORGANISM: Hepatitis B virus
            ( C ) INDIVIDUAL ISOLATE: adw2

( x ) PUBLICATION INFORMATION:
            ( A ) AUTHORS: Valenzuela, P, Quiroga, M, Zaldivar, J,
                    Gray, P, Ruter, W J.
            ( B ) TITLE: The nucleotide sequence of
                    the Hepatitis B viral genome and the
                    identification of the major viral genes
            ( C ) JOURNAL: In "Animal Virus Genetics", Fields, B N,
                    Jaenisch, R, Fox C F eds
            ( D ) VOLUME:
            ( F ) PAGES: 57-70
            ( G ) DATE: 1980
            ( K ) RELEVANT RESIDUES IN SEQ ID NO: 177 :FROM 1 TO 11

( x i ) SEQUENCE DESCRIPTION: SEQ ID NO: 177 :

A A G G T G G G A A  A                                                                                  1 1

( 2 ) INFORMATION FOR SEQ ID NO:178:

( i ) SEQUENCE CHARACTERISTICS:
            ( A ) LENGTH: 11 bases
            ( B ) TYPE: nucleic acid
            ( C ) STRANDEDNESS: single stranded
            ( D ) TOPOLOGY: linear ( i i ) MOLECULE TYPE: other nucleic acid
            ( A ) DESCRIPTION: third strand derived from Hepatitis B
                    isolate adw2 sequence region in Seq ID No 177

( i i i ) HYPOTHETICAL: yes ( i v ) ANTI-SENSE: no ( x ) PUBLICATION INFORMATION:
            ( K ) RELEVANT RESIDUES IN SEQ ID NO: 178 :FROM 1 TO 11

( x i ) SEQUENCE DESCRIPTION: SEQ ID NO: 178 :

T T C C G C C C T T  T                                                                                  1 1

( 2 ) INFORMATION FOR SEQ ID NO:179:

( i ) SEQUENCE CHARACTERISTICS:
        ( A ) LENGTH: 14 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus adw2 isolate,
            nucleotides 727 to 740

( i i i ) HYPOTHETICAL: no ( i v ) ANTI-SENSE: no ( v i ) ORIGINAL SOURCE:
        ( A ) ORGANISM: Hepatitis B virus
        ( C ) INDIVIDUAL ISOLATE: adw2

( x ) PUBLICATION INFORMATION:
        ( A ) AUTHORS: Valenzuela, P, Quiroga, M, Zaldivar, J,
            Gray, P, Ruter, W J.
        ( B ) TITLE: The nucleotide sequence of
            the Hepatitis B viral genome and the
            identification of the major viral genes
        ( C ) JOURNAL: In "Animal Virus Genetics", Fields, B N,
            Jaenisch, R, Fox C F eds
        ( D ) VOLUME:
        ( F ) PAGES: 57-70
        ( G ) DATE: 1980
        ( K ) RELEVANT RESIDUES IN SEQ ID NO: 179 :FROM 1 TO 14

( x i ) SEQUENCE DESCRIPTION: SEQ ID NO: 179 :

CTCCTTCCTT TCCT                                        14

( 2 ) INFORMATION FOR SEQ ID NO:180:

( i ) SEQUENCE CHARACTERISTICS:
        ( A ) LENGTH: 14 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from Hepatitis B
            isolate adw2 sequence region in Seq ID No 179

( i i i ) HYPOTHETICAL: yes ( i v ) ANTI-SENSE: no ( x ) PUBLICATION INFORMATION:
        ( K ) RELEVANT RESIDUES IN SEQ ID NO: 180 :FROM 1 TO 14

( x i ) SEQUENCE DESCRIPTION: SEQ ID NO: 180 :

TCCTTTCCTT CCTC                                        14

( 2 ) INFORMATION FOR SEQ ID NO:181:

( i ) SEQUENCE CHARACTERISTICS:
        ( A ) LENGTH: 12 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: hepatitis B virus adw2 isolate,
            nucleotides 807 to 818

( i i i ) HYPOTHETICAL: no ( i v ) ANTI-SENSE: no ( v i ) ORIGINAL SOURCE:

(A) ORGANISM: Hepatitis B virus
(C) INDIVIDUAL ISOLATE: adw2

(x) PUBLICATION INFORMATION:
(A) AUTHORS: Valenzuela, P, Quiroga, M, Zaldivar, J,
Gray, P, Ruter, W J.
(B) TITLE: The nucleotide sequence of
the Hepatitis B viral genome and the
identification of the major viral genes
(C) JOURNAL: In "Animal Virus Genetics", Fields, B N,
Jaenisch, R, Fox C F eds
(D) VOLUME:
(F) PAGES: 57-70
(G) DATE: 1980
(K) RELEVANT RESIDUES IN SEQ ID NO: 181 :FROM 1 TO 12

(xi) SEQUENCE DESCRIPTION: SEQ ID NO: 181 :

GAAAAGAGAA GA  12

(2) INFORMATION FOR SEQ ID NO:182:

(i) SEQUENCE CHARACTERISTICS:
(A) LENGTH: 12 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from Hepatitis B
isolate adw2 sequence region in Seq ID No 181

(iii) HYPOTHETICAL: yes (iv) ANTI-SENSE: no (x) PUBLICATION INFORMATION:
(K) RELEVANT RESIDUES IN SEQ ID NO: 182 :FROM 1 TO 12

(xi) SEQUENCE DESCRIPTION: SEQ ID NO: 182 :

CTTTTCTCTT CT  12

(2) INFORMATION FOR SEQ ID NO:183:

(i) SEQUENCE CHARACTERISTICS:
(A) LENGTH: 11 base pairs
(B) TYPE: nucleic acid
(C) STRANDEDNESS: double stranded
(D) TOPOLOGY: linear (ii) MOLECULE TYPE: genomic DNA
(A) DESCRIPTION: hepatitis B virus adw2 isolate,
nucleotides 1215 to 1225

(iii) HYPOTHETICAL: no (iv) ANTI-SENSE: no (vi) ORIGINAL SOURCE:
(A) ORGANISM: Hepatitis B virus
(C) INDIVIDUAL ISOLATE: adw2

(x) PUBLICATION INFORMATION:
(A) AUTHORS: Valenzuela, P, Quiroga, M, Zaldivar, J,
Gray, P, Ruter, W J.
(B) TITLE: The nucleotide sequence of
the Hepatitis B viral genome and the
identification of the major viral genes
(C) JOURNAL: In "Animal Virus Genetics", Fields, B N,
Jaenisch, R, Fox C F eds
(D) VOLUME:
(F) PAGES: 57-70
(G) DATE: 1980
(K) RELEVANT RESIDUES IN SEQ ID NO: 183 :FROM 1 TO 11

(xi) SEQUENCE DESCRIPTION: SEQ ID NO: 183 :

AGGAGTGGGA G                                                                    11

(2) INFORMATION FOR SEQ ID NO:184:

(i) SEQUENCE CHARACTERISTICS:
        (A) LENGTH: 11 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
            isolate adw2 sequence region in Seq ID No 183

(iii) HYPOTHETICAL: yes (iv) ANTI-SENSE: no (x) PUBLICATION INFORMATION:
        (K) RELEVANT RESIDUES IN SEQ ID NO: 184 :FROM 1 TO 11

(xi) SEQUENCE DESCRIPTION: SEQ ID NO: 184 :

TCCTCGCCCT C                                                                    11

(2) INFORMATION FOR SEQ ID NO:185:

(i) SEQUENCE CHARACTERISTICS:
        (A) LENGTH: 14 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: hepatitis B virus adw2 isolate,
            nucleotides 1810 to 1823

(iii) HYPOTHETICAL: no (iv) ANTI-SENSE: no (vi) ORIGINAL SOURCE:
        (A) ORGANISM: Hepatitis B virus
        (C) INDIVIDUAL ISOLATE: adw2

(x) PUBLICATION INFORMATION:
        (A) AUTHORS: Valenzuela, P, Quiroga, M, Zaldivar, J,
            Gray, P, Ruter, W J.
        (B) TITLE: The nucleotide sequence of
            the Hepatitis B viral genome and the
            identification of the major viral genes
        (C) JOURNAL: In "Animal Virus Genetics", Fields, B N,
            Jaenisch, R, Fox C F eds
        (D) VOLUME:
        (F) PAGES: 57-70
        (G) DATE: 1980
        (K) RELEVANT RESIDUES IN SEQ ID NO: 185 :FROM 1 TO 14

(xi) SEQUENCE DESCRIPTION: SEQ ID NO: 185 :

TTCCTCTTCA TCCT                                                                 14

(2) INFORMATION FOR SEQ ID NO:186:

(i) SEQUENCE CHARACTERISTICS:
        (A) LENGTH: 14 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Hepatitis B
            isolate adw2 sequence region in Seq ID No 185

(iii) HYPOTHETICAL: yes (iv) ANTI-SENSE: no (x) PUBLICATION INFORMATION:
 (K) RELEVANT RESIDUES IN SEQ ID NO: 186 :FROM 1 TO 14

(xi) SEQUENCE DESCRIPTION: SEQ ID NO: 186 :

TCCTGCTTCT CCTT     14

(2) INFORMATION FOR SEQ ID NO:187:

(i) SEQUENCE CHARACTERISTICS:
  (A) LENGTH: 12 base pairs
  (B) TYPE: nucleic acid
  (C) STRANDEDNESS: double stranded
  (D) TOPOLOGY: linear (ii) MOLECULE TYPE: genomic DNA
  (A) DESCRIPTION: hepatitis B virus adw2 isolate,
   nucleotides 1833 to 1844

(iii) HYPOTHETICAL: no (iv) ANTI-SENSE: no (vi) ORIGINAL SOURCE:
  (A) ORGANISM: Hepatitis B virus
  (C) INDIVIDUAL ISOLATE: adw2

(x) PUBLICATION INFORMATION:
  (A) AUTHORS: Valenzuela, P, Quiroga, M, Zaldivar, J,
   Gray, P, Ruter, W J.
  (B) TITLE: The nucleotide sequence of
   the Hepatitis B viral genome and the
   identification of the major viral genes
  (C) JOURNAL: In "Animal Virus Genetics", Fields, B N,
   Jaenisch, R, Fox C F eds
  (D) VOLUME:
  (F) PAGES: 57-70
  (G) DATE: 1980
  (K) RELEVANT RESIDUES IN SEQ ID NO: 187 :FROM 1 TO 12

(xi) SEQUENCE DESCRIPTION: SEQ ID NO: 187 :

CCTCATCTTC TT     12

(2) INFORMATION FOR SEQ ID NO:188:

(i) SEQUENCE CHARACTERISTICS:
  (A) LENGTH: 12 bases
  (B) TYPE: nucleic acid
  (C) STRANDEDNESS: single stranded
  (D) TOPOLOGY: linear (ii) MOLECULE TYPE: other nucleic acid
  (A) DESCRIPTION: third strand derived from Hepatitis B
   isolate adw2 sequence region in Seq ID No 187

(iii) HYPOTHETICAL: yes (iv) ANTI-SENSE: no (x) PUBLICATION INFORMATION:
  (K) RELEVANT RESIDUES IN SEQ ID NO: 188 :FROM 1 TO 12

(xi) SEQUENCE DESCRIPTION: SEQ ID NO: 188 :

TTCTTCTGCT CC     12

(2) INFORMATION FOR SEQ ID NO:189:

(i) SEQUENCE CHARACTERISTICS:
  (A) LENGTH: 12 base pairs
  (B) TYPE: nucleic acid
  (C) STRANDEDNESS: double stranded
  (D) TOPOLOGY: linear (ii) MOLECULE TYPE: genomic DNA -continued ( A ) DESCRIPTION: hepatitis B virus adw2 isolate,
nucleotides 2258 to 2269

( i i i ) HYPOTHETICAL: no ( i v ) ANTI-SENSE: no ( v i ) ORIGINAL SOURCE:
( A ) ORGANISM: Hepatitis B virus
( C ) INDIVIDUAL ISOLATE: adw2

( x ) PUBLICATION INFORMATION:
( A ) AUTHORS: Valenzuela, P, Quiroga, M, Zaldivar, J,
Gray, P, Ruter, W J.
( B ) TITLE: The nucleotide sequence of
the Hepatitis B viral genome and the
identification of the major viral genes
( C ) JOURNAL: In "Animal Virus Genetics", Fields, B N,
Jaenisch, R, Fox C F eds
( D ) VOLUME:
( F ) PAGES: 57-70
( G ) DATE: 1980
( K ) RELEVANT RESIDUES IN SEQ ID NO: 189 :FROM 1 TO 12

( x i ) SEQUENCE DESCRIPTION: SEQ ID NO: 189 :

AAAAGATGG GG                                                                                          12

( 2 ) INFORMATION FOR SEQ ID NO:190:

( i ) SEQUENCE CHARACTERISTICS:
( A ) LENGTH: 12 bases
( B ) TYPE: nucleic acid
( C ) STRANDEDNESS: single stranded
( D ) TOPOLOGY: linear ( i i ) MOLECULE TYPE: other nucleic acid
( A ) DESCRIPTION: third strand derived from Hepatitis B
isolate adw2 sequence region in Seq ID No 189

( i i i ) HYPOTHETICAL: yes ( i v ) ANTI-SENSE: no ( x ) PUBLICATION INFORMATION:
( K ) RELEVANT RESIDUES IN SEQ ID NO: 190 :FROM 1 TO 12

( x i ) SEQUENCE DESCRIPTION: SEQ ID NO: 190 :

TTTTCTGCC CC                                                                                          12

( 2 ) INFORMATION FOR SEQ ID NO:191:

( i ) SEQUENCE CHARACTERISTICS:
( A ) LENGTH: 13 base pairs
( B ) TYPE: nucleic acid
( C ) STRANDEDNESS: double stranded
( D ) TOPOLOGY: linear ( i i ) MOLECULE TYPE: genomic DNA
( A ) DESCRIPTION: hepatitis B virus adw2 isolate,
nucleotides 2497 to 2509

( i i i ) HYPOTHETICAL: no ( i v ) ANTI-SENSE: no ( v i ) ORIGINAL SOURCE:
( A ) ORGANISM: Hepatitis B virus
( C ) INDIVIDUAL ISOLATE: adw2

( x ) PUBLICATION INFORMATION:
( A ) AUTHORS: Valenzuela, P, Quiroga, M, Zaldivar, J,
Gray, P, Ruter, W J.
( B ) TITLE: The nucleotide sequence of
the Hepatitis B viral genome and the
identification of the major viral genes
( C ) JOURNAL: In "Animal Virus Genetics", Fields, B N, Jaenisch, R, Fox C F eds
- (D) VOLUME:
- (F) PAGES: 57-70
- (G) DATE: 1980
- (K) RELEVANT RESIDUES IN SEQ ID NO: 191 :FROM 1 TO 13

(xi) SEQUENCE DESCRIPTION: SEQ ID NO: 191 :

CTTTCACTTT CTC 13

(2) INFORMATION FOR SEQ ID NO:192:

- (i) SEQUENCE CHARACTERISTICS:
  - (A) LENGTH: 13 bases
  - (B) TYPE: nucleic acid
  - (C) STRANDEDNESS: single stranded
  - (D) TOPOLOGY: linear

- (ii) MOLECULE TYPE: other nucleic acid
  - (A) DESCRIPTION: third strand derived from Hepatitis B isolate adw2 sequence region in Seq ID No 191

- (iii) HYPOTHETICAL: yes

- (iv) ANTI-SENSE: no

- (x) PUBLICATION INFORMATION:
  - (K) RELEVANT RESIDUES IN SEQ ID NO: 192 :FROM 1 TO 13

(xi) SEQUENCE DESCRIPTION: SEQ ID NO: 192 :

CTCTTTCGCT TTC 13

(2) INFORMATION FOR SEQ ID NO:193:

- (i) SEQUENCE CHARACTERISTICS:
  - (A) LENGTH: 11 base pairs
  - (B) TYPE: nucleic acid
  - (C) STRANDEDNESS: double stranded
  - (D) TOPOLOGY: linear

- (ii) MOLECULE TYPE: genomic DNA
  - (A) DESCRIPTION: hepatitis B virus adw2 isolate, nucleotides 2897 to 2907

- (iii) HYPOTHETICAL: no

- (iv) ANTI-SENSE: no

- (vi) ORIGINAL SOURCE:
  - (A) ORGANISM: Hepatitis B virus
  - (C) INDIVIDUAL ISOLATE: adw2

- (x) PUBLICATION INFORMATION:
  - (A) AUTHORS: Valenzuela, P, Quiroga, M, Zaldivar, J, Gray, P, Ruter, W J.
  - (B) TITLE: The nucleotide sequence of the Hepatitis B viral genome and the identification of the major viral genes
  - (C) JOURNAL: In "Animal Virus Genetics", Fields, B N, Jaenisch, R, Fox C F eds
  - (D) VOLUME:
  - (F) PAGES: 57-70
  - (G) DATE: 1980
  - (K) RELEVANT RESIDUES IN SEQ ID NO: 193 :FROM 1 TO 11

(xi) SEQUENCE DESCRIPTION: SEQ ID NO: 193 :

TCCCCTTCTC C 11

(2) INFORMATION FOR SEQ ID NO:194:

- (i) SEQUENCE CHARACTERISTICS:
  - (A) LENGTH: 11 bases
  - (B) TYPE: nucleic acid
  - (C) STRANDEDNESS: single stranded
  - (D) TOPOLOGY: linear (  i  i  ) MOLECULE TYPE: other nucleic acid
        ( A ) DESCRIPTION: third strand derived from Hepatitis B
            isolate adw2 sequence region in Seq ID No 193

(  i  i  i  ) HYPOTHETICAL: yes (  i  v  ) ANTI-SENSE: no ( x ) PUBLICATION INFORMATION:
        ( K ) RELEVANT RESIDUES IN SEQ ID NO: 194 :FROM 1 TO 11

( x i ) SEQUENCE DESCRIPTION: SEQ ID NO: 194 :

C C T C T T C C C C  T                                                                                                       1 1

( 2 ) INFORMATION FOR SEQ ID NO:195:

( i ) SEQUENCE CHARACTERISTICS:
        ( A ) LENGTH: 11 base pairs
        ( B ) TYPE: nucleic acid
        ( C ) STRANDEDNESS: double stranded
        ( D ) TOPOLOGY: linear (  i  i  ) MOLECULE TYPE: genomic DNA
        ( A ) DESCRIPTION: hepatitis B virus adw2 isolate,
            nucleotides 3151 to 3161

(  i  i  i  ) HYPOTHETICAL: no (  i  v  ) ANTI-SENSE: no ( v i ) ORIGINAL SOURCE:
        ( A ) ORGANISM: Hepatitis B virus
        ( C ) INDIVIDUAL ISOLATE: adw2

( x ) PUBLICATION INFORMATION:
        ( A ) AUTHORS: Valenzuela, P, Quiroga, M, Zaldivar, J,
            Gray, P, Ruter, W J.
        ( B ) TITLE: The nucleotide sequence of
            the Hepatitis B viral genome and the
            identification of the major viral genes
        ( C ) JOURNAL: In "Animal Virus Genetics", Fields, B N,
            Jaenisch, R, Fox C F eds
        ( D ) VOLUME:
        ( F ) PAGES: 57-70
        ( G ) DATE: 1980
        ( K ) RELEVANT RESIDUES IN SEQ ID NO: 195 :FROM 1 TO 11

( x i ) SEQUENCE DESCRIPTION: SEQ ID NO: 195 :

G G G G G A G G A G  A                                                                                                       1 1

( 2 ) INFORMATION FOR SEQ ID NO:196:

( i ) SEQUENCE CHARACTERISTICS:
        ( A ) LENGTH: 11 bases
        ( B ) TYPE: nucleic acid
        ( C ) STRANDEDNESS: single stranded
        ( D ) TOPOLOGY: linear (  i  i  ) MOLECULE TYPE: other nucleic acid
        ( A ) DESCRIPTION: third strand derived from Hepatitis B
            isolate adw2 sequence region in Seq ID No 195

(  i  i  i  ) HYPOTHETICAL: yes (  i  v  ) ANTI-SENSE: no ( x ) PUBLICATION INFORMATION:
        ( K ) RELEVANT RESIDUES IN SEQ ID NO: 196 :FROM 1 TO 11

( x i ) SEQUENCE DESCRIPTION: SEQ ID NO: 196 :

C C C C C T C C T C  T                                                                                                       1 1

( 2 ) INFORMATION FOR SEQ ID NO:197:

( i ) SEQUENCE CHARACTERISTICS:
    ( A ) LENGTH: 14 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: hepatitis B virus adr isolate,
    nucleotides 274 to 287

( i i i ) HYPOTHETICAL: no ( i v ) ANTI-SENSE: no ( v i ) ORIGINAL SOURCE:
    ( A ) ORGANISM: Hepatitis B virus
    ( C ) INDIVIDUAL ISOLATE: adr ( x ) PUBLICATION INFORMATION:
    ( A ) AUTHORS: Fujiyama, A, Miyanohara, A, Nozaki, C,
    Toneyama, T,, Ohromo, N, Matsubara, K.
    ( B ) TITLE: Cloning and structural
    analysis of Hepatitis B virus DNAs subtype adr
    ( C ) JOURNAL: Nucleic Acids Research
    ( D ) VOLUME: 11
    ( F ) PAGES: 4601-4610
    ( G ) DATE: 1983
    ( K ) RELEVANT RESIDUES IN SEQ ID NO: 197 :FROM 1 TO 14

( x i ) SEQUENCE DESCRIPTION: SEQ ID NO: 197 :

TTCCTCTTCA TCCT 14

( 2 ) INFORMATION FOR SEQ ID NO:198:

( i ) SEQUENCE CHARACTERISTICS:
    ( A ) LENGTH: 14 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from Hepatitis B
    isolate adr sequence region in Seq ID No 197

( i i i ) HYPOTHETICAL: yes ( i v ) ANTI-SENSE: no ( x ) PUBLICATION INFORMATION:
    ( K ) RELEVANT RESIDUES IN SEQ ID NO: 198 :FROM 1 TO 14

( x i ) SEQUENCE DESCRIPTION: SEQ ID NO: 198 :

TCCTGCTTCT CCTT 14

( 2 ) INFORMATION FOR SEQ ID NO:199:

( i ) SEQUENCE CHARACTERISTICS:
    ( A ) LENGTH: 10 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: hepatitis B virus adr isolate,
    nucleotides 427 to 436

( i i i ) HYPOTHETICAL: no ( i v ) ANTI-SENSE: no ( v i ) ORIGINAL SOURCE:
    ( A ) ORGANISM: Hepatitis B virus
    ( C ) INDIVIDUAL ISOLATE: adr ( x ) PUBLICATION INFORMATION:

(A) AUTHORS: Fujiyama, A, Miyanohara, A, Nozaki, C,
    Toneyama, T,, Ohromo, N, Matsubara, K.
(B) TITLE: Cloning and structural
    analysis of Hepatitis B virus DNAs subtype adr
(C) JOURNAL: Nucleic Acids Research
(D) VOLUME: 11
(F) PAGES: 4601-4610
(G) DATE: 1983
(K) RELEVANT RESIDUES IN SEQ ID NO: 199 :FROM 1 TO 10

(x i) SEQUENCE DESCRIPTION: SEQ ID NO: 199 :

TTTCCCTCTT                                                                                          10

(2) INFORMATION FOR SEQ ID NO:200:

(i) SEQUENCE CHARACTERISTICS:
    (A) LENGTH: 10 bases
    (B) TYPE: nucleic acid
    (C) STRANDEDNESS: single stranded
    (D) TOPOLOGY: linear (i i) MOLECULE TYPE: other nucleic acid
    (A) DESCRIPTION: third strand derived from Hepatitis B
        isolate adr sequence region in Seq ID No 199

(i i i) HYPOTHETICAL: yes (i v) ANTI-SENSE: no (x) PUBLICATION INFORMATION:
    (K) RELEVANT RESIDUES IN SEQ ID NO: 200 :FROM 1 TO 10

(x i) SEQUENCE DESCRIPTION: SEQ ID NO: 200 :

TTCTCCCTTT                                                                                          10

(2) INFORMATION FOR SEQ ID NO:201:

(i) SEQUENCE CHARACTERISTICS:
    (A) LENGTH: 10 base pairs
    (B) TYPE: nucleic acid
    (C) STRANDEDNESS: double stranded
    (D) TOPOLOGY: linear (i i) MOLECULE TYPE: genomic DNA
    (A) DESCRIPTION: hepatitis B virus adr isolate,
        nucleotides 1236 to 1245

(i i i) HYPOTHETICAL: no (i v) ANTI-SENSE: no (v i) ORIGINAL SOURCE:
    (A) ORGANISM: Hepatitis B virus
    (C) INDIVIDUAL ISOLATE: adr (x) PUBLICATION INFORMATION:
    (A) AUTHORS: Fujiyama, A, Miyanohara, A, Nozaki, C,
        Toneyama, T,, Ohromo, N, Matsubara, K.
    (B) TITLE: Cloning and structural
        analysis of Hepatitis B virus DNAs subtype adr
    (C) JOURNAL: Nucleic Acids Research
    (D) VOLUME: 11
    (F) PAGES: 4601-4610
    (G) DATE: 1983
    (K) RELEVANT RESIDUES IN SEQ ID NO: 201 :FROM 1 TO 10

(x i) SEQUENCE DESCRIPTION: SEQ ID NO: 201 :

CCTCCTTTCC                                                                                          10

(2) INFORMATION FOR SEQ ID NO:202:

(i) SEQUENCE CHARACTERISTICS:
    (A) LENGTH: 10 bases
    (B) TYPE: nucleic acid (C) STRANDEDNESS: single stranded
(D) TOPOLOGY: linear (ii) MOLECULE TYPE: other nucleic acid
(A) DESCRIPTION: third strand derived from Hepatitis B
isolate adr sequence region in Seq ID No 201

(iii) HYPOTHETICAL: yes (iv) ANTI-SENSE: no (x) PUBLICATION INFORMATION:
(K) RELEVANT RESIDUES IN SEQ ID NO: 202 :FROM 1 TO 10

(xi) SEQUENCE DESCRIPTION: SEQ ID NO: 202 :

C C T T T C C T C C 10

(2) INFORMATION FOR SEQ ID NO:203:

(i) SEQUENCE CHARACTERISTICS:
(A) LENGTH: 10 base pairs
(B) TYPE: nucleic acid
(C) STRANDEDNESS: double stranded
(D) TOPOLOGY: linear (ii) MOLECULE TYPE: genomic DNA
(A) DESCRIPTION: hepatitis B virus adr isolate,
nucleotides 2103 to 2112

(iii) HYPOTHETICAL: no (iv) ANTI-SENSE: no (vi) ORIGINAL SOURCE:
(A) ORGANISM: Hepatitis B virus
(C) INDIVIDUAL ISOLATE: adr (x) PUBLICATION INFORMATION:
(A) AUTHORS: Fujiyama, A, Miyanohara, A, Nozaki, C,
Toneyama, T,, Ohromo, N, Matsubara, K.
(B) TITLE: Cloning and structural
analysis of Hepatitis B virus DNAs subtype adr
(C) JOURNAL: Nucleic Acids Research
(D) VOLUME: 11
(F) PAGES: 4601-4610
(G) DATE: 1983
(K) RELEVANT RESIDUES IN SEQ ID NO: 203 :FROM 1 TO 10

(xi) SEQUENCE DESCRIPTION: SEQ ID NO: 203 :

G G A A G A G A A A 10

(2) INFORMATION FOR SEQ ID NO:204:

(i) SEQUENCE CHARACTERISTICS:
(A) LENGTH: 10 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from Hepatitis B
isolate adr sequence region in Seq ID No 203

(iii) HYPOTHETICAL: yes (iv) ANTI-SENSE: no (x) PUBLICATION INFORMATION:
(K) RELEVANT RESIDUES IN SEQ ID NO: 204 :FROM 1 TO 10

(xi) SEQUENCE DESCRIPTION: SEQ ID NO: 204 :

C C T T C T C T T T 10

(2) INFORMATION FOR SEQ ID NO:205:

( i ) SEQUENCE CHARACTERISTICS:
    ( A ) LENGTH: 10 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: hepatitis B virus adr isolate,
        nucleotides 2241 to 2250

( i i i ) HYPOTHETICAL: no ( i v ) ANTI-SENSE: no ( v i ) ORIGINAL SOURCE:
    ( A ) ORGANISM: Hepatitis B virus
    ( C ) INDIVIDUAL ISOLATE: adr ( x ) PUBLICATION INFORMATION:
    ( A ) AUTHORS: Fujiyama, A, Miyanohara, A, Nozaki, C,
        Toneyama, T,, Ohromo, N, Matsubara, K.
    ( B ) TITLE: Cloning and structural
        analysis of Hepatitis B virus DNAs subtype adr
    ( C ) JOURNAL: Nucleic Acids Research
    ( D ) VOLUME: 11
    ( F ) PAGES: 4601-4610
    ( G ) DATE: 1983
    ( K ) RELEVANT RESIDUES IN SEQ ID NO: 205 :FROM 1 TO 10

( x i ) SEQUENCE DESCRIPTION: SEQ ID NO: 205 :

A G A A G A A G A A         1 0

( 2 ) INFORMATION FOR SEQ ID NO:206:

( i ) SEQUENCE CHARACTERISTICS:
    ( A ) LENGTH: 10 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from Hepatitis B
        isolate adr sequence region in Seq ID No 205

( i i i ) HYPOTHETICAL: yes ( i v ) ANTI-SENSE: no ( x ) PUBLICATION INFORMATION:
    ( K ) RELEVANT RESIDUES IN SEQ ID NO: 206 :FROM 1 TO 10

( x i ) SEQUENCE DESCRIPTION: SEQ ID NO: 206 :

T C T T C T T C T T         1 0

( 2 ) INFORMATION FOR SEQ ID NO:207:

( i ) SEQUENCE CHARACTERISTICS:
    ( A ) LENGTH: 11 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: hepatitis B virus adr isolate,
        nucleotides 2341 to 2351

( i i i ) HYPOTHETICAL: no ( i v ) ANTI-SENSE: no ( v i ) ORIGINAL SOURCE:
    ( A ) ORGANISM: Hepatitis B virus
    ( C ) INDIVIDUAL ISOLATE: adr ( x ) PUBLICATION INFORMATION:

(A) AUTHORS: Fujiyama, A, Miyanohara, A, Nozaki, C,
            Toneyama, T,, Ohromo, N, Matsubara, K.
(B) TITLE: Cloning and structural
            analysis of Hepatitis B virus DNAs subtype adr
(C) JOURNAL: Nucleic Acids Research
(D) VOLUME: 11
(F) PAGES: 4601-4610
(G) DATE: 1983
(K) RELEVANT RESIDUES IN SEQ ID NO: 207 :FROM 1 TO 11

(x i) SEQUENCE DESCRIPTION: SEQ ID NO: 207 :

AAGGTGGGAA A                                                                 11

(2) INFORMATION FOR SEQ ID NO:208:

(i) SEQUENCE CHARACTERISTICS:
    (A) LENGTH: 11 bases
    (B) TYPE: nucleic acid
    (C) STRANDEDNESS: single stranded
    (D) TOPOLOGY: linear (i i) MOLECULE TYPE: other nucleic acid
    (A) DESCRIPTION: third strand derived from Hepatitis B
            isolate adr sequence region in Seq ID No 207

(i i i) HYPOTHETICAL: yes (i v) ANTI-SENSE: no (x) PUBLICATION INFORMATION:
    (K) RELEVANT RESIDUES IN SEQ ID NO: 208 :FROM 1 TO 11

(x i) SEQUENCE DESCRIPTION: SEQ ID NO: 208 :

TTCCGCCCTT T                                                                 11

(2) INFORMATION FOR SEQ ID NO:209:

(i) SEQUENCE CHARACTERISTICS:
    (A) LENGTH: 12 base pairs
    (B) TYPE: nucleic acid
    (C) STRANDEDNESS: double stranded
    (D) TOPOLOGY: linear (i i) MOLECULE TYPE: genomic DNA
    (A) DESCRIPTION: hepatitis B virus adr isolate,
            nucleotides 2362 to 2373

(i i i) HYPOTHETICAL: no (i v) ANTI-SENSE: no (v i) ORIGINAL SOURCE:
    (A) ORGANISM: Hepatitis B virus
    (C) INDIVIDUAL ISOLATE: adr (x) PUBLICATION INFORMATION:
    (A) AUTHORS: Fujiyama, A, Miyanohara, A, Nozaki, C,
            Toneyama, T,, Ohromo, N, Matsubara, K.
    (B) TITLE: Cloning and structural
            analysis of Hepatitis B virus DNAs subtype adr
    (C) JOURNAL: Nucleic Acids Research
    (D) VOLUME: 11
    (F) PAGES: 4601-4610
    (G) DATE: 1983
    (K) RELEVANT RESIDUES IN SEQ ID NO: 209 :FROM 1 TO 12

(x i) SEQUENCE DESCRIPTION: SEQ ID NO: 209 :

CTTTATTCTT CT                                                                12

(2) INFORMATION FOR SEQ ID NO:210:

(i) SEQUENCE CHARACTERISTICS:
    (A) LENGTH: 12 bases
    (B) TYPE: nucleic acid (C) STRANDEDNESS: single stranded
(D) TOPOLOGY: linear (ii) MOLECULE TYPE: other nucleic acid
 (A) DESCRIPTION: third strand derived from Hepatitis B
  isolate adr sequence region in Seq ID No 209

(iii) HYPOTHETICAL: yes (iv) ANTI-SENSE: no (x) PUBLICATION INFORMATION:
 (K) RELEVANT RESIDUES IN SEQ ID NO: 210 :FROM 1 TO 12

(xi) SEQUENCE DESCRIPTION: SEQ ID NO: 210 :

TCTTCTTGTT TC                        12

(2) INFORMATION FOR SEQ ID NO:211:

(i) SEQUENCE CHARACTERISTICS:
 (A) LENGTH: 10 base pairs
 (B) TYPE: nucleic acid
 (C) STRANDEDNESS: double stranded
 (D) TOPOLOGY: linear (ii) MOLECULE TYPE: genomic DNA
 (A) DESCRIPTION: hepatitis B virus adr isolate,
  nucleotides 2653 to 2662

(iii) HYPOTHETICAL: no (iv) ANTI-SENSE: no (vi) ORIGINAL SOURCE:
 (A) ORGANISM: Hepatitis B virus
 (C) INDIVIDUAL ISOLATE: adr (x) PUBLICATION INFORMATION:
 (A) AUTHORS: Fujiyama, A, Miyanohara, A, Nozaki, C,
  Toneyama, T,, Ohromo, N, Matsubara, K.
 (B) TITLE: Cloning and structural
  analysis of Hepatitis B virus DNAs subtype adr
 (C) JOURNAL: Nucleic Acids Research
 (D) VOLUME: 11
 (F) PAGES: 4601-4610
 (G) DATE: 1983
 (K) RELEVANT RESIDUES IN SEQ ID NO: 211 :FROM 1 TO 10

(xi) SEQUENCE DESCRIPTION: SEQ ID NO: 211 :

AAGAGAGAAA                         10

(2) INFORMATION FOR SEQ ID NO:212:

(i) SEQUENCE CHARACTERISTICS:
 (A) LENGTH: 10 bases
 (B) TYPE: nucleic acid
 (C) STRANDEDNESS: single stranded
 (D) TOPOLOGY: linear (ii) MOLECULE TYPE: other nucleic acid
 (A) DESCRIPTION: third strand derived from Hepatitis B
  isolate adr sequence region in Seq ID No 211

(iii) HYPOTHETICAL: yes (iv) ANTI-SENSE: no (x) PUBLICATION INFORMATION:
 (K) RELEVANT RESIDUES IN SEQ ID NO: 212 :FROM 1 TO 10

(xi) SEQUENCE DESCRIPTION: SEQ ID NO: 212 :

TTCTCTCTTT                         10

(2) INFORMATION FOR SEQ ID NO:213:

(  i  ) SEQUENCE CHARACTERISTICS:
    ( A ) LENGTH: 19 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: hepatitis B virus adr isolate,
    nucleotides 3036 to 3054

( i i i ) HYPOTHETICAL: no ( i v ) ANTI-SENSE: no ( v i ) ORIGINAL SOURCE:
    ( A ) ORGANISM: Hepatitis B virus
    ( C ) INDIVIDUAL ISOLATE: adr ( x ) PUBLICATION INFORMATION:
    ( A ) AUTHORS: Fujiyama, A, Miyanohara, A, Nozaki, C,
    Toneyama, T,, Ohromo, N, Matsubara, K.
    ( B ) TITLE: Cloning and structural
    analysis of Hepatitis B virus DNAs subtype adr
    ( C ) JOURNAL: Nucleic Acids Research
    ( D ) VOLUME: 11
    ( F ) PAGES: 4601-4610
    ( G ) DATE: 1983
    ( K ) RELEVANT RESIDUES IN SEQ ID NO: 213 :FROM 1 TO 19

( x i ) SEQUENCE DESCRIPTION: SEQ ID NO: 213 :

CTCCCATCTC TCCACCTCT 19

( 2 ) INFORMATION FOR SEQ ID NO:214:

(  i  ) SEQUENCE CHARACTERISTICS:
    ( A ) LENGTH: 19 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from Hepatitis B
    isolate adr sequence region in Seq ID No 213

( i i i ) HYPOTHETICAL: yes ( i v ) ANTI-SENSE: no ( x ) PUBLICATION INFORMATION:
    ( K ) RELEVANT RESIDUES IN SEQ ID NO: 214 :FROM 1 TO 19

( x i ) SEQUENCE DESCRIPTION: SEQ ID NO: 214 :

TCTCCGCCTC TCTGCCCTC 19

( 2 ) INFORMATION FOR SEQ ID NO:215:

(  i  ) SEQUENCE CHARACTERISTICS:
    ( A ) LENGTH: 12 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: 23s rRNA gene from Escherichia coli
    ( Accession # M25458 ) nucleotides 212 to 223

( i i i ) HYPOTHETICAL: no ( i v ) ANTI-SENSE: no ( v i ) ORIGINAL SOURCE:
    ( A ) ORGANISM: Escherichia coli
    ( B ) STRAIN: MRE600

( x ) PUBLICATION INFORMATION:

(A) AUTHORS: Branlant, C, Krol, A, Machatt, M, A,
    Pouyet, J, Ebel, J P, Edwards, K, Koessel,
    H.
(B) TITLE: Primary and secondary
    structures of Escherichia coli MRE 600 23S
    ribosomal RNA Comparison with models of
    secondary structure for maize chloroplast 23S
    rRNA and for large portions of mouse and human
    16S mitochondrial rRNAs
(C) JOURNAL: Nucleic Acids Research
(D) VOLUME: 9
(F) PAGES: 4303-4324
(G) DATE: 1981
(K) RELEVANT RESIDUES IN SEQ ID NO: 215 :FROM 1 TO 12

(xi) SEQUENCE DESCRIPTION: SEQ ID NO: 215 :

GAGGAAAAGA AA                                                                12

(2) INFORMATION FOR SEQ ID NO:216:

(i) SEQUENCE CHARACTERISTICS:
    (A) LENGTH: 12 bases
    (B) TYPE: nucleic acid
    (C) STRANDEDNESS: single stranded
    (D) TOPOLOGY: linear (ii) MOLECULE TYPE: other nucleic acid
    (A) DESCRIPTION: third strand derived from E. coli 23s
        region in Seq ID No 215

(iii) HYPOTHETICAL: yes (iv) ANTI-SENSE: no (x) PUBLICATION INFORMATION:
    (K) RELEVANT RESIDUES IN SEQ ID NO: 216 :FROM 1 TO 12

(xi) SEQUENCE DESCRIPTION: SEQ ID NO: 216 :

CTCCTTTTCT TT                                                                12

(2) INFORMATION FOR SEQ ID NO:217:

(i) SEQUENCE CHARACTERISTICS:
    (A) LENGTH: 18 base pairs
    (B) TYPE: nucleic acid
    (C) STRANDEDNESS: double stranded
    (D) TOPOLOGY: linear (ii) MOLECULE TYPE: genomic DNA
    (A) DESCRIPTION: 23s rRNA gene from Escherichia coli
        (Accession # M25458) nucleotides 493 to 510

(iii) HYPOTHETICAL: no (iv) ANTI-SENSE: no (vi) ORIGINAL SOURCE:
    (A) ORGANISM: Escherichia coli
    (B) STRAIN: MRE600

(x) PUBLICATION INFORMATION:
    (A) AUTHORS: Branlant, C, Krol, A, Machatt, M, A,
        Pouyet, J, Ebel, J P, Edwards, K, Koessel,
        H.
    (B) TITLE: Primary and secondary
        structures of Escherichia coli MRE 600 23S
        ribosomal RNA Comparison with models of
        secondary structure for maize chloroplast 23S
        rRNA and for large portions of mouse and human
        16S mitochondrial rRNAs
    (C) JOURNAL: Nucleic Acids Research
    (D) VOLUME: 9
    (F) PAGES: 4303-4324
    (G) DATE: 1981
    (K) RELEVANT RESIDUES IN SEQ ID NO: 217 :FROM 1 TO 18

( x i ) SEQUENCE DESCRIPTION: SEQ ID NO: 217 :

GAGGGGAGTG AAAAAGAA 18

( 2 ) INFORMATION FOR SEQ ID NO:218:

( i ) SEQUENCE CHARACTERISTICS:
        ( A ) LENGTH: 18 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from E. coli 23s
            region in Seq ID No 217

( i i i ) HYPOTHETICAL: yes ( i v ) ANTI-SENSE: no ( x ) PUBLICATION INFORMATION:
        ( K ) RELEVANT RESIDUES IN SEQ ID NO: 218 :FROM 1 TO 18

( x i ) SEQUENCE DESCRIPTION: SEQ ID NO: 218 :

CTCCCCTCGC TTTTTCTT 18

( 2 ) INFORMATION FOR SEQ ID NO:219:

( i ) SEQUENCE CHARACTERISTICS:
        ( A ) LENGTH: 12 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: 23s rRNA gene from Escherichia coli
        ( A c c e s s i o n # M 2 5 4 5 8 ) nucleotides 785 to 796

( i i i ) HYPOTHETICAL: no ( i v ) ANTI-SENSE: no ( v i ) ORIGINAL SOURCE:
        ( A ) ORGANISM: Escherichia coli
        ( B ) STRAIN: MRE600

( x ) PUBLICATION INFORMATION:
        ( A ) AUTHORS: Branlant, C, Krol, A, Machatt, M, A,
            Pouyet, J, Ebel, J P, Edwards, K, Koessel,
            H.
        ( B ) TITLE: Primary and secondary
            structures of Escherichia coli MRE 600 23S
            ribosomal RNA Comparison with models of
            secondary structure for maize chloroplast 23S
            rRNA and for large portions of mouse and human
            16S mitochondrial rRNAs
        ( C ) JOURNAL: Nucleic Acids Research
        ( D ) VOLUME: 9
        ( F ) PAGES: 4303-4324
        ( G ) DATE: 1981
        ( K ) RELEVANT RESIDUES IN SEQ ID NO: 219 :FROM 1 TO 12

( x i ) SEQUENCE DESCRIPTION: SEQ ID NO: 219 :

GGGGGTGAAA GG 12

( 2 ) INFORMATION FOR SEQ ID NO:220:

( i ) SEQUENCE CHARACTERISTICS:
        ( A ) LENGTH: 12 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from E. coli 23s region in Seq ID No 219

(iii) HYPOTHETICAL: yes (iv) ANTI-SENSE: no (x) PUBLICATION INFORMATION:
  (K) RELEVANT RESIDUES IN SEQ ID NO: 220 :FROM 1 TO 12

(xi) SEQUENCE DESCRIPTION: SEQ ID NO: 220 :

CCCCCGCTTT CC 12

(2) INFORMATION FOR SEQ ID NO:221:

(i) SEQUENCE CHARACTERISTICS:
  (A) LENGTH: 11 base pairs
  (B) TYPE: nucleic acid
  (C) STRANDEDNESS: double stranded
  (D) TOPOLOGY: linear (ii) MOLECULE TYPE: genomic DNA
  (A) DESCRIPTION: 23s rRNA gene from Escherichia coli
    (Accession # M25458) nucleotides 982 to 992

(iii) HYPOTHETICAL: no (iv) ANTI-SENSE: no (vi) ORIGINAL SOURCE:
  (A) ORGANISM: Escherichia coli
  (B) STRAIN: MRE600

(x) PUBLICATION INFORMATION:
  (A) AUTHORS: Branlant, C, Krol, A, Machatt, M, A,
      Pouyet, J, Ebel, J P, Edwards, K, Koessel,
      H.
  (B) TITLE: Primary and secondary
      structures of Escherichia coli MRE 600 23S
      ribosomal RNA Comparison with models of
      secondary structure for maize chloroplast 23S
      rRNA and for large portions of mouse and human
      16S mitochondrial rRNAs
  (C) JOURNAL: Nucleic Acids Research
  (D) VOLUME: 9
  (F) PAGES: 4303-4324
  (G) DATE: 1981
  (K) RELEVANT RESIDUES IN SEQ ID NO: 221 :FROM 1 TO 11

(xi) SEQUENCE DESCRIPTION: SEQ ID NO: 221 :

GAAGAGGGAA A 11

(2) INFORMATION FOR SEQ ID NO:222:

(i) SEQUENCE CHARACTERISTICS:
  (A) LENGTH: 11 bases
  (B) TYPE: nucleic acid
  (C) STRANDEDNESS: single stranded
  (D) TOPOLOGY: linear (ii) MOLECULE TYPE: other nucleic acid
  (A) DESCRIPTION: third strand derived from E. coli 23s
      region in Seq ID No 221

(iii) HYPOTHETICAL: yes (iv) ANTI-SENSE: no (x) PUBLICATION INFORMATION:
  (K) RELEVANT RESIDUES IN SEQ ID NO: 222 :FROM 1 TO 11

(xi) SEQUENCE DESCRIPTION: SEQ ID NO: 222 :

CTTCTCCCTT T 11

(2) INFORMATION FOR SEQ ID NO:223:

( i ) SEQUENCE CHARACTERISTICS:
    ( A ) LENGTH: 10 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: 23s rRNA gene from Escherichia coli
    ( A c c e s s i o n # M 2 5 4 5 8 ) nucleotides 1410 to 1419

( i i i ) HYPOTHETICAL: no ( i v ) ANTI-SENSE: no ( v i ) ORIGINAL SOURCE:
    ( A ) ORGANISM: Escherichia coli
    ( B ) STRAIN: MRE600

( x ) PUBLICATION INFORMATION:
    ( A ) AUTHORS: Branlant, C, Krol, A, Machatt, M, A,
        Pouyet, J, Ebel, J P, Edwards, K, Koessel,
        H.
    ( B ) TITLE: Primary and secondary
        structures of Escherichia coli MRE 600 23S
        ribosomal RNA Comparison with models of
        secondary structure for maize chloroplast 23S
        rRNA and for large portions of mouse and human
        16S mitochondrial rRNAs
    ( C ) JOURNAL: Nucleic Acids Research
    ( D ) VOLUME: 9
    ( F ) PAGES: 4303-4324
    ( G ) DATE: 1981
    ( K ) RELEVANT RESIDUES IN SEQ ID NO: 223 :FROM 1 TO 10

( x i ) SEQUENCE DESCRIPTION: SEQ ID NO: 223 :

G A A G G G G G G A                 1 0

( 2 ) INFORMATION FOR SEQ ID NO:224:

( i ) SEQUENCE CHARACTERISTICS:
        ( A ) LENGTH: 10 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from E. coli 23s
            region in Seq ID No 223

( i i i ) HYPOTHETICAL: yes ( i v ) ANTI-SENSE: no ( x ) PUBLICATION INFORMATION:
        ( K ) RELEVANT RESIDUES IN SEQ ID NO: 224 :FROM 1 TO 10

( x i ) SEQUENCE DESCRIPTION: SEQ ID NO: 224 :

C T T C C C C C C T                 1 0

( 2 ) INFORMATION FOR SEQ ID NO:225:

( i ) SEQUENCE CHARACTERISTICS:
        ( A ) LENGTH: 11 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: 23s rRNA gene from Halococcus morrhuae
        ( A c c e s s i o n # X 0 5 4 8 1 ) nucleotides 181 to 191

( i i i ) HYPOTHETICAL: no ( i v ) ANTI-SENSE: no (v i) ORIGINAL SOURCE:
  (A) ORGANISM: Halococcus morrhuae (x) PUBLICATION INFORMATION:
  (A) AUTHORS: Leffers, H, Kjems, J, Ostergaard, L,
      Larsen, N, Garrett, R A.
  (B) TITLE: Evolutionary Relationship
      Amongst Archaebacteria: A Comparative Study of
      23 S Ribosomal RNAs of a Sulphur-dependent
      Extreme Thermophile, an Extreme Halophile and a
      Thermophilic Methanogen
  (C) JOURNAL: Journal of Molecular Biology
  (D) VOLUME: 195
  (F) PAGES: 43-61
  (G) DATE: 1987
  (K) RELEVANT RESIDUES IN SEQ ID NO: 225 :FROM 1 TO 11

(x i) SEQUENCE DESCRIPTION: SEQ ID NO: 225 :

A G G A A G A G A A  A                                                                                     11

(2) INFORMATION FOR SEQ ID NO:226:

(i) SEQUENCE CHARACTERISTICS:
      (A) LENGTH: 11 bases
      (B) TYPE: nucleic acid
      (C) STRANDEDNESS: single stranded
      (D) TOPOLOGY: linear (i i) MOLECULE TYPE: other nucleic acid
      (A) DESCRIPTION: third strand derived from H. morrhuae
          23s region in Seq ID No 225

(i i i) HYPOTHETICAL: yes (i v) ANTI-SENSE: no (x) PUBLICATION INFORMATION:
      (K) RELEVANT RESIDUES IN SEQ ID NO: 226 :FROM 1 TO 11

(x i) SEQUENCE DESCRIPTION: SEQ ID NO: 226 :

T C C T T C T C T T  T                                                                                     11

(2) INFORMATION FOR SEQ ID NO:227:

(i) SEQUENCE CHARACTERISTICS:
      (A) LENGTH: 12 base pairs
      (B) TYPE: nucleic acid
      (C) STRANDEDNESS: double stranded
      (D) TOPOLOGY: linear (i i) MOLECULE TYPE: genomic DNA
      (A) DESCRIPTION: 23s rRNA gene from Halococcus morrhuae
          (A c c e s s i o n   #   X 0 5 4 8 1 ) nucleotides 880 to 891

(i i i) HYPOTHETICAL: no (i v) ANTI-SENSE: no (v i) ORIGINAL SOURCE:
      (A) ORGANISM: Halococcus morrhuae (x) PUBLICATION INFORMATION:
      (A) AUTHORS: Leffers, H, Kjems, J, Ostergaard, L,
          Larsen, N, Garrett, R A.
      (B) TITLE: Evolutionary Relationship
          Amongst Archaebacteria: A Comparative Study of
          23 S Ribosomal RNAs of a Sulphur-dependent
          Extreme Thermophile, an Extreme Halophile and a
          Thermophilic Methanogen
      (C) JOURNAL: Journal of Molecular Biology
      (D) VOLUME: 195
      (F) PAGES: 43-61
      (G) DATE: 1987
      (K) RELEVANT RESIDUES IN SEQ ID NO: 227 :FROM 1 TO 12

(x i) SEQUENCE DESCRIPTION: SEQ ID NO: 227 :

AGGGGTGAAA GG 12

( 2 ) INFORMATION FOR SEQ ID NO:228:

( i ) SEQUENCE CHARACTERISTICS:
    ( A ) LENGTH: 12 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from H. morrhuae
      23s region in Seq ID No 227

( i i i ) HYPOTHETICAL: yes ( i v ) ANTI-SENSE: no ( x ) PUBLICATION INFORMATION:
    ( K ) RELEVANT RESIDUES IN SEQ ID NO: 228 :FROM 1 TO 12

( x i ) SEQUENCE DESCRIPTION: SEQ ID NO: 228 :

TCCCCGCTTT CC 12

( 2 ) INFORMATION FOR SEQ ID NO:229:

( i ) SEQUENCE CHARACTERISTICS:
    ( A ) LENGTH: 12 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: 23s rRNA gene from Halococcus morrhuae
      ( A c c e s s i o n # X 0 5 4 8 1 ) nucleotides 1628 to 1639

( i i i ) HYPOTHETICAL: no ( i v ) ANTI-SENSE: no ( v i ) ORIGINAL SOURCE:
    ( A ) ORGANISM: Halococcus morrhuae ( x ) PUBLICATION INFORMATION:
    ( A ) AUTHORS: Leffers, H, Kjems, J, Ostergaard, L,
      Larsen, N, Garrett, R A.
    ( B ) TITLE: Evolutionary Relationship
      Amongst Archaebacteria: A Comparative Study of
      23 S Ribosomal RNAs of a Sulphur-dependent
      Extreme Thermophile, an Extreme Halophile and a
      Thermophilic Methanogen
    ( C ) JOURNAL: Journal of Molecular Biology
    ( D ) VOLUME: 195
    ( F ) PAGES: 43-61
    ( G ) DATE: 1987
    ( K ) RELEVANT RESIDUES IN SEQ ID NO: 229 :FROM 1 TO 12

( x i ) SEQUENCE DESCRIPTION: SEQ ID NO: 229 :

GAGATAGAGA AA 12

( 2 ) INFORMATION FOR SEQ ID NO:230:

( i ) SEQUENCE CHARACTERISTICS:
    ( A ) LENGTH: 12 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from H. morrhuae
      23s region in Seq ID No 229

( i i i ) HYPOTHETICAL: yes (i v) ANTI-SENSE: no (x) PUBLICATION INFORMATION:
(K) RELEVANT RESIDUES IN SEQ ID NO: 230 :FROM 1 TO 12

(x i) SEQUENCE DESCRIPTION: SEQ ID NO: 230 :

CTCTGTCTCT TT 12

(2) INFORMATION FOR SEQ ID NO:231:

(i) SEQUENCE CHARACTERISTICS:
(A) LENGTH: 13 base pairs
(B) TYPE: nucleic acid
(C) STRANDEDNESS: double stranded
(D) TOPOLOGY: linear (i i) MOLECULE TYPE: genomic DNA
(A) DESCRIPTION: 23s rRNA gene from Halococcus morrhuae
(Accession # X05481) nucleotides 2551 to 2563

(i i i) HYPOTHETICAL: no (i v) ANTI-SENSE: no (v i) ORIGINAL SOURCE:
(A) ORGANISM: Halococcus morrhuae (x) PUBLICATION INFORMATION:
(A) AUTHORS: Leffers, H, Kjems, J, Ostergaard, L,
Larsen, N, Garrett, R A.
(B) TITLE: Evolutionary Relationship
Amongst Archaebacteria: A Comparative Study of
23 S Ribosomal RNAs of a Sulphur-dependent
Extreme Thermophile, an Extreme Halophile and a
Thermophilic Methanogen
(C) JOURNAL: Journal of Molecular Biology
(D) VOLUME: 195
(F) PAGES: 43-61
(G) DATE: 1987
(K) RELEVANT RESIDUES IN SEQ ID NO: 231 :FROM 1 TO 13

(x i) SEQUENCE DESCRIPTION: SEQ ID NO: 231 :

TTCCCTCCAT CCT 13

(2) INFORMATION FOR SEQ ID NO:232:

(i) SEQUENCE CHARACTERISTICS:
(A) LENGTH: 13 bases
(B) TYPE: nucleic acid
(C) STRANDEDNESS: single stranded
(D) TOPOLOGY: linear (i i) MOLECULE TYPE: other nucleic acid
(A) DESCRIPTION: third strand derived from H. morrhuae
23s region in Seq ID No 231

(i i i) HYPOTHETICAL: yes (i v) ANTI-SENSE: no (x) PUBLICATION INFORMATION:
(K) RELEVANT RESIDUES IN SEQ ID NO: 232 :FROM 1 TO 13

(x i) SEQUENCE DESCRIPTION: SEQ ID NO: 232 :

TCCTGCCTCC CTT 13

(2) INFORMATION FOR SEQ ID NO:233:

(i) SEQUENCE CHARACTERISTICS:
(A) LENGTH: 12 base pairs
(B) TYPE: nucleic acid
(C) STRANDEDNESS: double stranded
(D) TOPOLOGY: linear (i i) MOLECULE TYPE: genomic DNA
    (A) DESCRIPTION: 23s rRNA gene from Leptospira
        interrogans (Accession #X14249) nucleotides
        384 to 395

(i i i) HYPOTHETICAL: no (i v) ANTI-SENSE: no (v i) ORIGINAL SOURCE:
    (A) ORGANISM: Leptospira interrogans serovar canicola
    (B) STRAIN: moulton (x) PUBLICATION INFORMATION:
    (A) AUTHORS: Fukunga, M, Horie, I, Mifuchi, I.
    (B) TITLE: Nucleotide sequence of a 23s
        ribosomal RNA gene for Leptospira interrogans
        serovar canicola strain moulton
    (C) JOURNAL: Nucleic Acids Research
    (D) VOLUME: 17
    (F) PAGES: 2123-2123
    (G) DATE: 1989
    (K) RELEVANT RESIDUES IN SEQ ID NO: 233 :FROM 1 TO 12

(x i) SEQUENCE DESCRIPTION: SEQ ID NO: 233 :

AGAGGGTGAA AG                                                                12

(2) INFORMATION FOR SEQ ID NO:234:

(i) SEQUENCE CHARACTERISTICS:
    (A) LENGTH: 12 bases
    (B) TYPE: nucleic acid
    (C) STRANDEDNESS: single stranded
    (D) TOPOLOGY: linear (i i) MOLECULE TYPE: other nucleic acid
    (A) DESCRIPTION: third strand derived from L.
        interrogans 23s region in Seq ID No 233

(i i i) HYPOTHETICAL: yes (i v) ANTI-SENSE: no (x) PUBLICATION INFORMATION:
    (K) RELEVANT RESIDUES IN SEQ ID NO: 234 :FROM 1 TO 12

(x i) SEQUENCE DESCRIPTION: SEQ ID NO: 234 :

TCTCCCGCTT TC                                                                12

(2) INFORMATION FOR SEQ ID NO:235:

(i) SEQUENCE CHARACTERISTICS:
    (A) LENGTH: 17 base pairs
    (B) TYPE: nucleic acid
    (C) STRANDEDNESS: double stranded
    (D) TOPOLOGY: linear (i i) MOLECULE TYPE: genomic DNA
    (A) DESCRIPTION: 23s rRNA gene from Leptospira
        interrogans (Accession #X14249) nucleotides
        530 to 546

(i i i) HYPOTHETICAL: no (i v) ANTI-SENSE: no (v i) ORIGINAL SOURCE:
    (A) ORGANISM: Leptospira interrogans serovar canicola
    (B) STRAIN: moulton (x) PUBLICATION INFORMATION:
    (A) AUTHORS: Fukunga, M, Horie, I, Mifuchi, I.
    (B) TITLE: Nucleotide sequence of a 23s
        ribosomal RNA gene for Leptospira interrogans
        serovar canicola strain moulton
    (C) JOURNAL: Nucleic Acids Research (D) VOLUME: 17
(F) PAGES: 2123-2123
(G) DATE: 1989
(K) RELEVANT RESIDUES IN SEQ ID NO: 235 :FROM 1 TO 17

(xi) SEQUENCE DESCRIPTION: SEQ ID NO: 235 :

GAGGGAAAGG TGAAAAG                                                                 17

(2) INFORMATION FOR SEQ ID NO:236:

(i) SEQUENCE CHARACTERISTICS:
(A) LENGTH: 17 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from L.
interrogans 23s region in Seq ID No 235

(iii) HYPOTHETICAL: yes (iv) ANTI-SENSE: no (x) PUBLICATION INFORMATION:
(K) RELEVANT RESIDUES IN SEQ ID NO: 236 :FROM 1 TO 17

(xi) SEQUENCE DESCRIPTION: SEQ ID NO: 236 :

CTCCCTTTCC GCTTTTC                                                                 17

(2) INFORMATION FOR SEQ ID NO:237:

(i) SEQUENCE CHARACTERISTICS:
(A) LENGTH: 12 base pairs
(B) TYPE: nucleic acid
(C) STRANDEDNESS: double stranded
(D) TOPOLOGY: linear (ii) MOLECULE TYPE: genomic DNA
(A) DESCRIPTION: 23s rRNA gene from Leptospira
interrogans (Accession #X14249) nucleotides
842 to 853

(iii) HYPOTHETICAL: no (iv) ANTI-SENSE: no (vi) ORIGINAL SOURCE:
(A) ORGANISM: Leptospira interrogans serovar canicola
(B) STRAIN: moulton (x) PUBLICATION INFORMATION:
(A) AUTHORS: Fukunga, M, Horie, I, Mifuchi, I.
(B) TITLE: Nucleotide sequence of a 23s
ribosomal RNA gene for Leptospira interrogans
serovar canicola strain moulton
(C) JOURNAL: Nucleic Acids Research
(D) VOLUME: 17
(F) PAGES: 2123-2123
(G) DATE: 1989
(K) RELEVANT RESIDUES IN SEQ ID NO: 237 :FROM 1 TO 12

(xi) SEQUENCE DESCRIPTION: SEQ ID NO: 237 :

AGGGGTGAAA GG                                                                      12

(2) INFORMATION FOR SEQ ID NO:238:

(i) SEQUENCE CHARACTERISTICS:
(A) LENGTH: 12 bases
(B) TYPE: nucleic acid
(C) STRANDEDNESS: single stranded
(D) TOPOLOGY: linear (ii) MOLECULE TYPE: other nucleic acid (A) DESCRIPTION: third strand derived from L.
interrogans 23s region in Seq ID No 237

(iii) HYPOTHETICAL: yes (iv) ANTI-SENSE: no (x) PUBLICATION INFORMATION:
(K) RELEVANT RESIDUES IN SEQ ID NO: 238 :FROM 1 TO 12

(xi) SEQUENCE DESCRIPTION: SEQ ID NO: 238 :

TCCCCGCTTT CC 12

(2) INFORMATION FOR SEQ ID NO:239:

(i) SEQUENCE CHARACTERISTICS:
(A) LENGTH: 11 base pairs
(B) TYPE: nucleic acid
(C) STRANDEDNESS: double stranded
(D) TOPOLOGY: linear (ii) MOLECULE TYPE: genomic DNA
(A) DESCRIPTION: 23s rRNA gene from Leptospira
interrogans (Accession #X14249) nucleotides
1258 to 1268

(iii) HYPOTHETICAL: no (iv) ANTI-SENSE: no (vi) ORIGINAL SOURCE:
(A) ORGANISM: Leptospira interrogans serovar canicola
(B) STRAIN: moulton (x) PUBLICATION INFORMATION:
(A) AUTHORS: Fukunga, M, Horie, I, Mifuchi, I.
(B) TITLE: Nucleotide sequence of a 23s
ribosomal RNA gene for Leptospira interrogans
serovar canicola strain moulton
(C) JOURNAL: Nucleic Acids Research
(D) VOLUME: 17
(F) PAGES: 2123-2123
(G) DATE: 1989
(K) RELEVANT RESIDUES IN SEQ ID NO: 239 :FROM 1 TO 11

(xi) SEQUENCE DESCRIPTION: SEQ ID NO: 239 :

TTCTTTCTTC C 11

(2) INFORMATION FOR SEQ ID NO:240:

(i) SEQUENCE CHARACTERISTICS:
(A) LENGTH: 11 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from L.
interrogans 23s region in Seq ID No 239

(iii) HYPOTHETICAL: yes (iv) ANTI-SENSE: no (x) PUBLICATION INFORMATION:
(K) RELEVANT RESIDUES IN SEQ ID NO: 240 :FROM 1 TO 11

(xi) SEQUENCE DESCRIPTION: SEQ ID NO: 240 :

CCTTCTTTCT T 11

(2) INFORMATION FOR SEQ ID NO:241:

(i) SEQUENCE CHARACTERISTICS:
(A) LENGTH: 20 base pairs (B) TYPE: nucleic acid
(C) STRANDEDNESS: double stranded
(D) TOPOLOGY: linear (ii) MOLECULE TYPE: genomic DNA
(A) DESCRIPTION: 23s rRNA gene from Leptospira
interrogans (Accession #X14249) nucleotides
1295 to 1314

(iii) HYPOTHETICAL: no (iv) ANTI-SENSE: no (vi) ORIGINAL SOURCE:
(A) ORGANISM: Leptospira interrogans serovar canicola
(B) STRAIN: moulton (x) PUBLICATION INFORMATION:
(A) AUTHORS: Fukunga, M, Horie, I, Mifuchi, I.
(B) TITLE: Nucleotide sequence of a 23s
ribosomal RNA gene for Leptospira interrogans
serovar canicola strain moulton
(C) JOURNAL: Nucleic Acids Research
(D) VOLUME: 17
(F) PAGES: 2123-2123
(G) DATE: 1989
(K) RELEVANT RESIDUES IN SEQ ID NO: 241 :FROM 1 TO 20

(xi) SEQUENCE DESCRIPTION: SEQ ID NO: 241:

GGAGGAGTAA GAAATGAAGA 20

(2) INFORMATION FOR SEQ ID NO:242:

(i) SEQUENCE CHARACTERISTICS:
(A) LENGTH: 20 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from L.
interrogans 23s region in Seq ID No 241

(iii) HYPOTHETICAL: yes (iv) ANTI-SENSE: no (x) PUBLICATION INFORMATION:
(K) RELEVANT RESIDUES IN SEQ ID NO: 242 :FROM 1 TO 20

(xi) SEQUENCE DESCRIPTION: SEQ ID NO: 242 :

CCTCCTCGTT CTTTGCTTCT 20

(2) INFORMATION FOR SEQ ID NO:243:

(i) SEQUENCE CHARACTERISTICS:
(A) LENGTH: 13 base pairs
(B) TYPE: nucleic acid
(C) STRANDEDNESS: double stranded
(D) TOPOLOGY: linear (ii) MOLECULE TYPE: genomic DNA
(A) DESCRIPTION: 23s rRNA gene from Leptospira
interrogans (Accession #X14249) nucleotides
1758 to 1770

(iii) HYPOTHETICAL: no (iv) ANTI-SENSE: no (vi) ORIGINAL SOURCE:
(A) ORGANISM: Leptospira interrogans serovar canicola
(B) STRAIN: moulton (x) PUBLICATION INFORMATION:
(A) AUTHORS: Fukunga, M, Horie, I, Mifuchi, I.

(B) TITLE: Nucleotide sequence of a 23s
      ribosomal RNA gene for Leptospira interrogans
      serovar canicola strain moulton
(C) JOURNAL: Nucleic Acids Research
(D) VOLUME: 17
(F) PAGES: 2123-2123
(G) DATE: 1989
(K) RELEVANT RESIDUES IN SEQ ID NO: 243 :FROM 1 TO 13

(x i) SEQUENCE DESCRIPTION: SEQ ID NO: 243:

GGGATAAGGG AGA 13

(2) INFORMATION FOR SEQ ID NO:244:

(i) SEQUENCE CHARACTERISTICS:
    (A) LENGTH: 13 bases
    (B) TYPE: nucleic acid
    (C) STRANDEDNESS: single stranded
    (D) TOPOLOGY: linear (i i) MOLECULE TYPE: other nucleic acid
    (A) DESCRIPTION: third strand derived from L.
        interrogans 23s region in Seq ID No 243

(i i i) HYPOTHETICAL: yes (i v) ANTI-SENSE: no (x) PUBLICATION INFORMATION:
    (K) RELEVANT RESIDUES IN SEQ ID NO: 244 :FROM 1 TO 13

(x i) SEQUENCE DESCRIPTION: SEQ ID NO: 244 :

CCCTGTTCCC TCT 13

(2) INFORMATION FOR SEQ ID NO:245:

(i) SEQUENCE CHARACTERISTICS:
    (A) LENGTH: 12 base pairs
    (B) TYPE: nucleic acid
    (C) STRANDEDNESS: double stranded
    (D) TOPOLOGY: linear (i i) MOLECULE TYPE: genomic DNA
    (A) DESCRIPTION: 23s rRNA gene from Micrococcus luteus
        (Accession # X06484) nucleotides 214 to 225

(i i i) HYPOTHETICAL: no (i v) ANTI-SENSE: no (v i) ORIGINAL SOURCE:
    (A) ORGANISM: Micrococcus luteus
    (B) STRAIN: dsm 20030

(x) PUBLICATION INFORMATION:
    (A) AUTHORS: Regensburger, A, Ludwig, W, Frank, R,
        Bloecker, H, Schleifer, K H.
    (B) TITLE: Complete nucleotide sequence
        of a 23S ribosomal RNA gene from Micrococcus
        luteus
    (C) JOURNAL: Nucleic Acids Research
    (D) VOLUME: 16
    (F) PAGES: 2344-2344
    (G) DATE: 1988
    (K) RELEVANT RESIDUES IN SEQ ID NO: 245 :FROM 1 TO 12

(x i) SEQUENCE DESCRIPTION: SEQ ID NO: 245:

AGGAAGAGAA AA 12

(2) INFORMATION FOR SEQ ID NO:246:

(i) SEQUENCE CHARACTERISTICS:
    (A) LENGTH: 12 bases
    (B) TYPE: nucleic acid ( C ) STRANDEDNESS: single stranded
        ( D ) TOPOLOGY: linear ( i i ) MOLECULE TYPE: other nucleic acid
        ( A ) DESCRIPTION: third strand derived from M. luteus
            23s region in Seq ID No 245

( i i i ) HYPOTHETICAL: yes ( i v ) ANTI-SENSE: no ( x ) PUBLICATION INFORMATION:
        ( K ) RELEVANT RESIDUES IN SEQ ID NO: 246 :FROM 1 TO 12

( x i ) SEQUENCE DESCRIPTION: SEQ ID NO: 246 :

TCCTTCTCTT TT 12

( 2 ) INFORMATION FOR SEQ ID NO:247:

( i ) SEQUENCE CHARACTERISTICS:
        ( A ) LENGTH: 15 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: 23s rRNA gene from Micrococcus luteus
            ( A c c e s s i o n  #  X 0 6 4 8 4 ) nucleotides 572 to 586

( i i i ) HYPOTHETICAL: no ( i v ) ANTI-SENSE: no ( v i ) ORIGINAL SOURCE:
        ( A ) ORGANISM: Micrococcus luteus
        ( B ) STRAIN: dsm 20030

( x ) PUBLICATION INFORMATION:
        ( A ) AUTHORS: Regensburger, A, Ludwig, W, Frank, R,
            Bloecker, H, Schleifer, K H.
        ( B ) TITLE: Complete nucleotide sequence
            of a 23S ribosomal RNA gene from Micrococcus
            luteus
        ( C ) JOURNAL: Nucleic Acids Research
        ( D ) VOLUME: 16
        ( F ) PAGES: 2344-2344
        ( G ) DATE: 1988
        ( K ) RELEVANT RESIDUES IN SEQ ID NO: 247 :FROM 1 TO 15

( x i ) SEQUENCE DESCRIPTION: SEQ ID NO: 247:

GGGAGGGGAG TGAAA 15

( 2 ) INFORMATION FOR SEQ ID NO:248:

( i ) SEQUENCE CHARACTERISTICS:
        ( A ) LENGTH: 15 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from M. luteus
            23s region in Seq ID No 247

( i i i ) HYPOTHETICAL: yes ( i v ) ANTI-SENSE: no ( x ) PUBLICATION INFORMATION:
        ( K ) RELEVANT RESIDUES IN SEQ ID NO: 248 :FROM 1 TO 15

( x i ) SEQUENCE DESCRIPTION: SEQ ID NO: 248 :

CCCTCCCCTC GCTTT 15

( 2 ) INFORMATION FOR SEQ ID NO:249:

( i ) SEQUENCE CHARACTERISTICS:
  ( A ) LENGTH: 12 base pairs
  ( B ) TYPE: nucleic acid
  ( C ) STRANDEDNESS: double stranded
  ( D ) TOPOLOGY: linear ( i i ) MOLECULE TYPE: genomic DNA
  ( A ) DESCRIPTION: 23s rRNA gene from Micrococcus luteus
  ( A c c e s s i o n # X 0 6 4 8 4 ) nucleotides 859 to 870

( i i i ) HYPOTHETICAL: no ( i v ) ANTI-SENSE: no ( v i ) ORIGINAL SOURCE:
  ( A ) ORGANISM: Micrococcus luteus
  ( B ) STRAIN: dsm 20030

( x ) PUBLICATION INFORMATION:
  ( A ) AUTHORS: Regensburger, A, Ludwig, W, Frank, R,
   Bloecker, H, Schleifer, K H.
  ( B ) TITLE: Complete nucleotide sequence
   of a 23S ribosomal RNA gene from Micrococcus
   luteus
  ( C ) JOURNAL: Nucleic Acids Research
  ( D ) VOLUME: 16
  ( F ) PAGES: 2344-2344
  ( G ) DATE: 1988
  ( K ) RELEVANT RESIDUES IN SEQ ID NO: 249 :FROM 1 TO 12

( x i ) SEQUENCE DESCRIPTION: SEQ ID NO: 249:

AGGGGTGAAA GG   1 2

( 2 ) INFORMATION FOR SEQ ID NO:250:

( i ) SEQUENCE CHARACTERISTICS:
  ( A ) LENGTH: 12 bases
  ( B ) TYPE: nucleic acid
  ( C ) STRANDEDNESS: single stranded
  ( D ) TOPOLOGY: linear ( i i ) MOLECULE TYPE: other nucleic acid
  ( A ) DESCRIPTION: third strand derived from M. luteus
   23s region in Seq ID No 249

( i i i ) HYPOTHETICAL: yes ( i v ) ANTI-SENSE: no ( x ) PUBLICATION INFORMATION:
  ( K ) RELEVANT RESIDUES IN SEQ ID NO: 250 :FROM 1 TO 12

( x i ) SEQUENCE DESCRIPTION: SEQ ID NO: 250 :

TCCCCGCTTT CC   1 2

( 2 ) INFORMATION FOR SEQ ID NO:251:

( i ) SEQUENCE CHARACTERISTICS:
  ( A ) LENGTH: 12 base pairs
  ( B ) TYPE: nucleic acid
  ( C ) STRANDEDNESS: double stranded
  ( D ) TOPOLOGY: linear ( i i ) MOLECULE TYPE: genomic DNA
  ( A ) DESCRIPTION: 23s rRNA gene from Micrococcus luteus
  ( A c c e s s i o n # X 0 6 4 8 4 ) nucleotides 1009 to 1020

( i i i ) HYPOTHETICAL: no ( i v ) ANTI-SENSE: no ( v i ) ORIGINAL SOURCE:
  ( A ) ORGANISM: Micrococcus luteus
  ( B ) STRAIN: dsm 20030

( x ) PUBLICATION INFORMATION:
            ( A ) AUTHORS: Regensburger, A, Ludwig, W, Frank, R,
                Bloecker, H, Schleifer, K H.
            ( B ) TITLE: Complete nucleotide sequence
                of a 23S ribosomal RNA gene from Micrococcus
                luteus
            ( C ) JOURNAL: Nucleic Acids Research
            ( D ) VOLUME: 16
            ( F ) PAGES: 2344-2344
            ( G ) DATE: 1988
            ( K ) RELEVANT RESIDUES IN SEQ ID NO: 251 :FROM 1 TO 12

( x i ) SEQUENCE DESCRIPTION: SEQ ID NO: 251:

GGGAAGTGAG AG                                                                12

( 2 ) INFORMATION FOR SEQ ID NO:252:

( i ) SEQUENCE CHARACTERISTICS:
            ( A ) LENGTH: 12 bases
            ( B ) TYPE: nucleic acid
            ( C ) STRANDEDNESS: single stranded
            ( D ) TOPOLOGY: linear ( i i ) MOLECULE TYPE: other nucleic acid
            ( A ) DESCRIPTION: third strand derived from M. luteus
                23s region in Seq ID No 251

( i i i ) HYPOTHETICAL: yes ( i v ) ANTI-SENSE: no ( x ) PUBLICATION INFORMATION:
            ( K ) RELEVANT RESIDUES IN SEQ ID NO: 252 :FROM 1 TO 12

( x i ) SEQUENCE DESCRIPTION: SEQ ID NO: 252 :

CCCTTCGCTC TC                                                                12

( 2 ) INFORMATION FOR SEQ ID NO:253:

( i ) SEQUENCE CHARACTERISTICS:
            ( A ) LENGTH: 13 base pairs
            ( B ) TYPE: nucleic acid
            ( C ) STRANDEDNESS: double stranded
            ( D ) TOPOLOGY: linear ( i i ) MOLECULE TYPE: genomic DNA
            ( A ) DESCRIPTION: 23s rRNA gene from Micrococcus luteus
                ( A c c e s s i o n    #    X 0 6 4 8 4 ) nucleotides 1884 to 1896

( i i i ) HYPOTHETICAL: no ( i v ) ANTI-SENSE: no ( v i ) ORIGINAL SOURCE:
            ( A ) ORGANISM: Micrococcus luteus
            ( B ) STRAIN: dsm 20030

( x ) PUBLICATION INFORMATION:
            ( A ) AUTHORS: Regensburger, A, Ludwig, W, Frank, R,
                Bloecker, H, Schleifer, K H.
            ( B ) TITLE: Complete nucleotide sequence
                of a 23S ribosomal RNA gene from Micrococcus
                luteus
            ( C ) JOURNAL: Nucleic Acids Research
            ( D ) VOLUME: 16
            ( F ) PAGES: 2344-2344
            ( G ) DATE: 1988
            ( K ) RELEVANT RESIDUES IN SEQ ID NO: 253 :FROM 1 TO 13

( x i ) SEQUENCE DESCRIPTION: SEQ ID NO: 253:

GGGAGAAGGG GGG                                                               13

( 2 ) INFORMATION FOR SEQ ID NO:254:

( i ) SEQUENCE CHARACTERISTICS:
    ( A ) LENGTH: 13 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from M. luteus
        23s region in Seq ID No 253

( i i i ) HYPOTHETICAL: yes ( i v ) ANTI-SENSE: no ( x ) PUBLICATION INFORMATION:
    ( K ) RELEVANT RESIDUES IN SEQ ID NO: 254 :FROM 1 TO 13

( x i ) SEQUENCE DESCRIPTION: SEQ ID NO: 254 :

CCCTCTTCCC CCC                               13

( 2 ) INFORMATION FOR SEQ ID NO:255:

( i ) SEQUENCE CHARACTERISTICS:
    ( A ) LENGTH: 12 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: 23s rRNA gene from Micrococcus luteus
        ( A c c e s s i o n   #   X 0 6 4 8 4 ) nucleotides 2795 to 2806

( i i i ) HYPOTHETICAL: no ( i v ) ANTI-SENSE: no ( v i ) ORIGINAL SOURCE:
    ( A ) ORGANISM: Micrococcus luteus
    ( B ) STRAIN: dsm 20030

( x ) PUBLICATION INFORMATION:
    ( A ) AUTHORS: Regensburger, A, Ludwig, W, Frank, R,
        Bloecker, H, Schleifer, K H.
    ( B ) TITLE: Complete nucleotide sequence
        of a 23S ribosomal RNA gene from Micrococcus
        luteus
    ( C ) JOURNAL: Nucleic Acids Research
    ( D ) VOLUME: 16
    ( F ) PAGES: 2344-2344
    ( G ) DATE: 1988
    ( K ) RELEVANT RESIDUES IN SEQ ID NO: 255 :FROM 1 TO 12

( x i ) SEQUENCE DESCRIPTION: SEQ ID NO: 255:

TCCCTATCCT CT                                 12

( 2 ) INFORMATION FOR SEQ ID NO:256:

( i ) SEQUENCE CHARACTERISTICS:
    ( A ) LENGTH: 12 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from M. luteus
        23s region in Seq ID No 255

( i i i ) HYPOTHETICAL: yes ( i v ) ANTI-SENSE: no ( x ) PUBLICATION INFORMATION:
    ( K ) RELEVANT RESIDUES IN SEQ ID NO: 256 :FROM 1 TO 12

( x i ) SEQUENCE DESCRIPTION: SEQ ID NO: 256 :

TCTCCTGTCC CT                                                                                    12

(2) INFORMATION FOR SEQ ID NO:257:

(i) SEQUENCE CHARACTERISTICS:
        (A) LENGTH: 17 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: 23s rRNA gene from Frankia sp
        (Accession # M55343) nucleotides 3002 to 3018

(iii) HYPOTHETICAL: no (iv) ANTI-SENSE: no (vi) ORIGINAL SOURCE:
        (A) ORGANISM: Frankia sp.

(x) PUBLICATION INFORMATION:
        (A) AUTHORS: Normand, P.
        (B) TITLE: unpublished
        (C) JOURNAL:
        (D) VOLUME:
        (F) PAGES:
        (G) DATE: 1991
        (K) RELEVANT RESIDUES IN SEQ ID NO: 257 :FROM 1 TO 17

(xi) SEQUENCE DESCRIPTION: SEQ ID NO: 257:

GAGGGAAAGG TGAAAAG                                                                               17

(2) INFORMATION FOR SEQ ID NO:258:

(i) SEQUENCE CHARACTERISTICS:
        (A) LENGTH: 17 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from Frankia sp
            23s region in Seq ID No 257

(iii) HYPOTHETICAL: yes (iv) ANTI-SENSE: no (x) PUBLICATION INFORMATION:
        (K) RELEVANT RESIDUES IN SEQ ID NO: 258 :FROM 1 TO 17

(xi) SEQUENCE DESCRIPTION: SEQ ID NO: 258 :

CTCCCTTTCC GCTTTTC                                                                               17

(2) INFORMATION FOR SEQ ID NO:259:

(i) SEQUENCE CHARACTERISTICS:
        (A) LENGTH: 12 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: 23s rRNA gene from Frankia sp
        (Accession # M55343) nucleotides 3314 to 3325

(iii) HYPOTHETICAL: no (iv) ANTI-SENSE: no (vi) ORIGINAL SOURCE:
        (A) ORGANISM: Frankia sp.

(x) PUBLICATION INFORMATION:
  (A) AUTHORS: Normand, P.
  (B) TITLE: unpublished
  (C) JOURNAL:
  (D) VOLUME:
  (F) PAGES:
  (G) DATE: 1991
  (K) RELEVANT RESIDUES IN SEQ ID NO: 259 :FROM 1 TO 12

(xi) SEQUENCE DESCRIPTION: SEQ ID NO: 259:

AGGGGTGAAA GG    12

(2) INFORMATION FOR SEQ ID NO:260:

(i) SEQUENCE CHARACTERISTICS:
    (A) LENGTH: 12 bases
    (B) TYPE: nucleic acid
    (C) STRANDEDNESS: single stranded
    (D) TOPOLOGY: linear (ii) MOLECULE TYPE: other nucleic acid
    (A) DESCRIPTION: third strand derived from Frankia sp
        23s region in Seq ID No 259

(iii) HYPOTHETICAL: yes (iv) ANTI-SENSE: no (x) PUBLICATION INFORMATION:
    (K) RELEVANT RESIDUES IN SEQ ID NO: 260 :FROM 1 TO 12

(xi) SEQUENCE DESCRIPTION: SEQ ID NO: 260 :

TCCCCGCTTT CC    12

(2) INFORMATION FOR SEQ ID NO:261:

(i) SEQUENCE CHARACTERISTICS:
    (A) LENGTH: 12 base pairs
    (B) TYPE: nucleic acid
    (C) STRANDEDNESS: double stranded
    (D) TOPOLOGY: linear (ii) MOLECULE TYPE: genomic DNA
    (A) DESCRIPTION: 23s rRNA gene from Frankia sp
        (Accession # M55343) nucleotides 4444 to 4455

(iii) HYPOTHETICAL: no (iv) ANTI-SENSE: no (vi) ORIGINAL SOURCE:
    (A) ORGANISM: Frankia sp.

(x) PUBLICATION INFORMATION:
    (A) AUTHORS: Normand, P.
    (B) TITLE: unpublished
    (C) JOURNAL:
    (D) VOLUME:
    (F) PAGES:
    (G) DATE: 1991
    (K) RELEVANT RESIDUES IN SEQ ID NO: 261 :FROM 1 TO 12

(xi) SEQUENCE DESCRIPTION: SEQ ID NO: 261:

GGAGAAGGGG GG    12

(2) INFORMATION FOR SEQ ID NO:262:

(i) SEQUENCE CHARACTERISTICS:
    (A) LENGTH: 12 bases
    (B) TYPE: nucleic acid
    (C) STRANDEDNESS: single stranded
    (D) TOPOLOGY: linear (ii) MOLECULE TYPE: other nucleic acid (A) DESCRIPTION: third strand derived from Frankia sp
            23s region in Seq ID No 261

(iii) HYPOTHETICAL: yes (iv) ANTI-SENSE: no (x) PUBLICATION INFORMATION:
        (K) RELEVANT RESIDUES IN SEQ ID NO: 262 :FROM 1 TO 12

(xi) SEQUENCE DESCRIPTION: SEQ ID NO: 262 :

CCTCTTCCCC CC 12

(2) INFORMATION FOR SEQ ID NO:263:

(i) SEQUENCE CHARACTERISTICS:
        (A) LENGTH: 12 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: 23s rRNA gene from Rhodobacter
            capsulatus (Accession #X06485) nucleotides 842
            to 853

(iii) HYPOTHETICAL: no (iv) ANTI-SENSE: no (vi) ORIGINAL SOURCE:
        (A) ORGANISM: Rhodobacter capsulatus
        (B) STRAIN: dsm 938

(x) PUBLICATION INFORMATION:
        (A) AUTHORS: Regensburger, A, Ludwig, W, Frank, R,
            Bloecker, H, Schleifer, K H.
        (B) TITLE: Complete nucleotide sequence
            of a 23S ribosomal RNA gene from Rhodobacter
            capsulatus
        (C) JOURNAL: Nucleic Acids Research
        (D) VOLUME: 16
        (F) PAGES: 2343-2343
        (G) DATE: 1988
        (K) RELEVANT RESIDUES IN SEQ ID NO: 263 :FROM 1 TO 12

(xi) SEQUENCE DESCRIPTION: SEQ ID NO: 263:

AGGGGTGAAA GG 12

(2) INFORMATION FOR SEQ ID NO:264:

(i) SEQUENCE CHARACTERISTICS:
        (A) LENGTH: 12 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from R.
            capsulatus 23s region in Seq ID No 263

(iii) HYPOTHETICAL: yes (iv) ANTI-SENSE: no (x) PUBLICATION INFORMATION:
        (K) RELEVANT RESIDUES IN SEQ ID NO: 264 :FROM 1 TO 12

(xi) SEQUENCE DESCRIPTION: SEQ ID NO: 264 :

TCCCCGCTTT CC 12

(2) INFORMATION FOR SEQ ID NO:265:

(i) SEQUENCE CHARACTERISTICS:

( A ) LENGTH: 11 base pairs
                    ( B ) TYPE: nucleic acid
                    ( C ) STRANDEDNESS: double stranded
                    ( D ) TOPOLOGY: linear ( i i ) MOLECULE TYPE: genomic DNA
                    ( A ) DESCRIPTION: 23s rRNA gene from Rhodobacter
                            capsulatus (Accession #X06485) nucleotides
                            1038 to 1048

( i i i ) HYPOTHETICAL: no ( i v ) ANTI-SENSE: no ( v i ) ORIGINAL SOURCE:
                    ( A ) ORGANISM: Rhodobacter capsulatus
                    ( B ) STRAIN: dsm 938

( x ) PUBLICATION INFORMATION:
                    ( A ) AUTHORS: Regensburger, A, Ludwig, W, Frank, R,
                            Bloecker, H, Schleifer, K H.
                    ( B ) TITLE: Complete nucleotide sequence
                            of a 23S ribosomal RNA gene from Rhodobacter
                            capsulatus
                    ( C ) JOURNAL: Nucleic Acids Research
                    ( D ) VOLUME: 16
                    ( F ) PAGES: 2343-2343
                    ( G ) DATE: 1988
                    ( K ) RELEVANT RESIDUES IN SEQ ID NO: 265 :FROM 1 TO 11

( x i ) SEQUENCE DESCRIPTION: SEQ ID NO: 265:

GAAGAGGGAA A                                                                            1 1

( 2 ) INFORMATION FOR SEQ ID NO:266:

( i ) SEQUENCE CHARACTERISTICS:
                    ( A ) LENGTH: 11 bases
                    ( B ) TYPE: nucleic acid
                    ( C ) STRANDEDNESS: single stranded
                    ( D ) TOPOLOGY: linear ( i i ) MOLECULE TYPE: other nucleic acid
                    ( A ) DESCRIPTION: third strand derived from R.
                            capsulatus 23s region in Seq ID No 265

( i i i ) HYPOTHETICAL: yes ( i v ) ANTI-SENSE: no ( x ) PUBLICATION INFORMATION:
                    ( K ) RELEVANT RESIDUES IN SEQ ID NO: 266 :FROM 1 TO 11

( x i ) SEQUENCE DESCRIPTION: SEQ ID NO: 266 :

CTTCTCCCTT T                                                                            1 1

( 2 ) INFORMATION FOR SEQ ID NO:267:

( i ) SEQUENCE CHARACTERISTICS:
                    ( A ) LENGTH: 15 base pairs
                    ( B ) TYPE: nucleic acid
                    ( C ) STRANDEDNESS: double stranded
                    ( D ) TOPOLOGY: linear ( i i ) MOLECULE TYPE: genomic DNA
                    ( A ) DESCRIPTION: 23s rRNA gene from Rhodobacter
                            capsulatus (Accession #X06485) nucleotides
                            1401 to 1415

( i i i ) HYPOTHETICAL: no ( i v ) ANTI-SENSE: no ( v i ) ORIGINAL SOURCE:
                    ( A ) ORGANISM: Rhodobacter capsulatus
                    ( B ) STRAIN: dsm 938

( x ) PUBLICATION INFORMATION:
  ( A ) AUTHORS: Regensburger, A, Ludwig, W, Frank, R,
    Bloecker, H, Schleifer, K H.
  ( B ) TITLE: Complete nucleotide sequence
    of a 23S ribosomal RNA gene from Rhodobacter
    capsulatus
  ( C ) JOURNAL: Nucleic Acids Research
  ( D ) VOLUME: 16
  ( F ) PAGES: 2343-2343
  ( G ) DATE: 1988
  ( K ) RELEVANT RESIDUES IN SEQ ID NO: 267 :FROM 1 TO 15

( x i ) SEQUENCE DESCRIPTION: SEQ ID NO: 267:

AAAGAGGGTG AGAGA 15

( 2 ) INFORMATION FOR SEQ ID NO:268:

( i ) SEQUENCE CHARACTERISTICS:
    ( A ) LENGTH: 15 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from R.
      capsulatus 23s region in Seq ID No 267

( i i i ) HYPOTHETICAL: yes ( i v ) ANTI-SENSE: no ( x ) PUBLICATION INFORMATION:
    ( K ) RELEVANT RESIDUES IN SEQ ID NO: 268 :FROM 1 TO 15

( x i ) SEQUENCE DESCRIPTION: SEQ ID NO: 268 :

TTTCTCCCGC TCTCT 15

( 2 ) INFORMATION FOR SEQ ID NO:269:

( i ) SEQUENCE CHARACTERISTICS:
    ( A ) LENGTH: 16 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: 16s rRNA gene from Alcaligenes
      faecalis (Accession #M22508, M22467)
      nucleotides 190 to 205

( i i i ) HYPOTHETICAL: no ( i v ) ANTI-SENSE: no ( v i ) ORIGINAL SOURCE:
    ( A ) ORGANISM: Alcaligenes faecalis ( x ) PUBLICATION INFORMATION:
    ( A ) AUTHORS: Dewhirst, F E, Paster, B J, Bright,
      P.L.
    ( B ) TITLE: Chromobacterium, Eikenella,
      Kingella, Neisseria, Simonsiella and
      Vitreoscilla species comprise a major branch of
      the beta group Proteobacteria by 16S rRNA
      sequence comparison
    ( C ) JOURNAL: International Journal of Systematic
      Biology
    ( D ) VOLUME: 0
    ( F ) PAGES: 0-0
    ( G ) DATE: 1990
    ( K ) RELEVANT RESIDUES IN SEQ ID NO: 269 :FROM 1 TO 16

( x i ) SEQUENCE DESCRIPTION: SEQ ID NO: 269:

GGGGGAAAGG GGGGGA 16

( 2 ) INFORMATION FOR SEQ ID NO:270:

( i ) SEQUENCE CHARACTERISTICS:
  ( A ) LENGTH: 16 bases
  ( B ) TYPE: nucleic acid
  ( C ) STRANDEDNESS: single stranded
  ( D ) TOPOLOGY: linear ( i i ) MOLECULE TYPE: other nucleic acid
  ( A ) DESCRIPTION: third strand derived from A. faecalis
   16s region in Seq ID No 269

( i i i ) HYPOTHETICAL: yes ( i v ) ANTI-SENSE: no ( x ) PUBLICATION INFORMATION:
  ( K ) RELEVANT RESIDUES IN SEQ ID NO: 270 :FROM 1 TO 16

( x i ) SEQUENCE DESCRIPTION: SEQ ID NO: 270 :

CCCCCTTTCC CCCCCT                    16

( 2 ) INFORMATION FOR SEQ ID NO:271:

( i ) SEQUENCE CHARACTERISTICS:
  ( A ) LENGTH: 13 base pairs
  ( B ) TYPE: nucleic acid
  ( C ) STRANDEDNESS: double stranded
  ( D ) TOPOLOGY: linear ( i i ) MOLECULE TYPE: genomic DNA
  ( A ) DESCRIPTION: 16s rRNA gene from Alcaligenes
   faecalis (Accession #M22508, M22467)
   nucleotides 444 to 456

( i i i ) HYPOTHETICAL: no ( i v ) ANTI-SENSE: no ( v i ) ORIGINAL SOURCE:
  ( A ) ORGANISM: Alcaligenes faecalis ( x ) PUBLICATION INFORMATION:
  ( A ) AUTHORS: Dewhirst, F E, Paster, B J, Bright,
   P.L.
  ( B ) TITLE: Chromobacterium, Eikenella,
   Kingella, Neisseria, Simonsiella and
   Vitreoscilla species comprise a major branch of
   the beta group Proteobacteria by 16S rRNA
   sequence comparison
  ( C ) JOURNAL: International Journal of Systematic
   Biology
  ( D ) VOLUME: 0
  ( F ) PAGES: 0-0
  ( G ) DATE: 1990
  ( K ) RELEVANT RESIDUES IN SEQ ID NO: 271 :FROM 1 TO 13

( x i ) SEQUENCE DESCRIPTION: SEQ ID NO: 271:

AGAGAAGAAA AGG                      13

( 2 ) INFORMATION FOR SEQ ID NO:272:

( i ) SEQUENCE CHARACTERISTICS:
  ( A ) LENGTH: 13 bases
  ( B ) TYPE: nucleic acid
  ( C ) STRANDEDNESS: single stranded
  ( D ) TOPOLOGY: linear ( i i ) MOLECULE TYPE: other nucleic acid
  ( A ) DESCRIPTION: third strand derived from A. faecalis
   16s region in Seq ID No 271

( i i i ) HYPOTHETICAL: yes ( i v ) ANTI-SENSE: no (x) PUBLICATION INFORMATION:
            (K) RELEVANT RESIDUES IN SEQ ID NO: 272 :FROM 1 TO 13

(xi) SEQUENCE DESCRIPTION: SEQ ID NO: 272 :

TCTCTTCTTT TCC                                                                                                13

(2) INFORMATION FOR SEQ ID NO:273:

(i) SEQUENCE CHARACTERISTICS:
            (A) LENGTH: 11 base pairs
            (B) TYPE: nucleic acid
            (C) STRANDEDNESS: double stranded
            (D) TOPOLOGY: linear (ii) MOLECULE TYPE: genomic DNA
            (A) DESCRIPTION: 16s rRNA gene from Alcaligenes
                    faecalis (Accession #M22508, M22467)
                    nucleotides 592 to 602

(iii) HYPOTHETICAL: no (iv) ANTI-SENSE: no (vi) ORIGINAL SOURCE:
            (A) ORGANISM: Alcaligenes faecalis (x) PUBLICATION INFORMATION:
            (A) AUTHORS: Dewhirst, F E, Paster, B J, Bright,
                    P.L.
            (B) TITLE: Chromobacterium, Eikenella,
                    Kingella, Neisseria, Simonsiella and
                    Vitreoscilla species comprise a major branch of
                    the beta group Proteobacteria by 16S rRNA
                    sequence comparison
            (C) JOURNAL: International Journal of Systematic
                    Biology
            (D) VOLUME: 0
            (F) PAGES: 0-0
            (G) DATE: 1990
            (K) RELEVANT RESIDUES IN SEQ ID NO: 273 :FROM 1 TO 11

(xi) SEQUENCE DESCRIPTION: SEQ ID NO: 273:

GGAAAGAAAG A                                                                                                  11

(2) INFORMATION FOR SEQ ID NO:274:

(i) SEQUENCE CHARACTERISTICS:
            (A) LENGTH: 11 bases
            (B) TYPE: nucleic acid
            (C) STRANDEDNESS: single stranded
            (D) TOPOLOGY: linear (ii) MOLECULE TYPE: other nucleic acid
            (A) DESCRIPTION: third strand derived from A. faecalis
                    16s region in Seq ID No 273

(iii) HYPOTHETICAL: yes (iv) ANTI-SENSE: no (x) PUBLICATION INFORMATION:
            (K) RELEVANT RESIDUES IN SEQ ID NO: 274 :FROM 1 TO 11

(xi) SEQUENCE DESCRIPTION: SEQ ID NO: 274 :

CCAAACAAAC A                                                                                                  11

(2) INFORMATION FOR SEQ ID NO:275:

(i) SEQUENCE CHARACTERISTICS:
            (A) LENGTH: 14 base pairs
            (B) TYPE: nucleic acid
            (C) STRANDEDNESS: double stranded
            (D) TOPOLOGY: linear (i i) MOLECULE TYPE: genomic DNA
     (A) DESCRIPTION: 16s rRNA gene from Alcaligenes
         faecalis (Accession #M22508, M22467)
         nucleotides 663 to 676

(i i i) HYPOTHETICAL: no (i v) ANTI-SENSE: no (v i) ORIGINAL SOURCE:
     (A) ORGANISM: Alcaligenes faecalis (x) PUBLICATION INFORMATION:
     (A) AUTHORS: Dewhirst, F E, Paster, B J, Bright,
         P.L.
     (B) TITLE: Chromobacterium, Eikenella,
         Kingella, Neisseria, Simonsiella and
         Vitreoscilla species comprise a major branch of
         the beta group Proteobacteria by 16S rRNA
         sequence comparison
     (C) JOURNAL: International Journal of Systematic
         Biology
     (D) VOLUME: 0
     (F) PAGES: 0-0
     (G) DATE: 1990
     (K) RELEVANT RESIDUES IN SEQ ID NO: 275 :FROM 1 TO 14

(x i) SEQUENCE DESCRIPTION: SEQ ID NO: 275:

AGAGGGGGGT AGAA                                                              14

(2) INFORMATION FOR SEQ ID NO:276:

(i) SEQUENCE CHARACTERISTICS:
         (A) LENGTH: 14 bases
         (B) TYPE: nucleic acid
         (C) STRANDEDNESS: single stranded
         (D) TOPOLOGY: linear (i i) MOLECULE TYPE: other nucleic acid
         (A) DESCRIPTION: third strand derived from A. faecalis
             16s region in Seq ID No 275

(i i i) HYPOTHETICAL: yes (i v) ANTI-SENSE: no (x) PUBLICATION INFORMATION:
         (K) RELEVANT RESIDUES IN SEQ ID NO: 276 :FROM 1 TO 14

(x i) SEQUENCE DESCRIPTION: SEQ ID NO: 276 :

TCTCCCCCCG TCTT                                                              14

(2) INFORMATION FOR SEQ ID NO:277:

(i) SEQUENCE CHARACTERISTICS:
         (A) LENGTH: 15 base pairs
         (B) TYPE: nucleic acid
         (C) STRANDEDNESS: double stranded
         (D) TOPOLOGY: linear (i i) MOLECULE TYPE: genomic DNA
         (A) DESCRIPTION: 16s rRNA gene from Alcaligenes
             faecalis (Accession #M22508, M22467)
             nucleotides 1169 to 1183

(i i i) HYPOTHETICAL: no (i v) ANTI-SENSE: no (v i) ORIGINAL SOURCE:
         (A) ORGANISM: Alcaligenes faecalis (x) PUBLICATION INFORMATION:
         (A) AUTHORS: Dewhirst, F E, Paster, B J, Bright,
             P.L.

(B) TITLE: Chromobacterium, Eikenella,
    Kingella, Neisseria, Simonsiella and
    Vitreoscilla species comprise a major branch of
    the beta group Proteobacteria by 16S rRNA
    sequence comparison
(C) JOURNAL: International Journal of Systematic
    Biology
(D) VOLUME: 0
(F) PAGES: 0-0
(G) DATE: 1990
(K) RELEVANT RESIDUES IN SEQ ID NO: 277 :FROM 1 TO 15

(xi) SEQUENCE DESCRIPTION: SEQ ID NO: 277:

GGAGGAAGGT GGGGA                                                                    15

(2) INFORMATION FOR SEQ ID NO:278:

(i) SEQUENCE CHARACTERISTICS:
    (A) LENGTH: 15 bases
    (B) TYPE: nucleic acid
    (C) STRANDEDNESS: single stranded
    (D) TOPOLOGY: linear (ii) MOLECULE TYPE: other nucleic acid
    (A) DESCRIPTION: third strand derived from A. faecalis
        16s region in Seq ID No 277

(iii) HYPOTHETICAL: yes (iv) ANTI-SENSE: no (x) PUBLICATION INFORMATION:
    (K) RELEVANT RESIDUES IN SEQ ID NO: 278 :FROM 1 TO 15

(xi) SEQUENCE DESCRIPTION: SEQ ID NO: 278 :

CCTCCTTCCG CCCCT                                                                    15

(2) INFORMATION FOR SEQ ID NO:279:

(i) SEQUENCE CHARACTERISTICS:
    (A) LENGTH: 10 base pairs
    (B) TYPE: nucleic acid
    (C) STRANDEDNESS: double stranded
    (D) TOPOLOGY: linear (ii) MOLECULE TYPE: genomic DNA
    (A) DESCRIPTION: 16s rRNA gene from Coxiella burnetii
        (Accession # M21291) nucleotides 444 to 453

(iii) HYPOTHETICAL: no (iv) ANTI-SENSE: no (vi) ORIGINAL SOURCE:
    (A) ORGANISM: Coxiella burnetii (x) PUBLICATION INFORMATION (A) LENGTH: 10 bases
                (B) TYPE: nucleic acid
                (C) STRANDEDNESS: single stranded
                (D) TOPOLOGY: linear (ii) MOLECULE TYPE: other nucleic acid
                (A) DESCRIPTION: third strand derived from C. burnetii
                        16s region in Seq ID No 279

(iii) HYPOTHETICAL: yes (iv) ANTI-SENSE: no (x) PUBLICATION INFORMATION:
                (K) RELEVANT RESIDUES IN SEQ ID NO: 280 :FROM 1 TO 10

(xi) SEQUENCE DESCRIPTION: SEQ ID NO: 280 :

C C C C T T C T T T                                                                                     10

(2) INFORMATION FOR SEQ ID NO:281:

(i) SEQUENCE CHARACTERISTICS:
                (A) LENGTH: 10 base pairs
                (B) TYPE: nucleic acid
                (C) STRANDEDNESS: double stranded
                (D) TOPOLOGY: linear (ii) MOLECULE TYPE: genomic DNA
                (A) DESCRIPTION: 16s rRNA gene from Coxiella burnetii
                        (Accession # M21291) nucleotides 841 to 850

(iii) HYPOTHETICAL: no (iv) ANTI-SENSE: no (vi) ORIGINAL SOURCE:
                (A) ORGANISM: Coxiella burnetii (x) PUBLICATION INFORMATION:
                (A) AUTHORS: Weisburg, W G, Dobson, M E, Samuel, J E,
                        Dasch, G A, Mallavia, L P, Mandelco, L,
                        Sechrest, J E, Weiss, E, Woese, C R.
                (B) TITLE: Phylogenetic diversity of the
                        Rickettsiae
                (C) JOURNAL: Journal of Bacteriology
                (D) VOLUME: 171
                (F) PAGES: 4202-4206
                (G) DATE: 1989
                (K) RELEVANT RESIDUES IN SEQ ID NO: 281 :FROM 1 TO 10

(xi) SEQUENCE DESCRIPTION: SEQ ID NO: 281:

T T C C C T T C T T                                                                                     10

(2) INFORMATION FOR SEQ ID NO:282:

(i) SEQUENCE CHARACTERISTICS:
                (A) LENGTH: 10 bases
                (B) TYPE: nucleic acid
                (C) STRANDEDNESS: single stranded
                (D) TOPOLOGY: linear (ii) MOLECULE TYPE: other nucleic acid
                (A) DESCRIPTION: third strand derived from C. burnetii
                        16s region in Seq ID No 281

(iii) HYPOTHETICAL: yes (iv) ANTI-SENSE: no (x) PUBLICATION INFORMATION:
                (K) RELEVANT RESIDUES IN SEQ ID NO: 282 :FROM 1 TO 10

(xi) SEQUENCE DESCRIPTION: SEQ ID NO: 282 :

T T C T T C C C T T                                                                                     10

( 2 ) INFORMATION FOR SEQ ID NO:283:

( i ) SEQUENCE CHARACTERISTICS:
        ( A ) LENGTH: 15 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: 16s rRNA gene from Coxiella burnetii
        ( A c c e s s i o n # M 2 1 2 9 1 ) nucleotides 1174 to 1188

( i i i ) HYPOTHETICAL: no ( i v ) ANTI-SENSE: no ( v i ) ORIGINAL SOURCE:
        ( A ) ORGANISM: Coxiella burnetii ( x ) PUBLICATION INFORMATION:
        ( A ) AUTHORS: Weisburg, W G, Dobson, M E, Samuel, J E,
            Dasch, G A, Mallavia, L P, Mandelco, L,
            Sechrest, J E, Weiss, E, Woese, C R.
        ( B ) TITLE: Phylogenetic diversity of the
            Rickettsiae
        ( C ) JOURNAL: Journal of Bacteriology
        ( D ) VOLUME: 171
        ( F ) PAGES: 4202-4206
        ( G ) DATE: 1989
        ( K ) RELEVANT RESIDUES IN SEQ ID NO: 283 :FROM 1 TO 15

( x i ) SEQUENCE DESCRIPTION: SEQ ID NO: 283:

GGAGGAAGGT GGGGA            1 5

( 2 ) INFORMATION FOR SEQ ID NO:284:

( i ) SEQUENCE CHARACTERISTICS:
        ( A ) LENGTH: 15 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from C. burnetii
            16s region in Seq ID No 283

( i i i ) HYPOTHETICAL: yes ( i v ) ANTI-SENSE: no ( x ) PUBLICATION INFORMATION:
        ( K ) RELEVANT RESIDUES IN SEQ ID NO: 284 :FROM 1 TO 15

( x i ) SEQUENCE DESCRIPTION: SEQ ID NO: 284 :

CCTCCTTCCG CCCCT            1 5

( 2 ) INFORMATION FOR SEQ ID NO:285:

( i ) SEQUENCE CHARACTERISTICS:
        ( A ) LENGTH: 11 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: 16s rRNA gene from Clostridium
            pasteurianum (Accession #M23930) nucleotides
            129 to 139

( i i i ) HYPOTHETICAL: no ( i v ) ANTI-SENSE: no ( v i ) ORIGINAL SOURCE:
        ( A ) ORGANISM: Clostridium pasteurianum (x) PUBLICATION INFORMATION:
        (A) AUTHORS: Weisburg, W G, Tully, J G, Rose, D L,
            Petzel, J P, Oyaizu, H, Yang, D, Mandelco,
            L, Sechrest, J, Lawrence, T G, Van Etten, J,
            Maniloff, J, Woese, C R.
        (B) TITLE: A phylogenetic analysis of
            the mycoplasmas: Basis for their classification
        (C) JOURNAL: Journal of Bacteriology
        (D) VOLUME: 171
        (F) PAGES: 6455-6467
        (G) DATE: 1989
        (K) RELEVANT RESIDUES IN SEQ ID NO: 285 :FROM 1 TO 11

(xi) SEQUENCE DESCRIPTION: SEQ ID NO: 285:

AAAGAGGGGA A                                                                                        11

(2) INFORMATION FOR SEQ ID NO:286:

(i) SEQUENCE CHARACTERISTICS:
        (A) LENGTH: 11 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from C.
            pasteurianum 16s region in Seq ID No 285

(iii) HYPOTHETICAL: yes (iv) ANTI-SENSE: no (x) PUBLICATION INFORMATION:
        (K) RELEVANT RESIDUES IN SEQ ID NO: 286 :FROM 1 TO 11

(xi) SEQUENCE DESCRIPTION: SEQ ID NO: 286 :

TTTCTCCCCT T                                                                                        11

(2) INFORMATION FOR SEQ ID NO:287:

(i) SEQUENCE CHARACTERISTICS:
        (A) LENGTH: 10 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: 16s rRNA gene from Clostridium
            pasteurianum (Accession #M23930) nucleotides
            149 to 158

(iii) HYPOTHETICAL: no (iv) ANTI-SENSE: no (vi) ORIGINAL SOURCE:
        (A) ORGANISM: Clostridium pasteurianum (x) PUBLICATION INFORMATION:
        (A) AUTHORS: Weisburg, W G, Tully, J G, Rose, D L,
            Petzel, J P, Oyaizu, H, Yang, D, Mandelco,
            L, Sechrest, J, Lawrence, T G, Van Etten, J,
            Maniloff, J, Woese, C R.
        (B) TITLE: A phylogenetic analysis of
            the mycoplasmas: Basis for their classification
        (C) JOURNAL: Journal of Bacteriology
        (D) VOLUME: 171
        (F) PAGES: 6455-6467
        (G) DATE: 1989
        (K) RELEVANT RESIDUES IN SEQ ID NO: 287 :FROM 1 TO 10

(xi) SEQUENCE DESCRIPTION: SEQ ID NO: 287:

GAAAGGGAGA                                                                                          10

( 2 ) INFORMATION FOR SEQ ID NO:288:

( i ) SEQUENCE CHARACTERISTICS:
( A ) LENGTH: 10 bases
( B ) TYPE: nucleic acid
( C ) STRANDEDNESS: single stranded
( D ) TOPOLOGY: linear ( i i ) MOLECULE TYPE: other nucleic acid
( A ) DESCRIPTION: third strand derived from C.
pasteurianum 16s region in Seq ID No 287

( i i i ) HYPOTHETICAL: yes ( i v ) ANTI-SENSE: no ( x ) PUBLICATION INFORMATION:
( K ) RELEVANT RESIDUES IN SEQ ID NO: 288 :FROM 1 TO 10

( x i ) SEQUENCE DESCRIPTION: SEQ ID NO: 288 :

CTTTCCCTCT 10

( 2 ) INFORMATION FOR SEQ ID NO:289:

( i ) SEQUENCE CHARACTERISTICS:
( A ) LENGTH: 11 base pairs
( B ) TYPE: nucleic acid
( C ) STRANDEDNESS: double stranded
( D ) TOPOLOGY: linear ( i i ) MOLECULE TYPE: genomic DNA
( A ) DESCRIPTION: 16s rRNA gene from Clostridium
pasteurianum (Accession #M23930) nucleotides
459 to 469

( i i i ) HYPOTHETICAL: no ( i v ) ANTI-SENSE: no ( v i ) ORIGINAL SOURCE:
( A ) ORGANISM: Clostridium pasteurianum ( x ) PUBLICATION INFORMATION:
( A ) AUTHORS: Weisburg, W G, Tully, J G, Rose, D L,
Petzel, J P, Oyaizu, H, Yang, D, Mandelco,
L, Sechrest, J, Lawrence, T G, Van Etten, J,
Maniloff, J, Woese, C R.
( B ) TITLE: A phylogenetic analysis of
the mycoplasmas: Basis for their classification
( C ) JOURNAL: Journal of Bacteriology
( D ) VOLUME: 171
( F ) PAGES: 6455-6467
( G ) DATE: 1989
( K ) RELEVANT RESIDUES IN SEQ ID NO: 289 :FROM 1 TO 11

( x i ) SEQUENCE DESCRIPTION: SEQ ID NO: 289:

AAAGGAGGAA G 11

( 2 ) INFORMATION FOR SEQ ID NO:290:

( i ) SEQUENCE CHARACTERISTICS:
( A ) LENGTH: 11 bases
( B ) TYPE: nucleic acid
( C ) STRANDEDNESS: single stranded
( D ) TOPOLOGY: linear ( i i ) MOLECULE TYPE: other nucleic acid
( A ) DESCRIPTION: third strand derived from C.
pasteurianum 16s region in Seq ID No 289

( i i i ) HYPOTHETICAL: yes ( i v ) ANTI-SENSE: no ( x ) PUBLICATION INFORMATION:

-continued (K) RELEVANT RESIDUES IN SEQ ID NO: 290 :FROM 1 TO 11

(xi) SEQUENCE DESCRIPTION: SEQ ID NO: 290 :

TTTCCTCCTT C                                                                                          11

(2) INFORMATION FOR SEQ ID NO:291:

(i) SEQUENCE CHARACTERISTICS:
        (A) LENGTH: 12 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: 16s rRNA gene from Clostridium
            pasteurianum (Accession #M23930) nucleotides
            629 to 640

(iii) HYPOTHETICAL: no (iv) ANTI-SENSE: no (vi) ORIGINAL SOURCE:
        (A) ORGANISM: Clostridium pasteurianum (x) PUBLICATION INFORMATION:
        (A) AUTHORS: Weisburg, W G, Tully, J G, Rose, D L,
            Petzel, J P, Oyaizu, H, Yang, D, Mandelco,
            L, Sechrest, J, Lawrence, T G, Van Etten, J,
            Maniloff, J, Woese, C R.
        (B) TITLE: A phylogenetic analysis of
            the mycoplasmas: Basis for their classification
        (C) JOURNAL: Journal of Bacteriology
        (D) VOLUME: 171
        (F) PAGES: 6455-6467
        (G) DATE: 1989
        (K) RELEVANT RESIDUES IN SEQ ID NO: 291 :FROM 1 TO 12

(xi) SEQUENCE DESCRIPTION: SEQ ID NO: 291:

AGGAGAGGAA AG                                                                                          12

(2) INFORMATION FOR SEQ ID NO:292:

(i) SEQUENCE CHARACTERISTICS:
        (A) LENGTH: 12 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from C.
            pasteurianum 16s region in Seq ID No 291

(iii) HYPOTHETICAL: yes (iv) ANTI-SENSE: no (x) PUBLICATION INFORMATION:
        (K) RELEVANT RESIDUES IN SEQ ID NO: 292 :FROM 1 TO 12

(xi) SEQUENCE DESCRIPTION: SEQ ID NO: 292 :

TCCTCTCCTT TC                                                                                          12

(2) INFORMATION FOR SEQ ID NO:293:

(i) SEQUENCE CHARACTERISTICS:
        (A) LENGTH: 16 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: 16s rRNA gene from Clostridium
            pasteurianum (Accession #M23930) nucleotides 1141 to 1156

(iii) HYPOTHETICAL: no (iv) ANTI-SENSE: no (vi) ORIGINAL SOURCE:
    (A) ORGANISM: Clostridium pasteurianum (x) PUBLICATION INFORMATION:
    (A) AUTHORS: Weisburg, W G, Tully, J G, Rose, D L,
        Petzel, J P, Oyaizu, H, Yang, D, Mandelco,
        L, Sechrest, J, Lawrence, T G, Van Etten, J,
        Maniloff, J, Woese, C R.
    (B) TITLE: A phylogenetic analysis of
        the mycoplasmas: Basis for their classification
    (C) JOURNAL: Journal of Bacteriology
    (D) VOLUME: 171
    (F) PAGES: 6455-6467
    (G) DATE: 1989
    (K) RELEVANT RESIDUES IN SEQ ID NO: 293 :FROM 1 TO 16

(xi) SEQUENCE DESCRIPTION: SEQ ID NO: 293:

GGNAGGAAGG CGGGGA 16

(2) INFORMATION FOR SEQ ID NO:294:

(i) SEQUENCE CHARACTERISTICS:
    (A) LENGTH: 16 bases
    (B) TYPE: nucleic acid
    (C) STRANDEDNESS: single stranded
    (D) TOPOLOGY: linear (ii) MOLECULE TYPE: other nucleic acid
    (A) DESCRIPTION: third strand derived from C.
        pasteurianum 16s region in Seq ID No 293

(iii) HYPOTHETICAL: yes (iv) ANTI-SENSE: no (x) PUBLICATION INFORMATION:
    (K) RELEVANT RESIDUES IN SEQ ID NO: 294 :FROM 1 TO 16

(xi) SEQUENCE DESCRIPTION: SEQ ID NO: 294 :

CCNTCCTTCC GCCCCT 16

(2) INFORMATION FOR SEQ ID NO:295:

(i) SEQUENCE CHARACTERISTICS:
    (A) LENGTH: 11 base pairs
    (B) TYPE: nucleic acid
    (C) STRANDEDNESS: double stranded
    (D) TOPOLOGY: linear (ii) MOLECULE TYPE: genomic DNA
    (A) DESCRIPTION: 16s rRNA gene from Chlamydia psittaci
    (Accession # M13769) nucleotides 203 to 213

(iii) HYPOTHETICAL: no (iv) ANTI-SENSE: no (vi) ORIGINAL SOURCE:
    (A) ORGANISM: Chlamydia psittaci (x) PUBLICATION INFORMATION:
    (A) AUTHORS: Weisburg, W G, Hatch, T P, Woese, C R.
    (B) TITLE: Eubacterial Origin of
        Chlamydiae
    (C) JOURNAL: Journal of Bacteriology
    (D) VOLUME: 167
    (F) PAGES: 570-574
    (G) DATE: 1986
    (K) RELEVANT RESIDUES IN SEQ ID NO: 295 :FROM 1 TO 11

( x i ) SEQUENCE DESCRIPTION: SEQ ID NO: 295:

AAAGAAGGGG A                                                                                                    11

( 2 ) INFORMATION FOR SEQ ID NO:296:

( i ) SEQUENCE CHARACTERISTICS:
      ( A ) LENGTH: 11 bases
      ( B ) TYPE: nucleic acid
      ( C ) STRANDEDNESS: single stranded
      ( D ) TOPOLOGY: linear ( i i ) MOLECULE TYPE: other nucleic acid
      ( A ) DESCRIPTION: third strand derived from C. psittaci
          16s region in Seq ID No 295

( i i i ) HYPOTHETICAL: yes ( i v ) ANTI-SENSE: no ( x ) PUBLICATION INFORMATION:
      ( K ) RELEVANT RESIDUES IN SEQ ID NO:

(K) RELEVANT RESIDUES IN SEQ ID NO: 298 :FROM 1 TO 14

(xi) SEQUENCE DESCRIPTION: SEQ ID NO: 298 :

CCCTTGTTCT CTCT 14

(2) INFORMATION FOR SEQ ID NO:299:

(i) SEQUENCE CHARACTERISTICS:
        (A) LENGTH: 11 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: 16s rRNA gene from Chlamydia psittaci
        (Accession # M13769) nucleotides 595 to 605

(iii) HYPOTHETICAL: no (vi) ORIGINAL SOURCE:
(A) ORGANISM: Chlamydia psittaci (x) PUBLICATION INFORMATION:
(A) AUTHORS: Weisburg, W G, Hatch, T P, Woese, C R.
(B) TITLE: Eubacterial Origin of Chlamydiae
(C) JOURNAL: Journal of Bacteriology
(D) VOLUME: 167
(F) PAGES: 570-574
(G) DATE: 1986
(K) RELEVANT RESIDUES IN SEQ ID NO: 301 :FROM 1 TO 24

(xi) SEQUENCE DESCRIPTION: SEQ ID NO: 301:

AGAGGGTAGA TGGAGAAAAG GGAA 24

(2) INFORMATION FOR SEQ ID NO:302:

(i) SEQUENCE CHARACTERISTICS:
(A) LENGTH: 24 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from C. psittaci 16s region in Seq ID No 301

(iii) HYPOTHETICAL: yes (iv) ANTI-SENSE: no (x) PUBLICATION INFORMATION:
(K) RELEVANT RESIDUES IN SEQ ID NO: 302 :FROM 1 TO 24

(xi) SEQUENCE DESCRIPTION: SEQ ID NO: 302 :

TCTCCCGTCT GCCTCTTTTC CCTT 24

(2) INFORMATION FOR SEQ ID NO:303:

(i) SEQUENCE CHARACTERISTICS:
(A) LENGTH: 10 base pairs
(B) TYPE: nucleic acid
(C) STRANDEDNESS: double stranded
(D) TOPOLOGY: linear (ii) MOLECULE TYPE: genomic DNA
(A) DESCRIPTION: 16s rRNA gene from Chlamydia psittaci (Accession # M13769) nucleotides 1181 to 1190

(iii) HYPOTHETICAL: no (iv) ANTI-SENSE: no (vi) ORIGINAL SOURCE:
(A) ORGANISM: Chlamydia psittaci (x) PUBLICATION INFORMATION:
(A) AUTHORS: Weisburg, W G, Hatch, T P, Woese, C R.
(B) TITLE: Eubacterial Origin of Chlamydiae
(C) JOURNAL: Journal of Bacteriology
(D) VOLUME: 167
(F) PAGES: 570-574
(G) DATE: 1986
(K) RELEVANT RESIDUES IN SEQ ID NO: 303 :FROM 1 TO 10

(xi) SEQUENCE DESCRIPTION: SEQ ID NO: 303:

AGGAGGAAGG 10

(2) INFORMATION FOR SEQ ID NO:304:

(i) SEQUENCE CHARACTERISTICS:

(A) LENGTH: 10 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from C. psittaci 16s region in Seq ID No 303

(iii) HYPOTHETICAL: yes (iv) ANTI-SENSE: no (x) PUBLICATION INFORMATION:
(K) R ( 2 ) INFORMATION FOR SEQ ID NO:307:

( i ) SEQUENCE CHARACTERISTICS:
        ( A ) LENGTH: 11 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: 16s rRNA gene from Corynebacterium
            renale (Accession #M29553) nucleotides 997 to
            1007

( i i i ) HYPOTHETICAL: no ( i v ) ANTI-SENSE: no ( v i ) ORIGINAL SOURCE:
        ( A ) ORGANISM: Corynebacterium renale ( x ) PUBLICATION INFORMATION:
        ( A ) AUTHORS: Stahl, D A, Urbance, J W.
        ( B ) TITLE: The division between fast-
            and slow- growing species corresponds to natural
            relationships among the mycobacteria
        ( C ) JOURNAL: Journal of Bacteriology
        ( D ) VOLUME: 167
        ( F ) PAGES: 570-574
        ( G ) DATE: 1986
        ( K ) RELEVANT RESIDUES IN SEQ ID NO: 307 :FROM 1 TO 11

( x i ) SEQUENCE DESCRIPTION: SEQ ID NO: 307:

T C T T T C C C T T T                                       1 1

( 2 ) INFORMATION FOR SEQ ID NO:308:

( i ) SEQUENCE CHARACTERISTICS:
        ( A ) LENGTH: 11 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from C. renale
            16s region in Seq ID No 307

( i i i ) HYPOTHETICAL: yes ( i v ) ANTI-SENSE: no ( x ) PUBLICATION INFORMATION:
        ( K ) RELEVANT RESIDUES IN SEQ ID NO: 308 :FROM 1 TO 11

( x i ) SEQUENCE DESCRIPTION: SEQ ID NO: 308 :

T T T C C C T T T C T                                       1 1

( 2 ) INFORMATION FOR SEQ ID NO:309:

( i ) SEQUENCE CHARACTERISTICS:
        ( A ) LENGTH: 13 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: 16s rRNA gene from Corynebacterium
            renale (Accession #M29553) nucleotides 1152 to
            1164

( i i i ) HYPOTHETICAL: no ( i v ) ANTI-SENSE: no ( v i ) ORIGINAL SOURCE:
        ( A ) ORGANISM: Corynebacterium renale (x) PUBLICATION INFORMATION:
    (A) AUTHORS: Stahl, D A, Urbance, J W.
    (B) TITLE: The division between fast-
        and slow- growing species corresponds to natural
        relationships among the mycobacteria
    (C) JOURNAL: Journal of Bacteriology
    (D) VOLUME: 167
    (F) PAGES: 570-574
    (G) DATE: 1986
    (K) RELEVANT RESIDUES IN SEQ ID NO: 309 :FROM 1 TO 13

(xi) SEQUENCE DESCRIPTION: SEQ ID NO: 309:

AGGAAGGTGG GGA 13

(2) INFORMATION FOR SEQ ID NO:310:

(i) SEQUENCE CHARACTERISTICS:
    (A) LENGTH: 13 bases
    (B) TYPE: nucleic acid
    (C) STRANDEDNESS: single stranded
    (D) TOPOLOGY: linear (ii) MOLECULE TYPE: other nucleic acid
    (A) DESCRIPTION: third strand derived from C. renale
        16s region in Seq ID No 309

(iii) HYPOTHETICAL: yes (iv) ANTI-SENSE: no (x) PUBLICATION INFORMATION:
    (K) RELEVANT RESIDUES IN SEQ ID NO: 310 :FROM 1 TO 13

(xi) SEQUENCE DESCRIPTION: SEQ ID NO: 310 :

TCCTTCCGCC CCT 13

(2) INFORMATION FOR SEQ ID NO:311:

(i) SEQUENCE CHARACTERISTICS:
    (A) LENGTH: 15 base pairs
    (B) TYPE: nucleic acid
    (C) STRANDEDNESS: double stranded
    (D) TOPOLOGY: linear (ii) MOLECULE TYPE: genomic DNA
    (A) DESCRIPTION: 16s rRNA gene from Corynebacterium
        renale (Accession #M29553) nucleotides 1150 to
        1164

(iii) HYPOTHETICAL: no (iv) ANTI-SENSE: no (vi) ORIGINAL SOURCE:
    (A) ORGANISM: Corynebacterium renale (x) PUBLICATION INFORMATION:
    (A) AUTHORS: Stahl, D A, Urbance, J W.
    (B) TITLE: The division between fast-
        and slow- growing species corresponds to natural
        relationships among the mycobacteria
    (C) JOURNAL: Journal of Bacteriology
    (D) VOLUME: 167
    (F) PAGES: 570-574
    (G) DATE: 1986
    (K) RELEVANT RESIDUES IN SEQ ID NO: 311 :FROM 1 TO 15

(xi) SEQUENCE DESCRIPTION: SEQ ID NO: 311:

GNAGGAAGGT GGGGA 15

(2) INFORMATION FOR SEQ ID NO:312:

(i) SEQUENCE CHARACTERISTICS:

(A) LENGTH: 15 bases
(B) TYPE: nucleic acid
(C) STRANDEDNESS: single stranded
(D) TOPOLOGY: linear (i i) MOLECULE TYPE: other nucleic acid
(A) DESCRIPTION: third strand derived from C. renale 16s region in Seq ID No 311

(i i i) HYPOTHETICAL: yes (i v) ANTI-SENSE: no (x) PUBLICATION INFORMATION:
(K) RELEVANT RESIDUES IN SEQ ID NO: 312 :FROM 1 TO 15

(x i) SEQUENCE DESCRIPTION: SEQ ID NO: 312 :

CNTCCTTCCG CCCCT 15

(2) INFORMATION FOR SEQ ID NO:313:

(i) SEQUENCE CHARACTERISTICS:
(A) LENGTH: 12 base pairs
(B) TYPE: nucleic acid
(C) STRANDEDNESS: double stranded
(D) TOPOLOGY: linear (i i) MOLECULE TYPE: genomic DNA
(A) DESCRIPTION: 16s rRNA gene from Haemophilus influenzae (Accession #M35019, M59433 ) nucleotides 187 to 198

(i i i) HYPOTHETICAL: no (i v) ANTI-SENSE: no (v i) ORIGINAL SOURCE:
(A) ORGANISM: Haemophilus influenzae (x) PUBLICATION INFORMATION:
(A) AUTHORS: Dewhirst, F E, Paster, B J, La Fontaine, S, Rood, J I.
(B) TITLE: Transfer of Kingella indologenes (Snell and Lapage 1976) to the genus Suttonella gen nov as Suttonella indologenes comb nov transfer of Bacteroides nodosus (Beveridge 1941) to the genus Dichelobacter gen nov as Dichelobacter nodosus comb nov.
(C) JOURNAL: unpublished
(D) VOLUME:
(F) PAGES:
(G) DATE: 1991
(K) RELEVANT RESIDUES IN SEQ ID NO: 313 :FROM 1 TO 12

(x i) SEQUENCE DESCRIPTION: SEQ ID NO: 313:

GGAAGATGAA AG 12

(2) INFORMATION FOR SEQ ID NO:314:

(i) SEQUENCE CHARACTERISTICS:
(A) LENGTH: 12 bases
(B) TYPE: nucleic acid
(C) STRANDEDNESS: single stranded
(D) TOPOLOGY: linear (i i) MOLECULE TYPE: other nucleic acid
(A) DESCRIPTION: third strand derived from H. influenzae 16s region in Seq ID No 313

(i i i) HYPOTHETICAL: yes (i v) ANTI-SENSE: no (x) PUBLICATION INFORMATION:
(K) RELEVANT RESIDUES IN SEQ ID NO: 314 :FROM 1 TO 12

( x i ) SEQUENCE DESCRIPTION: SEQ ID NO: 314 :

CCTTCTGCTT TC                                                                                                    12

( 2 ) INFORMATION FOR SEQ ID NO:315:

( i ) SEQUENCE CHARACTERISTICS:
    ( A ) LENGTH: 12 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: 16s rRNA gene from Haemophilus
          influenzae (Accession #M35019, M59433 )
          nucleotides 406 to 417

( i i i ) HYPOTHETICAL: no ( i v ) ANTI-SENSE: no ( v i ) ORIGINAL SOURCE:
    ( A ) ORGANISM: Haemophilus influenzae ( x ) PUBLICATION INFORMATION:
    ( A ) AUTHORS: Dewhirst, F E, Paster, B J, La Fontaine,
          S, Rood, J I.
    ( B ) TITLE: Transfer of Kingella
          indologenes (Snell and Lapage 1976) to the
          genus Suttonella gen nov as Suttonella
          indologenes comb nov transfer of Bacteroides
          nodosus (Beveridge 1941) to the genus
          Dichelobacter gen nov as Dichelobacter nodosus
          comb nov.
    ( C ) JOURNAL: unpublished
    ( D ) VOLUME:
    ( F ) PAGES:
    ( G ) DATE: 1991
    ( K ) RELEVANT RESIDUES IN SEQ ID NO: 315 :FROM 1 TO 12

( x i ) SEQUENCE DESCRIPTION: SEQ ID NO: 315:

GAATGAAGAA GG                                                                                                    12

( 2 ) INFORMATION FOR SEQ ID NO:316:

( i ) SEQUENCE CHARACTERISTICS:
    ( A ) LENGTH: 12 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from H.
          influenzae 16s region in Seq ID No 315

( i i i ) HYPOTHETICAL: yes ( i v ) ANTI-SENSE: no ( x ) PUBLICATION INFORMATION:
    ( K ) RELEVANT RESIDUES IN SEQ ID NO: 316 :FROM 1 TO 12

( x i ) SEQUENCE DESCRIPTION: SEQ ID NO: 316 :

CTTGCTTCTT CC                                                                                                    12

( 2 ) INFORMATION FOR SEQ ID NO:317:

( i ) SEQUENCE CHARACTERISTICS:
    ( A ) LENGTH: 14 base pairs
    ( B ) TYPE: nucleic acid
    ( C ) STRANDEDNESS: double stranded
    ( D ) TOPOLOGY: linear ( i i ) MOLECULE TYPE: genomic DNA (A) DESCRIPTION: 16s rRNA gene from Haemophilus
    influenzae (Accession #M35019, M59433 )
    nucleotides 663 to 676

(i i i) HYPOTHETICAL: no (i v) ANTI-SENSE: no (v i) ORIGINAL SOURCE:
    (A) ORGANISM: Haemophilus influenzae (x) PUBLICATION INFORMATION:
    (A) AUTHORS: Dewhirst, F E, Paster, B J, La Fontaine,
        S, Rood, J I.
    (B) TITLE: Transfer of Kingella
        indologenes (Snell and Lapage 1976) to the
        genus Suttonella gen nov as Suttonella
        indologenes comb nov transfer of Bacteroides
        nodosus (Beveridge 1941) to the genus
        Dichelobacter gen nov as Dichelobacter nodosus
        comb nov.
    (C) JOURNAL: unpublished
    (D) VOLUME:
    (F) PAGES:
    (G) DATE: 1991
    (K) RELEVANT RESIDUES IN SEQ ID NO: 317 :FROM 1 TO 14

(x i) SEQUENCE DESCRIPTION: SEQ ID NO: 317:

AGGGAGGGGT AGAA                                                                14

(2) INFORMATION FOR SEQ ID NO:318:

(i) SEQUENCE CHARACTERISTICS:
        (A) LENGTH: 14 bases
        (B) TYPE: nucleic acid
        (C) STRANDEDNESS: single stranded
        (D) TOPOLOGY: linear (i i) MOLECULE TYPE: other nucleic acid
        (A) DESCRIPTION: third strand derived from H.
            influenzae 16s region in Seq ID No 317

(i i i) HYPOTHETICAL: yes (i v) ANTI-SENSE: no (x) PUBLICATION INFORMATION:
        (K) RELEVANT RESIDUES IN SEQ ID NO: 318 :FROM 1 TO 14

(x i) SEQUENCE DESCRIPTION: SEQ ID NO: 318 :

TCCCTCCCCG TCTT                                                                14

(2) INFORMATION FOR SEQ ID NO:319:

(i) SEQUENCE CHARACTERISTICS:
        (A) LENGTH: 12 base pairs
        (B) TYPE: nucleic acid
        (C) STRANDEDNESS: double stranded
        (D) TOPOLOGY: linear (i i) MOLECULE TYPE: genomic DNA
        (A) DESCRIPTION: 16s rRNA gene from Haemophilus
            influenzae (Accession #M35019, M59433 )
            nucleotides 1110 to 1121

(i i i) HYPOTHETICAL: no (i v) ANTI-SENSE: no (v i) ORIGINAL SOURCE:
        (A) ORGANISM: Haemophilus influenzae (x) PUBLICATION INFORMATION:
        (A) AUTHORS: Dewhirst, F E, Paster, B J, La Fontaine,
            S, Rood, J I.
        (B) TITLE: Transfer of Kingella -continued indologenes (Snell and Lapage 1976) to the
                         genus Suttonella gen nov as Suttonella
                         indologenes comb nov transfer of Bacteroides
                         nodosus (Beveridge 1941) to the genus
                         Dichelobacter gen nov as Dichelobacter nodosus
                         comb nov.
            ( C ) JOURNAL: unpublished
            ( D ) VOLUME:
            ( F ) PAGES:
            ( G ) DATE: 1991
            ( K ) RELEVANT RESIDUES IN SEQ ID NO: 319 :FROM 1 TO 12

( x i ) SEQUENCE DESCRIPTION: SEQ ID NO: 319:

C C C T T A T C C T   T T                                                                                     1 2

( 2 ) INFORMATION FOR SEQ ID NO:320:

( i ) SEQUENCE CHARACTERISTICS:
            ( A ) LENGTH: 12 bases
            ( B ) TYPE: nucleic acid
            ( C ) STRANDEDNESS: single stranded
            ( D ) TOPOLOGY: linear ( i i ) MOLECULE TYPE: other nucleic acid
            ( A ) DESCRIPTION: third strand derived from H.
                    influenzae 16s region in Seq ID No 319

( i i i ) HYPOTHETICAL: yes ( i v ) ANTI-SENSE: no ( x ) PUBLICATION INFORMATION:
            ( K ) RELEVANT RESIDUES IN SEQ ID NO: 320 :FROM 1 TO 12

( x i ) SEQUENCE DESCRIPTION: SEQ ID NO: 320 :

T T T C C T G T T C   C C                                                                                     1 2

( 2 ) INFORMATION FOR SEQ ID NO:321:

( i ) SEQUENCE CHARACTERISTICS:
            ( A ) LENGTH: 15 base pairs
            ( B ) TYPE: nucleic acid
            ( C ) STRANDEDNESS: double stranded
            ( D ) TOPOLOGY: linear ( i i ) MOLECULE TYPE: genomic DNA
            ( A ) DESCRIPTION: 16s rRNA gene from Haemophilus
                    influenzae (Accession #M35019, M59433 )
                    nucleotides 1172 to 1186

( i i i ) HYPOTHETICAL: no ( i v ) ANTI-SENSE: no ( v i ) ORIGINAL SOURCE:
            ( A ) ORGANISM: Haemophilus influenzae ( x ) PUBLICATION INFORMATION:
            ( A ) AUTHORS: Dewhirst, F E, Paster, B J, La Fontaine,
                    S, Rood, J I.
            ( B ) TITLE: Transfer of Kingella
                    indologenes (Snell and Lapage 1976) to the
                    genus Suttonella gen nov as Suttonella
                    indologenes comb nov transfer of Bacteroides
                    nodosus (Beveridge 1941) to the genus
                    Dichelobacter gen nov as Dichelobacter nodosus
                    comb nov.
            ( C ) JOURNAL: unpublished
            ( D ) VOLUME:
            ( F ) PAGES:
            ( G ) DATE: 1991
            ( K ) RELEVANT RESIDUES IN SEQ ID NO: 321 :FROM 1 TO 15

( x i ) SEQUENCE DESCRIPTION: SEQ ID NO: 321:

G G A G G A A G G T   N G G G A                                                                                    1 5

( 2 ) INFORMATION FOR SEQ ID NO:322:

( i ) SEQUENCE CHARACTERISTICS:
( A ) LENGTH: 15 bases
( B ) TYPE: nucleic acid
( C ) STRANDEDNESS: single stranded
( D ) TOPOLOGY: linear ( i i ) MOLECULE TYPE: other nucleic acid
( A ) DESCRIPTION: third strand derived from H.
influenzae 16s region in Seq ID No 321

( i i i ) HYPOTHETICAL: yes ( i v ) ANTI-SENSE: no ( x ) PUBLICATION INFORMATION:
( K ) RELEVANT RESIDUES IN SEQ ID NO: 322 :FROM 1 TO 15

( x i ) SEQUENCE DESCRIPTION: SEQ ID NO: 322 :

CCTCCTTCCG NCCCT 15

( 2 ) INFORMATION FOR SEQ ID NO:323:

( i ) SEQUENCE CHARACTERISTICS:
( A ) LENGTH: 14 base pairs
( B ) TYPE: nucleic acid
( C ) STRANDEDNESS: double stranded
( D ) TOPOLOGY: linear ( i i ) MOLECULE TYPE: genomic DNA
( A ) DESCRIPTION: 16s rRNA gene from Mycobacterium
paratuberculosis (Accession #M29569)
nucleotides 471 to 484

( i i i ) HYPOTHETICAL: no ( i v ) ANTI-SENSE: no ( v i ) ORIGINAL SOURCE:
( A ) ORGANISM: Mycobacterium paratuberculosis ( x ) PUBLICATION INFORMATION:
( A ) AUTHORS: Stahl, D A, Urbance, J W.
( B ) TITLE: The division between fast-
and slow- growing species corresponds to natural
relationships among the mycobacteria
( C ) JOURNAL: Journal of Bacteriology
( D ) VOLUME: 172
( F ) PAGES: 116-124
( G ) DATE: 1989
( K ) RELEVANT RESIDUES IN SEQ ID NO: 323 :FROM 1 TO 14

( x i ) SEQUENCE DESCRIPTION: SEQ ID NO: 323:

AGGTGGAGAA GAAG 14

( 2 ) INFORMATION FOR SEQ ID NO:324:

( i ) SEQUENCE CHARACTERISTICS:
( A ) LENGTH: 14 bases
( B ) TYPE: nucleic acid
( C ) STRANDEDNESS: single stranded
( D ) TOPOLOGY: linear ( i i ) MOLECULE TYPE: other nucleic acid
( A ) DESCRIPTION: third strand derived from M.
paratuberculosis 16s region in Seq ID No 323

( i i i ) HYPOTHETICAL: yes ( i v ) ANTI-SENSE: no ( x ) PUBLICATION INFORMATION:
( K ) RELEVANT RESIDUES IN SEQ ID NO: 324 :FROM 1 TO 14

(xi) SEQUENCE DESCRIPTION: SEQ ID NO: 324 :

TCCGCCTCTT CTTC                                                                 14

(2) INFORMATION FOR SEQ ID NO:325:

(i) SEQUENCE CHARACTERISTICS:
        (A) LENGTH: 11 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: 16s rRNA gene from Mycobacterium
            paratuberculosis (Accession #M29569)
            nucleotides 821 to 831

(iii) HYPOTHETICAL: no (iv) ANTI-SENSE: no (vi) ORIGINAL SOURCE:
        (A) ORGANISM: Mycobacterium paratuberculosis (x) PUBLICATION INFORMATION:
        (A) AUTHORS: Stahl, D A, Urbance, J W.
        (B) TITLE: The division between fast-
            and slow- growing species corresponds to natural
            relationships among the mycobacteria
        (C) JOURNAL: Journal of Bacteriology
        (D) VOLUME: 172
        (F) PAGES: 116-124
        (G) DATE: 1989
        (K) RELEVANT RESIDUES IN SEQ ID NO: 325 :FROM 1 TO 11

(xi) SEQUENCE DESCRIPTION: SEQ ID NO: 325:

TTTCCTTCCT T                                                                    11

(2) INFORMATION FOR SEQ ID NO:326:

(i) SEQUENCE CHARACTERISTICS:
        (A) LENGTH: 11 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: third strand derived from M.
            paratuberculosis 16s region in Seq ID No 325

(iii) HYPOTHETICAL: yes (iv) ANTI-SENSE: no (x) PUBLICATION INFORMATION:
        (K) RELEVANT RESIDUES IN SEQ ID NO: 326 :FROM 1 TO 11

(xi) SEQUENCE DESCRIPTION: SEQ ID NO: 326 :

TTCCTTCCTT T                                                                    11

(2) INFORMATION FOR SEQ ID NO:327:

(i) SEQUENCE CHARACTERISTICS:
        (A) LENGTH: 15 base pairs
        (B) TYPE: nucleic acid
        (C) STRANDEDNESS: double stranded
        (D) TOPOLOGY: linear (ii) MOLECULE TYPE: genomic DNA
        (A) DESCRIPTION: 16s rRNA gene from Mycobacterium
            paratuberculosis (Accession #M29569)
            nucleotides 1159 to 1173

(iii) HYPOTHETICAL: no (iv) ANTI-SENSE: no (vi) ORIGINAL SOURCE:
  (A) ORGANISM: Mycobacterium paratuberculosis (x) PUBLICATION INFORMATION:
  (A) AUTHORS: Stahl, D A, Urbance, J W.
  (B) TITLE: The division between fast-
      and slow- growing species corresponds to natural
      relationships among the mycobacteria
  (C) JOURNAL: Journal of Bacteriology
  (D) VOLUME: 172
  (F) PAGES: 116-124
  (G) DATE: 1989
  (K) RELEVANT RESIDUES IN SEQ ID NO: 327 :FROM 1 TO 15

(xi) SEQUENCE DESCRIPTION: SEQ ID NO: 327:

GGAGGAAGGT GGGGA                                                          15

(2) INFORMATION FOR SEQ ID NO:328:

(i) SEQUENCE CHARACTERISTICS:
    (A) LENGTH: 15 bases
    (B) TYPE: nucleic acid
    (C) STRANDEDNESS: single stranded
    (D) TOPOLOGY: linear (ii) MOLECULE TYPE: other nucleic acid
    (A) DESCRIPTION: third strand derived from M.
        paratuberculosis 16s region in Seq ID No 327

(iii) HYPOTHETICAL: yes (iv) ANTI-SENSE: no (x) PUBLICATION INFORMATION:
    (K) RELEVANT RESIDUES IN SEQ ID NO: 328 :FROM 1 TO 15

(xi) SEQUENCE DESCRIPTION: SEQ ID NO: 328 :

CCTCCTTCCG CCCCT                                                          15

(2) INFORMATION FOR SEQ ID NO:329:

(i) SEQUENCE CHARACTERISTICS:
    (A) LENGTH: 15 base pairs
    (B) TYPE: nucleic acid
    (C) STRANDEDNESS: double stranded
    (D) TOPOLOGY: linear (ii) MOLECULE TYPE: genomic DNA
    (A) DESCRIPTION: 16s rRNA gene from Mycoplasma
        pneumoniae (Accession #M29061) nucleotides
        1150 to 1164

(iii) HYPOTHETICAL: no (iv) ANTI-SENSE: no (vi) ORIGINAL SOURCE:
    (A) ORGANISM: Mycoplasma pneumoniae (x) PUBLICATION INFORMATION:
    (A) AUTHORS: Weisburg, W G, Tully, J G, Rose, D L,
        Petzel, J P, Oyaizu, H, Yang, D, Mandelco,
        L, Sechrest, J, Lawrence, T G, Van Etten, J,
        Maniloff, J, Woese, C R.
    (B) TITLE: A phylogenetic analysis of
        the mycoplasmas: Basis for their classification
    (C) JOURNAL: Journal of Bacteriology
    (D) VOLUME: 171
    (F) PAGES: 6455-6467
    (G) DATE: 1990
    (K) RELEVANT RESIDUES IN SEQ ID NO: 329 :FROM 1 TO 15

(xi) SEQUENCE DESCRIPTION: SEQ ID NO: 329:

GGAGGAAGGA AGGGA 15

(2) INFORMATION FOR SEQ ID NO:330:

(i) SEQUENCE CHARACTERISTICS:
  (A) LENGTH: 15 bases
  (B) TYPE: nucleic acid
  (C) STRANDEDNESS: single stranded
  (D) TOPOLOGY: linear (ii) MOLECULE TYPE: other nucleic acid
  (A) DESCRIPTION: third strand derived from M.
   pneumoniae 16s region in Seq ID No 329

(iii) HYPOTHETICAL: yes (iv) ANTI-SENSE: no (x) PUBLICATION INFORMATION:
  (K) RELEVANT RESIDUES IN SEQ ID NO: 330 :FROM 1 TO 15

(xi) SEQUENCE DESCRIPTION: SEQ ID NO: 330 :

CCTCCTTCCT TCCCT 15

(2) INFORMATION FOR SEQ ID NO:331:

(i) SEQUENCE CHARACTERISTICS:
  (A) LENGTH: 11 base pairs
  (B) TYPE: nucleic acid
  (C) STRANDEDNESS: double stranded
  (D) TOPOLOGY: linear (ii) MOLECULE TYPE: genomic DNA
  (A) DESCRIPTION: 16s rRNA gene from Neisseria
   gonorrhoeae (Accession #X07714) nucleotides
   189 to 199

(iii) HYPOTHETICAL: no (iv) ANTI-SENSE: no (vi) ORIGINAL SOURCE:
  (A) ORGANISM: Neisseria gonorrhoeae
  (B) STRAIN: NCTC 83785

(x) PUBLICATION INFORMATION:
  (A) AUTHORS: Rossau, R, Heyndrickx, L, van
   Heuverswyn, H.
  (B) TITLE: Nucleotide sequence of a 16s
   ribosomal RNA gene from Neisseria gonorrhoeae
  (C) JOURNAL: Nucleic Acids Research
  (D) VOLUME: 16
  (F) PAGES: 6227-6227
  (G) DATE: 1988
  (K) RELEVANT RESIDUES IN SEQ ID NO: 331 :FROM 1 TO 11

(xi) SEQUENCE DESCRIPTION: SEQ ID NO: 331:

GAGAGGGAAA G 11

(2) INFORMATION FOR SEQ ID NO:332:

(i) SEQUENCE CHARACTERISTICS:
  (A) LENGTH: 11 bases
  (B) TYPE: nucleic acid
  (C) STRANDEDNESS: single stranded
  (D) TOPOLOGY: linear (ii) MOLECULE TYPE: other nucleic acid
  (A) DESCRIPTION: third strand derived from N.
   gonorrhoeae 16s region in Seq ID No 331

(iii) HYPOTHETICAL: yes (iv) ANTI-SENSE: no ( x ) PUBLICATION INFORMATION:
 ( K ) RELEVANT RESIDUES IN SEQ ID NO: 332 :FROM 1 TO 11

( x i ) SEQUENCE DESCRIPTION: SEQ ID NO: 332 :

CTCTCCCTTT C                                                                                                                    11

( 2 ) INFORMATION FOR SEQ ID NO:333:

( i ) SEQUENCE CHARACTERISTICS:
  ( A ) LENGTH: 13 base pairs
  ( B ) TYPE: nucleic acid
  ( C ) STRANDEDNESS: double stranded
  ( D ) TOPOLOGY: linear ( i i ) MOLECULE TYPE: genomic DNA
  ( A ) DESCRIPTION: 16s rRNA gene from Neisseria
   gonorrhoeae (Accession #X07714) nucleotides
   445 to 457

( i i i ) HYPOTHETICAL: no ( i v ) ANTI-SENSE: no ( v i ) ORIGINAL SOURCE:
  ( A ) ORGANISM: Neisseria gonorrhoeae
  ( B ) STRAIN: NCTC 83785

( x ) PUBLICATION INFORMATION:
  ( A ) AUTHORS: Rossau, R, Heyndrickx, L, van
   Heuverswyn, H.
  ( B ) TITLE: Nucleotide sequence of a 16s
   ribosomal RNA gene from Neisseria gonorrhoeae
  ( C ) JOURNAL: Nucleic Acids Research
  ( D ) VOLUME: 16
  ( F ) PAGES: 6227-6227
  ( G ) DATE: 1988
  ( K ) RELEVANT RESIDUES IN SEQ ID NO: 333 :FROM 1 TO 13

( x i ) SEQUENCE DESCRIPTION: SEQ ID NO: 333:

AGGGAAGAAA AGG                                                                                                                    13

( 2 ) INFORMATION FOR SEQ ID NO:334:

( i ) SEQUENCE CHARACTERISTICS:
  ( A ) LENGTH: 13 bases
  ( B ) TYPE: nucleic acid
  ( C ) STRANDEDNESS: single stranded
  ( D ) TOPOLOGY: linear ( i i ) MOLECULE TYPE: other nucleic acid
  ( A ) DESCRIPTION: third strand derived from N.
   gonorrhoeae 16s region in Seq ID No 333

( i i i ) HYPOTHETICAL: yes ( i v ) ANTI-SENSE: no ( x ) PUBLICATION INFORMATION:
  ( K ) RELEVANT RESIDUES IN SEQ ID NO: 334 :FROM 1 TO 13

( x i ) SEQUENCE DESCRIPTION: SEQ ID NO: 334 :

TCCCTTCTTT TCC                                                                                                                    13

( 2 ) INFORMATION FOR SEQ ID NO:335:

( i ) SEQUENCE CHARACTERISTICS:
  ( A ) LENGTH: 14 base pairs
  ( B ) TYPE: nucleic acid
  ( C ) STRANDEDNESS: double stranded
  ( D ) TOPOLOGY: linear ( i i ) MOLECULE TYPE: genomic DNA
  ( A ) DESCRIPTION: 16s rRNA gene from Neisseria gonorrhoeae (Accession #X07714) nucleotides
            664 to 677

( i i i ) HYPOTHETICAL: no ( i v ) ANTI-SENSE: no ( v i ) ORIGINAL SOURCE:
            ( A ) ORGANISM: Neisseria gonorrhoeae
            ( B ) STRAIN: NCTC 83785

( x ) PUBLICATION INFORMATION:
            ( A ) AUTHORS: Rossau, R, Heyndrickx, L, van
                    Heuverswyn, H.
            ( B ) TITLE: Nucleotide sequence of a 16s
                    ribosomal RNA gene from Neisseria gonorrhoeae
            ( C ) JOURNAL: Nucleic Acids Research
            ( D ) VOLUME: 16
            ( F ) PAGES: 6227-6227
            ( G ) DATE: 1988
            ( K ) RELEVANT RESIDUES IN SEQ ID NO: 335 :FROM 1 TO 14

( x i ) SEQUENCE DESCRIPTION: SEQ ID NO: 335:

AGAGGGAGGT GGAA                                                                                    14

( 2 ) INFORMATION FOR SEQ ID NO:336:

( i ) SEQUENCE CHARACTERISTICS:
            ( A ) LENGTH: 14 bases
            ( B ) TYPE: nucleic acid
            ( C ) STRANDEDNESS: single stranded
            ( D ) TOPOLOGY: linear ( i i ) MOLECULE TYPE: other nucleic acid
            ( A ) DESCRIPTION: third strand derived from N.
                    gonorrhoeae 16s region in Seq ID No 335

( i i i ) HYPOTHETICAL: yes ( i v ) ANTI-SENSE: no ( x ) PUBLICATION INFORMATION:
            ( K ) RELEVANT RESIDUES IN SEQ ID NO: 336 :FROM 1 TO 14

( x i ) SEQUENCE DESCRIPTION: SEQ ID NO: 336 :

TCTCCCTCCG CCTT                                                                                    14

( 2 ) INFORMATION FOR SEQ ID NO:337:

( i ) SEQUENCE CHARACTERISTICS:
            ( A ) LENGTH: 15 base pairs
            ( B ) TYPE: nucleic acid
            ( C ) STRANDEDNESS: double stranded
            ( D ) TOPOLOGY: linear ( i i ) MOLECULE TYPE: genomic DNA
            ( A ) DESCRIPTION: 16s rRNA gene from Neisseria
                    gonorrhoeae (Accession #X07714) nucleotides
                    1174 to 1188

( i i i ) HYPOTHETICAL: no ( i v ) ANTI-SENSE: no ( v i ) ORIGINAL SOURCE:
            ( A ) ORGANISM: Neisseria gonorrhoeae
            ( B ) STRAIN: NCTC 83785

( x ) PUBLICATION INFORMATION:
            ( A ) AUTHORS: Rossau, R, Heyndrickx, L, van
                    Heuverswyn, H.
            ( B ) TITLE: Nucleotide sequence of a 16s
                    ribosomal RNA gene from Neisseria gonorrhoeae
            ( C ) JOURNAL: Nucleic Acids Research
            ( D ) VOLUME: 16
            ( F ) PAGES: 6227-6227

-continued ( G ) DATE: 1988
    ( K ) RELEVANT RESIDUES IN SEQ ID NO: 337 :FROM 1 TO 15

( x i ) SEQUENCE DESCRIPTION: SEQ ID NO: 337:

G G A G G A A G G T G G G G A                                 1 5

( 2 ) INFORMATION FOR SEQ ID NO:338:

( i ) SEQUENCE CHARACTERISTICS:
    ( A ) LENGTH: 15 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from N.
      gonorrhoeae 16s region in Seq ID No 337

( i i i ) HYPOTHETICAL: yes ( i v ) ANTI-SENSE: no ( x ) PUBLICATION INFORMATION:
    ( K ) RELEVANT RESIDUES IN SEQ ID NO: 338 :FROM 1 TO 15

( x i ) SEQUENCE DESCRIPTION: SEQ ID NO: 338 :

C C T C C T T C C G C C C C T                                 1 5

( 2 ) INFORMATION FOR SEQ ID NO:339:

( i ) SEQUENCE CHARACTERISTICS:
    ( A ) LENGTH: 12 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: 16s rRNA gene from Neisseria
      gonorrhoeae (Accession #X07714) nucleotides
      1415 to 1426

( i i i ) HYPOTHETICAL: no ( i v ) ANTI-SENSE: no ( v i ) ORIGINAL SOURCE:
    ( A ) ORGANISM: Neisseria gonorrhoeae ( x ) PUBLICATION INFORMATION:
    ( A ) AUTHORS: Rossau, R, Heyndrickx, L, van
      Heuverswyn, H.
    ( B ) TITLE: Nucleotide sequence of a 16s
      ribosomal RNA gene from Neisseria gonorrhoeae
    ( C ) JOURNAL: Nucleic Acids Research
    ( D ) VOLUME: 16
    ( F ) PAGES: 6227-6227
    ( G ) DATE: 1988
    ( K ) RELEVANT RESIDUES IN SEQ ID NO: 339 :FROM 1 TO 12

( x i ) SEQUENCE DESCRIPTION: SEQ ID NO: 339:

G G G A G T G G G G G A                                    1 2

( 2 ) INFORMATION FOR SEQ ID NO:340:

( i ) SEQUENCE CHARACTERISTICS:
    ( A ) LENGTH: 12 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from N.
      gonorrhoeae 16s region in Seq ID No 339

(i i i) HYPOTHETICAL: yes (i v) ANTI-SENSE: no (x) PUBLICATION INFORMATION:
    (K) RELEVANT RESIDUES IN SEQ ID NO: 340 :FROM 1 TO 12

(x i) SEQUENCE DESCRIPTION: SEQ ID NO: 340 :

CCCTCGCCCC CT  12

(2) INFORMATION FOR SEQ ID NO:341:

(i) SEQUENCE CHARACTERISTICS:
        (A) LENGTH: 11 base pairs
        (B) TYPE: nucleic acid
        (C) STRANDEDNESS: double stranded
        (D) TOPOLOGY: linear (i i) MOLECULE TYPE: genomic DNA
        (A) DESCRIPTION: 16s rRNA gene from Pseudomonas cepacea
        (Accession # M22518, M22467) nucleotides 486 to 496

(i i i) HYPOTHETICAL: no (i v) ANTI-SENSE: no (v i) ORIGINAL SOURCE:
        (A) ORGANISM: Pseudomonas cepacea
        (B) STRAIN: NCTC 83785

(x) PUBLICATION INFORMATION:
        (A) AUTHORS: Dewhirst, F E, Paster, B J, Bright, P L.
        (B) TITLE: Chromobacterium, Eikenella,
            Kingella, Neisseria, Simonsiella and
            Vitreoscilla species comprise a major branch of
            the beta group Proteobacteria by 16S rRNA
            sequence comparison
        (C) JOURNAL: International Journal of Systematic
            Bacteriology
        (D) VOLUME: 0
        (F) PAGES: 0-0
        (G) DATE: 1990
        (K) RELEVANT RESIDUES IN SEQ ID NO: 341 :FROM 1 TO 11

(x i) SEQUENCE DESCRIPTION: SEQ ID NO: 341:

GGAAGAATAA G  11

(2) INFORMATION FOR SEQ ID NO:342:

(i) SEQUENCE CHARACTERISTICS:
        (A) LENGTH: 11 bases
        (B) TYPE: nucleic acid
        (C) STRANDEDNESS: single stranded
        (D) TOPOLOGY: linear (i i) MOLECULE TYPE: other nucleic acid
        (A) DESCRIPTION: third strand derived from P. cepacea
            16s region in Seq ID No 341

(i i i) HYPOTHETICAL: yes (i v) ANTI-SENSE: no (x) PUBLICATION INFORMATION:
        (K) RELEVANT RESIDUES IN SEQ ID NO: 342 :FROM 1 TO 11

(x i) SEQUENCE DESCRIPTION: SEQ ID NO: 342 :

CCTTCTTGTT C  11

(2) INFORMATION FOR SEQ ID NO:343:

(i) SEQUENCE CHARACTERISTICS:
        (A) LENGTH: 15 base pairs (B) TYPE: nucleic acid
(C) STRANDEDNESS: double stranded
(D) TOPOLOGY: linear (ii) MOLECULE TYPE: genomic DNA
(A) DESCRIPTION: 16s rRNA gene from Pseudomonas cepacea
(Accession # M22518, M22467) nucleotides 1165 to 1179

(iii) HYPOTHETICAL: no (iv) ANTI-SENSE: no (vi) ORIGINAL SOURCE:
(A) ORGANISM: Pseudomonas cepacea (x) PUBLICATION INFORMATION:
(A) AUTHORS: Dewhirst, F E, Paster, B J, Bright, P L.
(B) TITLE: Chromobacterium, Eikenella,
Kingella, Neisseria, Simonsiella and
Vitreoscilla species comprise a major branch of
the beta group Proteobacteria by 16S rRNA
sequence comparison
(C) JOURNAL: International Journal of Systematic
Bacteriology
(D) VOLUME: 0
(F) PAGES: 0-0
(G) DATE: 1990
(K) RELEVANT RESIDUES IN SEQ ID NO: 343 :FROM 1 TO 15

(xi) SEQUENCE DESCRIPTION: SEQ ID NO: 343:

GGAGGAAGGT GGGGA                                                                15

(2) INFORMATION FOR SEQ ID NO:344:

(i) SEQUENCE CHARACTERISTICS:
(A) LENGTH: 15 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from P. cepacea
16s region in Seq ID No 343

(iii) HYPOTHETICAL: yes (iv) ANTI-SENSE: no (x) PUBLICATION INFORMATION:
(K) RELEVANT RESIDUES IN SEQ ID NO: 344 :FROM 1 TO 15

(xi) SEQUENCE DESCRIPTION: SEQ ID NO: 344 :

CCTCCTTCCG CCCCT                                                                15

(2) INFORMATION FOR SEQ ID NO:345:

(i) SEQUENCE CHARACTERISTICS:
(A) LENGTH: 17 base pairs
(B) TYPE: nucleic acid
(C) STRANDEDNESS: double stranded
(D) TOPOLOGY: linear (ii) MOLECULE TYPE: genomic DNA
(A) DESCRIPTION: 16s rRNA gene from Streptococcus
parasanguis (Accession #X53652) nucleotides
665 to 681

(iii) HYPOTHETICAL: no (iv) ANTI-SENSE: no (vi) ORIGINAL SOURCE:
(A) ORGANISM: Streptococcus parasanguis
(B) STRAIN: 85-81

( x ) PUBLICATION INFORMATION:
- ( A ) AUTHORS: Whiley, R A, Fraser, H Y, Douglas, C W I, Hardie, J M, Williams, A M, Collins, M D.
- ( B ) TITLE: Streptococcus parasanguis sp nov., an atypical viridans Streptococcus from human clinical specimens
- ( C ) JOURNAL: FEMS Microbiology Letters
- ( D ) VOLUME: 68
- ( F ) PAGES: 115-122
- ( G ) DATE: 1990
- ( K ) RELEVANT RESIDUES IN SEQ ID NO: 345 :FROM 1 TO 17

( x i ) SEQUENCE DESCRIPTION: SEQ ID NO: 345:

AGAAGGGGAG AGTGGAA 17

( 2 ) INFORMATION FOR SEQ ID NO:346:

( i ) SEQUENCE CHARACTERISTICS:
- ( A ) LENGTH: 17 bases
- ( B ) TYPE: nucleic acid
- ( C ) STRANDEDNESS: single stranded
- ( D ) TOPOLOGY: linear ( i i ) MOLECULE TYPE: other nucleic acid
- ( A ) DESCRIPTION: third strand derived from S. parasanguis 16s region in Seq ID No 345

( i i i ) HYPOTHETICAL: yes ( i v ) ANTI-SENSE: no ( x ) PUBLICATION INFORMATION:
- ( K ) RELEVANT RESIDUES IN SEQ ID NO: 346 :FROM 1 TO 17

( x i ) SEQUENCE DESCRIPTION: SEQ ID NO: 346 :

TCTTCCCCTC TCGCCTT 17

( 2 ) INFORMATION FOR SEQ ID NO:347:

( i ) SEQUENCE CHARACTERISTICS:
- ( A ) LENGTH: 15 base pairs
- ( B ) TYPE: nucleic acid
- ( C ) STRANDEDNESS: double stranded
- ( D ) TOPOLOGY: linear ( i i ) MOLECULE TYPE: genomic DNA
- ( A ) DESCRIPTION: 16s rRNA gene from Streptococcus parasanguis (Accession #X53652) nucleotides 1178 to 1192

( i i i ) HYPOTHETICAL: no ( i v ) ANTI-SENSE: no ( v i ) ORIGINAL SOURCE:
- ( A ) ORGANISM: Streptococcus parasanguis
- ( B ) STRAIN: 85-81

( x ) PUBLICATION INFORMATION:
- ( A ) AUTHORS: Whiley, R A, Fraser, H Y, Douglas, C W I, Hardie, J M, Williams, A M, Collins, M D.
- ( B ) TITLE: Streptococcus parasanguis sp nov., an atypical viridans Streptococcus from human clinical specimens
- ( C ) JOURNAL: FEMS Microbiology Letters
- ( D ) VOLUME: 68
- ( F ) PAGES: 115-122
- ( G ) DATE: 1990
- ( K ) RELEVANT RESIDUES IN SEQ ID NO: 347 :FROM 1 TO 15

( x i ) SEQUENCE DESCRIPTION: SEQ ID NO: 347:

GGAGGAAGGT GGGGA 15

( 2 ) INFORMATION FOR SEQ ID NO:348:

( i ) SEQUENCE CHARACTERISTICS:
   ( A ) LENGTH: 15 bases
   ( B ) TYPE: nucleic acid
   ( C ) STRANDEDNESS: single stranded
   ( D ) TOPOLOGY: linear ( i i ) MOLECULE TYPE: other nucleic acid
   ( A ) DESCRIPTION: third strand derived from S.
       parasanguis 16s region in Seq ID No 347

( i i i ) HYPOTHETICAL: yes ( i v ) ANTI-SENSE: no ( x ) PUBLICATION INFORMATION:
   ( K ) RELEVANT RESIDUES IN SEQ ID NO: 348 :FROM 1 TO 15

( x i ) SEQUENCE DESCRIPTION: SEQ ID NO: 348 :

CCTCCTTCCG CCCCT 15

( 2 ) INFORMATION FOR SEQ ID NO:349:

( i ) SEQUENCE CHARACTERISTICS:
      ( A ) LENGTH: 13 base pairs
      ( B ) TYPE: nucleic acid
      ( C ) STRANDEDNESS: double stranded
      ( D ) TOPOLOGY: linear ( i i ) MOLECULE TYPE: genomic DNA
      ( A ) DESCRIPTION: p53 gene, nucleotides 801-813

( i i i ) HYPOTHETICAL: no ( i v ) ANTI-SENSE: no ( v i ) ORIGINAL SOURCE:
      ( A ) ORGANISM: Homo sapiens ( x ) PUBLICATION INFORMATION:
      ( A ) AUTHORS: Harlow, E, Williamson, N M, Ralston, R,
          Helfman, D M, Adams T E.
      ( B ) TITLE: Molecular cloning and in
          vitro expression of a cDNA for human cellular
          tumor antigen p53
      ( C ) JOURNAL: Molecular and Cellular Biology
      ( D ) VOLUME: 5
      ( F ) PAGES: 1601-1610
      ( G ) DATE: 1985
      ( K ) RELEVANT RESIDUES IN SEQ ID NO: 349 :FROM 1 TO 13

( x i ) SEQUENCE DESCRIPTION: SEQ ID NO: 349:

GAGTGGAAGG AAA 13

( 2 ) INFORMATION FOR SEQ ID NO:350:

( i ) SEQUENCE CHARACTERISTICS:
      ( A ) LENGTH: 13 bases
      ( B ) TYPE: nucleic acid
      ( C ) STRANDEDNESS: single stranded
      ( D ) TOPOLOGY: linear ( i i ) MOLECULE TYPE: other nucleic acid
      ( A ) DESCRIPTION: third strand derived from p53 gene
          region in Seq ID No 349

( i i i ) HYPOTHETICAL: yes ( i v ) ANTI-SENSE: no ( x ) PUBLICATION INFORMATION:
      ( K ) RELEVANT RESIDUES IN SEQ ID NO: 350 :FROM 1 TO 13

( x i ) SEQUENCE DESCRIPTION: SEQ ID NO: 350 :

CTCGCCTTCC TTT 13

( 2 ) INFORMATION FOR SEQ ID NO:351:

( i ) SEQUENCE CHARACTERISTICS:
        ( A ) LENGTH: 12 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: p53 gene, nucleotides 1066-1077

( i i i ) HYPOTHETICAL: no ( i v ) ANTI-SENSE: no ( v i ) ORIGINAL SOURCE:
        ( A ) ORGANISM: Homo sapiens ( x ) PUBLICATION INFORMATION:
        ( A ) AUTHORS: Harlow, E, Williamson, N M, Ralston, R,
            Helfman, D M, Adams T E.
        ( B ) TITLE: Molecular cloning and in
            vitro expression of a cDNA for human cellular
            tumor antigen p53
        ( C ) JOURNAL: Molecular and Cellular Biology
        ( D ) VOLUME: 5
        ( F ) PAGES: 1601-1610
        ( G ) DATE: 1985
        ( K ) RELEVANT RESIDUES IN SEQ ID NO: 351 :FROM 1 TO 12

( x i ) SEQUENCE DESCRIPTION: SEQ ID NO: 351:

AGAGGAAGAG AA            12

( 2 ) INFORMATION FOR SEQ ID NO:352:

( i ) SEQUENCE CHARACTERISTICS:
        ( A ) LENGTH: 12 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from p53 gene
            region in Seq ID No 351

( i i i ) HYPOTHETICAL: yes ( i v ) ANTI-SENSE: no ( x ) PUBLICATION INFORMATION:
        ( K ) RELEVANT RESIDUES IN SEQ ID NO: 352 :FROM 1 TO 12

( x i ) SEQUENCE DESCRIPTION: SEQ ID NO: 352 :

TCTCCTTCTC TT            12

( 2 ) INFORMATION FOR SEQ ID NO:353:

( i ) SEQUENCE CHARACTERISTICS:
        ( A ) LENGTH: 12 base pairs
        ( B ) TYPE: nucleic acid
        ( C ) STRANDEDNESS: double stranded
        ( D ) TOPOLOGY: linear ( i i ) MOLECULE TYPE: genomic DNA
        ( A ) DESCRIPTION: p53 gene, nucleotides 1085-1096

( i i i ) HYPOTHETICAL: no ( i v ) ANTI-SENSE: no ( v i ) ORIGINAL SOURCE:
        ( A ) ORGANISM: Homo sapiens ( x ) PUBLICATION INFORMATION:

(A) AUTHORS: Harlow, E, Williamson, N M, Ralston, R,
    Helfman, D M, Adams T E.
(B) TITLE: Molecular cloning and in
    vitro expression of a cDNA for human cellular
    tumor antigen p53
(C) JOURNAL: Molecular and Cellular Biology
(D) VOLUME: 5
(F) PAGES: 1601-1610
(G) DATE: 1985
(K) RELEVANT RESIDUES IN SEQ ID NO: 353 :FROM 1 TO 12

(xi) SEQUENCE DESCRIPTION: SEQ ID NO: 353:

AAGAAAGGGG AG                                                          12

(2) INFORMATION FOR SEQ ID NO:354:

(i) SEQUENCE CHARACTERISTICS:
    (A) LENGTH: 12 bases
    (B) TYPE: nucleic acid
    (C) STRANDEDNESS: single stranded
    (D) TOPOLOGY: linear (ii) MOLECULE TYPE: other nucleic acid
    (A) DESCRIPTION: third strand derived from p53 gene
        region in Seq ID No 353

(iii) HYPOTHETICAL: yes (iv) ANTI-SENSE: no (x) PUBLICATION INFORMATION:
    (K) RELEVANT RESIDUES IN SEQ ID NO: 354 :FROM 1 TO 12

(xi) SEQUENCE DESCRIPTION: SEQ ID NO: 354 :

TTCTTTCCCC TC                                                          12

(2) INFORMATION FOR SEQ ID NO:355:

(i) SEQUENCE CHARACTERISTICS:
    (A) LENGTH: 11 base pairs
    (B) TYPE: nucleic acid
    (C) STRANDEDNESS: double stranded
    (D) TOPOLOGY: linear (ii) MOLECULE TYPE: genomic DNA
    (A) DESCRIPTION: p53 gene, nucleotides 1153-1163

(iii) HYPOTHETICAL: no (iv) ANTI-SENSE: no (vi) ORIGINAL SOURCE:
    (A) ORGANISM: Homo sapiens (x) PUBLICATION INFORMATION:
    (A) AUTHORS: Harlow, E, Williamson, N M, Ralston, R,
        Helfman, D M, Adams T E.
    (B) TITLE: Molecular cloning and in
        vitro expression of a cDNA for human cellular
        tumor antigen p53
    (C) JOURNAL: Molecular and Cellular Biology
    (D) VOLUME: 5
    (F) PAGES: 1601-1610
    (G) DATE: 1985
    (K) RELEVANT RESIDUES IN SEQ ID NO: 355 :FROM 1 TO 11

(xi) SEQUENCE DESCRIPTION: SEQ ID NO: 355:

CTCCTCTCCC C                                                           11

(2) INFORMATION FOR SEQ ID NO:356:

(i) SEQUENCE CHARACTERISTICS:
    (A) LENGTH: 11 bases
    (B) TYPE: nucleic acid (C) STRANDEDNESS: single stranded
(D) TOPOLOGY: linear (ii) MOLECULE TYPE: other nucleic acid
(A) DESCRIPTION: third strand derived from p53 gene region in Seq ID No 355

(iii) HYPOTHETICAL: yes (iv) ANTI-SENSE: no (x) PUBLICATION INFORMATION:
(K) RELEVANT RESIDUES IN SEQ ID NO: 356 :FROM 1 TO 11

(xi) SEQUENCE DESCRIPTION: SEQ ID NO: 356 :

CCCCTCTCCT C 11

(2) INFORMATION FOR SEQ ID NO:357:

(i) SEQUENCE CHARACTERISTICS:
(A) LENGTH: 10 base pairs
(B) TYPE: nucleic acid
(C) STRANDEDNESS: double stranded
(D) TOPOLOGY: linear (ii) MOLECULE TYPE: genomic DNA
(A) DESCRIPTION: p53 gene, nucleotides 1168-1177

(iii) HYPOTHETICAL: no (iv) ANTI-SENSE: no (vi) ORIGINAL SOURCE:
(A) ORGANISM: Homo sapiens (x) PUBLICATION INFORMATION:
(A) AUTHORS: Harlow, E, Williamson, N M, Ralston, R, Helfman, D M, Adams T E.
(B) TITLE: Molecular cloning and in vitro expression of a cDNA for human cellular tumor antigen p53
(C) JOURNAL: Molecular and Cellular Biology
(D) VOLUME: 5
(F) PAGES: 1601-1610
(G) DATE: 1985
(K) RELEVANT RESIDUES IN SEQ ID NO: 357 :FROM 1 TO 10

(xi) SEQUENCE DESCRIPTION: SEQ ID NO: 357:

AAAGAAGAAA 10

(2) INFORMATION FOR SEQ ID NO:358:

(i) SEQUENCE CHARACTERISTICS:
(A) LENGTH: 10 bases
(B) TYPE: nucleic acid
(C) STRANDEDNESS: single stranded
(D) TOPOLOGY: linear (ii) MOLECULE TYPE: other nucleic acid
(A) DESCRIPTION: third strand derived from p53 gene region in Seq ID No 357

(iii) HYPOTHETICAL: yes (iv) ANTI-SENSE: no (x) PUBLICATION INFORMATION:
(K) RELEVANT RESIDUES IN SEQ ID NO: 358 :FROM 1 TO 10

(xi) SEQUENCE DESCRIPTION: SEQ ID NO: 358 :

TTTCTTCTTT 10

(2) INFORMATION FOR SEQ ID NO:359:

( i ) SEQUENCE CHARACTERISTICS:
    ( A ) LENGTH: 27 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: p53 gene, nucleotides 1427-1453

( i i i ) HYPOTHETICAL: no ( i v ) ANTI-SENSE: no ( v i ) ORIGINAL SOURCE:
    ( A ) ORGANISM: Homo sapiens ( x ) PUBLICATION INFORMATION:
    ( A ) AUTHORS: Harlow, E, Williamson, N M, Ralston, R,
        Helfman, D M, Adams T E.
    ( B ) TITLE: Molecular cloning and in
        vitro expression of a cDNA for human cellular
        tumor antigen p53
    ( C ) JOURNAL: Molecular and Cellular Biology
    ( D ) VOLUME: 5
    ( F ) PAGES: 1601-1610
    ( G ) DATE: 1985
    ( K ) RELEVANT RESIDUES IN SEQ ID NO: 359 :FROM 1 TO 27

( x i ) SEQUENCE DESCRIPTION: SEQ ID NO: 359:

CCTCCCACCC CCATCTCTCC CTCCCCT                27

( 2 ) INFORMATION FOR SEQ ID NO:360:

( i ) SEQUENCE CHARACTERISTICS:
    ( A ) LENGTH: 27 bases
    ( B ) TYPE: nucleic acid
    ( C ) STRANDEDNESS: single stranded
    ( D ) TOPOLOGY: linear ( i i ) MOLECULE TYPE: other nucleic acid
    ( A ) DESCRIPTION: third strand derived from p53 gene
        region in Seq ID No 359

( i i i ) HYPOTHETICAL: yes ( i v ) ANTI-SENSE: no ( x ) PUBLICATION INFORMATION:
    ( K ) RELEVANT RESIDUES IN SEQ ID NO: 360 :FROM 1 TO 27

( x i ) SEQUENCE DESCRIPTION: SEQ ID NO: 360 :

TCCCCTCCCT CTCTGCCCCC GCCCTCC                27

( 2 ) INFORMATION FOR SEQ ID NO:361:

( i ) SEQUENCE CHARACTERISTICS:
    ( A ) LENGTH: 23 base pairs
    ( B ) TYPE: nucleic acid
    ( C ) STRANDEDNESS: double stranded
    ( D ) TOPOLOGY: linear ( i i ) MOLECULE TYPE: genomic DNA
    ( A ) DESCRIPTION: p53 gene, nucleotides 1581-1603

( i i i ) HYPOTHETICAL: no ( i v ) ANTI-SENSE: no ( v i ) ORIGINAL SOURCE:
    ( A ) ORGANISM: Homo sapiens ( x ) PUBLICATION INFORMATION:
    ( A ) AUTHORS: Harlow, E, Williamson, N M, Ralston, R,
        Helfman, D M, Adams T E.
    ( B ) TITLE: Molecular cloning and in
        vitro expression of a cDNA for human cellular tumor antigen p53
( C ) JOURNAL: Molecular and Cellular Biology
( D ) VOLUME: 5
( F ) PAGES: 1601-1610
( G ) DATE: 1985
( K ) RELEVANT RESIDUES IN SEQ ID NO: 361 :FROM 1 TO 23

( x i ) SEQUENCE DESCRIPTION: SEQ ID NO: 361:

GGGGAGGAGG ATGGGGAGTA GGA 23

( 2 ) INFORMATION FOR SEQ ID NO:362:

( i ) SEQUENCE CHARACTERISTICS:
        ( A ) LENGTH: 23 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: third strand derived from p53 gene
            region in Seq ID No 361

( i i i ) HYPOTHETICAL: yes ( i v ) ANTI-SENSE: no ( x ) PUBLICATION INFORMATION:
        ( K ) RELEVANT RESIDUES IN SEQ ID NO: 362 :FROM 1 TO 23

( x i ) SEQUENCE DESCRIPTION: SEQ ID NO: 362 :

CCCCTCCTCC TGCCCCTCGT CCT 23

( 2 ) INFORMATION FOR SEQ ID NO:363:

( i ) SEQUENCE CHARACTERISTICS:
        ( A ) LENGTH: 33 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: collector strand ( i i i ) HYPOTHETICAL: yes ( i v ) ANTI-SENSE: no ( x ) PUBLICATION INFORMATION:
        ( K ) RELEVANT RESIDUES IN SEQ ID NO: 363 :FROM 1 TO 33

( x i ) SEQUENCE DESCRIPTION: SEQ ID NO: 363 :

GCAAGCAACA GTTACTGCGA CGTGAGGTAT ATG 33

( 2 ) INFORMATION FOR SEQ ID NO:364:

( i ) SEQUENCE CHARACTERISTICS:
        ( A ) LENGTH: 17 bases
        ( B ) TYPE: nucleic acid
        ( C ) STRANDEDNESS: single stranded
        ( D ) TOPOLOGY: linear ( i i ) MOLECULE TYPE: other nucleic acid
        ( A ) DESCRIPTION: reporter strand ( i i i ) HYPOTHETICAL: yes ( i v ) ANTI-SENSE: no ( x ) PUBLICATION INFORMATION:
        ( K ) RELEVANT RESIDUES IN SEQ ID NO: 364 :FROM 1 TO 17

( x i ) SEQUENCE DESCRIPTION: SEQ ID NO: 364 :

AGTTGAACGT CGCATCC 17

(2) INFORMATION FOR SEQ ID NO:365:

(i) SEQUENCE CHARACTERISTICS:
        (A) LENGTH: 22 bases
        (B) TYPE: nucleic acid
        (C) STRANDEDNESS: single stranded
        (D) TOPOLOGY: linear (ii) MOLECULE TYPE: other nucleic acid
        (A) DESCRIPTION: tester strand (iii) HYPOTHETICAL: yes (iv) ANTI-SENSE: no (x) PUBLICATION INFORMATION:
        (K) RELEVANT RESIDUES IN SEQ ID NO: 365 :FROM 1 TO 22

(xi) SEQUENCE DESCRIPTION: SEQ ID NO: 365 :

```
ATACCTCACG TCGCAGTAAC TG                                    22
```

We claim:

1. A method of assaying genetic sequences, which comprises introducing a sample containing double stranded DNA to be assayed into an aqueous medium containing at least one complex comprising an anchor DNA strand anchored to a support matrix, said anchor strand being hybridized with a reporter DNA strand having a detectable label, a portion of the anchor strand or the reporter strand consisting of a selected sequence of bases selected to form a triple strand structure with a portion of double stranded DNA to be assayed, whereby said reporter strand is displaced from said complex upon formation of said triple strand structure, and detecting displaced reporter strands to determine the presence of said double stranded DNA.

2. A method of assaying genetic sequences, which comprises providing at least one anchor/reporter hybrid, wherein the anchor comprises a single strand DNA molecule coupled at one end to a solid support, the reporter comprises a single strand DNA molecule having at or near one end a label which is an assayable molecule or particle, a portion of the reporter strand being hybridized to the anchor strand and either the anchor strand or the reporter strand having an unhybridized free end, said free end comprising a nucleotide sequence selected to to form a triple strand structure with a portion of double stranded DNA sequence to be assayed;

maintaining said anchor/reporter hybrid in an aqueous buffer medium in a container;

adding to the medium a sample containing double stranded DNA to be assayed;

incubating the medium for a time and at a temperature effective for forming a triple strand structure between said selected nucleotide sequence and said portion of said particular double stranded DNA sequence when present, whereby said reporter is displaced from said anchor/reporter hybrid upon formation of said triple strand structure; and determining the presence of said double stranded DNA sequence in the sample by detecting the labels of displaced reporters.

3. A method according to claim 2, wherein the free end comprising said selected nucleotide sequence is a free 5'-end of the reporter DNA strand.

4. A method according to claim 2, wherein said selected nucleotide sequence comprises at least 10 bases.

5. A method according to claim 2, further comprising providing at least one standard by assaying a control comprising a known amount of a known double stranded DNA sequence.

6. A method according to claim 5, which comprises simultaneously assaying said double stranded DNA sequence to be assayed in said sample and said control DNA sequence in the same container by use of two differing types of anchor/reporter hybrids having differently detectable labels and respectively having a nucleotide sequence selected to form a triple strand structure with said sample DNA or with said control.

7. A method according to claim 5, which comprises detecting the amount of reporters displaced as a result of formation of triple strand structures with the particular double stranded DNA sequences to be assayed in the sample, and determining the amount of said double stranded DNA sequences in the sample by comparison with said standard.

8. A method according to claim 2, which comprises simultaneously assaying in the same container two or more different genetic sequences in a sample by use of correspondingly differing types of anchor/reporter hybrids having different detectable labels and respectively having a nucleotide sequence selected to form forming a triple strand structure with each different genetic sequence to be assayed.

9. A method according to claim 2, further comprising adding a protein to the anchor/reporter hybrid which promotes formation of a triple strand structure between the selected nucleotide sequence and the added double stranded DNA.

10. A method according to claim 9, wherein the added protein is RecA protein of *Escherichia coli*.

11. A method according to claim 2, wherein the reporter label is fluorescent.

12. A method according to claim 11, wherein the label of the reporter strand is a particle which is a polymeric microsphere comprising fluorescent compounds or elements.

13. A method according to claim 11, which comprises removing at least a portion of the aqueous medium after incubating, passing the removed liquid through a narrow tube exposed to light and determining the amount of reporters by detecting the fluorescence of their labels.

14. A method according to claim 13, wherein said light is a laser beam and which comprises carrying out the detection automatically.

15. A method of assaying genetic sequences, which comprises combining in an aqueous medium a double stranded DNA to be assayed fixed to a support, a protein which promotes formation of a triple strand structure and at least one reporter DNA strand having a detectable label, a portion of the reporter strand consisting of a selected sequence of bases which forms a triple strand structure with a portion of the double stranded DNA to be assayed, incubating the medium, washing to remove unbound reporter, and detecting bound reporter strands to determine the presence of said double stranded DNA.

\* \* \* \* \*